US010428060B2

(12) United States Patent
Glenn et al.

(10) Patent No.: US 10,428,060 B2
(45) **Date of Patent: *Oct. 1, 2019**

(54) PI-KINASE INHIBITORS WITH ANTI-INFECTIVE ACTIVITY

(71) Applicants: The Board of Trustees of the Leland Stanford Junior University, Stanford, CA (US); The Regents of the University of California, Oakland, CA (US)

(72) Inventors: Jeffrey S. Glenn, Palo Alto, CA (US); Michael A. Gelman, New York, NY (US); Brandon Tavshanjian, San Francisco, CA (US); Kevan Shokat, San Francisco, CA (US); Ingrid Choong, Los Altos, CA (US)

(73) Assignees: The Board of Trustees of the Leland Stanford Junior University, Stanford, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,965

(22) Filed: Feb. 9, 2018

(65) Prior Publication Data

US 2018/0170924 A1 Jun. 21, 2018

Related U.S. Application Data

(63) Continuation of application No. 15/055,403, filed on Feb. 26, 2016, now Pat. No. 9,926,309, which is a continuation-in-part of application No. 14/348,864, filed as application No. PCT/US2012/059023 on Oct. 5, 2012, now Pat. No. 9,309,236.

(60) Provisional application No. 61/543,538, filed on Oct. 5, 2011.

(51) Int. Cl.

| | |
|---|---|
| ***C07D 277/44*** | (2006.01) |
| ***C07D 417/04*** | (2006.01) |
| ***C07D 417/12*** | (2006.01) |
| ***C07D 417/14*** | (2006.01) |
| ***C07D 277/46*** | (2006.01) |
| ***C07D 277/42*** | (2006.01) |

(52) U.S. Cl.

CPC ......... *C07D 417/14* (2013.01); *C07D 277/42* (2013.01); *C07D 277/44* (2013.01); *C07D 277/46* (2013.01); *C07D 417/04* (2013.01); *C07D 417/12* (2013.01)

(58) Field of Classification Search

CPC ... C07D 277/44; C07D 417/04; C07D 417/12
See application file for complete search history.

(56) References Cited

U.S. PATENT DOCUMENTS

| | | | |
|---|---|---|---|
| 7,361,669 B2 | 4/2008 | Scarborough et al. | |
| 7,687,637 B2 | 3/2010 | Bruce et al. | |
| 7,868,188 B2 | 1/2011 | Bengtsson et al. | |
| 8,088,806 B2 | 1/2012 | Zhang et al. | |
| 8,106,209 B2 | 1/2012 | Liu et al. | |
| 8,404,684 B2 | 3/2013 | Bruce et al. | |
| 9,309,236 B2 | 4/2016 | Glenn et al. | |
| 9,926,309 B2 * | 3/2018 | Glenn .................. | C07D 417/14 |
| 2004/0186148 A1 | 9/2004 | Shankar et al. | |
| 2005/0228020 A1 | 10/2005 | Miyamoto et al. | |
| 2007/0212717 A1 | 9/2007 | Kukolj et al. | |
| 2009/0029997 A1 | 1/2009 | Quattropani et al. | |
| 2009/0076009 A1 | 3/2009 | Arnould et al. | |
| 2009/0163469 A1 | 6/2009 | Caravatti et al. | |
| 2010/0010057 A1 | 1/2010 | Moffat et al. | |
| 2010/0093690 A1 | 4/2010 | Bruce et al. | |
| 2011/0124693 A1 | 5/2011 | Bloomfield et al. | |
| 2012/0135997 A1 | 5/2012 | Kato et al. | |
| 2015/0175562 A1 | 6/2015 | Gege et al. | |

FOREIGN PATENT DOCUMENTS

| | | |
|---|---|---|
| WO | 1996/23783 A1 | 8/1996 |
| WO | 2003/018536 A1 | 3/2003 |
| WO | 2003/072557 A1 | 9/2003 |
| WO | 2004/080377 A2 | 9/2004 |

(Continued)

OTHER PUBLICATIONS

Schickli et al., Human Vaccines, vol. 5, Issue 9, pp. 582-591, Sep. 2009 (Year: 2009).*

(Continued)

*Primary Examiner* — Laura L Stockton
(74) *Attorney, Agent, or Firm* — Bret E. Field; Bozicevic, Field & Francis LLP

(57) ABSTRACT

Compounds and methods are provided for the treatment of pathogen infections. In some embodiments, the anti-infective compounds have broad spectrum activity against a variety of infective diseases, where the diseases are caused by pathogens containing a basic amino acid PIP-2 pincer (BAAPP) domain that interacts with phosphatidylinositol 4,5-bisphosphate (PIP-2) to mediate pathogen replication. Also provided are methods of inhibiting a PI4-kinase and methods of inhibiting viral infection. In some embodiments, the compound is a PI4-kinase inhibiting compound that is a 5-aryl-thiazole or a 5-hetereoaryl-thiazole. The subject compounds may be formulated or provided to a subject in combination with a second anti-infective agent, e.g. interferon, ribivarin, and the like.

21 Claims, No Drawings

Specification includes a Sequence Listing.

(56) References Cited

FOREIGN PATENT DOCUMENTS

| | | | |
|---|---|---|---|
| WO | 2005/044797 | A1 | 5/2005 |
| WO | 2006/051270 | A1 | 5/2006 |
| WO | 2007/070600 | A2 | 6/2007 |
| WO | 2007/073497 | A2 | 6/2007 |
| WO | 2007/129048 | A1 | 11/2007 |
| WO | 2008/020227 | A2 | 2/2008 |
| WO | 2008/154601 | A1 | 12/2008 |
| WO | 2010/008739 | A1 | 1/2010 |
| WO | 2010/066324 | A1 | 6/2010 |
| WO | 2011/007819 | A1 | 1/2011 |
| WO | 2013/052845 | A1 | 4/2013 |

OTHER PUBLICATIONS

Anthony P. Cardile, Travis K. Warren, Karen A. Martins, Ronald B. Reisler, and Sina Bavari, Annual Review of Pharmacology and Toxicology, 2017, 57(1), 329-348 (Year: 2017).*

Du et al. {Vaccines for the prevention against the threat of MERS-CoV, Expert Review of Vaccines, 2016, 15:9, 1123-1134 (Year: 2016).*

Chemical Abstracts Registry No. 329792-54-3, indexed in the Registry file on STN CAS Online Apr. 3, 2001.

Jamieson et al. "A drug targeting only p110α can block phosphoinositide 3-kinase signalling and tumour growth in certain cell types", Biochemical Journal, Aug. 15, 2011, pp. 53-62, 438(1), Portland Press Limited, London, England.

Miller et al., "Shaping Development of Autophagy Inhibitors with the Structure of the Lipid Kinase Vps34", Science, Mar. 26, 2010, pp. 1638-1642, 327(5973), and the Supporting Online Material (33 pages) including Materials, Methods, Figs. S1 to S11, Table S1 and References, http://science.sciencemag.org/content/sci/suppl/2010/03/23/327.5973.1638.DC1/Miller.SOM.pdf., American Association for the Advancement of Science, Washington, D.C.

* cited by examiner

PI-KINASE INHIBITORS WITH ANTI-INFECTIVE ACTIVITY

CROSS REFERENCE TO RELATED APPLICATIONS

This application claims benefit and is a Continuation of application Ser. No. 15/055,403 filed Jan. 26, 2016, which is a continuation-in part of U.S. patent application Ser. No. 14/348,864, filed Mar. 31, 2014, now U.S. Pat. No. 9,309,236, issued Apr. 12, 2016, which is a 371 application and claims the benefit of PCT Application No. PCT/US2012/059023, filed Oct. 5, 2012, which claims benefit of U.S. Provisional Patent Application No. 61/543,538, filed Oct. 5, 2011, which applications are incorporated herein by reference in their entirety.

FEDERALLY SPONSORED RESEARCH AND DEVELOPMENT

This invention was made with Government support under contracts AI007502, AI088793, AI097322, AI099245, AI109662, and DK007056 awarded by the National Institutes of Health. The Government has certain rights in the invention.

INTRODUCTION

The rapid rise in the number of emerging pathogens in the world's population represents a serious global health problem and underscores the need to develop broad spectrum anti-infectives that target common components of large classes of pathogens. For example, it is estimated that more than 2% of the world's population is currently infected with the Hepatitis C Virus (HCV). One of the outstanding characteristics of HCV is its ability to establish chronic infections in 65-80% of infected patients. Chronic infection with HCV can lead to serious sequelae including chronic active hepatitis, cirrhosis and hepatocellular carcinoma—usually manifested 10, 20 and 25 years respectively after the initial infection. End stage liver disease from HCV has become the leading indication for liver transplantation in North America, and it has been suggested that there will be a 2-3 fold increase in liver transplantation in 10 years as a result of cirrhosis from hepatitis C.

Anti-infective agents for use in treating various infective diseases are of interest. Also of interest are anti-infective agents for specifically treating one or more pathogen-caused infective diseases, such as hepatitis C.

SUMMARY

Compounds and methods are provided for the treatment of pathogen infections, which include, without limitation, viruses and other pathogens that utilize intracellular replication mechanisms, e.g. hepatitis C virus (HCV), *Plasmodium falciparum*, rhinovirus, and the like. In some embodiments, the anti-infective compounds have broad spectrum activity against a variety of infective diseases, where the diseases are caused by pathogens containing a basic amino acid PIP2 pincer (BAAPP) domain that interacts with phosphatidylinositol 4,5-bisphosphate ($PI(4,5)P_2$) to mediate replication.

Also provided are methods of inhibiting a PI4-kinase and methods of inhibiting viral infection in a subject. In some embodiments, the compound is a PI4-kinase inhibiting compound that is a 5-aryl or heteroaryl-thiazole, e.g., as described herein. In certain embodiments the compound is a 2-amino-5-phenylthiazole compound. In certain embodiments the compound is a 2-amino-5-pyridylthiazole compound. The subject compounds may be formulated or provided to a subject in combination with one or more additional anti-infective agents, e.g. interferon, ribavirin, and the like. The subject compounds find use in the treatment of a variety of viruses such as a virus from the Picornaviridae, Flaviviridae, Caliciviridae, Filoviridae, Hepeviridae or Coronavirinae families. For treatment of viruses such as HCV, the compounds may be formulated to specifically target the liver, e.g. by conjugation with polyarginine or a bile acid, or as pro-drugs designed to be activated by enzymes resident in the liver.

These and other advantages and features of the disclosure will become apparent to those persons skilled in the art upon reading the details of the compositions and methods of use, which are more fully described below.

DEFINITIONS

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The Basic Amino Acid PIP2 Pincer (BAAPP) domain, as described by Glenn et al., "PIP-2 Inhibition-Based Antiviral and Anti-Hyperlipidemic Therapies" WO2009/148541, and which is herein incorporated by reference in its entirety, provides a mechanism by which a protein or peptide recognizes (including but not limited to binding, as well as activation or suppression of activity) PIP2 (phosphatidylinositol 4,5-bisphosphate [PtdIns(4,5)P2], PI(4,5)P2). Alterations or variations of the BAAPP domain may result in recognition of other phosphatidylinositol variants.

Phosphoinositides, such as phosphatidylinositol (PI)-4-phosphate (PI(4)P) and PI-4,5-bisphosphate ($PI(4,5)P_2$, or "PIP2"), are enriched in various specific plasma membrane and intracellular locations. The steady state location and abundance of specific PI isoform pools within the cell is regulated by a family of PI-kinases and phosphatases. There are least 4 human PI4-kinases, with family members PI4KIIIα and PI4KIIIβ being primarily localized to ER and Golgi-derived membranes where they contribute to the PI(4)P and $PI(4,5)P_2$ pools associated with these membranes, and with family members PI4KIIα and PI4KIIβ contributing primarily to other pools.

The BAAPP domain mediates specific interaction with PIP2, resulting in a conformational change in the BAAPP domain that affects a key pathogen regulator. In HCV, replication complexes are established at intracellular PIP2-enriched sites, and point mutations in the BAAPP domain abrogate PIP2 binding and HCV RNA replication. Such critical dependence on PIP2 is widespread among pathogens. Targeting specific intracellular PIP2 pools by siRNA-mediated knockdown of enzymes responsible for PIP2 production—such as PI4KIIIα and PI4KIIIβ—abrogates HCV replication, yet is well tolerated by the host cell.

Molecules that inhibit the enzymatic pathways responsible for production of PIP-2 are of interest for use in the methods of the disclosure. Such inhibitors include, without limitation, inhibitors of phosphatidylinositol 4-kinase III alpha (see, for example Berger et al. (2009) PNAS 106: 7577-7582, herein specifically incorporated by reference) and inhibitors of phosphatidylinositol 4-kinase III beta.

BAAPP domains have been identified in multiple organisms, including but not limited to pathogens such as viruses, bacteria, fungi and parasites, as well as hosts, such as the human BAAPP domain peptides, molecules that mimic the BAAPP domain, enzymes involved in PIP-2 metabolism, and molecules that inhibit or activate the BAAPP domain act in treating infectious diseases as well as affecting host physiology or pathophysiology.

Examples of proteins having a BAAPP domain include, without limitation, the 2C protein of Picornaviridae, Rhinovirus 14, Rhinovirus B, Rhinovirus C, PolioVirus, Enterovirus A, Enterovirus B, Enterovirus C, Enterovirus D, Enterovirus 71, and Coxsackie A virus 18. The core protein of Japanese Encephalitis Virus, West Nile Virus, Dengue Virus 1, Dengue Virus 2, Dengue Virus 3, and Dengue Virus 4 have BAAPP domains, as does the *P. falciparum* PfNDH2 protein. In the Flaviviridae, the NS4B AH 1 of HCV; the NS5A protein of HCV which has a BAAPP domain that comprises the conserved lysine residues at residue 20 and 26 of the processed protein, for example a peptide with the amino acid sequence SGSWLRDVWDWICTVLTDFK-TWLQSKLL (SEQ ID NO:1) that includes the lysine residues K20 and K26. Other BAAPP-domain harboring pathogens include HAV, Vaccinia, Ebola virus, *F. Tularensis*, influenza virus polymerase protein, Variola major (smallpox), Sin Nombre virus (hantavirus), *Pseudomonas aeruginosa*, CMV.

NS5 encoding viruses include without limitation flaviviruses, pestiviruses and hepatitis C viruses, e.g. yellow fever virus (YFV); Dengue virus, including Dengue types 1-4; Japanese Encephalitis virus; Murray Valley Encephalitis virus; St. Louis Encephalitis virus; West Nile virus; tickborne encephalitis virus; Hepatitis C virus; Kunjin virus; Central European encephalitis virus; Russian spring-summer encephalitis virus; Powassan virus; Kyasanur Forest disease virus; and Omsk hemorrhagic fever virus.

By "Flaviviridae virus" is meant any virus of the Flaviviridae family, including those viruses that infect humans and non-human animals. The polynucleotide and polypeptide sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

By "Picornaviridae virus" is meant any virus of the Picornaviridae family, including those viruses that infect humans and non-human animals, including, but not limited to, enteroviruses. The polynucleotide and polypeptide sequences encoding these viruses are well known in the art, and may be found at NCBI's GenBank database.

By "Caliciviridae virus" is meant any virus of the Caliciviridae family, including those viruses that infect humans and non-human animals, such as norovirus. The polynucleotide and polypeptide sequences encoding these viruses are well known in the art, and may be found at NCBI's GenBank database.

By "Filoviridae virus" is meant any virus of the Filoviridae family, including those viruses that infect humans and non-human animals, such as ebola virus. The polynucleotide and polypeptide sequences encoding these viruses are well known in the art, and may be found at NCBI's GenBank database.

By "Hepeviridae virus" is meant any virus of the Hepeviridae family, including those viruses that infect humans and non-human animals, such as hepevirus (e.g., HEV). The polynucleotide and polypeptide sequences encoding these viruses are well known in the art, and may be found at NCBI's GenBank database.

By "Coronavirinae virus" is meant any virus of the Coronavirinae family, including those viruses that infect humans and non-human animals, such as betacoronovirus (e.g., SARS and MERS). The polynucleotide and polypeptide sequences encoding these viruses are well known in the art, and may be found at NCBI's GenBank database.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in viral titers).

The terms “individual,” “host,” “subject,” and “patient” are used interchangeably herein, and refer to an animal, including, but not limited to, human and non-human primates, including simians and humans; rodents, including rats and mice; bovines; equines; ovines; felines; canines; and the like. “Mammal” means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms “determining,” “measuring,” “assessing,” and “assaying” are used interchangeably and include both quantitative and qualitative determinations.

The terms “polypeptide” and “protein”, used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms “nucleic acid molecule” and “polynucleotide” are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A “therapeutically effective amount” or “efficacious amount” means the amount of a compound that, when administered to a mammal or other subject for treating a disease, condition, or disorder, is sufficient to effect such treatment for the disease, condition, or disorder. The “therapeutically effective amount” will vary depending on the compound, the disease and its severity and the age, weight, etc., of the subject to be treated.

The term “unit dosage form,” as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A “pharmaceutically acceptable excipient,” “pharmaceutically acceptable diluent,” “pharmaceutically acceptable carrier,” and “pharmaceutically acceptable adjuvant” means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. “A pharmaceutically acceptable excipient, diluent, carrier and adjuvant” as used in the specification and claims includes both one and more than one such excipient, diluent, carrier, and adjuvant.

As used herein, a “pharmaceutical composition” is meant to encompass a composition suitable for administration to a subject, such as a mammal, especially a human. In general a “pharmaceutical composition” is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase “having the formula” or “having the structure” is not intended to be limiting and is used in the same way that the term “comprising” is commonly used. The term “independently selected from” is used herein to indicate that the recited elements, e.g., R groups or the like, can be identical or different.

As used herein, the terms “may,” “optional,” “optionally,” or “may optionally” mean that the subsequently described circumstance may or may not occur, so that the description includes instances where the circumstance occurs and instances where it does not. For example, the phrase “optionally substituted” means that a non-hydrogen substituent may or may not be present on a given atom, and, thus, the description includes structures wherein a non-hydrogen substituent is present and structures wherein a non-hydrogen substituent is not present.

“Acyl” refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the “acetyl” group $CH_3C(O)$—

The term “alkyl” as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term “lower alkyl” intends an alkyl group of 1 to 6 carbon atoms. “Substituted alkyl” refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(═O)— moiety). The terms “heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, $—S(O)_n—$ (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, $—SO_2$-alkyl, $—SO_2$-aryl, $—SO_2$-heteroaryl, and $—NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing "Lower alkylene" refers to alkylene linkages containing from 1 to 6 carbon atoms. Examples include, methylene ($—CH_2—$), ethylene ($—CH_2CH_2—$), propylene ($—CH_2CH_2CH_2—$), 2-methylpropylene ($—CH_2—CH(CH_3)—CH_2—$), hexylene ($—(CH_2)_6—$) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —$CO_2H$ or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cylcoalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N═N+═N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR═NH where R=hydrogen, C1-C24 alkyl, C5-C20 aryl, C6-C20 alkaryl, C6-C20 aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—NO2), nitroso (—NO), sulfo (—$SO_2$—OH), sulfonato (—$SO_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—$SO_2$-aryl), phosphono (—P(O)$(OH)_2$), phosphonato (—P(O)$(O—)_2$), phosphinato (—P(O)(O—)), phospho (—$PO_2$), and phosphino (—$PH_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═$NR^{70}$, ═N—$OR^{70}$, ═$N_2$ or ═S) on saturated carbon atoms in the specified group or radical are, unless otherwise specified, —$R^{60}$, halo, ═O, —$OR^{70}$, —$SR^{70}$, —$NR^{80}R^{80}$, trihalomethyl, —CN, —OCN, —SCN, —NO, —$NO_2$, ═$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1H$, $^2H$ (i.e., D) and $^3H$ (i.e., T), and reference to C is meant to include $^{12}C$ and all isotopes of carbon (such as $^{13}C$).

Definitions of other terms and concepts appear throughout the detailed description below.

DETAILED DESCRIPTION OF THE EMBODIMENTS

As summarized above, compounds and methods are provided for the treatment of pathogen infections, where the compound inhibits an enzyme in the phosphatidylinositol 4,5-bisphosphate (PIP-2) synthetic pathway, including without limitation selective inhibition of PI4-kinase. In some embodiments, the anti-infective compounds have broad spectrum activity against a variety of infective diseases, where the diseases are caused by pathogens containing a basic amino acid PIP-2 pincer (BAAPP) domain that interacts with phosphatidylinositol 4,5-bisphosphate (PIP-2) to mediate replication. In certain cases, the compounds have activity against one or more viruses selected from the Picornaviridae, Flaviviridae, Caliciviridae, Filoviridae, Hepeviridae and Coronavirinae families.

In some embodiments, an anti-infective compound that is a PI4-kinase inhibiting compound is contacted with a pathogen, in a dose and for a period of time sufficient to inhibit replication. Contacting may be performed in vitro or in vivo. Such PI4-kinase inhibiting compounds may inhibit pathogen replication by inhibiting the production of PIP-2.

In some embodiments a method of inhibiting a PI4-kinase, including but not limited to a class III PI4-kinase, are provided, where a compound of the invention is brought into contact with a PI4-kinase in a dose and for a period of time sufficient to inhibit activity of the enzyme.

Also provided are pharmaceutical compositions that include the subject compounds, where a compound of the present disclosure can be formulated with a pharmaceutically acceptable excipient. Formulations may be provided in a unit dose, where the dose provides an amount of the compound effective to achieve a desired result, including without limitation inhibition of pathogen replication.

These compounds and methods find use in a variety of applications in which inhibition of a PI-kinase is desired.

Compounds

As summarized above, aspects of the disclosure include PI4-kinase inhibitor compounds. In some cases, the compounds include a 5-aryl-thiazole or a 5-heteroaryl-thiazole core structure. The 5-aryl or 5-heteroaryl ring may be a 6-membered heteroaryl (e.g., pyridyl) or phenyl ring that includes at least a further substituent meta to the thiazole ring substituent. The thiazole ring of the core structure may include further substituents at the 2- and/or 4-positions of the ring. In some embodiments, the PI4-kinase inhibitor compounds are 2-amino-5-phenylthiazole compounds that include a thiazole ring having an amino substituent at the 2-position of the ring, and a phenyl substituent at the 5-position of the ring. In some embodiments, the PI4-kinase inhibitor compounds are 2-amino-5-pyridyl-thiazole compounds that include a thiazole ring having an amino substituent at the 2-position of the ring, and a pyridyl substituent at the 5-position of the ring. In some embodiments, the compound includes further substituents, such as a substituent at either the 4 or 5-position of the thiazole ring. The aryl ring of the core structure (e.g., 5-phenyl or pyridyl ring) may be further substituted with any convenient substituents including but not limited to alkyl, acyloxy, aminoalkoxy, cyano, halogen, hydroxyl, nitro, —NHCOR, —$SO_2NHR$, —CONHR or —$NHSO_2R$, where R is alkyl, heteroalkyl, heterocycle or aryl. Exemplary 5-aryl-thiazole compounds are set forth in the following structures and formulae I-XLIX.

In some cases, the subject compound is described by the structure of formula (Ia):

(Ia)

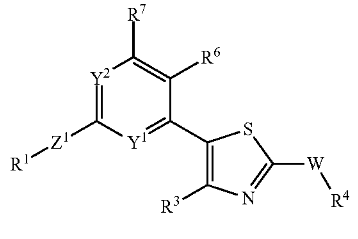

where:

$Z^1$ and W are each independently a covalent bond or a linking functional group;

$Y^1$ and $Y^2$ are each independently $CR^2$ or N;

$R^1$ is selected from hydrogen, an alkyl, a substituted alkyl, an aryl, a substituted aryl, an alkyl-heterocycle, a substituted heterocycle, a heterocycle and a substituted heterocycle;

$R^3$ is selected from hydrogen and an alkyl;

$R^4$ is selected from an alkyl, a substituted alkyl, an aralkyl, a substituted aralkyl, an aryl, a substituted aryl, an alkyl-cycloalkyl, a substituted alkyl-cyclohexyl, a cycloalkyl, a substituted cycloalkyl, an alkyl-heterocycle, a substituted alkyl-heterocycle, a heterocycle, a substituted heterocycle, an amino, a substituted amino, an alkoxy and a substituted alkoxy; and $R^2$, $R^6$ and $R^7$ are independently selected from hydrogen, an alkyl, a substituted alkyl, an aryl, a substituted aryl, a hydroxy, an alkoxy, a substituted alkoxy, an aryloxy, a substituted aryloxy, a heterocycle, a substituted heterocycle, a cyano, a halogen, an amino, a substituted amino, an acyl, an acyloxy, an amido, and a nitro.

In some cases, the subject compound is described by the structure of formula (Ib):

(Ib)

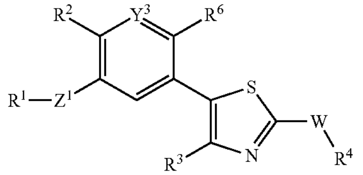

where:

$Z^1$ and W are each independently a covalent bond or a linking functional group;

$Y^3$ is $CR^7$ or N;

$R^1$ is selected from hydrogen, an alkyl, a substituted alkyl, an aryl, a substituted aryl, an alkyl-heterocycle, a substituted heterocycle, a heterocycle and a substituted heterocycle;

$R^3$ is selected from hydrogen and an alkyl;

$R^4$ is selected from an alkyl, a substituted alkyl, an aralkyl, a substituted aralkyl, an aryl, a substituted aryl, an alkyl-cycloalkyl, a substituted alkyl-cyclohexyl, a cycloalkyl, a substituted cycloalkyl, an alkyl-heterocycle, a substituted alkyl-heterocycle, a heterocycle, a substituted heterocycle, an amino, a substituted amino, an alkoxy and a substituted alkoxy; and $R^2$, $R^6$ and $R^7$ are independently selected from hydrogen, an alkyl, a substituted alkyl, an aryl, a substituted aryl, a hydroxy, an alkoxy, a substituted alkoxy, an aryloxy, a substituted aryloxy, a heterocycle, a substituted heterocycle, a cyano, a halogen, an amino, a substituted amino, an acyl, an acyloxy, an amido, and a nitro.

In certain embodiments, in formula (Ia) or (Ib), $R^1$ to $R^7$ are independently selected from corresponding groups as depicted in any of the structures of Table 1.

In some embodiments, in formula (Ia), $Y^1$ is CH and $Y^2$ is $CR^2$, such that the compound is described by the formula (IIa):

(IIa)

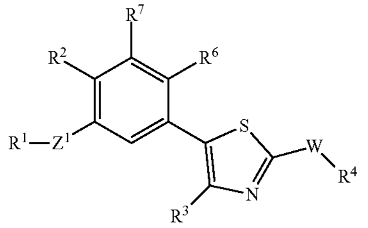

where:

$Z^1$ and W are each independently a covalent bond or a linking functional group;

$R^1$ is selected from an alkyl, an aryl, an alkyl-heterocycle and a heterocycle;

$R^2$ is selected from hydrogen, a halogen, an alkyl, a substituted alkyl, an alkoxy and a substituted alkoxy;

$R^3$ is selected from hydrogen and an alkyl;

$R^4$ is selected from an alkyl, an aralkyl, an aryl, an alkyl-cycloalkyl, a cycloalkyl, an alkyl-heterocycle, a heterocycle; and $R^6$ and $R^7$ are independently selected from hydrogen, an alkyl, an aryl, a hydroxy, an alkoxy, an aryloxy, a heterocycle, a cyano, a halogen, an amino, an acyl, an acyloxy, an amido and nitro.

In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments, $R^3$ and $R^6$ are selected such that they form a 6-membered ring as part of a fused tricyclic aryl-thiazole core structure.

In some embodiments, $R^1$ is not a hydroxy-substituted alkyl group, such as $-(CH_2)_2-OH$.

In some embodiments, $R^1$ is selected from hydrogen, an alkyl, an aryl (e.g., a phenyl), an alkyl-heterocycle and a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some embodiments, $R^1$ is selected from hydrogen, a substituted lower alkyl (e.g., a substituted methyl or ethyl), a phenyl, a cycloalkyl, a pyridyl and a pyrimidinyl.

In some instances, $R^4$ is $-(CH_2)_n-R^{10}$, where n is 0, 1, 2 or 3; and $R^{10}$ is a cycloalkyl or a hetercycle (e.g., a 5- or 6-membered saturated N-containing heterocycle). In certain cases, $R^{10}$ is selected from a cyclohexyl, a cyclopentyl, a cyclopropyl, a lower alkyl, a pyrrolidinyl and a piperidinyl.

In some embodiments, the subject compound is described by the structure of formula (IIb):

(IIb)

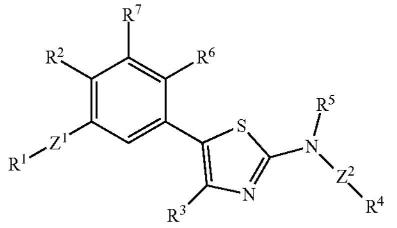

where:

$Z^1$ and $Z^2$ are each independently a covalent bond or a linking functional group;

$R^1$ is selected from hydrogen, an alkyl, a substituted alkyl (e.g., a substituted ethyl, or a heterocycle-substituted lower alkyl), an aryl (e.g., a phenyl), a substituted aryl, a heterocycle (e.g., a pyridyl, a pyrimidinyl) and a substituted heterocycle;

$R^2$ is selected from hydrogen, a halogen, an alkyl, a substituted alkyl, an alkoxy and a substituted alkoxy;

$R^3$ and $R^5$ are selected from hydrogen and an alkyl (e.g., a lower alkyl such as a methyl);

$R^4$ is selected from an alkyl (e.g., a cycloalkyl such as cycloheptyl, cyclohexyl, cyclopentyl, cyclopropyl or a lower alkyl such as methyl, ethyl or tert-butyl), an aralkyl (e.g., a benzyl or a phenylethyl), an aryl, an alkyl-heterocycle, a heterocycle, an amino and an alkoxy; and $R^6$ and $R^7$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments, in formula (IIb), $R^1$ to $R^4$ are independently selected from corresponding groups as depicted in any of the structures of Table 1.

The linking functional group may be any convenient bivalent group. Linking functional groups of interest include, but are not limited to, an amino, an amido, an ester, a carbonyloxy, an ether, a carbamate, a sulfonamide, a carbonyl, a sulfonyl, a sulfinyl, or the like. In some embodiments, the linking functional group is described by one of the following formulas: $-SO_2NR-$, $-NR-$, $-NRC(=O)-$, or $-NRC(=O)NR-$ where each R is independently H, an alkyl, a cycloalkyl, a heterocycle, a heterocycloalkyl, an aryl or a heteroaryl; $-O-$; $-C(=O)-$; $-C(=O)X-$ where X is NR, O or S and where R is H or an alkyl; $-S(=O)-$ or $-SO_2-$; where for each of the formulae depicted it is understood that both possible orientations of a functional group are included. In some embodiments, in formula (I), $Z^1$ is $-SO_2NH-$ or $-CONH-$ and W is a covalent bond, $-NR-$ or $-NRC(=O)-$, where R is H or an alkyl. In some embodiments, in formula (II), $Z^1$ is $-NHSO_2-$ or $-SO_2NH-$; and $Z^2$ is a covalent bond or $-C(=O)-$.

In some embodiments, $R^1$ is described by the formula $-(CH_2)_n-CH(R^8)-CHR^9$, where $R^8$ is hydrogen or a lower alkyl (e.g., methyl) and $R^9$ is hydrogen, an aryl (e.g., a phenyl) or a heterocycle (e.g., pyridyl (e.g., 3-pyridyl), pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl); and n is 0, 1, 2 or 3. In some embodiments, n is 0. In certain embodiments, $R^1$ is a substituted ethyl group, for example, a group described by one of the following structures:

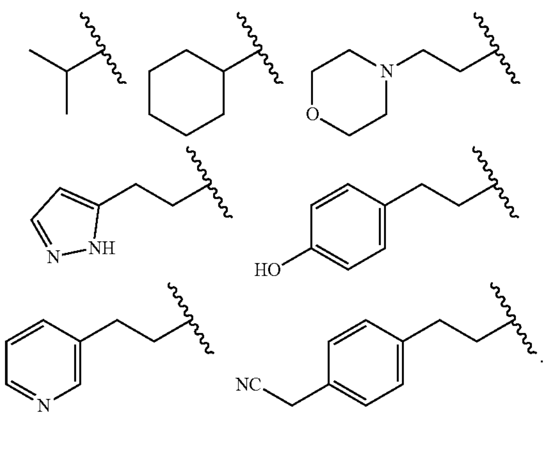

In other embodiments, $R^1$ is described by the formula:

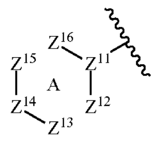

where A is a 6-membered aryl, heteroaryl, heterocyclyl, or cycloalkyl, where $Z^{11}$-$Z^{16}$ are independently selected from N, CR', NR and CR'R", where R is H or alkyl, and R' and R" are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In some embodiments, $R^1$ is described by the following formula:

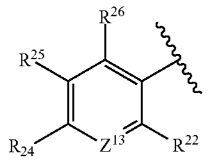

where $Z^{13}$ is $CR^{23}$ or N, where $R^{22}$-$R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In certain embodiments, $R^1$ is described by the following formula:

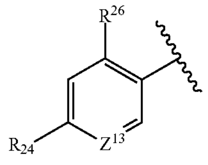

where $Z^{13}$ is $CR^{23}$ or N, where $R^{23}$, $R^{24}$ and $R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In some embodiments, $R^1$ is described by the following formula:

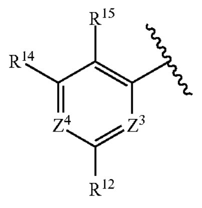

where $Z^3$ is N or $CR^{11}$; $Z^4$ is N or $CR^{13}$; and $R^{11}$ to $R^{15}$ are each independently selected from where $R^{22}$-$R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{11}$ to $R^{15}$ are each independently selected from hydrogen, an alkyl, an alkoxy, an acyloxy, a cyano, a halogen, and hydroxyl. In certain embodiments, $Z^3$ is $CR^{11}$, $Z^4$ is $CR^{13}$; $R^{11}$, $R^{14}$ and $R^{15}$ are each hydrogen; $R^{12}$ is hydrogen, an alkoxy (e.g., methoxy) or a halogen (e.g., fluoro); and $R^{13}$ is selected from hydrogen, acetyloxy, hydroxy, methoxy, cyano-methyl and halogen (e.g., fluoro). In certain embodiments, $Z^4$ is N. In certain embodiments, $Z^3$ and $Z^4$ are each N.

In some instances, $R^1$ is described by the following formula:

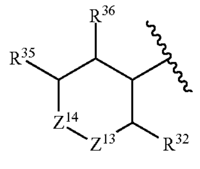

where $Z^{13}$ and $Z^{14}$ are each independently CR'R" or NR, where R is H or alkyl, and $R^{32}$, $R^{35}$, $R^{36}$, R' and R" are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{32}$, $R^{35}$, $R^{36}$, R' and R" are each independently selected from hydrogen, an alkyl, an alkoxy, an acyloxy, a cyano, a halogen, and hydroxyl.

In certain embodiments, $R^1$ is described by one of the following formulas:

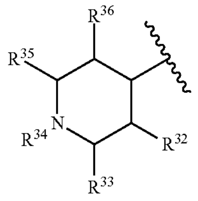
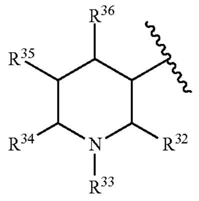

In some embodiments, in formulae (Ia), (Ib), (IIa) or (IIb), $R^2$ is methoxy. In some embodiments, in formulae (Ia), (Ib), (IIa) or (IIb), $R^3$ is methyl.

In some embodiments, in formula (IIb), $Z^2$ is a covalent bond or —C(═O)—, and $R^4$ is a lower alkyl (trifluoromethyl, tert-butyl, methyl, ethyl), a cycloalkyl (e.g., cyclopentyl, 1-fluoro-cyclopentyl or cyclohexyl) or —$CH_2$-cycloalkyl, a heterocycle (e.g., a N-linked saturated heterocycle such as N-pyrollidinyl, N-morpholino), or an amino (e.g., an amino-alkyl such as N-amino-cyclopentyl). In some embodiments, in formula (IIb), $R^4$ is described by the formula —$NR^{16}R^{17}$, wherein $R^{16}$ and $R^{17}$ are each independently selected from hydrogen, an alkyl, a cycloalkyl, and wherein optionally $R^{16}$ and $R^{17}$ are cyclically linked (e.g., to form a N-heterocyclyl). In some embodiments, in formula (IIb), $Z^2$ is a covalent bond; and $R^4$ is an alkyl or an alkyl-cycloalkyl (e.g., 1-cyclopentyl-methyl-). In some embodiments, in formula (IIb), $R^4$ is selected from methyl, trifluoromethyl, ethyl, tert-butyl, cyclopentyl, N-pyrrolidinyl, N-morpholinyl, N-amino-cyclopentyl and 1-fluoro-cyclopentyl. In certain embodiments, in formula (IIb), $R^5$ is hydrogen. In certain embodiments, in formula (II), $R^6$ and $R^7$ are each hydrogen.

In some instances, the compound is described by the structure of formula (III):

(III)

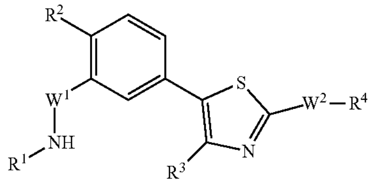

where $R^1$ is selected from hydrogen, an alkyl, an aryl, an alkyl-heterocycle and a heterocycle; $R^2$ is selected from hydrogen, a halogen, an alkyl, a substituted alkyl, an alkoxy and a substituted alkoxy; $R^3$ is alkyl; $R^5$ is H or alkyl; $R^4$ is lower alkyl, cycloalkyl, -alkyl-cycloalkyl, heterocyclyl or alkyl-heterocyclyl (e.g., —$(CH_2)_n$-cycloalkyl or —$(CH_2)_n$-heterocycyl, where n is 0, 1 or 2); $W^1$ is —$SO_2$— or —C(═O)—; and $W^2$ is a covalent bond, —NH—, or —NHCO—. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments, in formula (III), $R^1$ is described by the following structure:

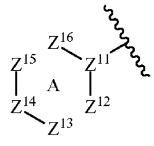

where A is a 6-membered aryl, heteroaryl, heterocyclyl, or cycloalkyl, where $Z^{11}$-$Z^{16}$ are independently selected from N, CR', NR and CR'R", where R is H or alkyl, and R' and R" are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In some embodiments, in formula (III), $R^1$ is described by one of the following structures:

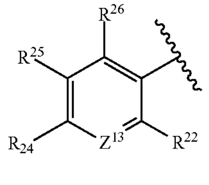
or
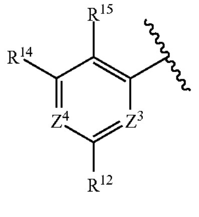

where $Z^{13}$ is $CR^{23}$ or N, where $Z^3$ is N or $CR^{11}$; $Z^4$ is N or $CR^{13}$; and $R^{11}$ to $R^{15}$ and $R^{23}$-$R^{26}$ are each independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In certain embodiments, in formula (III), $R^1$ is described by the following:

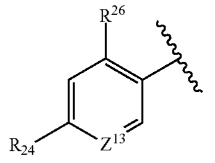

where $Z^{13}$ is $CR^{23}$ or N, and $R^{23}$, $R^{24}$ and $R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{23}$, $R^{24}$ and $R^{26}$ are independently selected from H, alkyl (e.g., methyl or ethyl), alkoxy (e.g., methoxy or ethoxy) and halo (e.g., fluoro or chloro). In certain cases, $Z^{13}$ is selected from CH and N.

In certain embodiments, in formula (III), $R^1$ to $R^4$ are independently selected from corresponding groups as depicted in any of the structures of Table 1.

In some cases, the compound is described by the structure of formula (IV):

(IV)

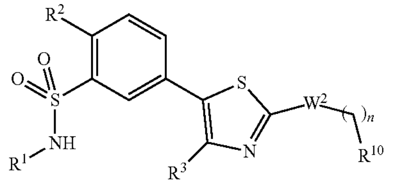

where: $R^1$ is $-(CH_2)_n-R^{20}$, where $R^{20}$ is an aryl, a cycloalkyl or a heterocycle and n is 0, 1 or 2; $R^2$ is selected from hydrogen, a halogen, an alkyl, a substituted alkyl, an alkoxy and a substituted alkoxy; $R^3$ is H or alkyl; $W^2$ is a covalent bond, —NH—, or —NHCO—; n is 0, 1, 2 or 3; and $R^{10}$ is a cycloalkyl or a heterocycle. In certain cases, in formula (IV), $R^1$ is a phenyl, a pyridyl, a diazinyl, a piperidinyl, a piperazinyl, or a pyrriloidinyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain cases, in formula (IV), $R^1$ is described by the following structure:

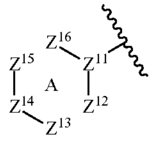

where A is a 6-membered aryl, heteroaryl, heterocyclyl, or cycloalkyl, where $Z^{11}$-$Z^{16}$ are independently selected from N, CR', NR and CR'R", where R is H or alkyl, and R' and R" are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro.

In some cases, the compound is described by the structure of formula (V):

(V)

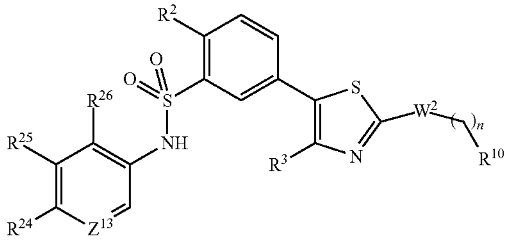

where: $R^2$ is selected from hydrogen, a halogen, an alkyl, a substituted alkyl, an alkoxy and a substituted alkoxy; $R^3$ is lower alkyl, $W^2$ is a covalent bond, —NH—, or —NHCO—; n is 0, 1 or 2; $Z^{13}$ is N or $CR^{23}$, $R^{10}$ is a cycloalkyl or a heterocycle; and $R^{23}$-$R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{23}$-$R^{26}$ are independently selected from hydrogen, halo, alkyl, and alkoxy. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some instances, the compound is described by the structure of one of formulae (VI), (VII) or (VIII):

(VI)

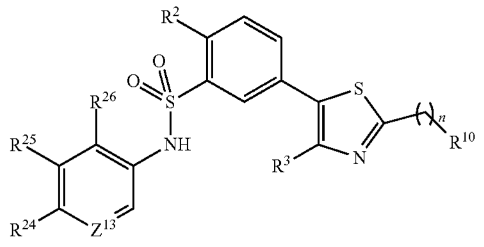

(VII)

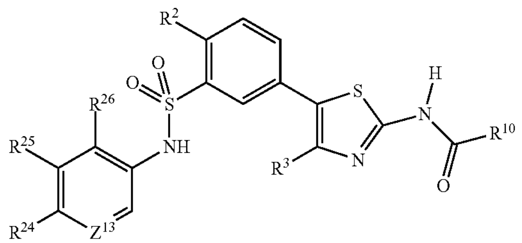

-continued (VIII)

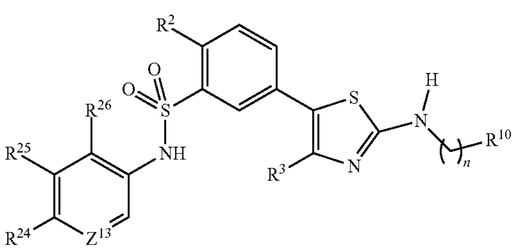

where: $R^2$ is selected from hydrogen, a halogen, an alkyl, a substituted alkyl, an alkoxy and a substituted alkoxy; $R^3$ is lower alkyl, n is 0, 1 or 2; $Z^{13}$ is N or $CR^{23}$, $R^{10}$ is a cycloalkyl or a heterocycle; and $R^{23}$-$R^{26}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{23}$-$R^{26}$ are independently selected from hydrogen, halo, alkyl, and alkoxy. In certain instances, $R^{10}$ is a cyclopentyl, a cyclohexyl, a piperidinyl or a pyrrolidinyl. In certain embodiments, in formulae (IV)-(VIII), $R^2$ is methoxy. In certain embodiments, in formulae (IV)-(VIII), $R^3$ is methyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments, in formulae (IV)-(VIII), $Z^{13}$, $R^{23}$-$R^{26}$, $R^2$, $R^3$ and $R^{10}$ are independently selected from corresponding groups as depicted in any of the structures of Table 1.

In some cases, the compound is described by the structure of formula (IX):

(IX)

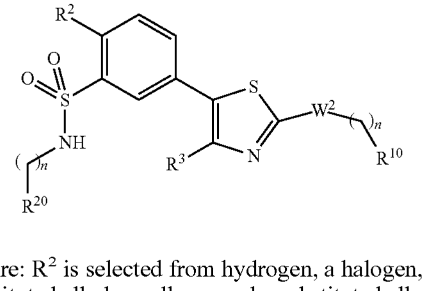

where: $R^2$ is selected from hydrogen, a halogen, an alkyl, a substituted alkyl, an alkoxy and a substituted alkoxy; $R^3$ is lower alkyl; $W^2$ is a covalent bond, —NH—, or —NHCO—; each n is independently 0, 1 or 2; $Z^{13}$ is N or $CR^{23}$; $R^{10}$ is a cycloalkyl or a heterocycle; and $R^{20}$ is an aryl, a cycloalkyl or a heterocycle. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain cases, $R^{20}$ and $R^{10}$ are independently described by the following structure:

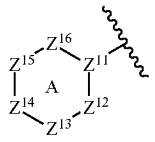

where A is a 6-membered aryl, heteroaryl, heterocyclyl, or cycloalkyl, where $Z^{11}$-$Z^{16}$ are independently selected from N, CR', NR and CR'R", where R is H, an alkyl, a cycloalkyl, a heterocycloalkyl, an aryl or a heteroaryl; and R' and R" are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, $R^{20}$ is a phenyl, a pyridyl, a diazinyl, a piperidinyl, a piperazinyl, or a pyrrolidinyl.

In some instances, the compound is described by the structure of one of formulae (X), (XI) or (XII):

(X)

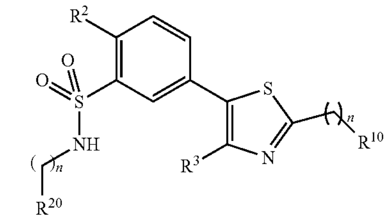

(XI)

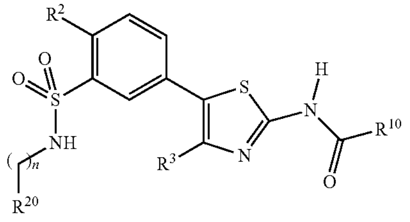

(XII)

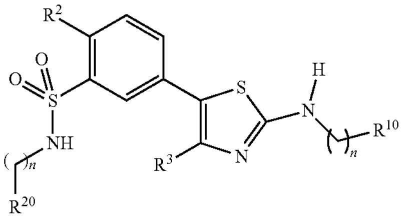

where $R^2$ is selected from hydrogen, a halogen, an alkyl, a substituted alkyl, an alkoxy and a substituted alkoxy; $R^3$ is a lower alkyl, each n is independently 0, 1 or 2; $R^{10}$ is a cycloalkyl or a heterocycle; and $R^{20}$ is an aryl, a cycloalkyl or a heterocycle. In certain embodiments, $R^{20}$ is a phenyl, a pyridyl, a diazinyl, a piperidinyl, a piperazinyl, or a pyrrolidinyl.

In certain instances, $R^{10}$ is a cyclopentyl, a cyclohexyl, a piperidinyl or a pyrrolidinyl. In certain instances, $R^{20}$ is a phenyl, or a pyridyl. In certain embodiments, in formulae (IX)-(XII), $R^2$ is methoxy. In certain embodiments, in formulae (IX)-(XII), $R^3$ is methyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments, the compound is described by the structure of formula (XIII):

(XIII)

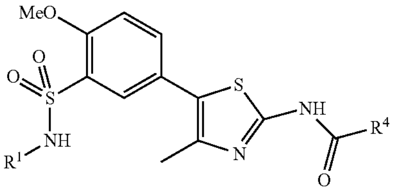

where $R^1$ is an alkyl, an aryl, an alkyl-heterocycle or a heterocycle; and $R^4$ is an alkyl, an aralkyl, an aryl, an alkyl-cycloalkyl, a cycloalkyl, an alkyl-heterocycle, or a heterocycle. In certain instances, $R^4$ is a cyclopentyl, a cyclohexyl, a piperidinyl or a pyrrolidinyl. In certain instances, $R^1$ is a phenyl or a pyridiyl.

In certain embodiments, in formulae (I)-(XIII), $R^1$ or $R^{20}$ is described by one of the following structures:

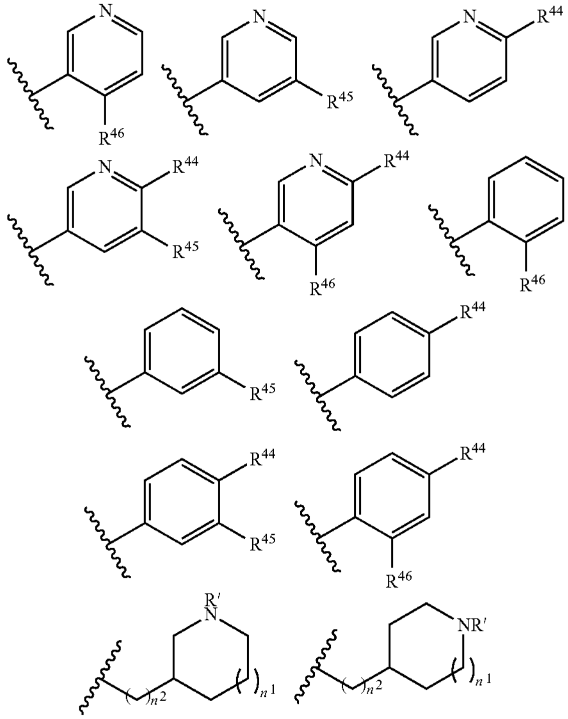

where $R^{44}$-$R^{46}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro; R' is hydrogen, an alkyl, an aryl or a heterocycle; $n^2$ is 0, 1, 2 or 3, and $n^1$ is 0, 1 or 2; and $R^4$ is $-(CH_2)_n$-cycloalkyl (e.g., cyclopropyl, cyclopentyl or cyclohexyl), $-(CH_2)_n$-heterocycle (e.g., piperidinyl, a piperazinyl, or a pyrriloidinyl), or lower alkyl, where each n is independently 0, 1, 2 or 3. In certain embodiments, in formula (XIII), n is 1.

In certain embodiments, in formula (XIII), $R^1$ and $R^4$ are independently selected from corresponding groups as depicted in any of the structures of Table 1.

In certain embodiments, the compound is described by one of the following structures:

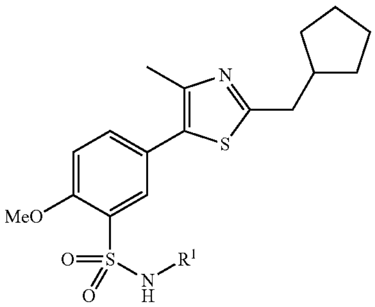

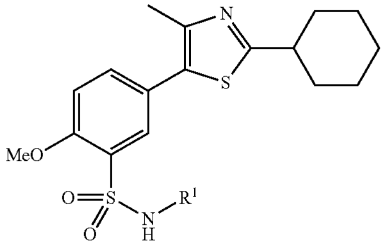

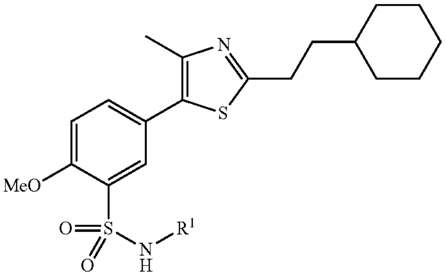

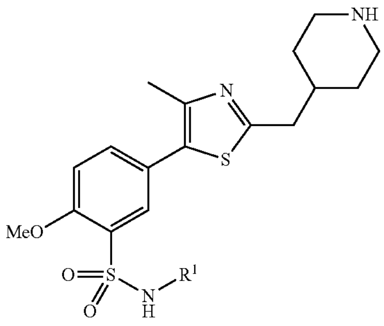

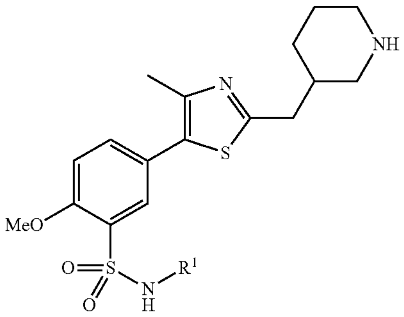

-continued

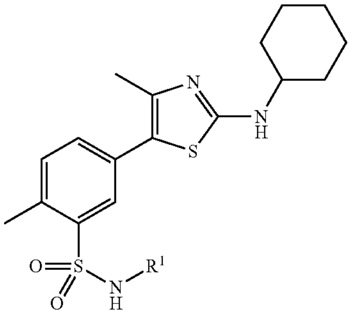

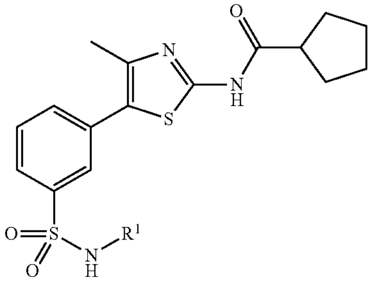

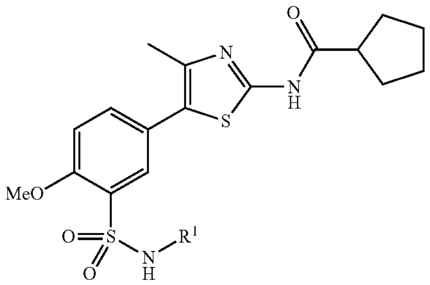

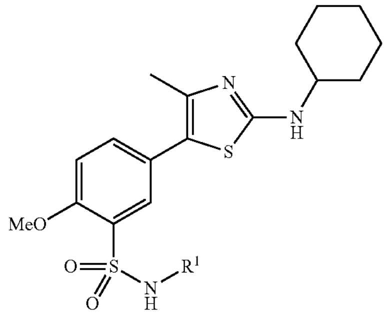

where $R^1$ is selected from a phenyl, a pyridyl, a diazinyl, a piperidinyl, a piperazinyl, a pyrriloidinyl and $-(CH_2)_n-R^{20}$ where $R^{20}$ is an aryl, a cycloalkyl or a heterocycle and n is 0, 1 or 2.

In certain embodiments, in the nine structures depicted above, $R^1$ is described by one of the following structures:

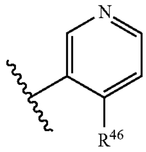 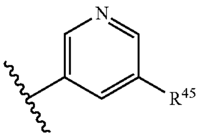 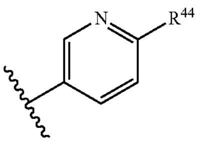

-continued

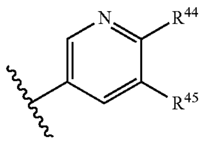 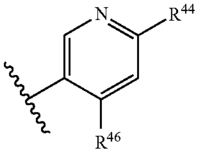 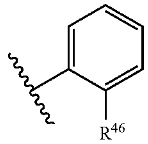

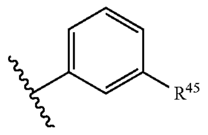 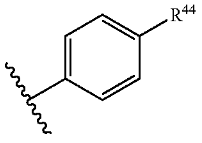

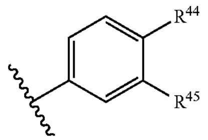 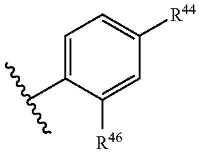

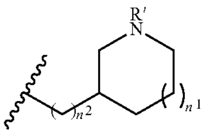 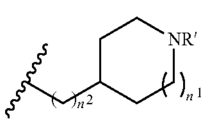

where $R^{44}$-$R^{46}$ are independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro; R' is hydrogen, an alkyl, an aryl or a heterocycle; $n^2$ is 0, 1, 2 or 3, and $n^1$ is 0, 1 or 2. In certain embodiments, $R^{44}$-$R^{46}$ are independently selected from H, an alkyl, an alkoxy, hydroxyl, and a halo (e.g., fluoro or chloro).

In some embodiments, the compound is described by the structure of formula (XIV):

(XIV)

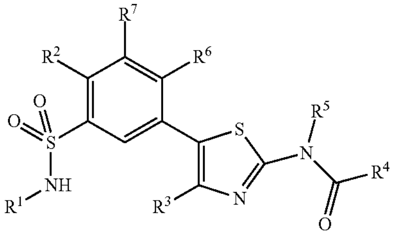

where $R^1$ is a phenyl, a pyridyl (e.g., 4-pyridyl or 3-pyridyl) or a pyrimidinyl (e.g., a 4-pyrimidinyl or 3-pyrimidinyl). In some embodiments, in formula (XIV), $R^5$-$R^7$ are each hydrogen. In certain embodiments, in formula (XIV), $R^1$ to $R^5$ are independently selected from corresponding groups as depicted in any of the structures of Table 1. In some embodiments, in formula (XIV), $R^1$ is a phenyl, and $R^5$-$R^7$ are each hydrogen.

In some embodiments, the compound is described by the structure of formula (XIVb):

(XIVb)

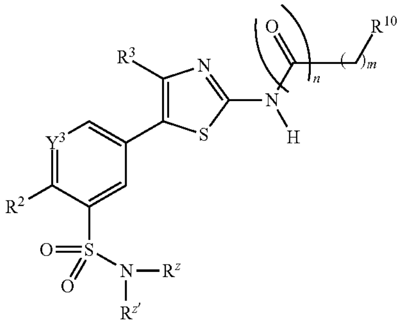

wherein n is 0 or 1; m is 0 or 1; $R^2$, $R^3$, $Y^3$ and $R^{10}$ are as defined herein; $R^z$ and $R^{z'}$ are cyclically linked and together form a 5- or 6-membered saturated heterocycle with the N to which they are attached (e.g., a pyrrolidinyl ring or a piperidinyl ring), where the heterocycle is optionally substituted (e.g., substituted with an amino, a hydroxy, a substituted alkoxy, an alkoxy, a substituted alkyl or an alkyl group). In certain instances, n is 1 and m is 1 and $R^{10}$ is a cycloalkyl or a substituted cycloalkyl. In certain instances, n is 1 and m is 0 and $R^{10}$ is a cycloalkyl or a substituted cycloalkyl. In certain instances, n is 0 and m is 0 and $R^{10}$ is a cycloalkyl or a substituted cycloalkyl. In certain instances, n is 0 and m is 1 and $R^{10}$ is a cycloalkyl or a substituted cycloalkyl.

In certain embodiments, the compound is described by the structure of formula (XV):

(XV)

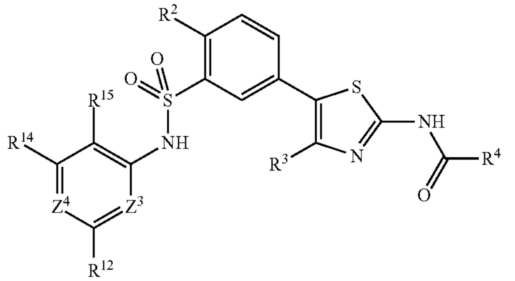

where $Z^3$ is N or $CR^{11}$; $Z^4$ is N or $CR^{13}$; and $R^{11}$-$R^{15}$ are each independently selected from hydrogen, an alkyl (e.g., a lower alkyl such as methyl or trifluoromethyl), an aryl, a hydroxy, an alkoxy, an aryloxy, a heterocycle, a cyano, a halogen (e.g., fluoro, chloro or bromo), an amino (e.g., $-NMe_2$), an acyl, an acyloxy, an amido, or a nitro. In some embodiments, in formula (XV), $R^2$ is selected from hydrogen, a halogen, an alkyl, a substituted alkyl, an alkoxy and a substituted alkoxy (e.g., methoxy). In some embodiments, in formula (XV), $R^3$ is an alkyl (e.g., methyl). In some embodiments, in formula (XV), $Z^4$ is $CR^{13}$ and $Z^3$ is $CR^{11}$. In some embodiments, in formula (XV), $Z^4$ is N and $Z^3$ is $CR^{11}$. In some embodiments, in formula (XV), $Z^3$ and $Z^4$ are each N. In some embodiments, in formula (XV), $R^{11}$-$R^{15}$ are each independently selected from hydrogen, an alkoxy (e.g., methoxy), a halogen (e.g., fluoro), acyloxy (e.g., acetyloxy), hydroxy and cyano-alkyl (e.g., cyano-methyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments, the subject compound is described by the structure of formula (XVI):

(XVI)

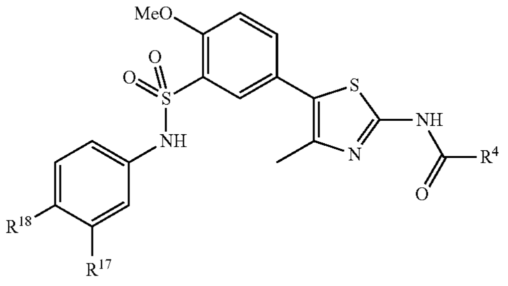

where $R^{17}$ is hydrogen, an alkoxy (e.g., methoxy) or a halogen (e.g., fluoro); and $R^{18}$ is selected from hydrogen, acetyloxy, hydroxy, methoxy, cyano-methyl and halogen (e.g., fluoro). In some embodiments, in formula (XVI), $R^4$ is selected from methyl, trifluoromethyl, ethyl, tert-butyl, cyclopentyl, N-pyrrolidinyl, N-morpholinyl, N-amino-cyclopentyl and 1-fluoro-cyclopentyl; and $R^{17}$ and $R^{18}$ are independently selected from hydrogen, methoxy, fluoro, acetyloxy, hydroxy, and cyano-methyl.

In some embodiments, the subject compound is described by the structure of formula (XVII):

(XVII)

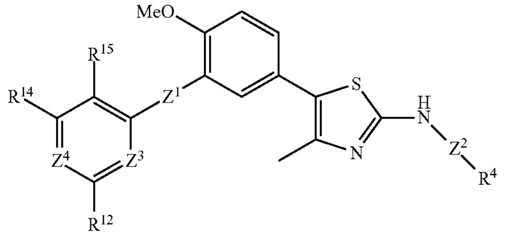

wherein: $Z^1$ is $-NHSO_2-$ or $-SO_2NH-$; $Z^2$ is a covalent bond or $-C(=O)-$; $Z^3$ is N or $CR^{11}$; $Z^4$ is N or $CR^{13}$; and $R^{11}$ to $R^{15}$ are each independently selected from hydrogen, an alkyl, an aryl, a hydroxy, an alkoxy, an aryloxy, a heterocycle, a cyano, a halogen (e.g., fluoro, chloro or bromo), an amino, an acyl, an acyloxy, an amido, and a nitro. In certain embodiments, in formula (XVII), $R^{11}$ to $R^{15}$ are each independently selected from hydrogen, an alkoxy, an acyloxy, a halogen, and hydroxyl. In some embodiments, in formula (XVII), $Z^3$ is $CR^{11}$, $Z^4$ is $CR^{13}$; $R^{11}$, $R^{12}$, $R^{14}$ and $R^{15}$ are each hydrogen; and $R^{13}$ is selected from hydrogen, acetyloxy, hydroxy, methoxy and halogen (e.g., fluoro). In some embodiments, in formula (XVII), $Z^3$ is $CR^{11}$, $Z^4$ is N, and $R^{11}$, $R^{12}$, $R^{14}$ and $R^{15}$ are each hydrogen. In some embodiments, in formula (XVII), $Z^3$ and $Z^4$ are each N, and $R^{12}$, $R^{14}$ and $R^{15}$ are each hydrogen. In some embodiments, in formula (XVII), $Z^2$ is a covalent bond or $-C(=O)-$, and $R^4$ is a lower alkyl (e.g., trifluoromethyl, tert-butyl), a cycloalkyl (e.g., cyclopentyl or 1-fluoro-cyclopentyl) or $-CH_2$-cycloalkyl (e.g., $-CH_2$-cyclopentyl), a heterocycle (e.g., a N-linked saturated heterocycle such as N-pyrrolidino or N-morpholino), or an amino (e.g., an amino-alkyl such as N-amino-cyclopentyl). In some embodiments, in formula (XVII), $Z^2$ is —C(═O)—, and $R^4$ is described by the formula —$NR^{16}R^{17}$, where $R^{16}$ and $R^{17}$ are each independently selected from hydrogen, an alkyl, and a cycloalkyl, wherein optionally $R^{16}$ and $R^{17}$ are cyclically linked (e.g., to form a N-heterocyclyl). In some embodiments, in formula (XVII), $Z^2$ is a single bond; and $R^4$ is an alkyl or a cycloalkyl-alkyl (e.g., 1-cyclopentyl-methyl). In some embodiments, in formula (XVII), $Z^2$ is —C(═O)—, and $R^4$ is selected from trifluoromethyl, ethyl, tert-butyl, N-pyrrolidinyl, N-morpholinyl, N-amino-cyclopentyl and 1-fluoro-cyclopentyl.

In some embodiments, the subject compound is described by the structure of formula (XVIII):

(XVIII)

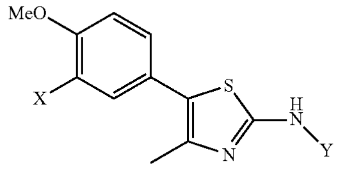

where X and Y are independently selected from the substituents groups shown below:

X =

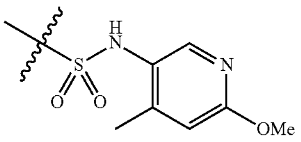

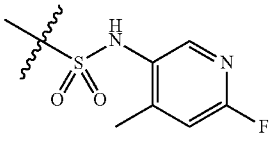

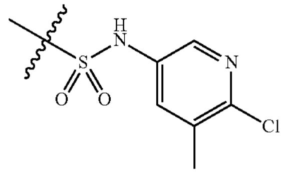

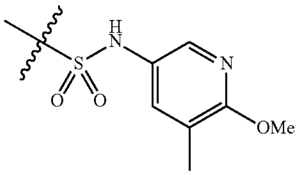

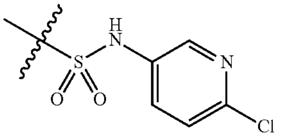

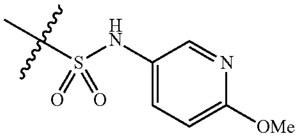

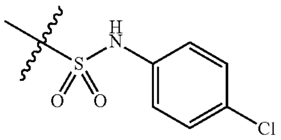

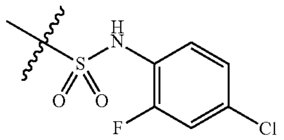

-continued

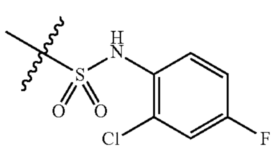

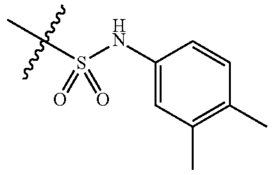

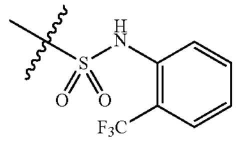

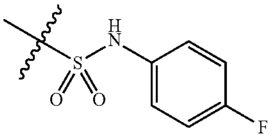

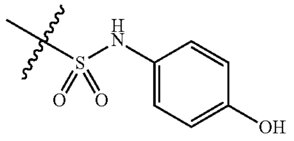

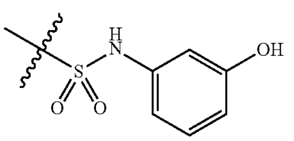

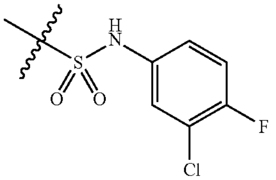

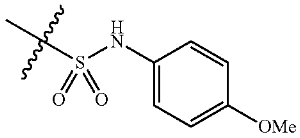

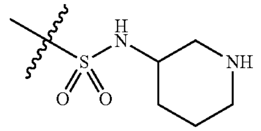

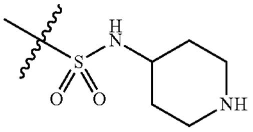

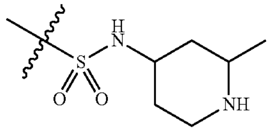

1

Y =

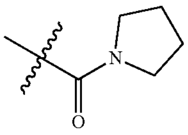

2

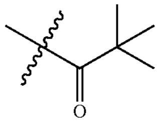

3

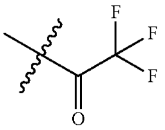

4

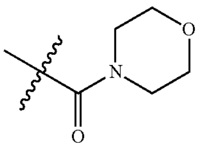

5

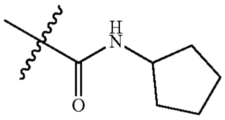

-continued

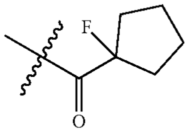

6

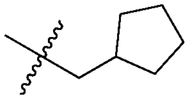

7

In certain embodiments, in formula (XVIII), $R^1$ and $R^4$ are independently selected from corresponding groups as depicted in any of the structures of Table 1. In some embodiments, the subject compound is described by the structure of compound PT423, shown in Table 1. In some embodiments, the subject compound is described by one of the structures labeled M1, M2, and M3 in FIG. 2.

In some instances of formula (Ib), the compound has the formula (XXI):

(XXI)

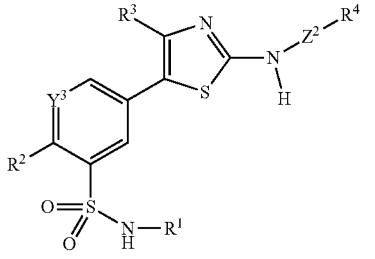

wherein: $R^2$ is selected from hydrogen, a halogen, an alkyl, a substituted alkyl, an alkoxy and a substituted alkoxy; $R^3$ is hydrogen, a lower alkyl (e.g., methyl) or a substituted lower alkyl; $Y^3$ is CH or N; $Z^2$ is absent, CO or $SO_2$; $R^1$ is an aryl, a substituted aryl (e.g., a substituted phenyl), an alkyl, a substituted alkyl, a cycloalkyl, a substituted cycloalkyl (e.g., a substituted cyclohexyl), a heterocycle (e.g., a tetrahydropyran or a piperidinyl) or a substituted heterocycle; and $R^4$ is selected from alkyl, substituted alkyl, cycloalkyl, substituted cycloalkyl, alkyl-cycloalkyl, substituted alkyl-cycloalkyl, aryl, substituted aryl, heterocycle, substituted heterocycle, alkyl-heterocycle (e.g., $—CH_2$-(4-tetrahydropyran)) and substituted alkyl-heterocycle; or a prodrug thereof, or a pharmaceutically acceptable salt thereof. In certain instances, $Z^2$ is absent. In certain instances, $Z^2$ is $—C(=O)—$. In certain instances, $Z^2$ is $—S(=O)_2—$. In certain instances, $R^1$ is a phenyl, a substituted phenyl, a cyclohexyl, a substituted cyclohexyl, a piperidinyl (e.g., a 3-piperidinyl or a 4-piperidinyl) or a substituted piperidinyl (e.g., a substituted 3-piperidinyl or substituted 4-piperidinyl). In certain instances, $R^1$ is a substituted phenyl. In certain instances, $R^1$ is a substituted alkyl, e.g., a substituted lower alkyl. In certain instances, $R^4$ is a cyclohexyl, a substituted cyclohexyl, a tetrahydropyran, a benzyl, a substituted benzyl, a phenyl, a substituted phenyl, a methylene-cyclohexane and a substituted methylene-cyclohexane. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XXI), the compound has formula (XXII):

(XXII)

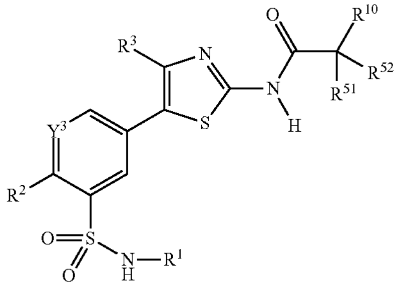

wherein: $R^2$ is selected from hydrogen, a halogen, an alkyl, a substituted alkyl, an alkoxy and a substituted alkoxy; $R^{10}$ is selected from cycloalkyl, substituted cycloalkyl, heterocycle (e.g., 4-tetrahydropyran) and substituted heterocycle; and $R^{51}$ and $R^{52}$ are independently selected from H, halogen (e.g., fluoro), alkyl (e.g., lower alkyl) and substituted alkyl. In certain instances, $R^1$ is a phenyl, a substituted phenyl, a cyclohexyl, a substituted cyclohexyl, a piperidinyl (e.g., a 3-piperidinyl or a 4-piperidinyl) or a substituted piperidinyl (e.g., a substituted 3-piperidinyl or substituted 4-piperidinyl). In certain instances, $R^1$ is a substituted phenyl. In certain instances, $R^1$ is a substituted alkyl, e.g., a substituted lower alkyl. In certain instances, $R^{10}$ is a cyclohexyl, a substituted cyclohexyl, a tetrahydropyran, a benzyl, a substituted benzyl, a phenyl, a substituted phenyl, a methylene-cyclohexane and a substituted methylene-cyclohexane. In certain instances, $R^{51}$ and $R^{52}$ are each hydrogen. In certain instances, $R^{51}$ is hydrogen and $R^{52}$ is alkyl or substituted alkyl (e.g., methyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XXII), the compound has formula (XXIII):

(XXIII)

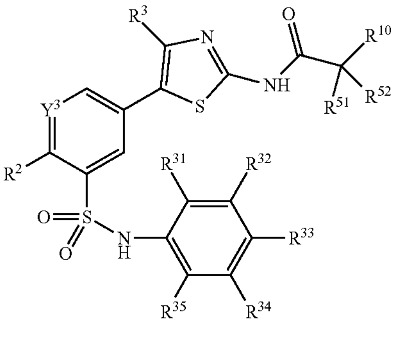

wherein: $R^2$ is selected from hydrogen, a halogen, an alkyl, a substituted alkyl, an alkoxy and a substituted alkoxy; $R^{31}$-$R^{35}$ are independently selected from hydrogen, halogen (e.g., fluoro), alkyl, substituted alkyl, hydroxy, alkoxy, substituted alkoxy, acyl, substituted acyl and —$CO_2R$, wherein R is H, alkyl or substituted alkyl. In certain instances, $R^{31}$ and $R^{33}$ are halogen (e.g., fluoro or chloro). In certain instances, $R^{31}$ and $R^{35}$ are halogen (e.g., fluoro or chloro). In certain instances, $R^{31}$ is halogen (e.g., fluoro or chloro). In certain instances, 3 or 4 of $R^{31}$-$R^{35}$ are hydrogen. In certain instances, $R^{51}$ and $R^{52}$ are each hydrogen. In certain instances, $R^{51}$ is hydrogen and $R^{52}$ is alkyl or substituted alkyl (e.g., methyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formulae (XXII) or (XXIII), the compound has the formula (XXIV) or formula (XXV):

(XXIV)

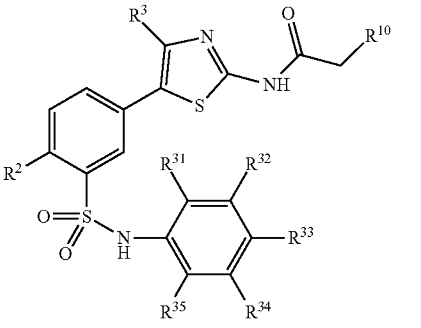

(XXV)

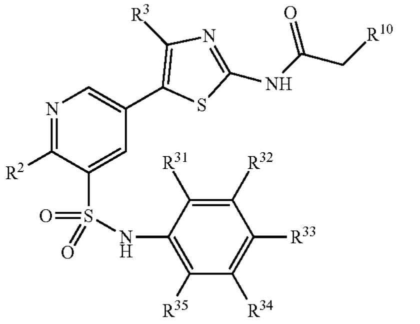

wherein: one and only one of $R^{33}$ and $R^{34}$ is hydroxy; and $R^2$ is selected from hydrogen, a halogen, an alkyl, a substituted alkyl, an alkoxy and a substituted alkoxy. In certain instances, $R^{33}$ is hydroxy. In certain instances, $R^{34}$ is hydroxy. In certain instances, 3, 4 or 5 of $R^{31}$-$R^{35}$ are hydrogen. In certain cases, $R^{10}$ is a cyclohexyl or substituted cyclohexyl. In certain cases, $R^{10}$ is tetrahydropyran (e.g., 4-tetrahydropyranyl) or substituted tetrahydropyran (e.g., substituted 4-tetrahydropyranyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XXIV) and formula (XXV), the compound has one of the formulae (XXVI)-(XXVIII):

(XXVI)

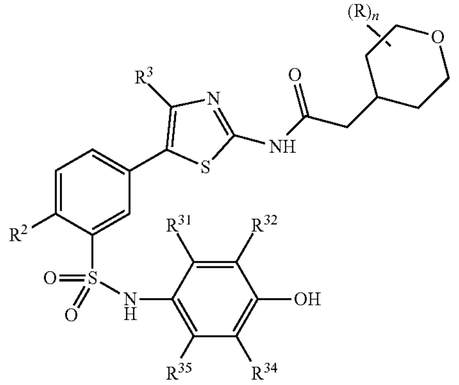

(XXVII)

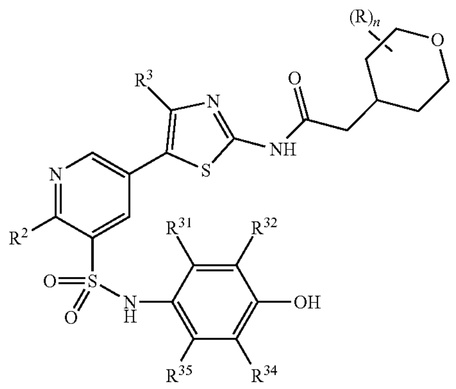

(XXVIII)

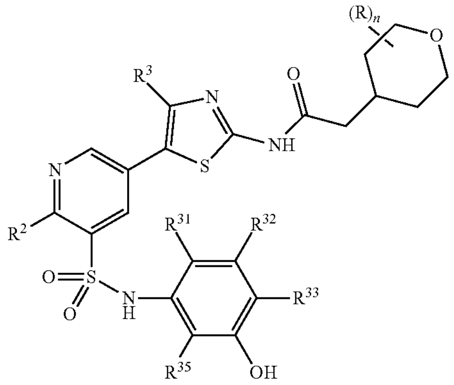

wherein: $R^2$ is selected from hydrogen, a halogen, an alkyl, a substituted alkyl, an alkoxy and a substituted alkoxy; $R^{31}$, $R^{32}$, $R^{34}$ and $R^{35}$ are independently selected from hydrogen and halogen (e.g., fluoro); and $(R)_n$ is one or more optional substituents each independently selected from alkyl, substituted alkyl, hydroxyl, alkoxy, substituted alkoxy, halogen (e.g., fluoro or chloro), and $CO_2R''$ where R'' is hydrogen, alkyl or substituted alkyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. In certain embodiments, the compound has one of the following structures:

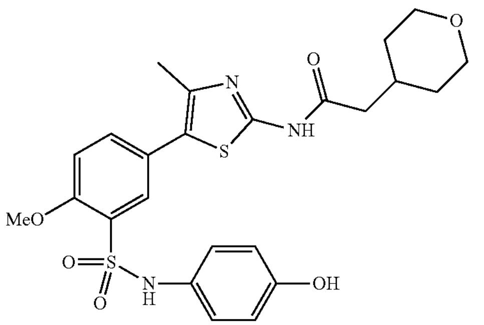

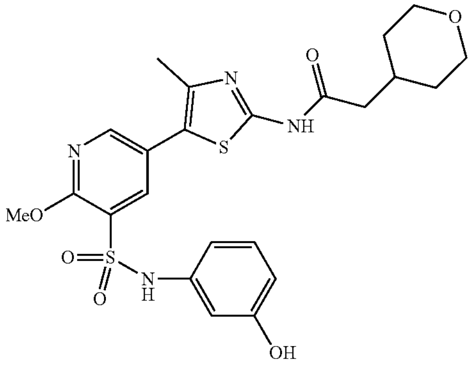

or

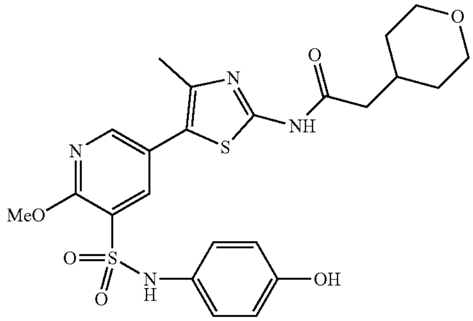

, or a prodrug thereof, or a pharmaceutically acceptable salt thereof.

In certain embodiments of formula (XXIII), the compound has formula (XXIX):

(XXIX)

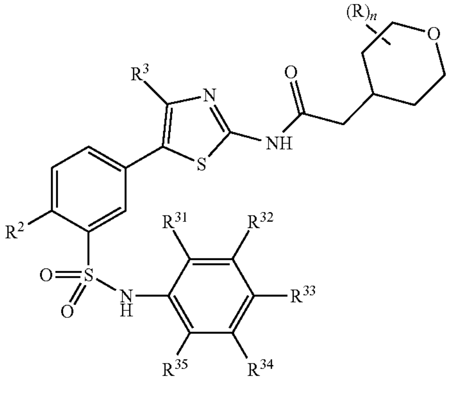

wherein: $R^2$ is selected from hydrogen, a halogen, an alkyl, a substituted alkyl, an alkoxy and a substituted alkoxy; $R^{31}$-$R^{35}$ are independently selected from hydrogen and halogen (e.g., fluoro or chloro), wherein 0, 1 or 2 of $R^{31}$-$R^{35}$ are halogen; and $(R)_n$ is one or more optional substituents each independently selected from alkyl, substituted alkyl, hydroxyl, alkoxy, substituted alkoxy, halogen (e.g., fluoro or chloro) and $CO_2R''$ wherein R" is hydrogen, alkyl or substituted alkyl. In certain instances, $R^{31}$ and $R^{33}$ are halogen (e.g., fluoro or chloro). In certain instances, $R^{31}$ and $R^{35}$ are halogen (e.g., fluoro or chloro). In certain instances, $R^{31}$ is halogen (e.g., fluoro or chloro). In certain instances, 3 or 4 of $R^{31}$-$R^{35}$ are hydrogen. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XXII), the compound has formula (XXX):

(XXX)

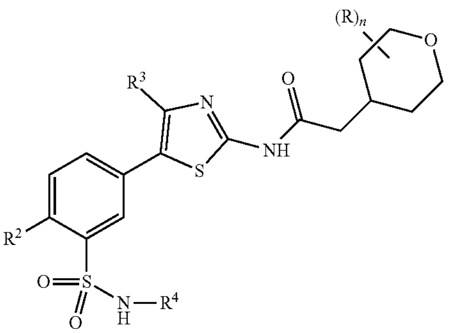

wherein: $R^2$ is selected from hydrogen, a halogen, an alkyl, a substituted alkyl, an alkoxy and a substituted alkoxy; $R^4$ is a lower alkyl or a substituted lower alkyl (e.g., an isopropyl); and $(R)_n$ is one or more optional substituents each independently selected from alkyl, substituted alkyl, hydroxyl, alkoxy, substituted alkoxy, halogen (e.g., fluoro or chloro), and $CO_2R''$ where R" is hydrogen, alkyl or substituted alkyl. In certain instances, n is 0. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XXII), the compound has the formula (XXXI):

(XXXI)

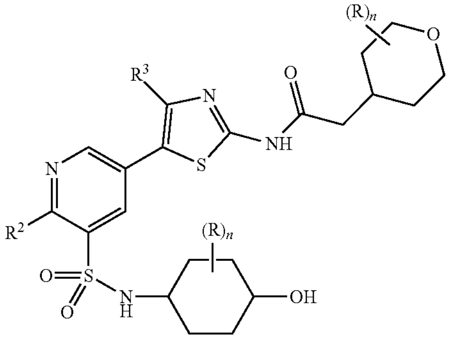

wherein: $R^2$ is selected from hydrogen, a halogen, an alkyl, a substituted alkyl, an alkoxy and a substituted alkoxy; each $(R)_n$ is one or more optional substituents each independently selected from alkyl, substituted alkyl, hydroxyl, alkoxy, substituted alkoxy, halogen (e.g., fluoro or chloro) and $CO_2R''$ where R'' is hydrogen, alkyl or substituted alkyl. In certain instances, each n is 0. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments, the compound has the structure:

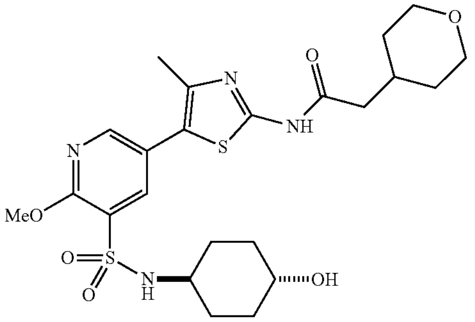 [SMILES: COc1ncc(-c2sc(NC(=O)CC3CCOCC3)nc2C)cc1S(=O)(=O)N[C@H]1CC[C@H](O)CC1]

or a prodrug thereof, or a pharmaceutically acceptable salt thereof.

In certain embodiments of formula (XXIII), the compound has the formula (XXXII):

(XXXII)

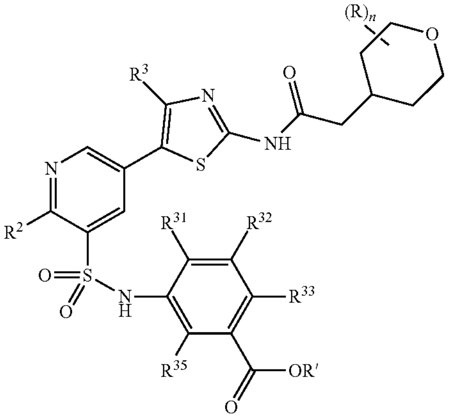

wherein: $R^2$ is selected from hydrogen, a halogen, an alkyl, a substituted alkyl, an alkoxy and a substituted alkoxy; $R^{31}$-$R^{33}$ and $R^{35}$are independently selected from hydrogen and halogen (e.g., fluoro); $(R)_n$ is one or more optional substituents each independently selected from alkyl, substituted alkyl, hydroxyl, alkoxy, substituted alkoxy, halogen (e.g., fluoro or chloro) and $CO_2R''$ where R'' is hydrogen, alkyl or substituted alkyl; and R' is H, alkyl or substituted alkyl. In certain embodiments, R' is a lower alkyl. In certain cases, R' is ethyl. In certain cases, R' is methyl. In certain embodiments, n is 0. In certain embodiments, $R^{31}$-$R^{33}$ and $R^{35}$ are each hydrogen. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. In certain embodiments, the compound has the structure:

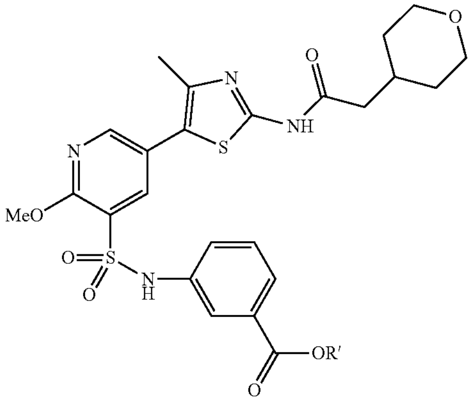

wherein R' is H, a lower alkyl or a substituted lower alkyl; or a prodrug thereof, or a pharmaceutically acceptable salt thereof. In certain cases, R' is hydrogen. In certain cases, R' is lower alkyl. In certain cases, R' is ethyl. In certain cases, R' is methyl.

In some embodiments, the compound has the following structure:

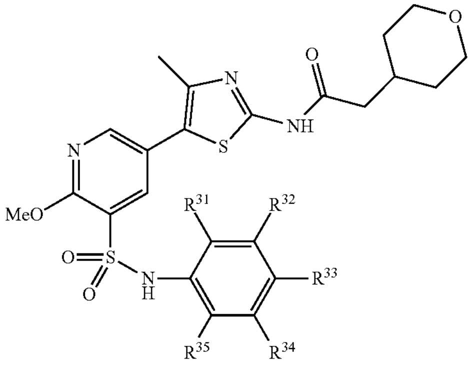

where $R^{31}$-$R^{35}$ are selected from one of the following embodiments:

| Embodiment | $R^{31}$ | $R^{32}$ | $R^{33}$ | $R^{34}$ | $R^{35}$ |
|---|---|---|---|---|---|
| 1 | H | H | H | H | H |
| 2 | F | H | F | H | H |
| 3 | Cl | H | H | H | H |
| 4 | Cl | H | Cl | H | H |
| 5 | Cl | H | H | H | Cl |

In certain embodiments of formula (XXI), the compound has the formula (XXXIII) or formula (XXXIV):

(XXXIII)

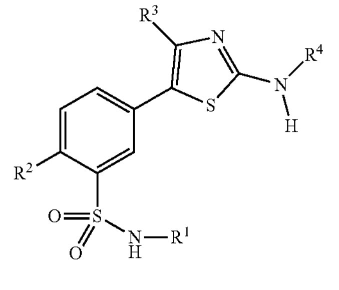

(XXXIV)

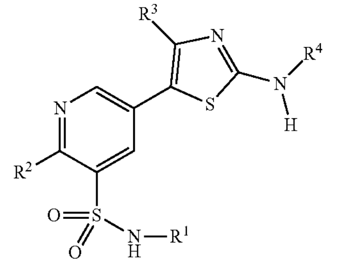

wherein: $R^2$ is selected from hydrogen, a halogen, an alkyl, a substituted alkyl, an alkoxy and a substituted alkoxy; $R^3$ is hydrogen, a lower alkyl (e.g., methyl) or a substituted lower alkyl; $R^1$ is an aryl, a substituted aryl, (e.g., a substituted phenyl), a cycloalkyl, a substituted cycloalkyl (e.g., a substituted cyclohexyl), a heterocycle (e.g., a tetrahydropyran or a piperidinyl) or a substituted heterocycle; and $R^4$ is selected from cycloalkyl, substituted cycloalkyl, alkyl-cycloalkyl, substituted alkyl-cycloalkyl, heterocycle, substituted heterocycle, alkyl-heterocycle (e.g., —$CH_2$-(4-tetrahydropyran)) and substituted alkyl-heterocycle. In certain instances, $R^1$ is a phenyl, a substituted phenyl, a cyclohexyl, a substituted cyclohexyl, a piperidinyl (e.g., a 3-piperidinyl or a 4-piperidinyl) or a substituted piperidinyl (e.g., a substituted 3-piperidinyl or substituted 4-piperidinyl). In certain instances, $R^1$ is a substituted phenyl. In certain instances, $R^4$ is a cyclohexyl, a substituted cyclohexyl, a tetrahydropyran, a methylene-tetrahydropyran, a substituted tetrahydropyran, a substituted methylene-tetrahydropyran, a benzyl, a substituted benzyl, a phenyl, a substituted phenyl, a methylene-cyclohexane and a substituted methylene-cyclohexane. In certain instances, $R^4$ is cycloheptyl or a substituted cycloheptyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formulae (XXXIII) or (XXXIV), the compound has one of the formula (XXXV) and formula (XXXVI):

(XXXV)

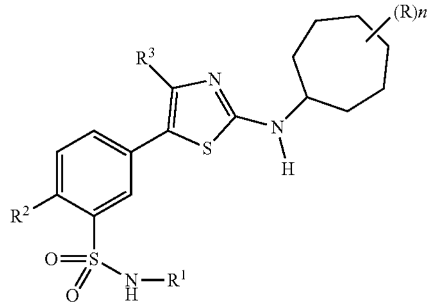

(XXXVI)

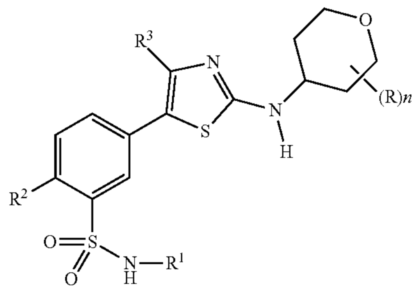

wherein: $R^2$ is selected from hydrogen, a halogen, an alkyl, a substituted alkyl, an alkoxy and a substituted alkoxy; $(R)_n$ is one or more optional substituents each independently selected from alkyl, substituted alkyl, hydroxyl, alkoxy, substituted alkoxy, halogen (e.g., fluoro or chloro), and $CO_2R''$ where R'' is hydrogen, alkyl and substituted alkyl. In certain instances, n is 0. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments of formula (XXXV) and formula (XXXVI), the compound has one of the formula (XXXVII) and formula (XXXVIII):

(XXXVII)

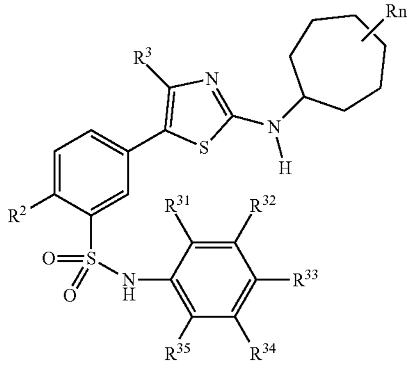

-continued (XXXVIII)

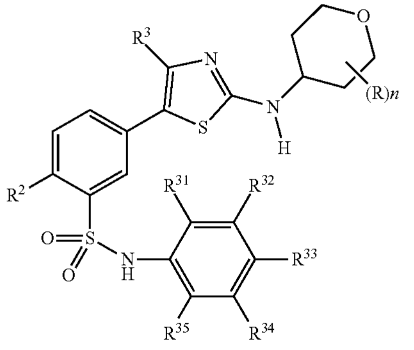

wherein: $R^2$ is selected from hydrogen, a halogen, an alkyl, a substituted alkyl, an alkoxy and a substituted alkoxy; $R^{31}$-$R^{35}$ are independently selected from hydrogen, halogen (e.g., fluoro), alkyl, substituted alkyl, hydroxy, alkoxy, substituted alkoxy, acyl, substituted acyl and —$CO_2R$, wherein R is H, alkyl or substituted alkyl. In certain embodiments of formula (XXXVII) and formula (XXXVIII), $R^{31}$-$R^{35}$ are independently selected from hydrogen, methyl, halogen (e.g., fluoro or chloro) and hydroxy. In certain instances, $R^{31}$ and $R^{33}$ are halogen (e.g., fluoro or chloro). In certain instances, $R^{31}$ and $R^{35}$ are halogen (e.g., fluoro or chloro). In certain instances, $R^{31}$ is halogen (e.g., fluoro or chloro). In certain instances, 3 or 4 of $R^{31}$-$R^{35}$ are hydrogen. In certain embodiments of formula (XXXVII) and formula (XXXVIII), $R^{31}$ and $R^{35}$ are independently lower alkyl or substituted lower alkyl (e.g., methyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. In certain instances, the compound has the structure:

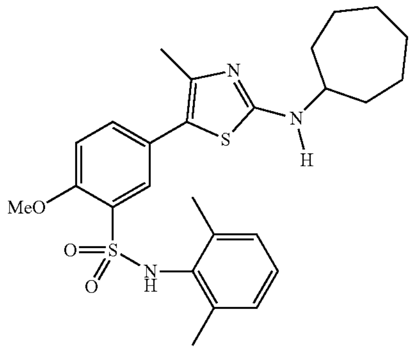 [SMILES: COc1ccc(-c2sc(NC3CCCCCC3)nc2C)cc1S(=O)(=O)Nc1c(C)cccc1C]

or a prodrug thereof, or a pharmaceutically acceptable salt thereof.

In some embodiments, the compound has one of the following structures:

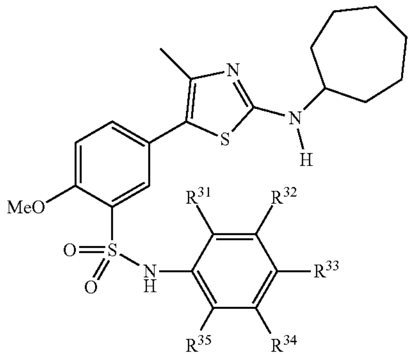

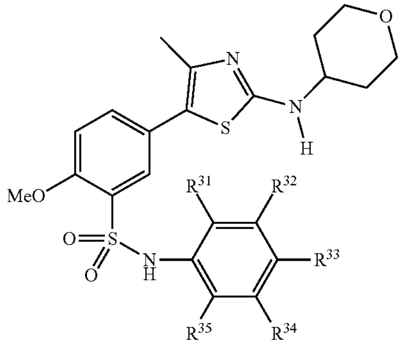

where $R^{31}$-$R^{35}$ are selected from one of the following embodiments:

| Embodiment | $R^{31}$ | $R^{32}$ | $R^{33}$ | $R^{34}$ | $R^{35}$ |
|---|---|---|---|---|---|
| 1 | Cl | H | H | H | Cl |
| 2 | Cl | H | H | H | F |
| 3 | Cl | H | Cl | H | H |
| 4 | Cl | H | H | H | H |
| 5 | Me | H | OH | H | H |
| 6 | Cl | H | OH | H | H |

In some embodiments of formula (XXI), the compound has the formula (XXXIX):

(XXXIX)

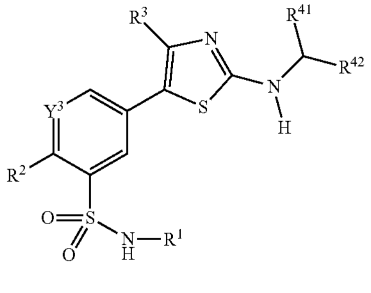

wherein: $R^2$ is selected from hydrogen, a halogen, an alkyl, a substituted alkyl, an alkoxy and a substituted alkoxy; $R^{41}$ is hydrogen, a lower alkyl or a substituted lower alkyl (e.g., methyl); and $R^{42}$ is selected from cycloalkyl, substituted cycloalkyl, alkyl-cycloalkyl, substituted alkyl-cycloalkyl, heterocycle, substituted heterocycle, alkyl-heterocycle (e.g., —$CH_2$-(4-tetrahydropyran)) and substituted alkyl-heterocycle. In certain cases, $Y^3$ is N. In certain cases, $Y^3$ is CH. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. In certain embodiments of formula (XXXIX), the compound has the formula (XL) or (XLI):

(XL)

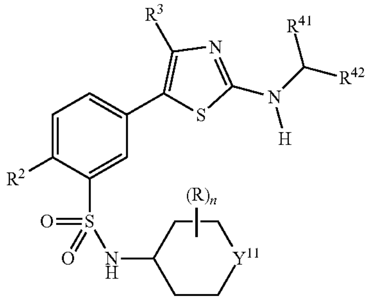

(XLI)

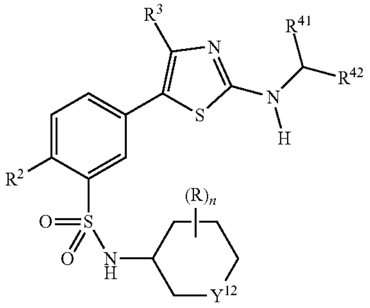

wherein: $R^2$ is selected from hydrogen, a halogen, an alkyl, a substituted alkyl, an alkoxy and a substituted alkoxy; $Y^{11}$ and $Y^{12}$ are selected from $CR''_2$, NR" and O, wherein each R" is independently H, R, an acyl or a substituted acyl; each R is independently H, an alkyl, a substituted alkyl, an alkoxy or a halogen (e.g., a fluoro); and n is 0, 1, 2, 3 or 4. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In certain embodiments of formula (XL) or (XLI), the compound has the formulae (XLII) or (XLIII):

(XLII)

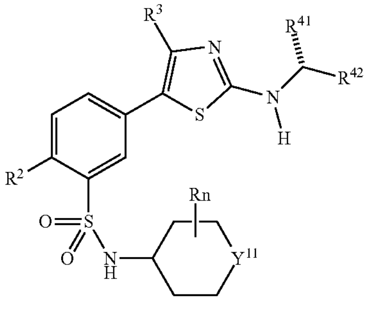

-continued (XLIII)

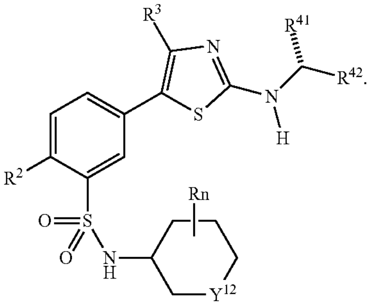

In some instances, $Y^{11}$ and $Y^{12}$ are each NH. In certain cases, n is 0 (e.g., there are no R groups present). In some instances of formulae (XL)-(XLIII), $(R)_n$ is 4-$CO_2R'$, wherein R' is hydrogen or lower alkyl (e.g., ethyl). In certain embodiments of formulae (XXXIX)-(XLIII), $R^{41}$ is methyl; and $R^{42}$ is selected from cyclohexyl, substituted cyclohexyl, —$CH_2$-cyclohexyl and substituted —$CH_2$-cyclohexyl. In certain embodiments, the compound has one of the following structures:

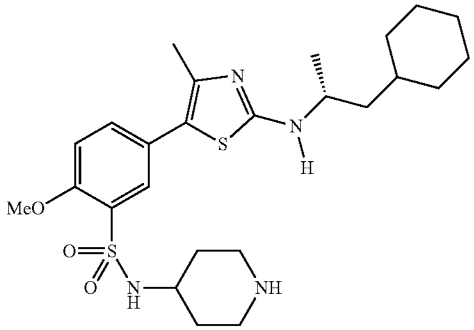

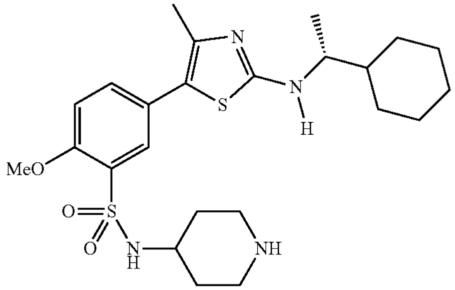

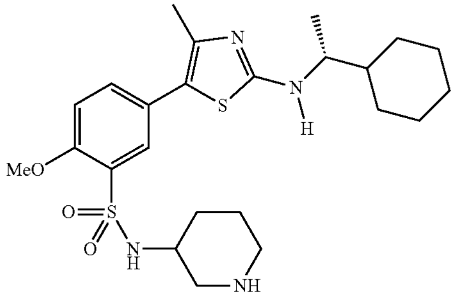

or a prodrug thereof, or a pharmaceutically acceptable salt thereof.

In certain embodiments of formula (XXXIX), the compound has one of the formula (XLIV) and formula (XLV):

(XLIV)

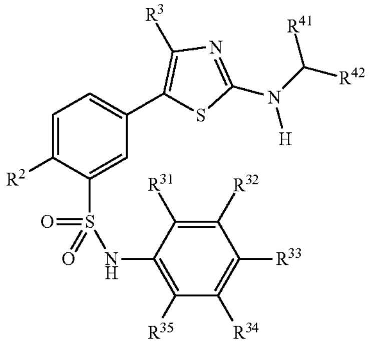

(XLV)

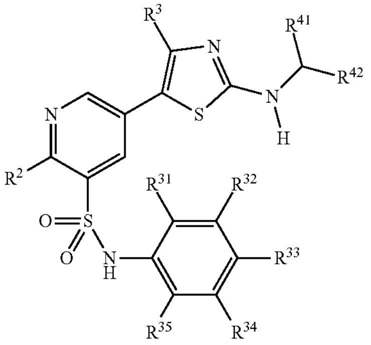

wherein: $R^{31}$-$R^{35}$ are independently selected from hydrogen, halogen (e.g., fluoro), alkyl, substituted alkyl, hydroxy, alkoxy, substituted alkoxy, acyl, substituted acyl and —$CO_2R$, wherein R is H, alkyl or substituted alkyl. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. In certain embodiments of formula (XLIV) or formula (XLV), the compound has one of the formula (XLVI) and formula (XLVII):

(XLVI)

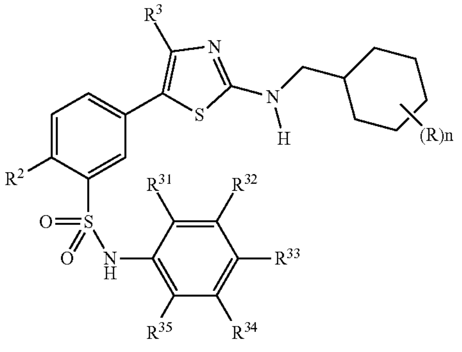

-continued (XLVII)

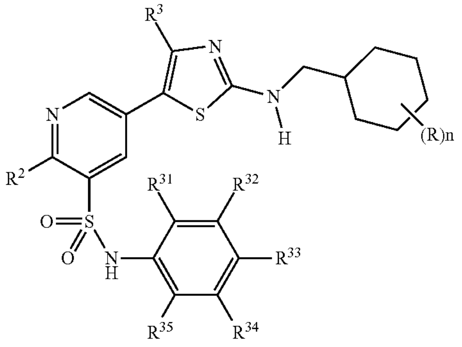

wherein: $(R)_n$ is one or more optional substituents each independently selected from alkyl, substituted alkyl, hydroxyl, alkoxy, substituted alkoxy, halogen (e.g., fluoro or chloro) and $CO_2R''$ where R'' is hydrogen, alkyl or substituted alkyl. In certain instances of formula (XLVI) and formula (XLVII), $R^{31}$-$R^{35}$ are independently selected from hydrogen, methyl, halogen (e.g., fluoro or chloro) and hydroxy. In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments, the compound has the following structure:

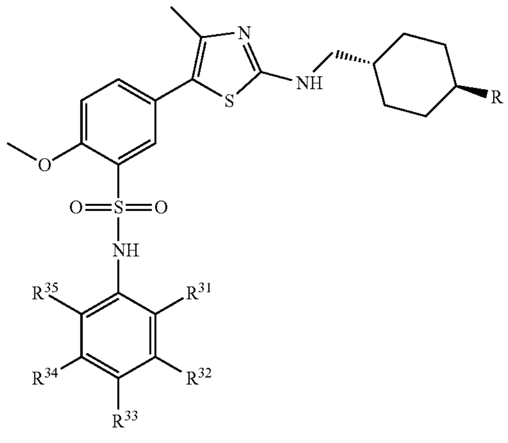

where R and $R^{31}$-$R^{35}$ are selected from one of the following embodiments:

| Embodiment | R | $R^{31}$ | $R^{32}$ | $R^{33}$ | $R^{34}$ | $R^{35}$ |
|---|---|---|---|---|---|---|
| 1 | $CO_2Et$ | H | H | OH | H | H |
| 2 | $CO_2Et$ | H | H | H | H | H |
| 3 | $CO_2Et$ | F | H | F | H | H |
| 4 | $CO_2Et$ | Cl | H | H | H | H |
| 5 | $CO_2Et$ | Cl | H | Cl | H | H |
| 6 | $CO_2Et$ | Cl | H | H | H | Cl |
| 7 | H | H | H | OH | H | H |
| 8 | H | H | H | H | H | H |
| 9 | H | F | H | F | H | H |
| 10 | H | Cl | H | H | H | H |

-continued

| Embodiment | R | $R^{31}$ | $R^{32}$ | $R^{33}$ | $R^{34}$ | $R^{35}$ |
|---|---|---|---|---|---|---|
| 11 | H | Cl | H | Cl | H | H |
| 12 | H | Cl | H | H | H | Cl |

In some embodiments, the compound has the following structure:

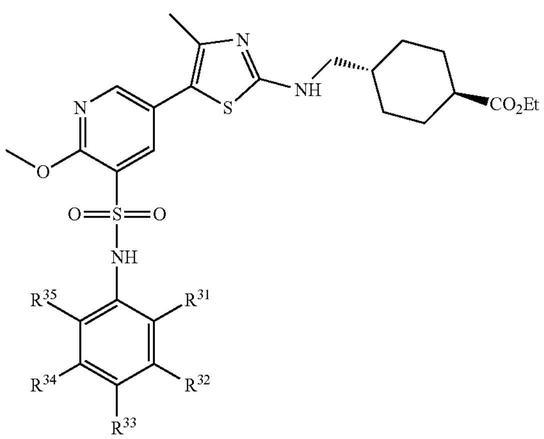

where $R^{31}$-$R^{35}$ are selected from one of the following embodiments:

| Embodiment | $R^{31}$ | $R^{32}$ | $R^{33}$ | $R^{34}$ | $R^{35}$ |
|---|---|---|---|---|---|
| 1 | H | H | OH | H | H |
| 2 | H | H | H | H | H |
| 3 | F | H | F | H | H |
| 4 | Cl | H | H | H | H |
| 5 | Cl | H | Cl | H | H |
| 6 | Cl | H | H | H | Cl |

In certain instances of formula (XXI), the compound has one of the formula (XLVIII) or formula (XLIX):

(XLVIII)

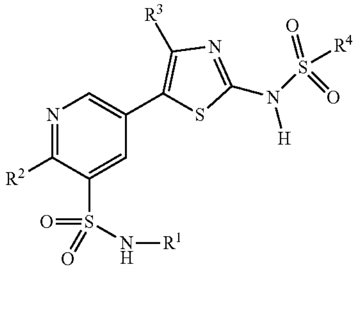

-continued (XLIX)

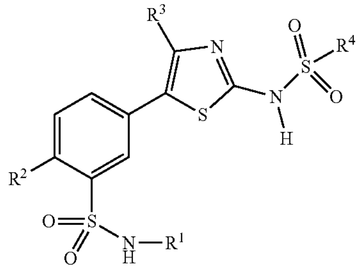

wherein $R^1$ is selected from aryl and substituted aryl. In certain instances of formula (XLVIII) or formula (XLIX): $R^4$ is methyl, isopropyl, cyclohexyl, substituted cyclohexyl, phenyl, substituted phenyl, benzyl, substituted benzyl or —$CH_2$-4-tetrahydropyran. In certain instances of formula (XLVIII) or formula (XLIX): $R^1$ is a substituted phenyl (e.g., 4-hydroxy-phenyl). In certain embodiments, $R^2$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe. Also provided are compounds based on any of the structure and formulae depicted herein having OMe at the $R^2$ position, which have an analogous structure but with one Me, Cl, Br, $CHF_2$, $CF_3$ and $CH_2F$ appearing at the $R^2$ position instead of this OMe group.

In some embodiments, the compound has the following structure:

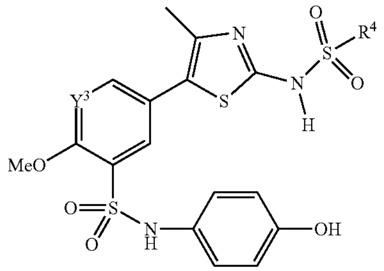

where $Y^3$ and $R^4$ are selected from one of the following embodiments:

| Embodiment | $Y^3$ | $R^4$ |
|---|---|---|
| 1 | CH | methyl |
| 2 | CH | isopropyl |
| 3 | CH | cyclohexyl |
| 4 | CH | phenyl |
| 5 | CH | benzyl |
| 6 | CH | —$CH_2$-(4-tetrahydropyran) |
| 7 | N | methyl |
| 8 | N | isopropyl |
| 9 | N | cyclohexyl |
| 10 | N | phenyl |
| 11 | N | benzyl |
| 12 | N | —$CH_2$-(4-tetrahydropyran) |

In some embodiments of any one of the formulae (Ia)-(XLIX), $R^2$ is methoxy. In some embodiments of any one of the formulae (Ia)-(XLIX), $R^3$ is methyl. In some embodiments of any one of the formulae (Ia)-(XLIX), $R^2$ is methoxy and $R^3$ is methyl. In some embodiments of any one of the formulae (Ia)-(XLIX), $R^2$ is a halogen (e.g., Cl or Br). In some embodiments of any one of the formulae (Ia)-(XLIX), $R^2$ is a substituted lower alkyl. In some embodiments of any one of the formulae (Ia)-(XLIX), $R^2$ is $CF_3$. In some embodiments of any one of the formulae (Ia)-(XLIX), $R^2$ is $CHF_2$. In some embodiments of any one of the formulae (Ia)-(XLIX), $R^2$ is $CH_2F$. In some embodiments of any one of the formulae (Ia)-(XLIX), $R^2$ is a lower alkyl. In some embodiments of any one of the formulae (Ia)-(XLIX), $R^2$ is methyl.

In certain embodiments, the compound is described by the structure of one of the compounds of Table 1. It is understood that any of the compounds shown in Table 1 may be present in a salt form, such as a trifluoroacetate salt (e.g., $CF_3COOH$ salt). In some cases, the salt form of the compound is a pharmaceutically acceptable salt.

TABLE 1

| Compounds | | |
|---|---|---|
| Compound | Structure | Name |
| S-1 | 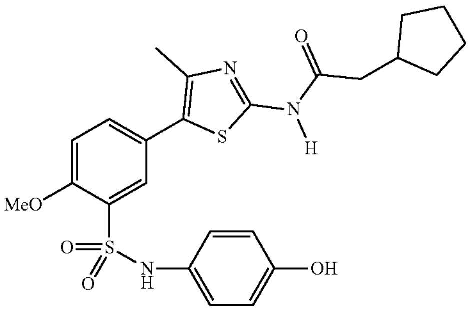 [SMILES: COc1ccc(-c2sc(NC(=O)CC3CCCC3)nc2C)cc1S(=O)(=O)Nc1ccc(O)cc1] | 2-cyclopentyl-N-[5-[3-[(4-hydroxyphenyl)sulfamoyl]-4-methoxy-phenyl]-4-methyl-thiazol-2-yl]acetamide |
| S-2 | 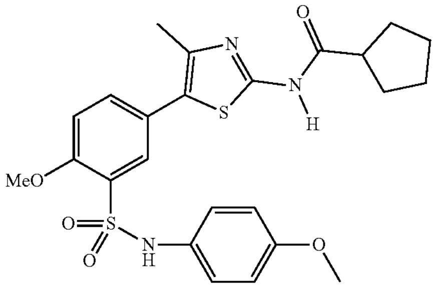 [SMILES: COc1ccc(NS(=O)(=O)c2cc(-c3sc(NC(=O)C4CCCC4)nc3C)ccc2OC)cc1] | N-[5-[4-methoxy-3-[(4-methoxyphenyl)sulfamoyl]phenyl]-4-methyl-thiazol-2-yl]cyclopentanecarboxamide |
| S-3 | 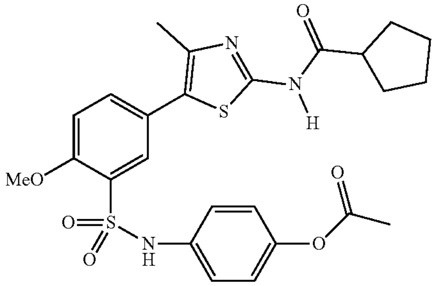 [SMILES: COc1ccc(-c2sc(NC(=O)C3CCCC3)nc2C)cc1S(=O)(=O)Nc1ccc(OC(C)=O)cc1] | [4-[[5-[2-(cyclopentanecarbonylamino)-4-methyl-thiazol-5-yl]-2-methoxy-phenyl]sulfonylamino]phenyl] acetate |
| S-4 | 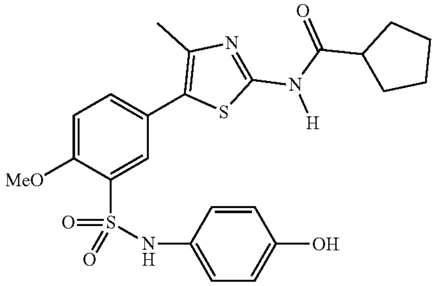 [SMILES: COc1ccc(-c2sc(NC(=O)C3CCCC3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]cyclopentanecarboxamide |

TABLE 1-continued

| Compounds | | |
|---|---|---|
| Compound | Structure | Name |
| S-5 | 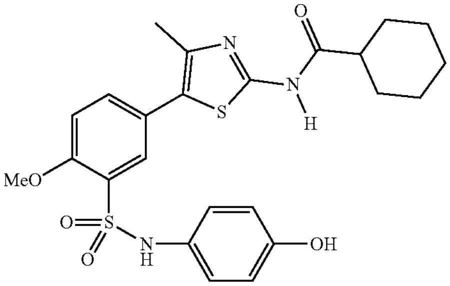 [SMILES: COc1ccc(-c2sc(NC(=O)C3CCCCC3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]cyclohexanecarboxamide |
| S-6 | 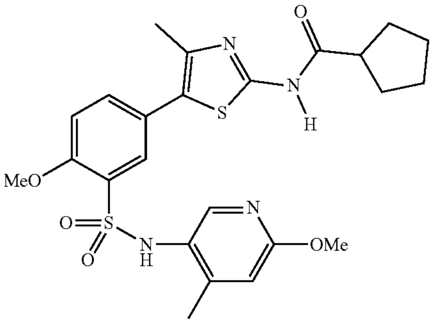 [SMILES: COc1cc(C)c(NS(=O)(=O)c2cc(-c3sc(NC(=O)C4CCCC4)nc3C)ccc2OC)cn1] | N-[5-[4-methoxy-3-[(6-methoxy-4-methyl-3-pyridyl)sulfamoyl]phenyl]-4-methyl-thiazol-2-yl]cyclopentanecarboxamide |
| S-7 | 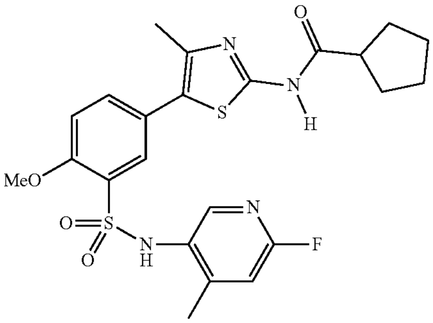 [SMILES: COc1ccc(-c2sc(NC(=O)C3CCCC3)nc2C)cc1S(=O)(=O)Nc1cnc(F)cc1C] | N-[5-[3-[(6-fluoro-4-methyl-3-pyridyl)sulfamoyl]-4-methoxy-phenyl]-4-methyl-thiazol-2-yl]cyclopentanecarboxamide |
| S-8 | 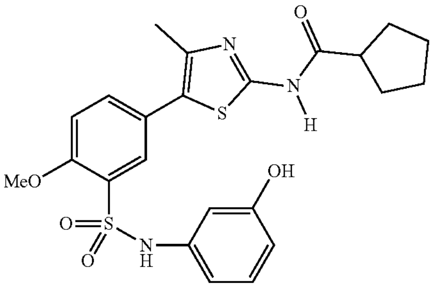 [SMILES: COc1ccc(-c2sc(NC(=O)C3CCCC3)nc2C)cc1S(=O)(=O)Nc1cccc(O)c1] | N-[5-[3-[(3-hydroxyphenyl)sulfamoyl]-4-methoxy-phenyl]-4-methyl-thiazol-2-yl]cyclopentanecarboxamide |
| S-9 | 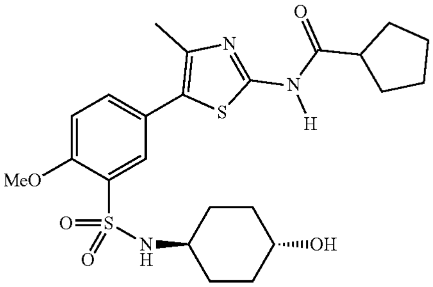 [SMILES: COc1ccc(-c2sc(NC(=O)C3CCCC3)nc2C)cc1S(=O)(=O)N[C@H]1CC[C@H](O)CC1] | N-[5-[3-[(4-hydroxycyclohexyl)sulfamoyl]-4-methoxy-phenyl]-4-methyl-thiazol-2-yl]cyclopentanecarboxamide |

TABLE 1-continued

| Compounds | | |
|---|---|---|
| Compound | Structure | Name |
| S-10 | 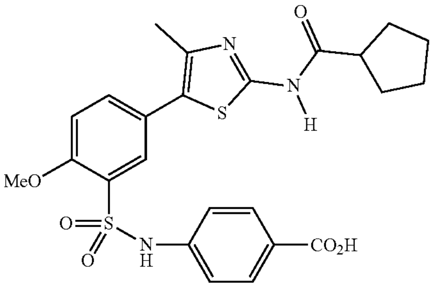 [SMILES: COc1ccc(-c2sc(NC(=O)C3CCCC3)nc2C)cc1S(=O)(=O)Nc1ccc(C(=O)O)cc1] | 4-[[5-[2-(cyclopentanecarbonylamino)-4-methyl-thiazol-5-yl]-2-methoxy-phenyl]sulfonylamino]benzoic acid |
| S-11 | 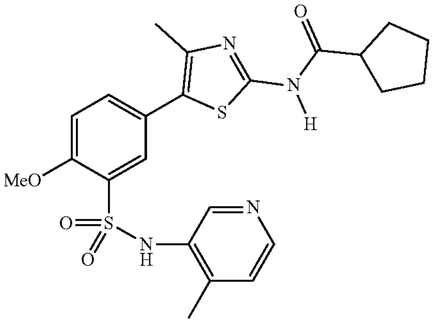 [SMILES: COc1ccc(-c2sc(NC(=O)C3CCCC3)nc2C)cc1S(=O)(=O)Nc1cnccc1C] | N-[5-[4-methoxy-3-[(4-methyl-3-pyridyl]sulfamoyl]phenyl]-4-methyl-thiazol-2-yl]cyclopentanecarboxamide |
| S-12 | 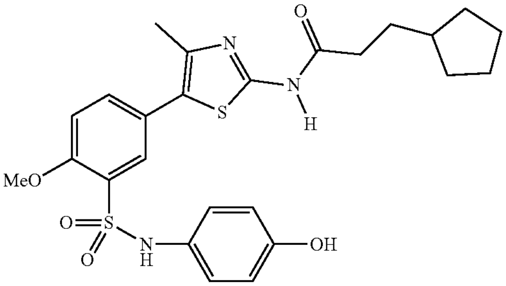 [SMILES: COc1ccc(-c2sc(NC(=O)CCC3CCCC3)nc2C)cc1S(=O)(=O)Nc1ccc(O)cc1] | 3-cyclopentyl-N-[5-[3-[(4-hydroxyphenyl)sulfamoyl]-4-methoxy-phenyl]-4-methyl-thiazol-2-yl]propanamide |
| S-13 | 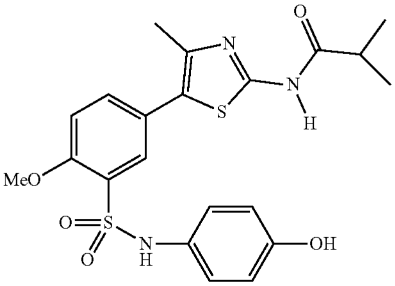 [SMILES: COc1ccc(-c2sc(NC(=O)C(C)C)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]-2-methyl-propanamide |
| S-14 | 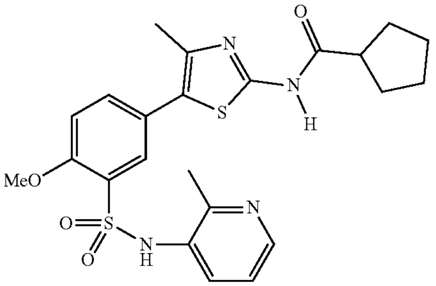 [SMILES: COc1ccc(-c2sc(NC(=O)C3CCCC3)nc2C)cc1S(=O)(=O)Nc1cccnc1C] | N-[5-[4-methoxy-3-[(2-methyl-3-pyridyl)sulfamoyl]phenyl]-4-methyl-thiazol-2-yl]cyclopentanecarboxamide |

TABLE 1-continued

| Compounds | | |
|---|---|---|
| Compound | Structure | Name |
| S-15 | 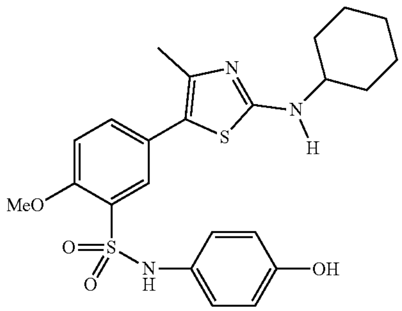 [SMILES: COc1ccc(-c2sc(NC3CCCCC3)nc2C)cc1S(=O)(=O)Nc1ccc(O)cc1] | 5-[2-(cyclohexylamino)-4-methyl-thiazol-5-yl]-N-(4-hydroxyphenyl)-2-methoxy-benzenesulfonamide |
| S-16 | 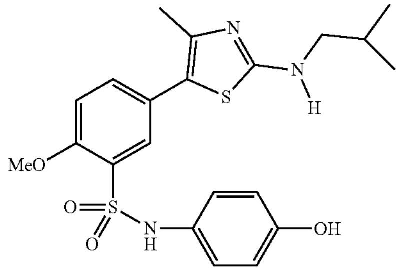 [SMILES: COc1ccc(-c2sc(NCC(C)C)nc2C)cc1S(=O)(=O)Nc1ccc(O)cc1] | N-(4-hydroxyphenyl)-5-[2-(isobutylamino)-4-methyl-thiazol-5-yl]-2-methoxy-benzenesulfonamide |
| S-17 | 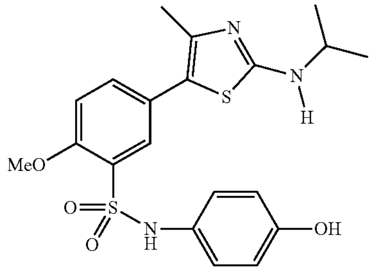 [SMILES: COc1ccc(-c2sc(NC(C)C)nc2C)cc1S(=O)(=O)Nc1ccc(O)cc1] | N-(4-hydroxyphenyl)-5-[2-(isopropylamino)-4-methyl-thiazol-5-yl]-2-methoxy-benzenesulfonamide |
| S-18 | 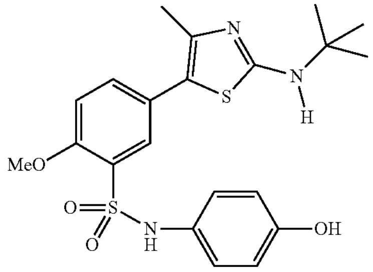 [SMILES: COc1ccc(-c2sc(NC(C)(C)C)nc2C)cc1S(=O)(=O)Nc1ccc(O)cc1] | 5-[2-(tert-butylamino)-4-methyl-thiazol-5-yl]-N-(4-hydroxyphenyl)-2-methoxy-benzenesulfonamide |
| S-19 | 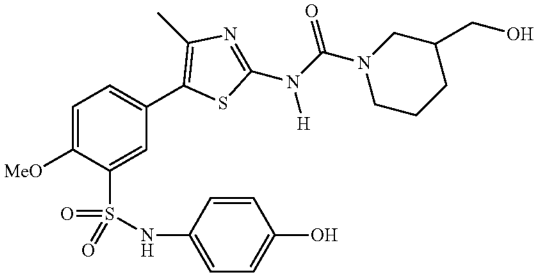 [SMILES: COc1ccc(-c2sc(NC(=O)N3CCCC(CO)C3)nc2C)cc1S(=O)(=O)Nc1ccc(O)cc1] | 3-(hydroxymethyl)-N-[5-[3-[(4-hydroxyphenyl)sulfamoyl]-4-methoxy-phenyl]-4-methyl-thiazol-2-yl]piperidine-1-carboxamide |

TABLE 1-continued

| Compounds | | |
|---|---|---|
| Compound | Structure | Name |
| S-20 | 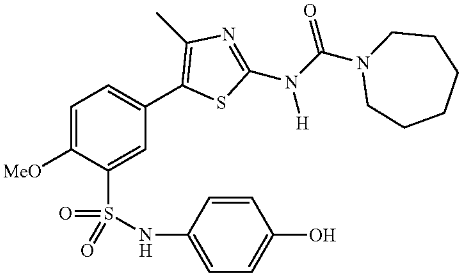 [SMILES: COc1ccc(-c2sc(NC(=O)N3CCCCCC3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]azepane-1-carboxamide |
| S-21 | 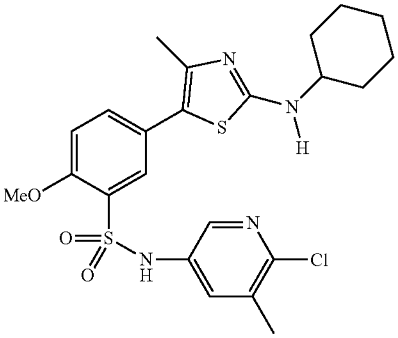 [SMILES: COc1ccc(-c2sc(NC3CCCCC3)nc2C)cc1S(=O)(=O)Nc1cnc(Cl)c(C)c1] | N-(6-chloro-5-methyl-3-pyridyl)-5-[2-(cyclohexylamino)-4-methyl-thiazol-5-yl]-2-methoxy-benzenesulfonamide |
| S-22 | 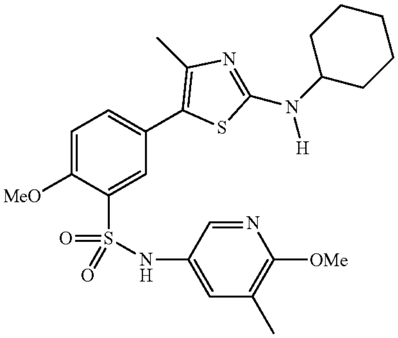 [SMILES: COc1ccc(-c2sc(NC3CCCCC3)nc2C)cc1S(=O)(=O)Nc1cnc(OC)c(C)c1] | 5-[2-(cyclohexylamino)-4-methyl-thiazol-5-yl]-2-methoxy-N-(6-methoxy-5-methyl-3-pyridyl)benzenesulfonamide |
| S-23 | 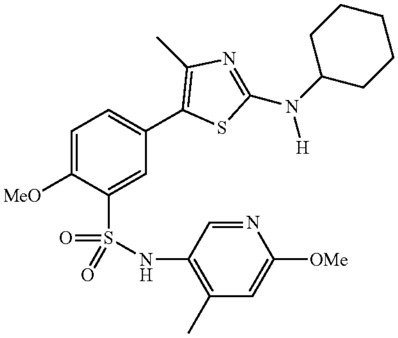 [SMILES: COc1cc(C)c(NS(=O)(=O)c2cc(-c3sc(NC4CCCCC4)nc3C)ccc2OC)cn1] | 5-[2-(cyclohexylamino)-4-methyl-thiazol-5-yl]-2-methoxy-N-(6-methoxy-4-methyl-3-pyridyl)benzenesulfonamide |

TABLE 1-continued

| Compounds | | |
|---|---|---|
| Compound | Structure | Name |
| S-24 | 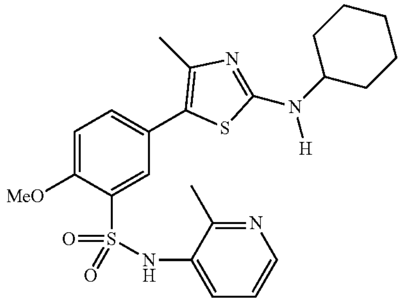 [SMILES: COc1ccc(-c2sc(NC3CCCCC3)nc2C)cc1S(=O)(=O)Nc1cccnc1C] | 5-[2-(cyclohexylamino)-4-methyl-thiazol-5-yl]-2-methoxy-N-(2-methyl-3-pyridyl)benzenesulfonamide |
| S-25 | 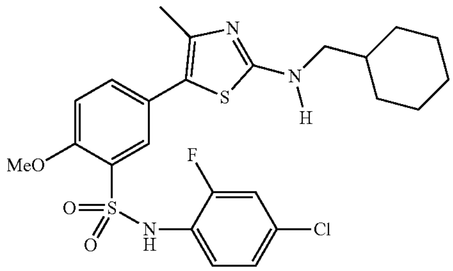 [SMILES: COc1ccc(-c2sc(NCC3CCCCC3)nc2C)cc1S(=O)(=O)Nc1ccc(Cl)cc1F] | N-(4-chloro-2-fluoro-phenyl)-5-[2-(cyclohexylmethylamino)-4-methyl-thiazol-5-yl]-2-methoxy-benzenesulfonamide |
| S-26 | 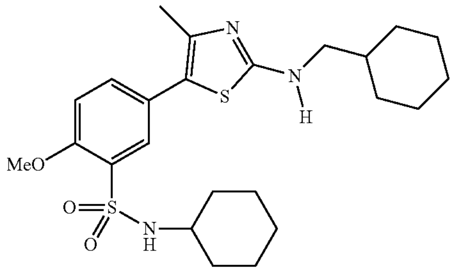 [SMILES: COc1ccc(-c2sc(NCC3CCCCC3)nc2C)cc1S(=O)(=O)NC1CCCCC1] | N-cyclohexyl-5-[2-(cyclohexylmethylamino)-4-methyl-thiazol-5-yl]-2-methoxy-benzenesulfonamide |
| S-27 | 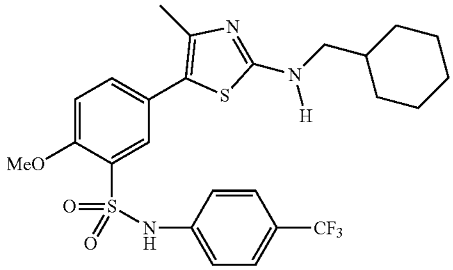 [SMILES: COc1ccc(-c2sc(NCC3CCCCC3)nc2C)cc1S(=O)(=O)Nc1ccc(C(F)(F)F)cc1] | 5-[2-(cyclohexylmethylamino)-4-methyl-thiazol-5-yl]-2-methoxy-N-[4-(trifluoromethyl)phenyl]benzenesulfonamide |
| S-28 | 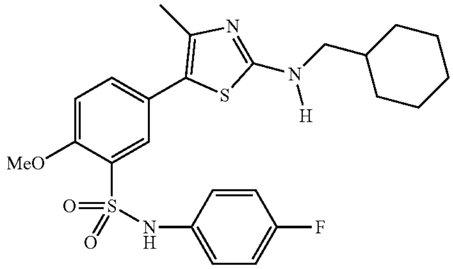 [SMILES: COc1ccc(-c2sc(NCC3CCCCC3)nc2C)cc1S(=O)(=O)Nc1ccc(F)cc1] | 5-[2-(cyclohexylmethylamino)-4-methyl-thiazol-5-yl]-N-(4-fluorophenyl)-2-methoxy-benzenesulfonamide |

TABLE 1-continued

| Compounds | | |
|---|---|---|
| Compound | Structure | Name |
| S-29 | 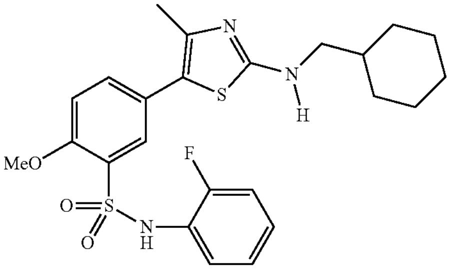 [SMILES: COc1ccc(-c2sc(NCC3CCCCC3)nc2C)cc1S(=O)(=O)Nc1ccccc1F] | 5-[2-(cyclohexylmethylamino)-4-methyl-thiazol-5-yl]-N-(2-fluorophenyl)-2-methoxy-benzenesulfonamide |
| S-30 | 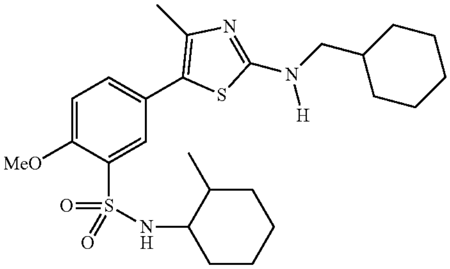 [SMILES: COc1ccc(-c2sc(NCC3CCCCC3)nc2C)cc1S(=O)(=O)NC1CCCCC1C] | 5-[2-(cyclohexylmethylamino)-4-methyl-thiazol-5-yl]-2-methoxy-N-(2-methylcyclohexyl)benzenesulfonamide |
| S-31 | 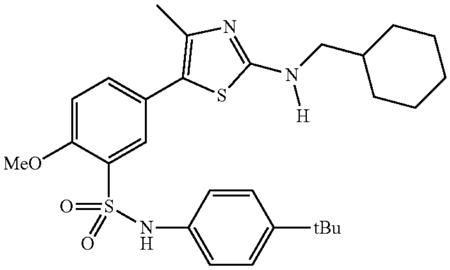 [SMILES: COc1ccc(-c2sc(NCC3CCCCC3)nc2C)cc1S(=O)(=O)Nc1ccc(C(C)(C)C)cc1] | N-(4-tert-butylphenyl)-5-[2-(cyclohexylmethylamino)-4-methyl-thiazol-5-yl]-2-methoxy-benzenesulfonamide; 2,2,2-trifluoroacetic acid |
| S-32 | 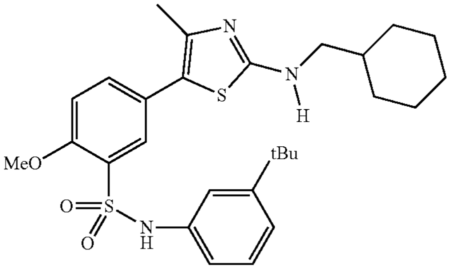 [SMILES: COc1ccc(-c2sc(NCC3CCCCC3)nc2C)cc1S(=O)(=O)Nc1cccc(C(C)(C)C)c1] | N-(3-tert-butylphenyl)-5-[2-(cyclohexylmethylamino)-4-methyl-thiazol-5-yl]-2-methoxy-benzenesulfonamide; 2,2,2-trifluoroacetic acid |
| S-33 | 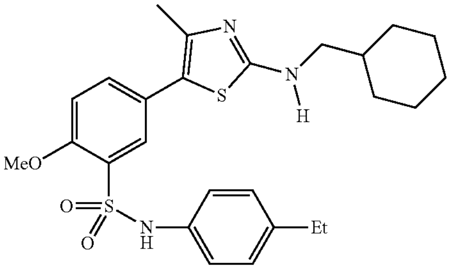 [SMILES: CCc1ccc(NS(=O)(=O)c2cc(-c3sc(NCC4CCCCC4)nc3C)ccc2OC)cc1] | 5-[2-(cyclohexylmethylamino)-4-methyl-thiazol-5-yl]-N-(4-ethylphenyl)-2-methoxy-benzenesulfonamide; 2,2,2-trifluoroacetic acid |

TABLE 1-continued

| Compounds | | |
|---|---|---|
| Compound | Structure | Name |
| S-34 | 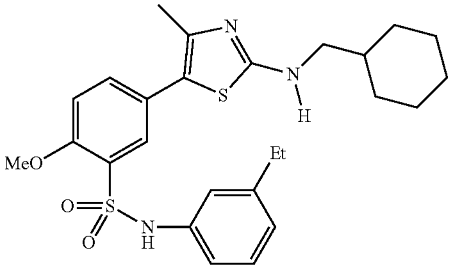 [SMILES: CCc1cccc(NS(=O)(=O)c2cc(-c3sc(NCC4CCCCC4)nc3C)ccc2OC)c1] | 5-[2-(cyclohexylmethylamino)-4-methyl-thiazol-5-yl]-N-(3-ethylphenyl)-2-methoxy-benzenesulfonamide |
| S-35 | 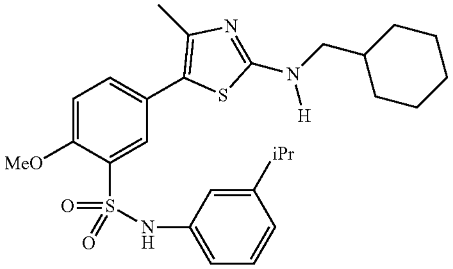 [SMILES: COc1ccc(-c2sc(NCC3CCCCC3)nc2C)cc1S(=O)(=O)Nc1cccc(C(C)C)c1] | 5-[2-(cyclohexylmethylamino)-4-methyl-thiazol-5-yl]-N-(3-isopropylphenyl)-2-methoxy-benzenesulfonamide |
| S-36 | 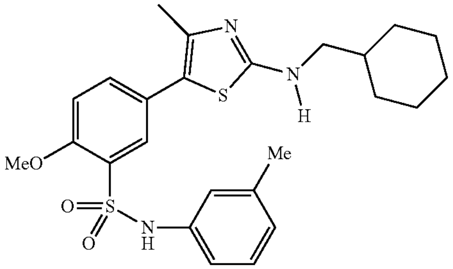 [SMILES: COc1ccc(-c2sc(NCC3CCCCC3)nc2C)cc1S(=O)(=O)Nc1cccc(C)c1] | 5-[2-(cyclohexylmethylamino)-4-methyl-thiazol-5-yl]-2-methoxy-N-(m-tolyl)benzenesulfonamide |
| S-37 | 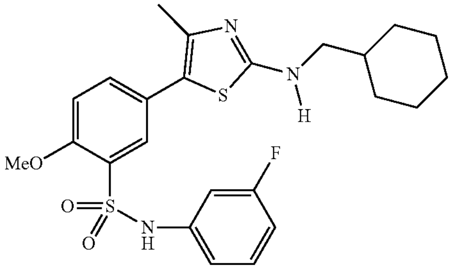 [SMILES: COc1ccc(-c2sc(NCC3CCCCC3)nc2C)cc1S(=O)(=O)Nc1cccc(F)c1] | 5-[2-(cyclohexylmethylamino)-4-methyl-thiazol-5-yl]-N-(3-fluorophenyl)-2-methoxy-benzenesulfonamide |
| S-38 | 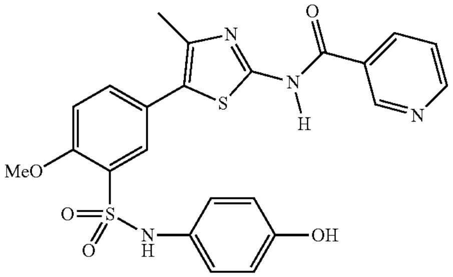 [SMILES: COc1ccc(-c2sc(NC(=O)c3cccnc3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]pyridine-3-carboxamide |

TABLE 1-continued

| Compounds | | |
|---|---|---|
| Compound | Structure | Name |
| S-39 | 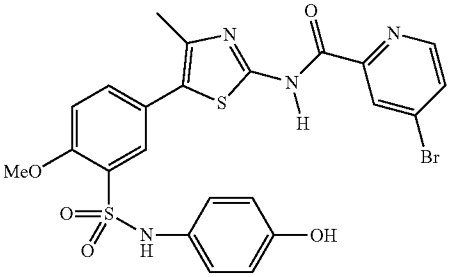 [SMILES: COc1ccc(-c2sc(NC(=O)c3cc(Br)ccn3)nc2C)cc1S(=O)(=O)Nc1ccc(O)cc1] | 4-bromo-N-[5-[3-[(4-hydroxyphenyl)sulfamoyl]-4-methoxy-phenyl]-4-methyl-thiazol-2-yl]pyridine-2-carboxamide |
| S-40 | 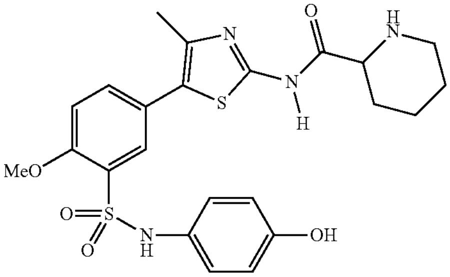 [SMILES: COc1ccc(-c2sc(NC(=O)C3CCCCN3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]piperidine-2-carboxamide |
| S-41 | 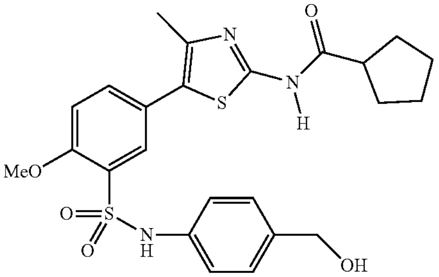 [SMILES: COc1ccc(-c2sc(NC(=O)C3CCCC3)nc2C)cc1S(=O)(=O)Nc1ccc(CO)cc1] | N-[5-[3-[[4-(hydroxymethyl)phenyl]sulfamoyl]-4-methoxy-phenyl]-4-methyl-thiazol-2-yl]cyclopentanecarboxamide |
| S-42 | 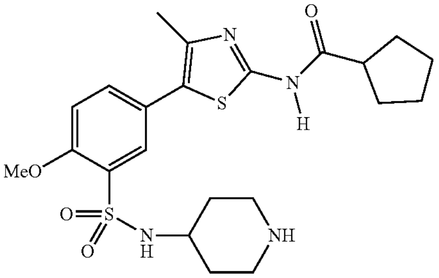 [SMILES: COc1ccc(-c2sc(NC(=O)C3CCCC3)nc2C)cc1S(=O)(=O)NC1CCNCC1] | N-[5-[4-methoxy-3-(4-piperidylsulfamoyl)phenyl]-4-methyl-thiazol-2-yl]cyclopentanecarboxamide |
| S-43 | 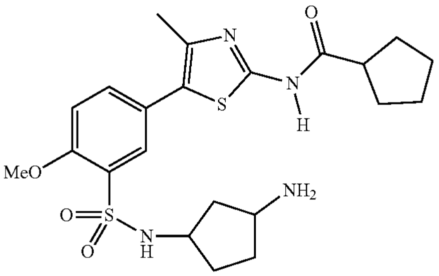 [SMILES: COc1ccc(-c2sc(NC(=O)C3CCCC3)nc2C)cc1S(=O)(=O)NC1CCC(N)C1] | N-[5-[3-(3-aminopyrrolidin-1-yl)sulfonyl-4-methoxy-phenyl]-4-methyl-thiazol-2-yl]cyclopentanecarboxamide |

TABLE 1-continued

| Compounds | | |
|---|---|---|
| Compound | Structure | Name |
| S-44 | 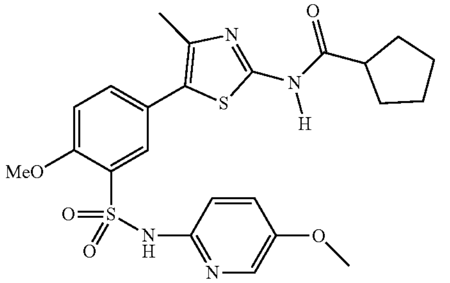 [SMILES: COc1ccc(NS(=O)(=O)c2cc(-c3sc(NC(=O)C4CCCC4)nc3C)ccc2OC)nc1] | N-[5-[4-methoxy-3-[(5-methoxy-2-pyridyl)sulfamoyl]phenyl]-4-methyl-thiazol-2-yl]cyclopentanecarboxamide |
| S-45 | 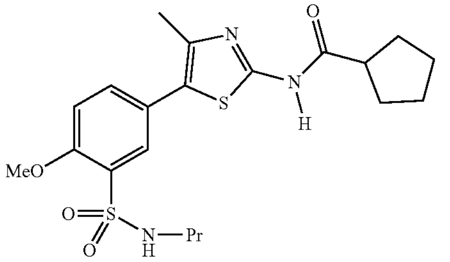 | N-[5-[4-methoxy-3-(propylsulfamoyl)phenyl]-4-methyl-thiazol-2-yl]cyclopentanecarboxamide |
| S-46 | 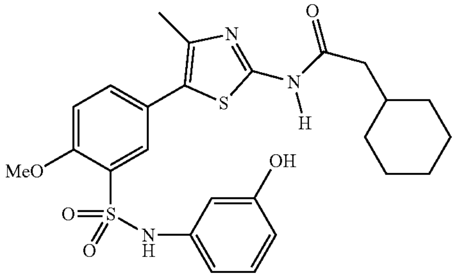 [SMILES: COc1ccc(-c2sc(NC(=O)CC3CCCCC3)nc2C)cc1S(=O)(=O)Nc1cccc(O)c1] | 2-cyclohexyl-N-[5-[3-[(3-hydroxyphenyl)sulfamoyl]-4-methoxy-phenyl]-4-methyl-thiazol-2-yl]acetamide |
| S-47 | 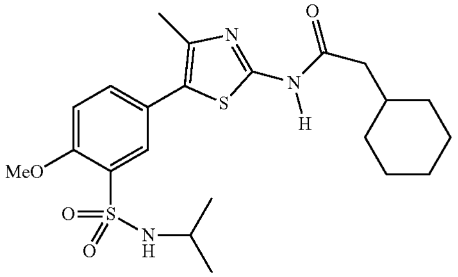 [SMILES: COc1ccc(-c2sc(NC(=O)CC3CCCCC3)nc2C)cc1S(=O)(=O)NC(C)C] | 2-cyclohexyl-N-[5-[3-(isopropylsulfamoyl)-4-methoxy-phenyl]-4-methyl-thiazol-2-yl]acetamide |
| S-48 | 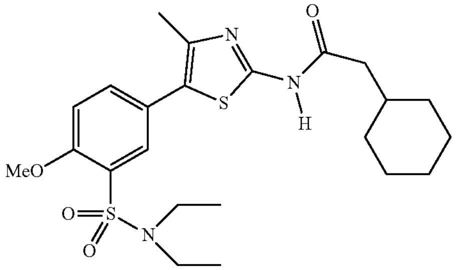 [SMILES: CCN(CC)S(=O)(=O)c1cc(-c2sc(NC(=O)CC3CCCCC3)nc2C)ccc1OC] | 2-cyclohexyl-N-[5-[3-(diethylsulfamoyl)-4-methoxy-phenyl]-4-methyl-thiazol-2-yl]acetamide |

TABLE 1-continued

| Compounds | | |
|---|---|---|
| Compound | Structure | Name |
| S-49 | 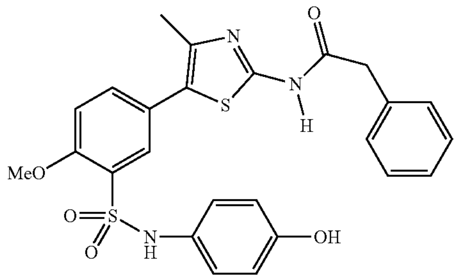 [SMILES: COc1ccc(-c2sc(NC(=O)Cc3ccccc3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]-2-phenyl-acetamide |
| S-50 | 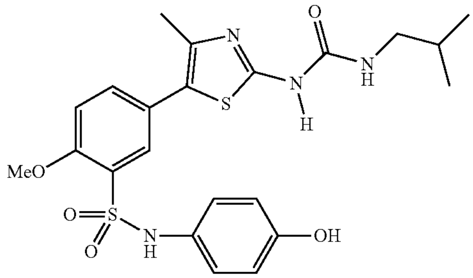 [SMILES: COc1ccc(-c2sc(NC(=O)NCC(C)C)nc2C)cc1S(=O)(=O)Nc1ccc(O)cc1] | 1-[5-[3-[(4-hydroxyphenyl)sulfamoyl]-4-methoxy-phenyl]-4-methyl-thiazol-2-yl]-3-isobutyl-urea |
| S-51 | 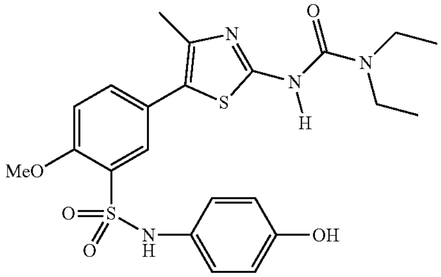 [SMILES: CCN(CC)C(=O)Nc1nc(C)c(-c2ccc(OC)c(S(=O)(=O)Nc3ccc(O)cc3)c2)s1] | 1,1-diethyl-3-[5-[3-[(4-hydroxyphenyl)sulfamoyl]-4-methoxy-phenyl]-4-methyl-thiazol-2-yl]urea |
| S-52 | 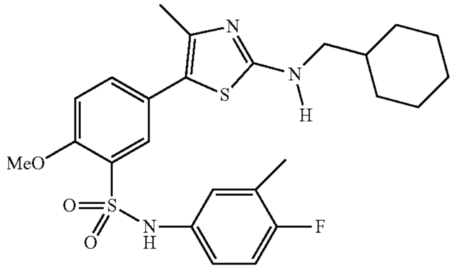 [SMILES: COc1ccc(-c2sc(NCC3CCCCC3)nc2C)cc1S(=O)(=O)Nc1ccc(F)c(C)c1] | 5-[2-(cyclohexylmethylamino)-4-methyl-thiazol-5-yl]-N-(4-fluoro-3-methyl-phenyl)-2-methoxy-benzenesulfonamide; 2,2,2-trifluoroacetic acid |
| S-53 | 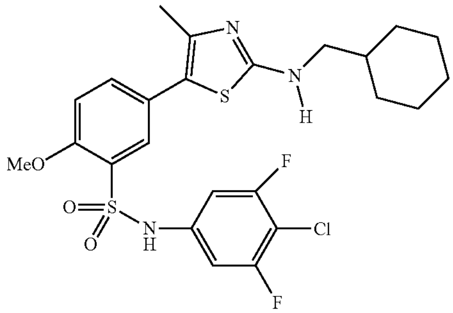 [SMILES: COc1ccc(-c2sc(NCC3CCCCC3)nc2C)cc1S(=O)(=O)Nc1cc(F)c(Cl)c(F)c1] | N-(4-chloro-3,5-difluoro-phenyl)-5-[2-(cyclohexylmethylamino)-4-methyl-thiazol-5-yl]-2-methoxy-benzenesulfonamide |

TABLE 1-continued

| Compounds | | |
|---|---|---|
| Compound | Structure | Name |
| S-54 | 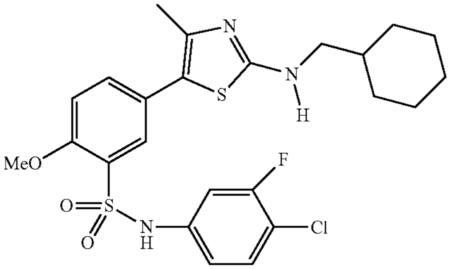 [SMILES: COc1ccc(-c2sc(NCC3CCCCC3)nc2C)cc1S(=O)(=O)Nc1ccc(Cl)c(F)c1] | N-(4-chloro-3-fluoro-phenyl)-5-[2-(cyclohexylmethylamino)-4-methyl-thiazol-5-yl]-2-methoxy-benzenesulfonamide |
| S-55 | 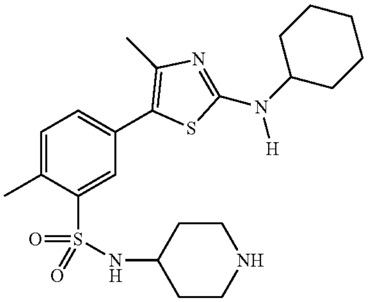 [SMILES: Cc1ccc(-c2sc(NC3CCCCC3)nc2C)cc1S(=O)(=O)NC1CCNCC1] | 5-[2-(cyclohexylamino)-4-methyl-thiazol-5-yl]-2-methyl-N-(4-piperidyl)benzenesulfonamide |
| S-56 | 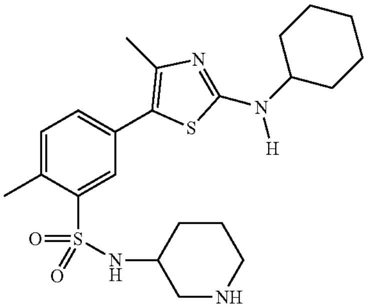 [SMILES: Cc1ccc(-c2sc(NC3CCCCC3)nc2C)cc1S(=O)(=O)NC1CCCNC1] | 5-[2-(cyclohexylamino)-4-methyl-thiazol-5-yl]-2-methyl-N-(3-piperidyl)benzenesulfonamide |
| S-57 | 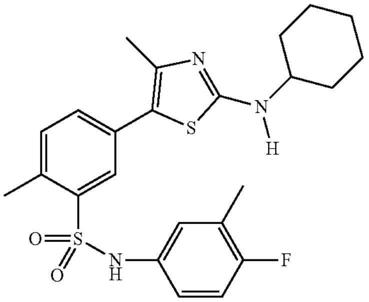 [SMILES: Cc1cc(NS(=O)(=O)c2cc(-c3sc(NC4CCCCC4)nc3C)ccc2C)ccc1F] | 5-[2-(cyclohexylamino)-4-methyl-thiazol-5-yl]-N-(4-fluoro-3-methyl-phenyl)-2-methyl-benzenesulfonamide; 2,2,2-trifluoroacetic acid |
| S-58 | 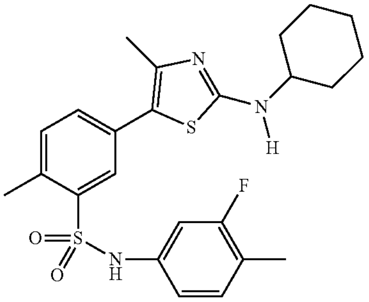 [SMILES: Cc1ccc(NS(=O)(=O)c2cc(-c3sc(NC4CCCCC4)nc3C)ccc2C)cc1F] | 5-[2-(cyclohexylamino)-4-methyl-thiazol-5-yl]-N-(3-fluoro-4-methyl-phenyl)-2-methyl-benzenesulfonamide |

TABLE 1-continued

| Compounds | | |
|---|---|---|
| Compound | Structure | Name |
| S-59 | 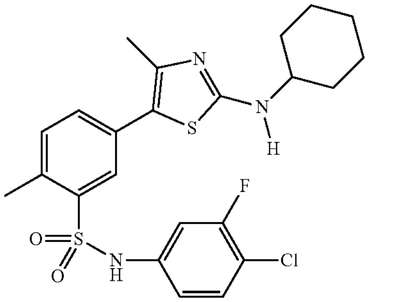 [SMILES: Cc1ccc(-c2sc(NC3CCCCC3)nc2C)cc1S(=O)(=O)Nc1ccc(Cl)c(F)c1] | N-(4-chloro-3-fluoro-phenyl)-5-[2-(cyclohexylamino)-4-methyl-thiazol-5-yl]-2-methyl-benzenesulfonamide |
| S-60 | 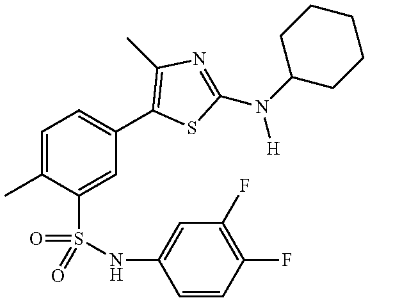 [SMILES: Cc1ccc(-c2sc(NC3CCCCC3)nc2C)cc1S(=O)(=O)Nc1ccc(F)c(F)c1] | 5-[2-(cyclohexylamino)-4-methyl-thiazol-5-yl]-N-(3,4-difluorophenyl)-2-methyl-benzenesulfonamide |
| S-61 | 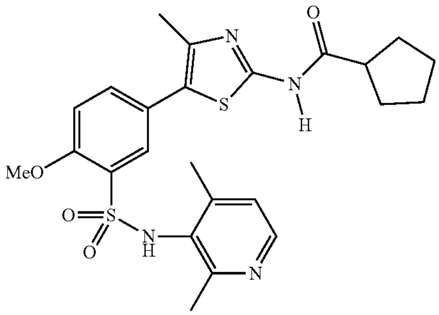 [SMILES: COc1ccc(-c2sc(NC(=O)C3CCCC3)nc2C)cc1S(=O)(=O)Nc1c(C)ccnc1C] | N-[5-[3-[(2,4-dimethyl-3-pyridyl)sulfamoyl]-4-methoxy-phenyl]-4-methyl-thiazol-2-yl]cyclopentanecarboxamide |
| S-62 | 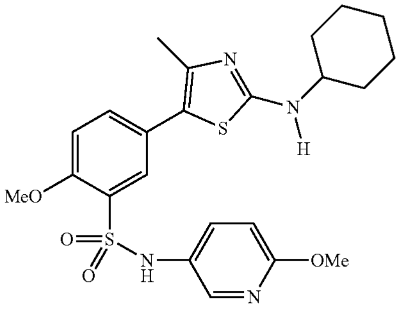 [SMILES: COc1ccc(NS(=O)(=O)c2cc(-c3sc(NC4CCCCC4)nc3C)ccc2OC)cn1] | 5-[2-(cyclohexylamino)-4-methyl-thiazol-5-yl]-2-methoxy-N-(6-methoxy-3-pyridyl)benzenesulfonamide |
| S-63 | 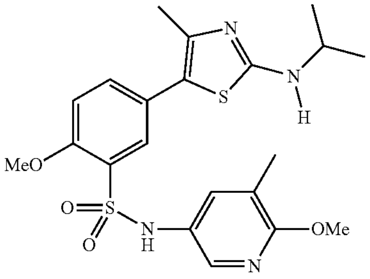 [SMILES: COc1ccc(-c2sc(NC(C)C)nc2C)cc1S(=O)(=O)Nc1cnc(OC)c(C)c1] | 5-[2-(isopropylamino)-4-methyl-thiazol-5-yl]-2-methoxy-N-(6-methoxy-5-methyl-3-pyridyl)benzenesulfonamide |

TABLE 1-continued

| Compounds | | |
|---|---|---|
| Compound | Structure | Name |
| S-64 | 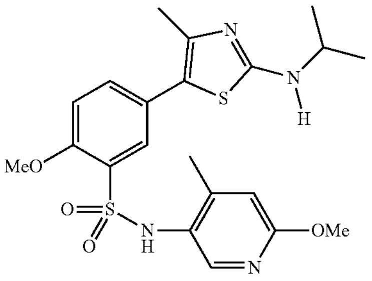 [SMILES: COc1cc(C)c(NS(=O)(=O)c2cc(-c3sc(NC(C)C)nc3C)ccc2OC)cn1] | 5-[2-(isopropylamino)-4-methyl-thiazol-5-yl]-2-methoxy-N-(6-methoxy-4-methyl-3-pyridyl)benzenesulfonamide |
| S-65 | 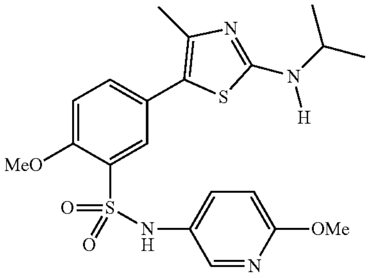 [SMILES: COc1ccc(NS(=O)(=O)c2cc(-c3sc(NC(C)C)nc3C)ccc2OC)cn1] | 5-[2-(isopropylamino)-4-methyl-thiazol-5-yl]-2-methoxy-N-(6-methoxy-3-pyridyl)benzenesulfonamide; 2,2,2-trifluoroacetic acid |
| S-66 | 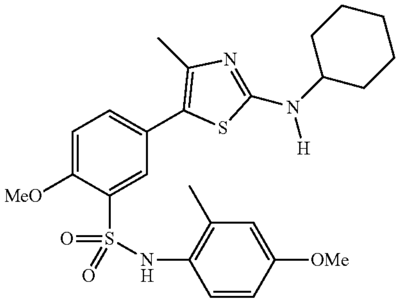 [SMILES: COc1ccc(NS(=O)(=O)c2cc(-c3sc(NC4CCCCC4)nc3C)ccc2OC)c(C)c1] | 5-[2-(cyclohexylamino)-4-methyl-thiazol-5-yl]-2-methoxy-N-(4-methoxy-2-methyl-phenyl)benzenesulfonamide; 2,2,2-trifluoroacetic acid |
| S-67 | 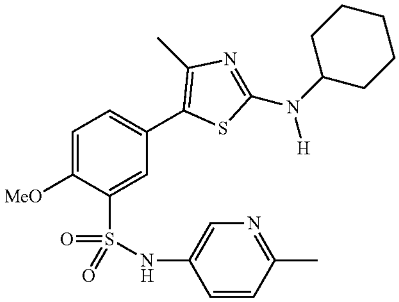 [SMILES: COc1ccc(-c2sc(NC3CCCCC3)nc2C)cc1S(=O)(=O)Nc1ccc(C)nc1] | 5-[2-(cyclohexylamino)-4-methyl-thiazol-5-yl]-2-methoxy-N-(6-methyl-3-pyridyl)benzenesulfonamide; 2,2,2-trifluoroacetic acid |
| S-68 | 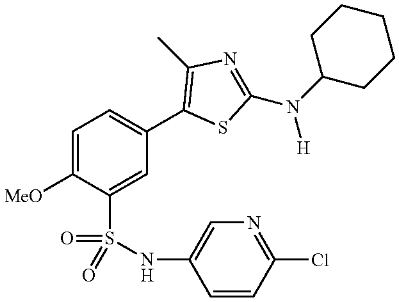 [SMILES: COc1ccc(-c2sc(NC3CCCCC3)nc2C)cc1S(=O)(=O)Nc1ccc(Cl)nc1] | N-(6-chloro-3-pyridyl)-5-[2-(cyclohexylamino)-4-methyl-thiazol-5-yl]-2-methoxy-benzenesulfonamide; 2,2,2-trifluoroacetic acid |

TABLE 1-continued

| Compounds | | |
|---|---|---|
| Compound | Structure | Name |
| S-69 | 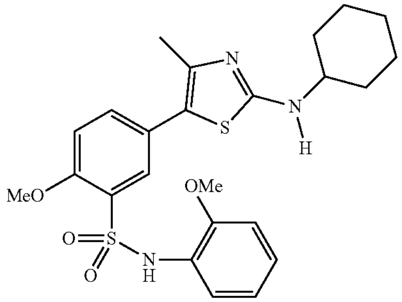 [SMILES: COc1ccccc1NS(=O)(=O)c1cc(-c2sc(NC3CCCCC3)nc2C)ccc1OC] | 5-[2-(cyclohexylamino)-4-methyl-thiazol-5-yl]-2-methoxy-N-(2-methoxyphenyl)benzenesulfonamide; 2,2,2-trifluoroacetic acid |
| S-70 | 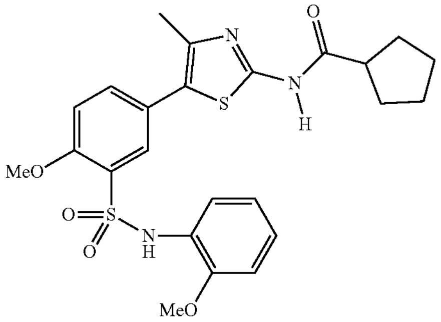 [SMILES: COc1ccccc1NS(=O)(=O)c1cc(-c2sc(NC(=O)C3CCCC3)nc2C)ccc1OC] | N-[5-[4-methoxy-3-[(2-methoxyphenyl)sulfamoyl]phenyl]-4-methyl-thiazol-2-yl]cyclopentanecarboxamide |
| S-71 | 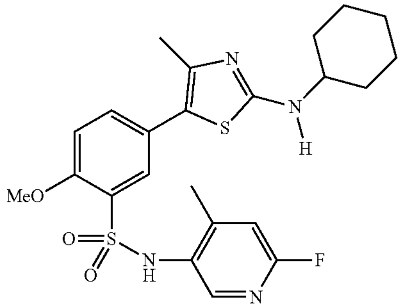 [SMILES: COc1ccc(-c2sc(NC3CCCCC3)nc2C)cc1S(=O)(=O)Nc1cnc(F)cc1C] | 5-[2-(cyclohexylamino)-4-methyl-thiazol-5-yl]-N-(6-fluoro-4-methyl-3-pyridyl)-2-methoxy-benzenesulfonamide |
| S-72 | 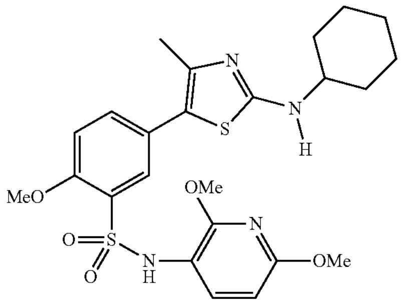 [SMILES: COc1ccc(NS(=O)(=O)c2cc(-c3sc(NC4CCCCC4)nc3C)ccc2OC)c(OC)n1] | 5-[2-(cyclohexylamino)-4-methyl-thiazol-5-yl]-N-(2,6-dimethoxy-3-pyridyl)-2-methoxy-benzenesulfonamide |

TABLE 1-continued

| Compounds | | |
|---|---|---|
| Compound | Structure | Name |
| S-73 | 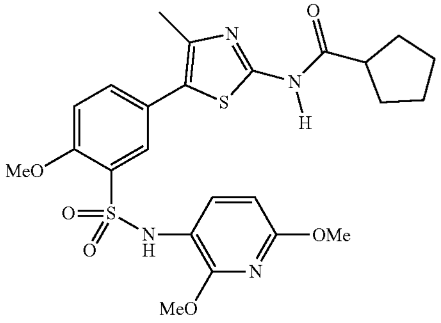 [SMILES: COc1ccc(NS(=O)(=O)c2cc(-c3sc(NC(=O)C4CCCC4)nc3C)ccc2OC)c(OC)n1] | N-[5-[3-[(2,6-dimethoxy-3-pyridyl)sulfamoyl]-4-methoxy-phenyl]-4-methyl-thiazol-2-yl]cyclopentanecarboxamide |
| S-74 | 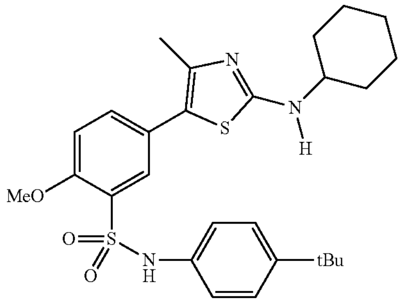 [SMILES: COc1ccc(-c2sc(NC3CCCCC3)nc2C)cc1S(=O)(=O)Nc1ccc(C(C)(C)C)cc1] | N-(4-tert-butylphenyl)-5-[2-(cyclohexylamino)-4-methyl-thiazol-5-yl]-2-methoxy-benzenesulfonamide |
| S-75 | 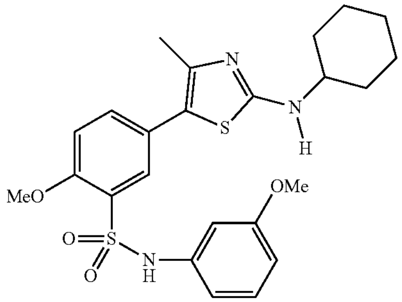 [SMILES: COc1cccc(NS(=O)(=O)c2cc(-c3sc(NC4CCCCC4)nc3C)ccc2OC)c1] | 5-[2-(cyclohexylamino)-4-methyl-thiazol-5-yl]-2-methoxy-N-(3-methoxyphenyl)benzenesulfonamide |
| S-76 | 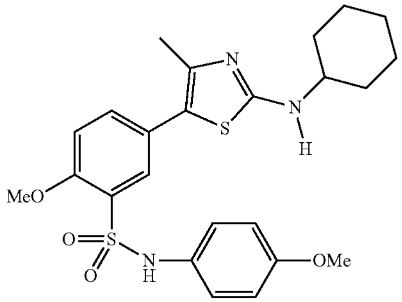 [SMILES: COc1ccc(NS(=O)(=O)c2cc(-c3sc(NC4CCCCC4)nc3C)ccc2OC)cc1] | 5-[2-(cyclohexylamino)-4-methyl-thiazol-5-yl]-2-methoxy-N-(4-methoxyphenyl)benzenesulfonamide |
| S-77 | 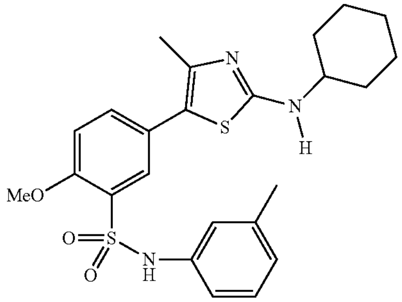 [SMILES: COc1ccc(-c2sc(NC3CCCCC3)nc2C)cc1S(=O)(=O)Nc1cccc(C)c1] | 5-[2-(cyclohexylamino)-4-methyl-thiazol-5-yl]-2-methoxy-N-(m-tolyl)benzenesulfonamide |

TABLE 1-continued

| Compounds | | |
|---|---|---|
| Compound | Structure | Name |
| S-78 | 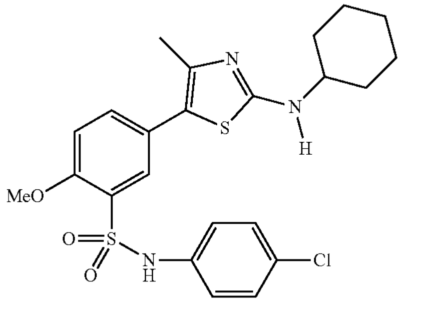 [SMILES: COc1ccc(-c2sc(NC3CCCCC3)nc2C)cc1S(=O)(=O)Nc1ccc(Cl)cc1] | N-(4-chlorophenyl)-5-[2-(cyclohexylamino)-4-methyl-thiazol-5-yl]-2-methoxy-benzenesulfonamide |
| S-79 | 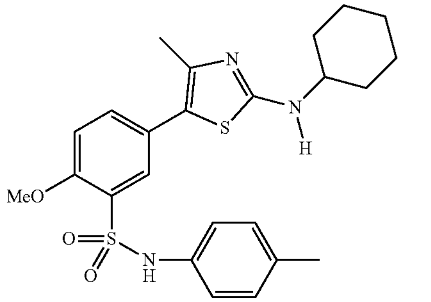 [SMILES: COc1ccc(-c2sc(NC3CCCCC3)nc2C)cc1S(=O)(=O)Nc1ccc(C)cc1] | 5-[2-(cyclohexylamino)-4-methyl-thiazol-5-yl]-2-methoxy-N-(p-tolyl)benzenesulfonamide |
| S-80 | 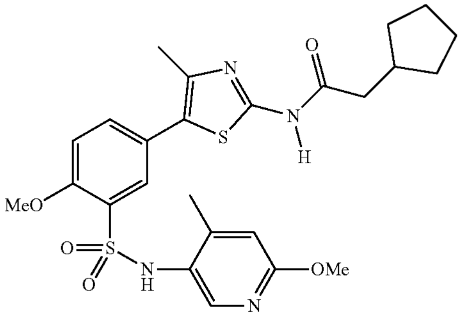 [SMILES: COc1cc(C)c(NS(=O)(=O)c2cc(-c3sc(NC(=O)CC4CCCC4)nc3C)ccc2OC)cn1] | 2-cyclopentyl-N-[5-[4-methoxy-3-[(6-methoxy-4-methyl-3-pyridyl)sulfamoyl]phenyl]-4-methyl-thiazol-2-yl]acetamide |
| S-81 | 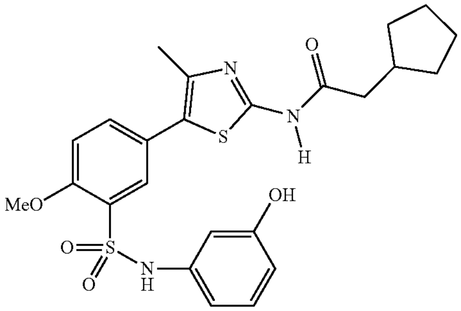 [SMILES: COc1ccc(-c2sc(NC(=O)CC3CCCC3)nc2C)cc1S(=O)(=O)Nc1cccc(O)c1] | 2-cyclopentyl-N-[5-[3-[(3-hydroxyphenyl)sulfamoyl]-4-methoxy-phenyl]-4-methyl-thiazol-2-yl]acetamide |

TABLE 1-continued

| Compounds | | |
|---|---|---|
| Compound | Structure | Name |
| S-82 | 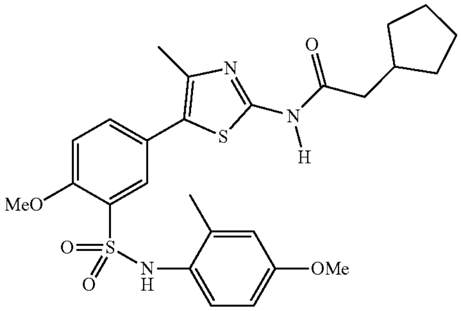 [SMILES: COc1ccc(NS(=O)(=O)c2cc(-c3sc(NC(=O)CC4CCCC4)nc3C)ccc2OC)c(C)c1] | 2-cyclopentyl-N-[5-[4-methoxy-3-[(4-methoxy-2-methyl-phenyl)sulfamoyl]phenyl]-4-methyl-thiazol-2-yl]acetamide |
| S-83 | 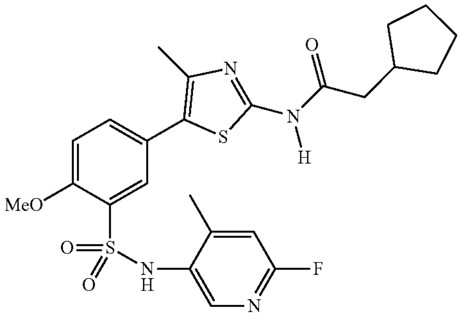 [SMILES: COc1ccc(-c2sc(NC(=O)CC3CCCC3)nc2C)cc1S(=O)(=O)Nc1cnc(F)cc1C] | 2-cyclopentyl-N-[5-[3-[(6-fluoro-4-methyl-3-pyridyl)sulfamoyl]-4-methoxy-phenyl]-4-methyl-thiazol-2-yl]acetamide; 2,2,2-trifluoroacetic acid |
| S-84 | 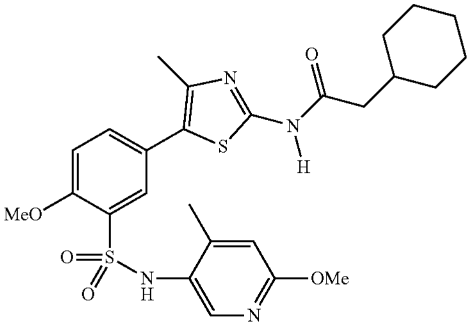 [SMILES: COc1cc(C)c(NS(=O)(=O)c2cc(-c3sc(NC(=O)CC4CCCCC4)nc3C)ccc2OC)cn1] | 2-cyclohexyl-N-[5-[4-methoxy-3-[(6-methoxy-4-methyl-3-pyridyl)sulfamoyl]phenyl]-4-methyl-thiazol-2-yl]acetamide; 2,2,2-trifluoroacetic acid |
| S-85 | 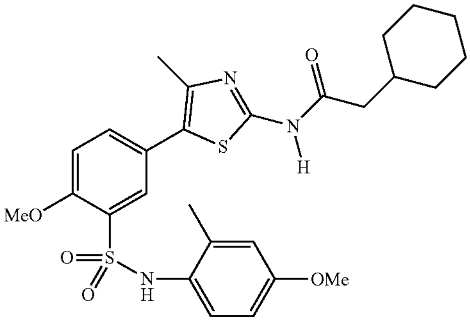 [SMILES: COc1ccc(NS(=O)(=O)c2cc(-c3sc(NC(=O)CC4CCCCC4)nc3C)ccc2OC)c(C)c1] | 2-cyclohexyl-N-[5-[4-methoxy-3-[(4-methoxy-2-methyl-phenyl)sulfamoyl]phenyl]-4-methyl-thiazol-2-yl]acetamide |

TABLE 1-continued

| Compounds | | |
|---|---|---|
| Compound | Structure | Name |
| S-86 | 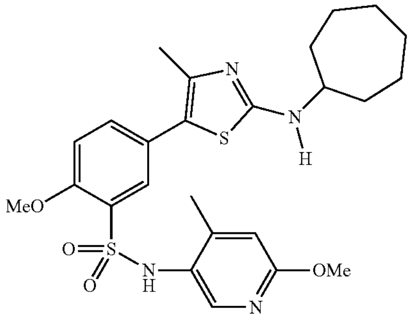 [SMILES: COc1cc(C)c(NS(=O)(=O)c2cc(-c3sc(NC4CCCCCC4)nc3C)ccc2OC)cn1] | 5-[2-(cycloheptylamino)-4-methyl-thiazol-5-yl]-2-methoxy-N-(6-methoxy-4-methyl-3-pyridyl)benzenesulfonamide; 2,2,2-trifluoroacetic acid |
| S-87 | 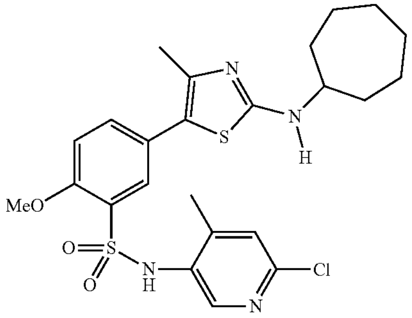 [SMILES: COc1ccc(-c2sc(NC3CCCCCC3)nc2C)cc1S(=O)(=O)Nc1cnc(Cl)cc1C] | N-(6-chloro-5-methyl-3-pyridyl)-5-[2-(cycloheptylamino)-4-methyl-thiazol-5-yl]-2-methoxy-benzenesulfonamide; 2,2,2-trifluoroacetic acid |
| S-88 | 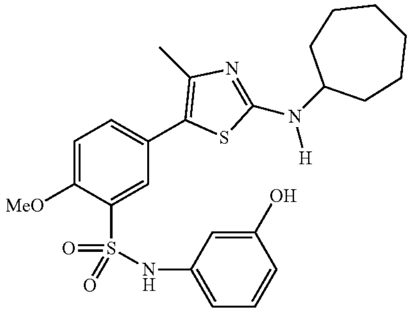 [SMILES: COc1ccc(-c2sc(NC3CCCCCC3)nc2C)cc1S(=O)(=O)Nc1cccc(O)c1] | 5-[2-(cycloheptylamino)-4-methyl-thiazol-5-yl]-N-(3-hydroxyphenyl)-2-methoxy-benzenesulfonamide; 2,2,2-trifluoroacetic acid |
| S-89 | 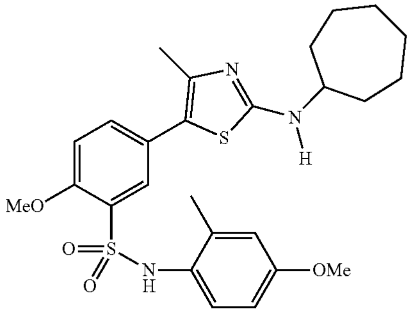 [SMILES: COc1ccc(NS(=O)(=O)c2cc(-c3sc(NC4CCCCCC4)nc3C)ccc2OC)c(C)c1] | 5-[2-(cycloheptylamino)-4-methyl-thiazol-5-yl]-2-methoxy-N-(4-methoxy-2-methyl-phenyl)benzenesulfonamide; 2,2,2-trifluoroactic acid |

TABLE 1-continued

| Compounds | | |
|---|---|---|
| Compound | Structure | Name |
| S-90 | 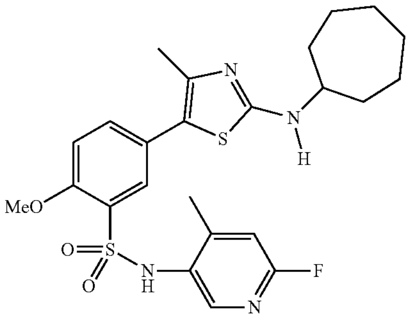 [SMILES: COc1ccc(-c2sc(NC3CCCCCC3)nc2C)cc1S(=O)(=O)Nc1cnc(F)cc1C] | 5-[2-(cycloheptylamino)-4-methyl-thiazol-5-yl]-N-(6-fluoro-4-methyl-3-pyridyl)-2-methoxy-benzenesulfonamide |
| S-91 | 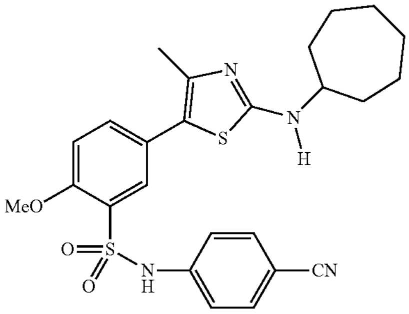 [SMILES: COc1ccc(-c2sc(NC3CCCCCC3)nc2C)cc1S(=O)(=O)Nc1ccc(C#N)cc1] | N-(4-cyanophenyl)-5-[2-(cycloheptylamino)-4-methyl-thiazol-5-yl]-2-methoxy-benzenesulfonamide; 2,2,2-trifluoroacetic acid |
| S-92 | 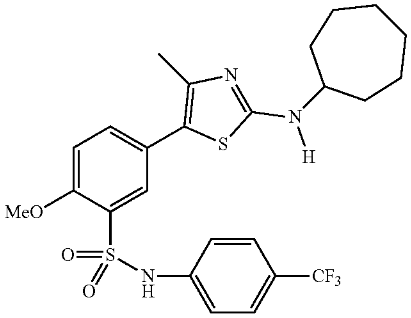 [SMILES: COc1ccc(-c2sc(NC3CCCCCC3)nc2C)cc1S(=O)(=O)Nc1ccc(C(F)(F)F)cc1] | 5-[2-(cycloheptylamino)-4-methyl-thiazol-5-yl]-2-methoxy-N-[4-(trifluoromethyl)phenyl]benzenesulfonamide |
| S-93 | 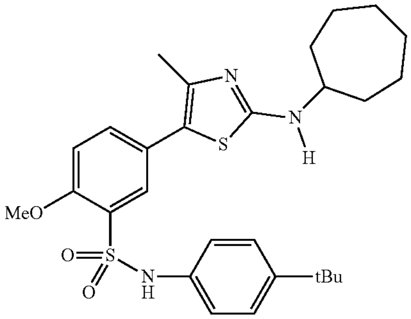 [SMILES: COc1ccc(-c2sc(NC3CCCCCC3)nc2C)cc1S(=O)(=O)Nc1ccc(C(C)(C)C)cc1] | N-(4-tert-butylphenyl)-5-[2-(cycloheptylamino)-4-methyl-thiazol-5-yl]-2-methoxy-benzenesulfonamide |

TABLE 1-continued

| Compounds | | |
|---|---|---|
| Compound | Structure | Name |
| S-94 | 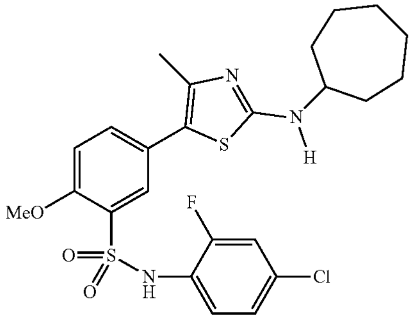 [SMILES: COc1ccc(-c2sc(NC3CCCCCC3)nc2C)cc1S(=O)(=O)Nc1ccc(Cl)cc1F] | N-(4-chloro-2-fluoro-phenyl)-5-[2-(cycloheptylamino)-4-methyl-thiazol-5-yl]-2-methoxy-benzenesulfonamide; 2,2,2-trifluoroacetic acid |
| S-95 | 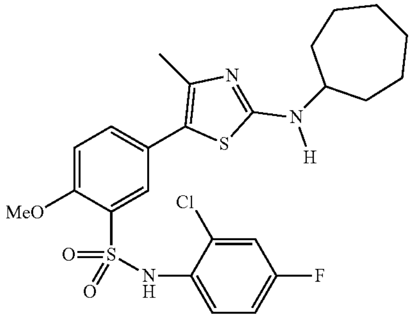 [SMILES: COc1ccc(-c2sc(NC3CCCCCC3)nc2C)cc1S(=O)(=O)Nc1ccc(F)cc1Cl] | N-(2-chloro-4-fluoro-phenyl)-5-[2-(cycloheptylamino)-4-methyl-thiazol-5-yl]-2-methoxy-benzenesulfonamide; 2,2,2-trifluoroacetic acid |
| S-96 | 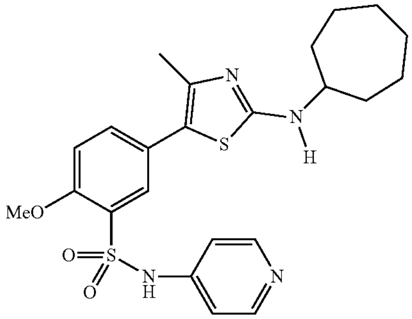 [SMILES: COc1ccc(-c2sc(NC3CCCCCC3)nc2C)cc1S(=O)(=O)Nc1ccncc1] | 5-[2-(cycloheptylamino)-4-methyl-thiazol-5-yl]-2-methoxy-N-(4-pyridyl)benzenesulfonamide; 2,2,2-trifluoroacetic acid |
| S-97 | 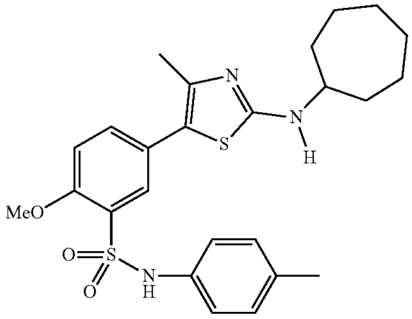 [SMILES: COc1ccc(-c2sc(NC3CCCCCC3)nc2C)cc1S(=O)(=O)Nc1ccc(C)cc1] | 5-[2-(cycloheptylamino)-4-methyl-thiazol-5-yl]-2-methoxy-N-(p-tolyl)benzenesulfonamide; 2,2,2-trifluoroacetic acid |

TABLE 1-continued

| Compounds | | |
|---|---|---|
| Compound | Structure | Name |
| S-98 | 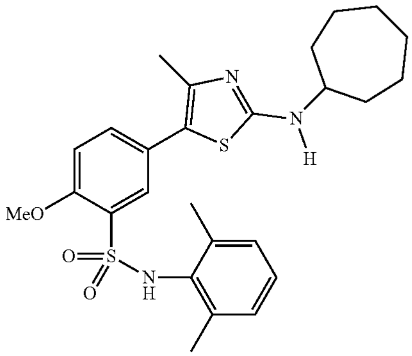 [SMILES: COc1ccc(-c2sc(NC3CCCCCC3)nc2C)cc1S(=O)(=O)Nc1c(C)cccc1C] | 5-[2-(cycloheptylamino)-4-methyl-thiazol-5-yl]-N-(2,6-dimethylphenyl)-2-methoxy-benzenesulfonamide; 2,2,2-trifluoroacetic acid |
| S-99 | 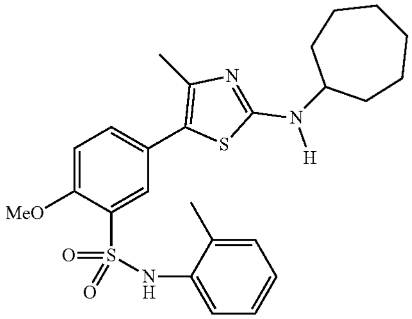 [SMILES: COc1ccc(-c2sc(NC3CCCCCC3)nc2C)cc1S(=O)(=O)Nc1ccccc1C] | 5-[2-(cycloheptylamino)-4-methyl-thiazol-5-yl]-2-methoxy-N-(o-tolyl)benzenesulfonamide; 2,2,2-trifluoroacetic acid |
| S-100 | 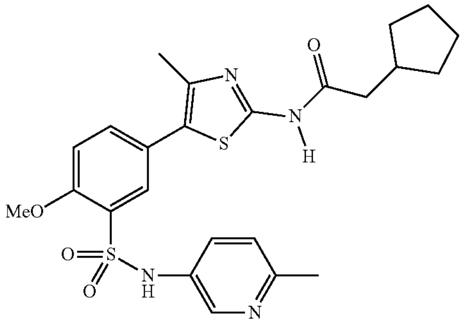 [SMILES: COc1ccc(-c2sc(NC(=O)CC3CCCC3)nc2C)cc1S(=O)(=O)Nc1ccc(C)nc1] | 2-cyclopentyl-N-[5-[4-methoxy-3-[(6-methyl-3-pyridyl)sulfamoyl]phenyl]-4-methyl-thiazol-2-yl]acetamide; 2,2,2-trifluoroacetic acid |
| S-101 | 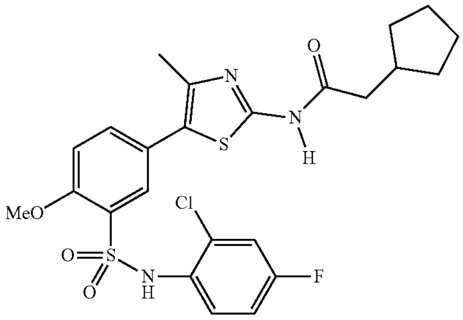 [SMILES: COc1ccc(-c2sc(NC(=O)CC3CCCC3)nc2C)cc1S(=O)(=O)Nc1ccc(F)cc1Cl] | N-[5-[3-[(2-chloro-4-fluoro-phenyl)sulfamoyl]-4-methoxy-phenyl]-4-methyl-thiazol-2-yl]-2-cyclopentyl-acetamide |

TABLE 1-continued

| Compounds | | |
|---|---|---|
| Compound | Structure | Name |
| S-102 | 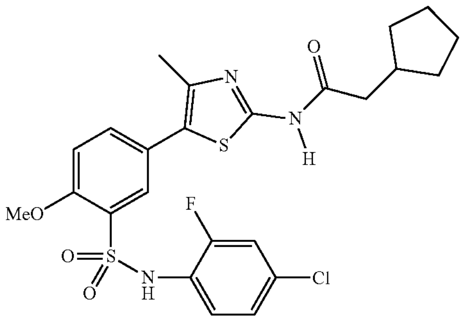 [SMILES: COc1ccc(-c2sc(NC(=O)CC3CCCC3)nc2C)cc1S(=O)(=O)Nc1ccc(Cl)cc1F] | N-[5-[3-[(4-chloro-2-fluoro-phenyl)sulfamoyl]-4-methoxy-phenyl]-4-methyl-thiazol-2-yl]-2-cyclopentyl-acetamide |
| S-103 | 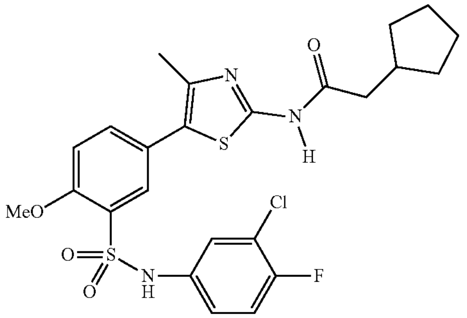 [SMILES: COc1ccc(-c2sc(NC(=O)CC3CCCC3)nc2C)cc1S(=O)(=O)Nc1ccc(F)c(Cl)c1] | N-[5-[3-[(3-chloro-4-fluoro-phenyl)sulfamoyl]-4-methoxy-phenyl]-4-methyl-thiazol-2-yl]-2-cyclopentyl-acetamide |
| S-104 | 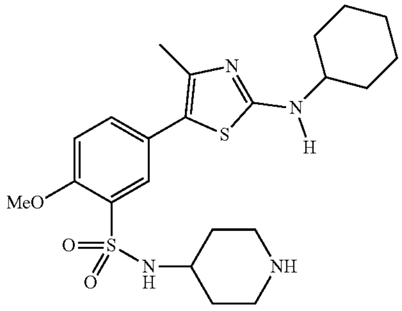 [SMILES: COc1ccc(-c2sc(NC3CCCCC3)nc2C)cc1S(=O)(=O)NC1CCNCC1] | 5-[2-(cyclohexylamino)-4-methyl-thiazol-5-yl]-2-methoxy-N-(4-piperidyl)benzenesulfonamide |
| S-105 | 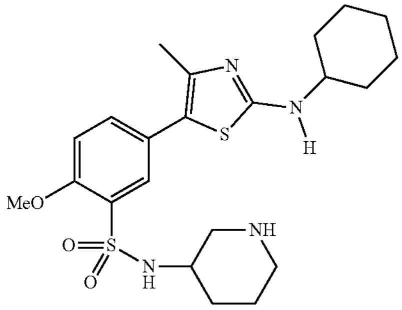 [SMILES: COc1ccc(-c2sc(NC3CCCCC3)nc2C)cc1S(=O)(=O)NC1CCCNC1] | 5-[2-(cyclohexylamino)-4-methyl-thiazol-5-yl]-2-methoxy-N-(3-piperidyl)benzenesulfonamide |

TABLE 1-continued

| Compounds | | |
|---|---|---|
| Compound | Structure | Name |
| S-106 | 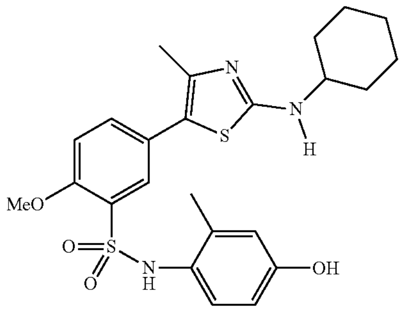 [SMILES: COc1ccc(-c2sc(NC3CCCCC3)nc2C)cc1S(=O)(=O)Nc1ccc(O)cc1C] | 5-[2-(cyclohexylamino)-4-methyl-thiazol-5-yl]-N-(4-hydroxy-2-methyl-phenyl)-2-methoxy-benzenesulfonamide |
| S-107 | 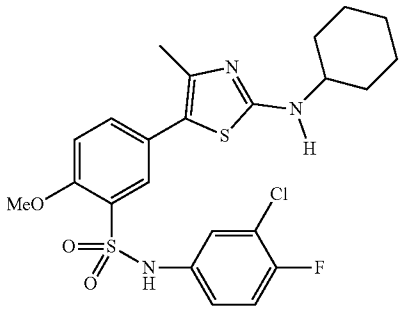 [SMILES: COc1ccc(-c2sc(NC3CCCCC3)nc2C)cc1S(=O)(=O)Nc1ccc(F)c(Cl)c1] | N-(3-chloro-4-fluoro-phenyl)-5-[2-(cyclohexylamino)-4-methyl-thiazol-5-yl]-2-methoxy-benzenesulfonamide |
| S-108 | 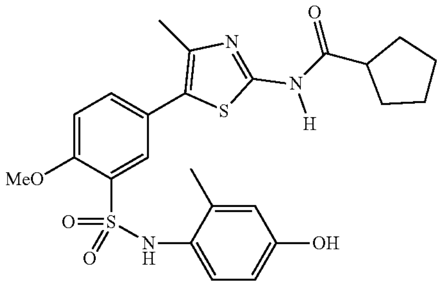 [SMILES: COc1ccc(-c2sc(NC(=O)C3CCCC3)nc2C)cc1S(=O)(=O)Nc1ccc(O)cc1C] | N-[5-[3-[(4-hydroxy-2-methyl-phenyl)sulfamoyl]-4-methoxy-phenyl]-4-methyl-thiazol-2-yl]cyclopentanecarboxamide |
| S-109 | 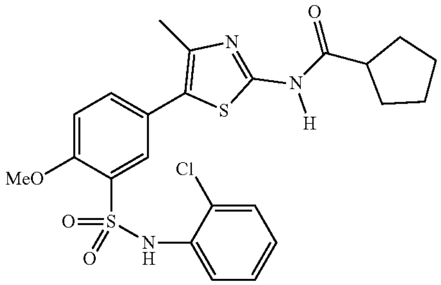 [SMILES: COc1ccc(-c2sc(NC(=O)C3CCCC3)nc2C)cc1S(=O)(=O)Nc1ccccc1Cl] | N-[5-[3-[(2-chlorophenyl)sulfamoyl]-4-methoxy-phenyl]-4-methyl-thiazol-2-yl]cyclopentanecarboxamide |
| S-110 | 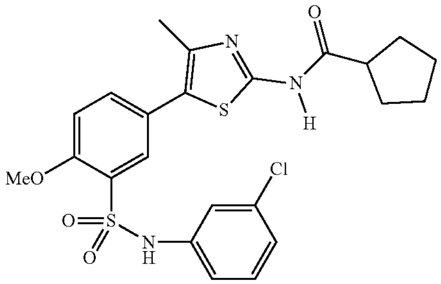 [SMILES: COc1ccc(-c2sc(NC(=O)C3CCCC3)nc2C)cc1S(=O)(=O)Nc1cccc(Cl)c1] | N-[5-[3-[(3-chlorophenyl)sulfamoyl]-4-methoxy-phenyl]-4-methyl-thiazol-2-yl]cyclopentanecarboxamide |

TABLE 1-continued

| Compounds | | |
|---|---|---|
| Compound | Structure | Name |
| S-111 | 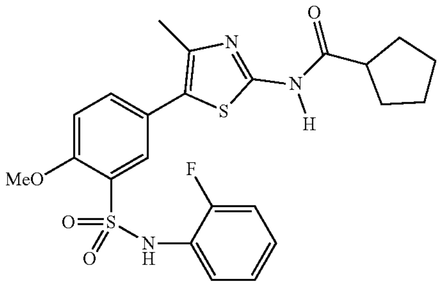 [SMILES: COc1ccc(-c2sc(NC(=O)C3CCCC3)nc2C)cc1S(=O)(=O)Nc1ccccc1F] | N-[5-[3-[(2-fluorophenyl)sulfamoyl]-4-methoxy-phenyl]-4-methyl-thiazol-2-yl]cyclopentanecarboxamide |
| S-112 | 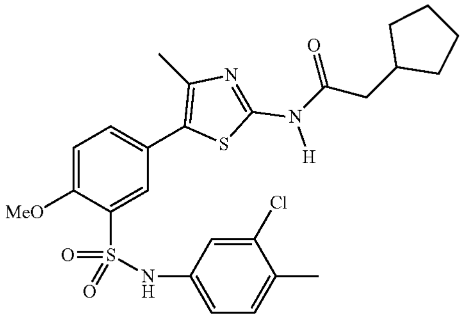 [SMILES: COc1ccc(-c2sc(NC(=O)CC3CCCC3)nc2C)cc1S(=O)(=O)Nc1ccc(C)c(Cl)c1] | N-[5-[3-[(3-chloro-4-methyl-phenyl)sulfamoyl]-4-methoxy-phenyl]-4-methyl-thiazol-2-yl]-2-cyclopentyl-acetamide |
| S-113 | 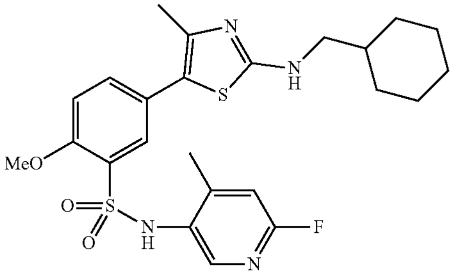 [SMILES: COc1ccc(-c2sc(NCC3CCCCC3)nc2C)cc1S(=O)(=O)Nc1cnc(F)cc1C] | 5-[2-(cyclohexylmethylamino)-4-methyl-thiazol-5-yl]-N-(6-fluoro-4-methyl-3-pyridyl)-2-methoxy-benzenesulfonamide |
| S-114 | 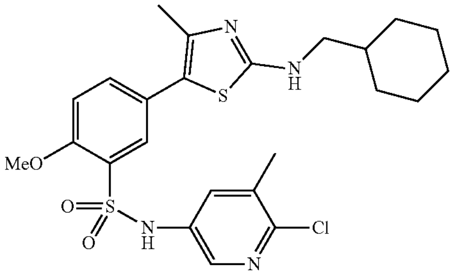 [SMILES: COc1ccc(-c2sc(NCC3CCCCC3)nc2C)cc1S(=O)(=O)Nc1cnc(Cl)c(C)c1] | N-(6-chloro-5-methyl-3-pyridyl)-5-[2-(cyclohexylmethylamino)-4-methyl-thiazol-5-yl]-2-methoxy-benzenesulfonamide |
| S-115 | 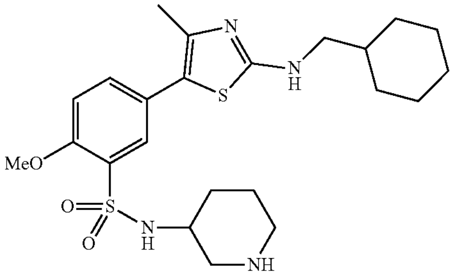 [SMILES: COc1ccc(-c2sc(NCC3CCCCC3)nc2C)cc1S(=O)(=O)NC1CCCNC1] | 5-[2-(cyclohexylmethylamino)-4-methyl-thiazol-5-yl]-2-methoxy-N-(3-piperidyl)benzenesulfonamide |

TABLE 1-continued

| Compounds | | |
|---|---|---|
| Compound | Structure | Name |
| S-116 | 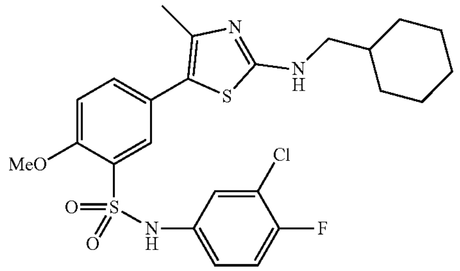 [SMILES: COc1ccc(-c2sc(NCC3CCCCC3)nc2C)cc1S(=O)(=O)Nc1ccc(F)c(Cl)c1] | N-(3-chloro-4-fluoro-phenyl)-5-[2-(cyclohexylmethylamino)-4-methyl-thiazol-5-yl]-2-methoxy-benzenesulfonamide |
| S-117 | 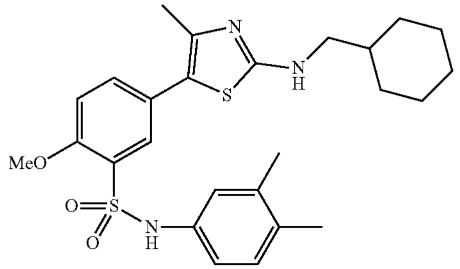 [SMILES: COc1ccc(-c2sc(NCC3CCCCC3)nc2C)cc1S(=O)(=O)Nc1ccc(C)c(C)c1] | 5-[2-(cyclohexylmethylamino)-4-methyl-thiazol-5-yl]-N-(3,4-dimethylphenyl)-2-methoxy-benzenesulfonamide |
| S-118 | 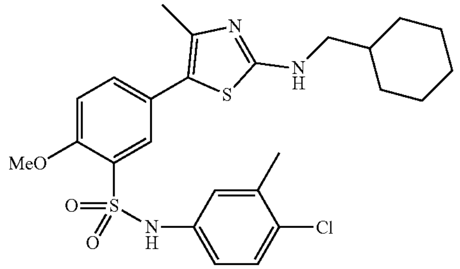 [SMILES: COc1ccc(-c2sc(NCC3CCCCC3)nc2C)cc1S(=O)(=O)Nc1ccc(Cl)c(C)c1] | N-(4-chloro-3-methyl-phenyl)-5-[2-(cyclohexylmethylamino)-4-methyl-thiazol-5-yl]-2-methoxy-benzenesulfonamide |
| S-119 | 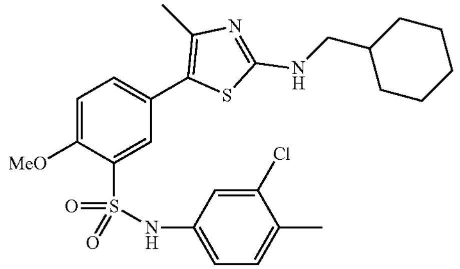 [SMILES: COc1ccc(-c2sc(NCC3CCCCC3)nc2C)cc1S(=O)(=O)Nc1ccc(C)c(Cl)c1] | N-(3-chloro-4-methyl-phenyl)-5-[2-(cyclohexylmethylamino)-4-methyl-thiazol-5-yl]-2-methoxy-benzenesulfonamide |
| S-120 | 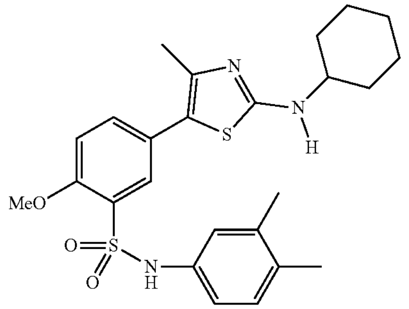 [SMILES: COc1ccc(-c2sc(NC3CCCCC3)nc2C)cc1S(=O)(=O)Nc1ccc(C)c(C)c1] | 5-[2-(cyclohexylamino)-4-methyl-thiazol-5-yl]-N-(3,4-dimethylphenyl)-2-methoxy-benzenesulfonamide |

TABLE 1-continued

| Compounds | | |
|---|---|---|
| Compound | Structure | Name |
| S-121 | 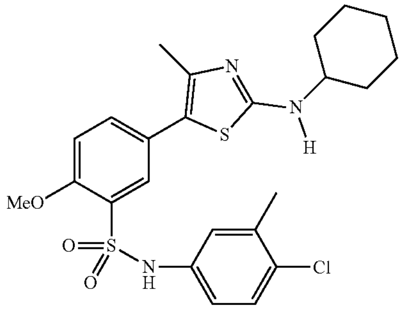 [SMILES: COc1ccc(-c2sc(NC3CCCCC3)nc2C)cc1S(=O)(=O)Nc1ccc(Cl)c(C)c1] | N-(4-chloro-3-methyl-phenyl)-5-[2-(cyclohexylamino)-4-methyl-thiazol-5-yl]-2-methoxy-benzenesulfonamide |
| S-122 | 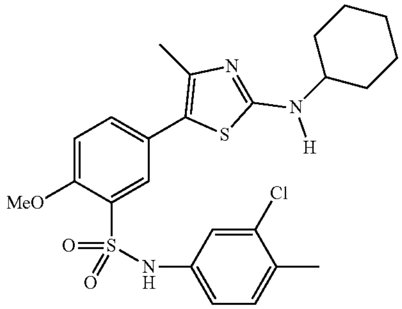 [SMILES: COc1ccc(-c2sc(NC3CCCCC3)nc2C)cc1S(=O)(=O)Nc1ccc(C)c(Cl)c1] | N-(3-chloro-4-methyl-phenyl)-5-[2-(cyclohexylamino)-4-methyl-thiazol-5-yl]-2-methoxy-benzenesulfonamide |
| S-123 | 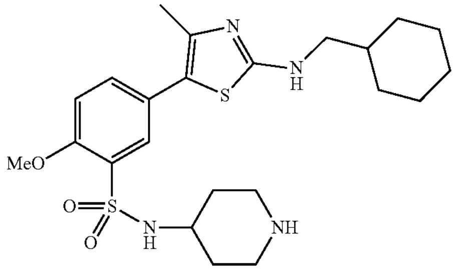 [SMILES: COc1ccc(-c2sc(NCC3CCCCC3)nc2C)cc1S(=O)(=O)NC1CCNCC1] | 5-[2-(cyclohexylmethylamino)-4-methyl-thiazol-5-yl]-2-methoxy-N-(4-piperidyl)benzenesulfonamide |
| S-124 | 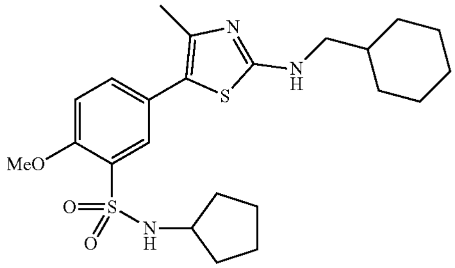 [SMILES: COc1ccc(-c2sc(NCC3CCCCC3)nc2C)cc1S(=O)(=O)NC1CCCC1] | 5-[2-(cyclohexylmethylamino)-4-methyl-thiazol-5-yl]-N-cyclopentyl-2-methoxy-benzenesulfonamide |
| S-125 | 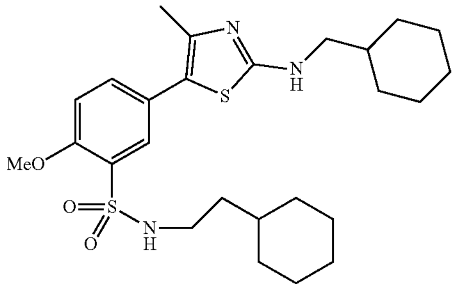 [SMILES: COc1ccc(-c2sc(NCC3CCCCC3)nc2C)cc1S(=O)(=O)NCCC1CCCCC1] | N-(2-cyclohexylethyl)-5-[2-(cyclohexylmethylamino)-4-methyl-thiazol-5-yl]-2-methoxy-benzenesulfonamide |

TABLE 1-continued

| Compound | Structure | Name |
|---|---|---|
| S-126 | 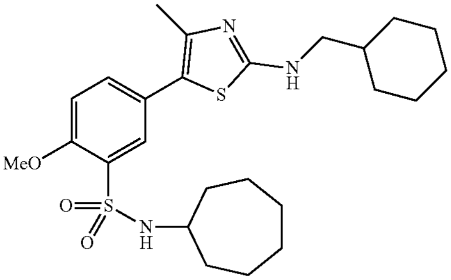 [SMILES: COc1ccc(-c2sc(NCC3CCCCC3)nc2C)cc1S(=O)(=O)NC1CCCCCC1] | N-cycloheptyl-5-[2-(cyclohexylmethylamino)-4-methyl-thiazol-5-yl]-2-methoxy-benzenesulfonamide |
| S-127 | 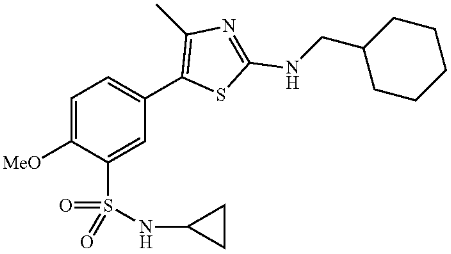 [SMILES: COc1ccc(-c2sc(NCC3CCCCC3)nc2C)cc1S(=O)(=O)NC1CC1] | 5-[2-(cyclohexylmethylamino)-4-methyl-thiazol-5-yl]-N-cyclopropyl-2-methoxy-benzenesulfonamide |
| S-128 | 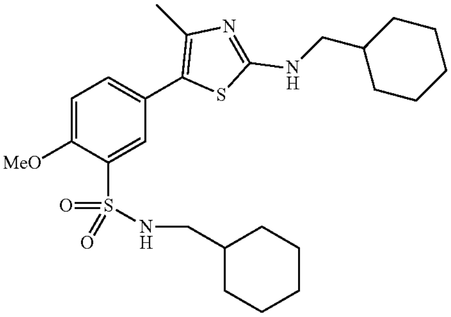 [SMILES: COc1ccc(-c2sc(NCC3CCCCC3)nc2C)cc1S(=O)(=O)NCC1CCCCC1] | N-(cyclohexylmethyl)-5-[2-(cyclohexylmethylamino)-4-methyl-thiazol-5-yl]-2-methoxy-benzenesulfonamide |
| S-129 | 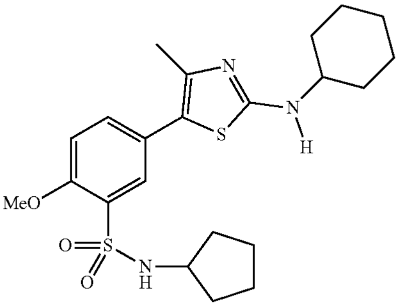 [SMILES: COc1ccc(-c2sc(NC3CCCCC3)nc2C)cc1S(=O)(=O)NC1CCCC1] | 5-[2-(cyclohexylamino)-4-methyl-thiazol-5-yl]-N-cyclopentyl-2-methoxy-benzenesulfonamide |
| S-130 | 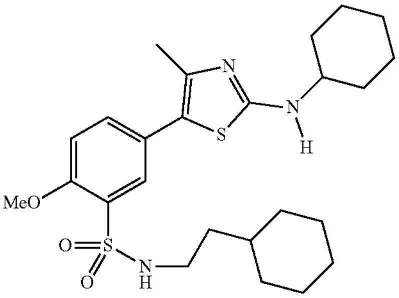 [SMILES: COc1ccc(-c2sc(NC3CCCCC3)nc2C)cc1S(=O)(=O)NCCC1CCCCC1] | 5-[2-(cyclohexylamino)-4-methyl-thiazol-5-yl]-N-(2-cyclohexylethyl)-2-methoxy-benzenesulfonamide |

TABLE 1-continued

| Compounds | | |
|---|---|---|
| Compound | Structure | Name |
| S-131 | 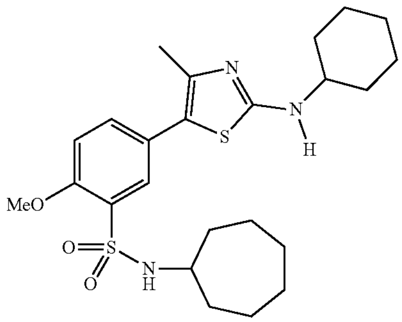 [SMILES: COc1ccc(-c2sc(NC3CCCCC3)nc2C)cc1S(=O)(=O)NC1CCCCCC1] | N-cycloheptyl-5-[2-(cyclohexylamino)-4-methyl-thiazol-5-yl]-2-methoxy-benzenesulfonamide |
| S-132 | 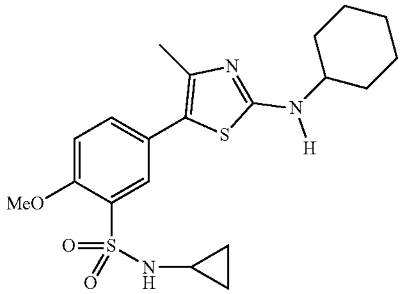 [SMILES: COc1ccc(-c2sc(NC3CCCCC3)nc2C)cc1S(=O)(=O)NC1CC1] | 5-[2-(cyclohexylamino)-4-methyl-thiazol-5-yl]-N-cyclopropyl-2-methoxy-benzenesulfonamide |
| S-133 | 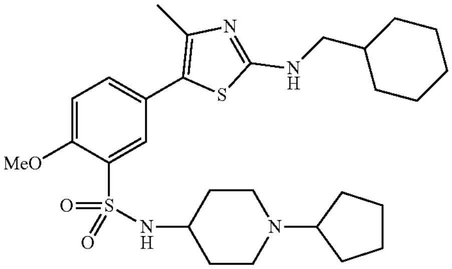 [SMILES: COc1ccc(-c2sc(NCC3CCCCC3)nc2C)cc1S(=O)(=O)NC1CCN(C2CCCC2)CC1] | 5-[2-(cyclohexylmethylamino)-4-methyl-thiazol-5-yl]-N-(1-cyclopentyl-4-piperidyl)-2-methoxy-benzenesulfonamide |
| S-134 | 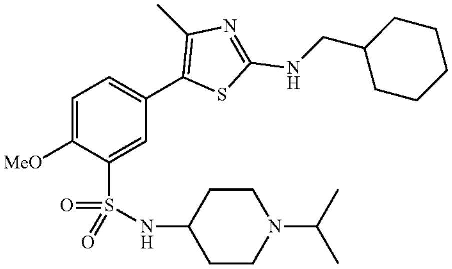 [SMILES: COc1ccc(-c2sc(NCC3CCCCC3)nc2C)cc1S(=O)(=O)NC1CCN(C(C)C)CC1] | 5-[2-(cyclohexylmethylamino)-4-methyl-thiazol-5-yl]-N-(1-isopropyl-4-piperidyl)-2-methoxy-benzenesulfonamide |
| S-135 | 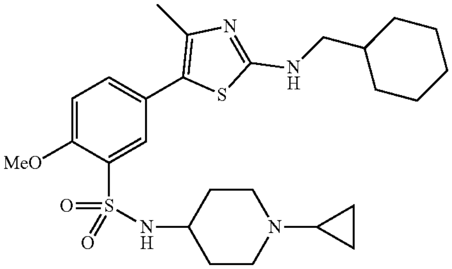 [SMILES: COc1ccc(-c2sc(NCC3CCCCC3)nc2C)cc1S(=O)(=O)NC1CCN(C2CC2)CC1] | 5-[2-(cyclohexylmethylamino)-4-methyl-thiazol-5-yl]-N-(1-cyclopropyl-4-piperidyl)-2-methoxy-benzenesulfonamide |

TABLE 1-continued

| Compounds | | |
|---|---|---|
| Compound | Structure | Name |
| S-136 | 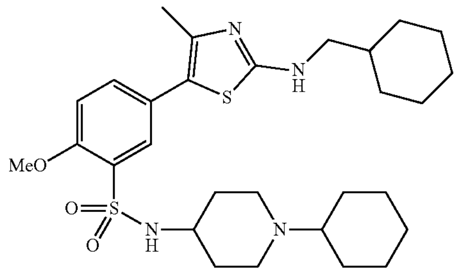 [SMILES: COc1ccc(-c2sc(NCC3CCCCC3)nc2C)cc1S(=O)(=O)NC1CCN(C2CCCCC2)CC1] | 5-[2-(cyclohexylmethylamino)-4-methyl-thiazol-5-yl]-N-(1-cyclohexyl-4-piperidyl)-2-methoxy-benzenesulfonamide |
| S-137 | 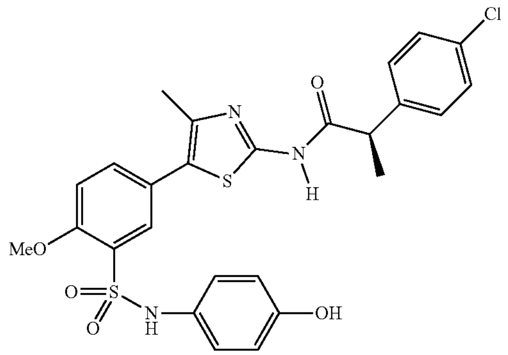 [SMILES: COc1ccc(-c2sc(NC(=O)[C@H](C)c3ccc(Cl)cc3)nc2C)cc1S(=O)(=O)Nc1ccc(O)cc1] | (2R)-2-(4-chlorophenyl)-N-[5-[3-[(4-hydroxyphenyl)sulfamoyl]-4-methoxy-phenyl]-4-methyl-thiazol-2-yl]propanamide |
| S-138 | 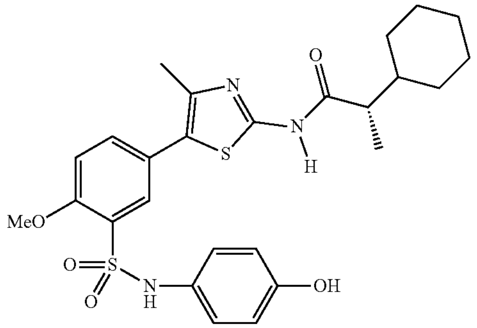 [SMILES: COc1ccc(-c2sc(NC(=O)[C@@H](C)C3CCCCC3)nc2C)cc1S(=O)(=O)Nc1ccc(O)cc1] | (2S)-2-cyclohexyl-N-[5-[3-[(4-hydroxyphenyl)sulfamoyl]-4-methoxy-phenyl]-4-methyl-thiazol-2-yl]propanamide |
| S-139 | 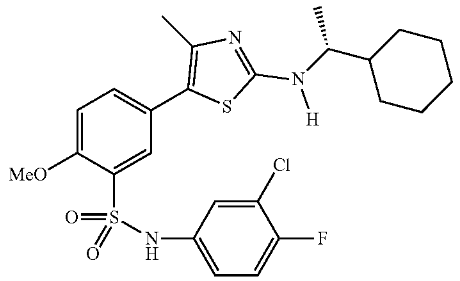 [SMILES: COc1ccc(-c2sc(N[C@H](C)C3CCCCC3)nc2C)cc1S(=O)(=O)Nc1ccc(F)c(Cl)c1] | N-(3-chloro-4-fluoro-phenyl)-5-[2-[[(1R)-1-cyclohexylethyl]amino]-4-methyl-thiazol-5-yl]-2-methoxy-benzenesulfonamide |
| S-140 | 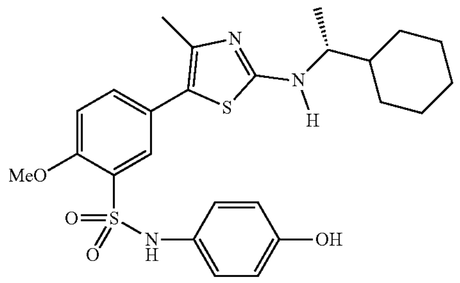 [SMILES: COc1ccc(-c2sc(N[C@H](C)C3CCCCC3)nc2C)cc1S(=O)(=O)Nc1ccc(O)cc1] | 5-[2-[[(1R)-1-cyclohexylethyl]amino]-4-methyl-thiazol-5-yl]-N-(4-hydroxyphenyl)-2-methoxy-benzenesulfonamide |

TABLE 1-continued

| Compounds | | |
|---|---|---|
| Compound | Structure | Name |
| S-141 | 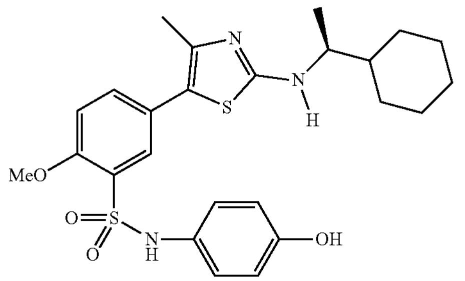 [SMILES: COc1ccc(-c2sc(N[C@@H](C)C3CCCCC3)nc2C)cc1S(=O)(=O)Nc1ccc(O)cc1] | 5-[2-[[(1S)-1-cyclohexylethyl]amino]-4-methyl-thiazol-5-yl]-N-(4-hydroxyphenyl)-2-methoxy-benzenesulfonamide |
| S-142 | 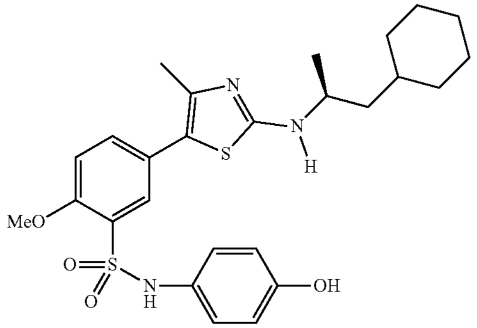 [SMILES: COc1ccc(-c2sc(N[C@@H](C)CC3CCCCC3)nc2C)cc1S(=O)(=O)Nc1ccc(O)cc1] | 5-[2-[[(1S)-2-cyclohexyl-1-methyl-ethyl]amino]-4-methyl-thiazol-5-yl]-N-(4-hydroxyphenyl)-2-methoxy-benzenesulfonamide |
| S-143 | 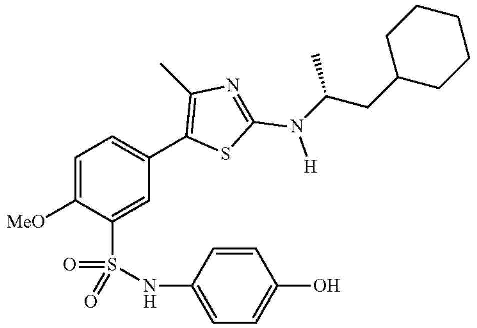 [SMILES: COc1ccc(-c2sc(N[C@H](C)CC3CCCCC3)nc2C)cc1S(=O)(=O)Nc1ccc(O)cc1] | 5-[2-[[(1R)-2-cyclohexyl-1-methyl-ethyl]amino]-4-methyl-thiazol-5-yl]-N-(4-hydroxyphenyl)-2-methoxy-benzenesulfonamide |
| S-144 | 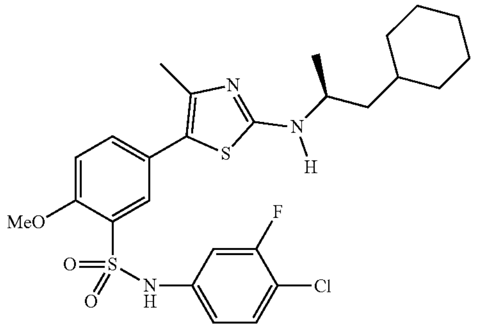 [SMILES: COc1ccc(-c2sc(N[C@@H](C)CC3CCCCC3)nc2C)cc1S(=O)(=O)Nc1ccc(Cl)c(F)c1] | N-(4-chloro-3-fluoro-phenyl)-5-[2-[[(1S)-2-cyclohexyl-1-methyl-ethyl]amino]-4-methyl-thiazol-5-yl]-2-methoxy-benzenesulfonamide |

TABLE 1-continued

| Compounds | | |
|---|---|---|
| Compound | Structure | Name |
| S-145 | 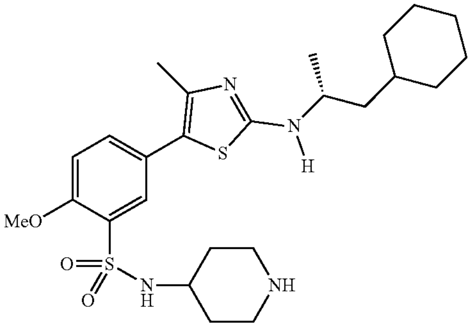 [SMILES: COc1ccc(-c2sc(N[C@H](C)CC3CCCCC3)nc2C)cc1S(=O)(=O)NC1CCNCC1] | 5-[2-[[(1R)-2-cyclohexyl-1-methyl-ethyl]amino]-4-methyl-thiazol-5-yl]-2-methoxy-N-(4-piperidyl)benzenesulfonamide |
| S-146 | 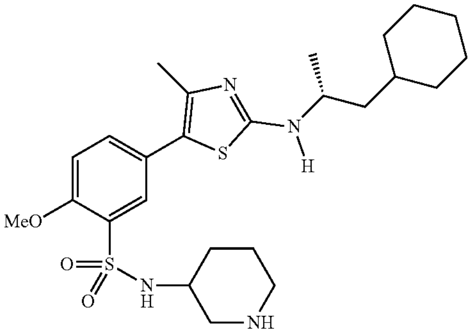 [SMILES: COc1ccc(-c2sc(N[C@H](C)CC3CCCCC3)nc2C)cc1S(=O)(=O)NC1CCCNC1] | 5-[2-[[(1R)-2-cyclohexyl-1-methyl-ethyl]amino]-4-methyl-thiazol-5-yl]-2-methoxy-N-(3-piperidyl)benzenesulfonamide |
| S-147 | 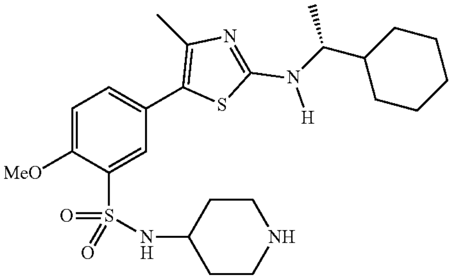 [SMILES: COc1ccc(-c2sc(N[C@H](C)C3CCCCC3)nc2C)cc1S(=O)(=O)NC1CCNCC1] | 5-[2-[[(1R)-1-cyclohexylethyl]amino]-4-methyl-thiazol-5-yl]-2-methoxy-N-(4-piperidyl)benzenesulfonamide |
| S-148 | 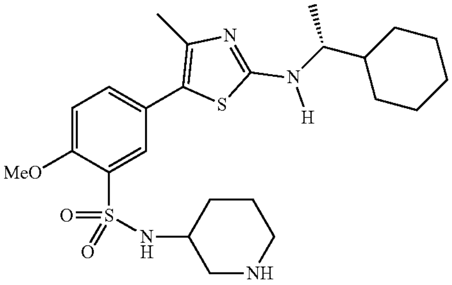 [SMILES: COc1ccc(-c2sc(N[C@H](C)C3CCCCC3)nc2C)cc1S(=O)(=O)NC1CCCNC1] | 5-[2-[[(1R)-1-cyclohexylethyl]amino]-4-methyl-thiazol-5-yl]-2-methoxy-N-(3-piperidyl)benzenesulfonamide |

TABLE 1-continued

| Compounds | | |
|---|---|---|
| Compound | Structure | Name |
| S-149 | 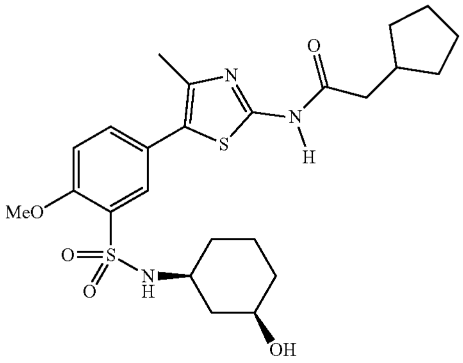 [SMILES: COc1ccc(-c2sc(NC(=O)CC3CCCC3)nc2C)cc1S(=O)(=O)N[C@H]1CCC[C@@H](O)C1] | 2-cyclopentyl-N-[5-[3-[[(1S,3R)-3-hydroxycyclohexyl]sulfamoyl]-4-methoxy-phenyl]-4-methyl-thiazol-2-yl]acetamide |
| S-150 | 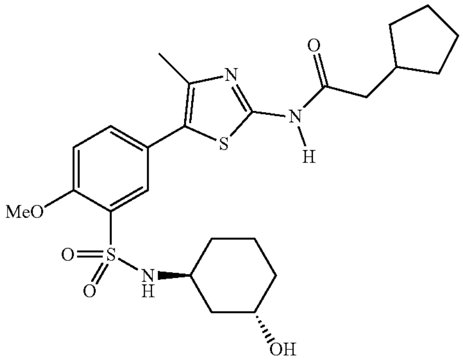 [SMILES: COc1ccc(-c2sc(NC(=O)CC3CCCC3)nc2C)cc1S(=O)(=O)N[C@H]1CCC[C@H](O)C1] | 2-cyclopentyl-N-[5-[3-[[(1S,3S)-3-hydroxycyclohexyl]sulfamoyl]-4-methoxy-phenyl]-4-methyl-thiazol-2-yl]acetamide |
| S-151 | 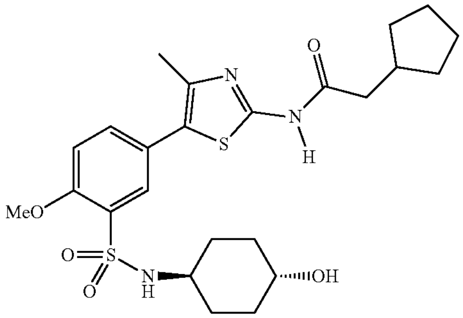 [SMILES: COc1ccc(-c2sc(NC(=O)CC3CCCC3)nc2C)cc1S(=O)(=O)N[C@H]1CC[C@H](O)CC1] | 2-cyclopentyl-N-[5-[3-[(4-hydroxycyclohexyl)sulfamoyl]-4-methoxy-phenyl]-4-methyl-thiazol-2-yl]acetamide |
| S-152 | 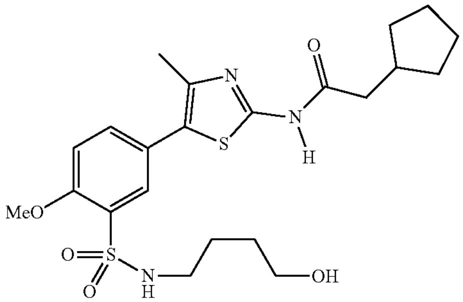 [SMILES: COc1ccc(-c2sc(NC(=O)CC3CCCC3)nc2C)cc1S(=O)(=O)NCCCCO] | 2-cyclopentyl-N-[5-[3-(4-hydroxybutylsulfamoyl)-4-methoxy-phenyl]-4-methyl-thiazol-2-yl]acetamide |

TABLE 1-continued

| Compounds | | |
|---|---|---|
| Compound | Structure | Name |
| S-153 | 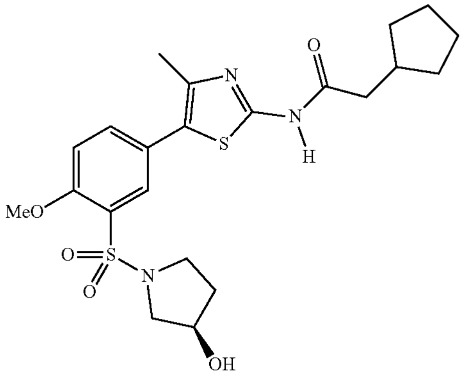 [SMILES: COc1ccc(-c2sc(NC(=O)CC3CCCC3)nc2C)cc1S(=O)(=O)N1CC[C@@H](O)C1] | 2-cyclopentyl-N-[5-[3-[(3R)-3-hydroxypyrrolidin-1-yl]sulfonyl-4-methoxy-phenyl]-4-methyl-thiazol-2-yl]acetamide |
| S-154 | 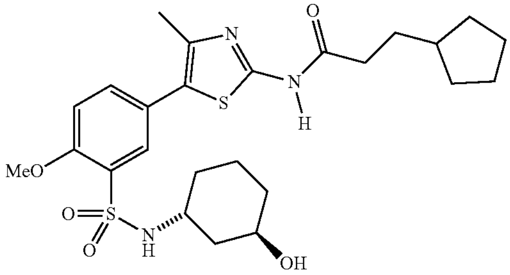 | 3-cyclopentyl-N-[5-[3-[[(1R,3R)-3-hydroxycyclohexyl]sulfamoyl]-4-methoxy-phenyl]-4-methyl-thiazol-2-yl]propanamide |
| S-155 | 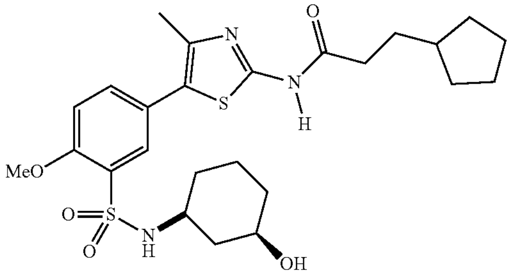 | 3-cyclopentyl-N-[5-[3-[[(1S,3R)-3-hydroxycyclohexyl]sulfamoyl]-4-methoxy-phenyl]-4-methyl-thiazol-2-yl]propanamide |
| S-156 | 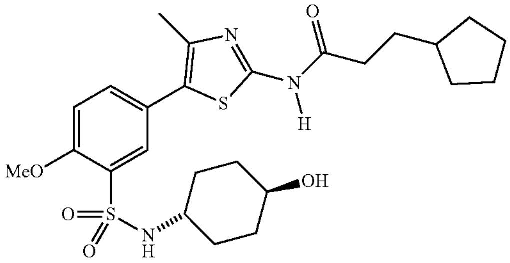 | 3-cyclopentyl-N-[5-[3-[(4-hydroxycyclohexyl)sulfamoyl]-4-methoxy-phenyl]-4-methyl-thiazol-2-yl]propanamide |
| S-157 | 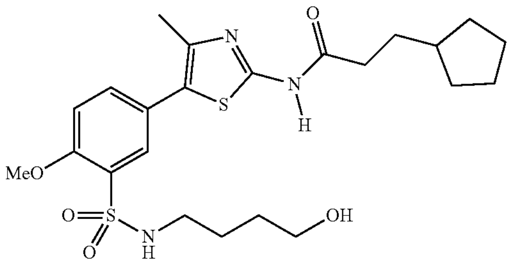 [SMILES: COc1ccc(-c2sc(NC(=O)CCC3CCCC3)nc2C)cc1S(=O)(=O)NCCCCO] | 3-cyclopentyl-N-[5-[3-(4-hydroxybutylsulfamoyl)-4-methoxy-phenyl]-4-methyl-thiazol-2-yl]propanamide |

TABLE 1-continued

| Compounds | | |
|---|---|---|
| Compound | Structure | Name |
| S-158 | 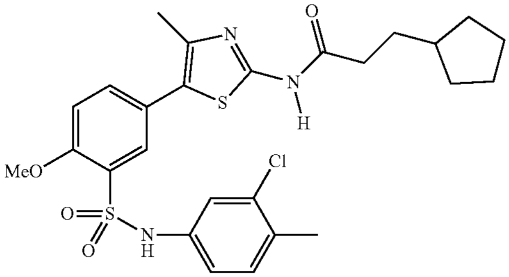 [SMILES: COc1ccc(-c2sc(NC(=O)CCC3CCCC3)nc2C)cc1S(=O)(=O)Nc1ccc(C)c(Cl)c1] | 3-cyclopentyl-N-[5-[3-[(3-hydroxy-4-methyl-phenyl)sulfamoyl]-4-methoxy-phenyl]-4-methyl-thiazol-2-yl]propanamide |
| S-159 | 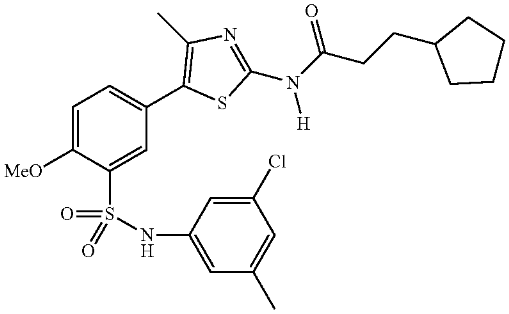 [SMILES: COc1ccc(-c2sc(NC(=O)CCC3CCCC3)nc2C)cc1S(=O)(=O)Nc1cc(C)cc(Cl)c1] | 3-cyclopentyl-N-[5-[3-[(3-hydroxy-5-methyl-phenyl)sulfamoyl]-4-methoxy-phenyl]-4-methyl-thiazol-2-yl]propanamide |
| S-160 | 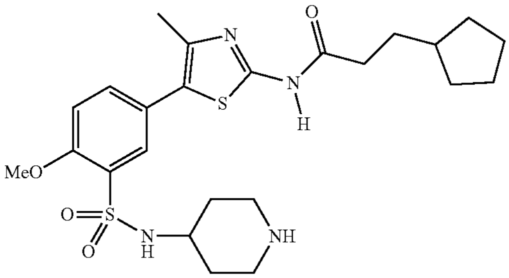 [SMILES: COc1ccc(-c2sc(NC(=O)CCC3CCCC3)nc2C)cc1S(=O)(=O)NC1CCNCC1] | 3-cyclopentyl-N-[5-[4-methoxy-3-(4-piperidylsulfamoyl)phenyl]-4-methyl-thiazol-2-yl]propanamide |
| S-161 | 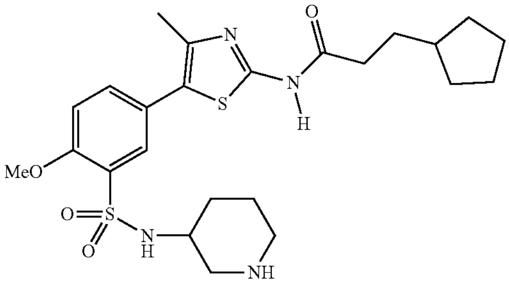 [SMILES: COc1ccc(-c2sc(NC(=O)CCC3CCCC3)nc2C)cc1S(=O)(=O)NC1CCCNC1] | 3-cyclopentyl-N-[5-[4-methoxy-3-(3-piperidylsulfamoyl)phenyl]-4-methyl-thiazol-2-yl]propanamide |
| S-162 | 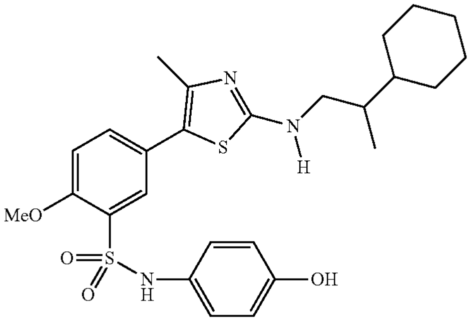 [SMILES: COc1ccc(-c2sc(NCC(C)C3CCCCC3)nc2C)cc1S(=O)(=O)Nc1ccc(O)cc1] | 5-[2-(2-cyclohexylpropylamino)-4-methyl-thiazol-5-yl]-N-(4-hydroxyphenyl)-2-methoxy-benzenesulfonamide |

TABLE 1-continued

| Compounds | | |
|---|---|---|
| Compound | Structure | Name |
| S-163 | 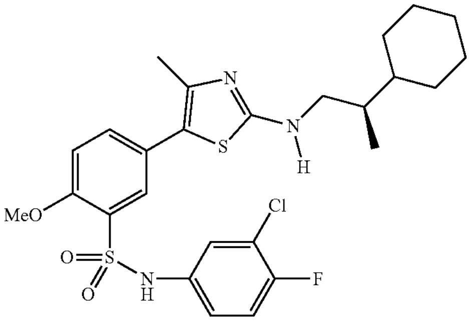 [SMILES: COc1ccc(-c2sc(NC[C@H](C)C3CCCCC3)nc2C)cc1S(=O)(=O)Nc1ccc(F)c(Cl)c1] | N-(3-chloro-4-fluoro-phenyl)-5-[2-[[(2R)-2-cyclohexylpropyl]amino]-4-methyl-thiazol-5-yl]-2-methoxy-benzenesulfonamide |
| S-164 | 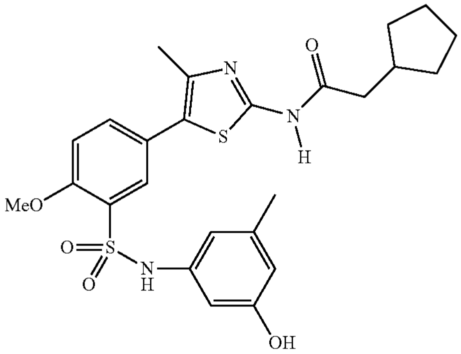 [SMILES: COc1ccc(-c2sc(NC(=O)CC3CCCC3)nc2C)cc1S(=O)(=O)Nc1cc(C)cc(O)c1] | 2-cyclopentyl-N-[5-[3-[(3-hydroxy-5-methyl-phenyl)sulfamoyl]-4-methoxy-phenyl]-4-methyl-thiazol-2-yl]acetamide |
| S-165 | 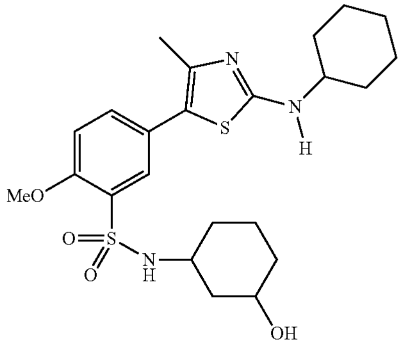 [SMILES: COc1ccc(-c2sc(NC3CCCCC3)nc2C)cc1S(=O)(=O)NC1CCCC(O)C1] | 5-[2-(cyclohexylamino)-4-methyl-thiazol-5-yl]-N-(3-hydroxycyclohexyl)-2-methoxy-benzenesulfonamide |
| S-166 | 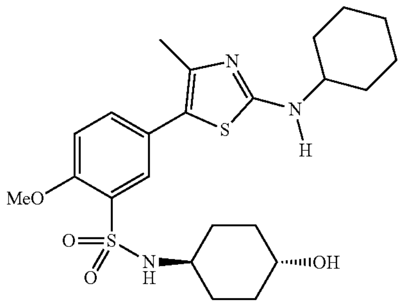 [SMILES: COc1ccc(-c2sc(NC3CCCCC3)nc2C)cc1S(=O)(=O)N[C@H]1CC[C@H](O)CC1] | 5-[2-(cyclohexylamino)-4-methyl-thiazol-5-yl]-N-(4-hydroxycyclohexyl)-2-methoxy-benzenesulfonamide |

TABLE 1-continued

| Compounds | | |
|---|---|---|
| Compound | Structure | Name |
| S-167 | 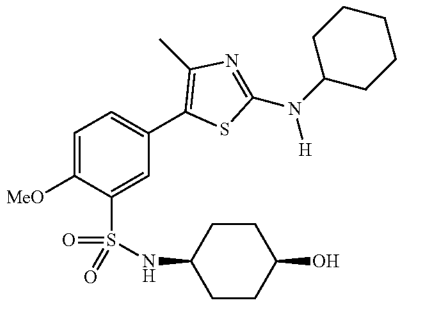 [SMILES: COc1ccc(-c2sc(NC3CCCCC3)nc2C)cc1S(=O)(=O)N[C@H]1CC[C@@H](O)CC1] | 5-[2-(cyclohexylamino)-4-methyl-thiazol-5-yl]-N-(4-hydroxycyclohexyl)-2-methoxy-benzenesulfonamide |
| S-168 | 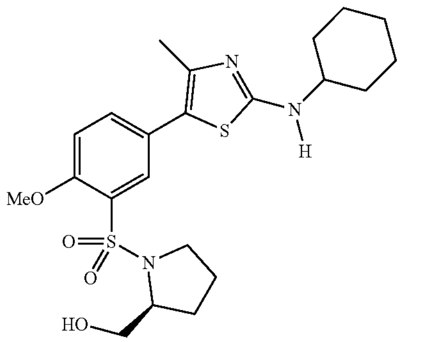 [SMILES: COc1ccc(-c2sc(NC3CCCCC3)nc2C)cc1S(=O)(=O)N1CCC[C@H]1CO] | [(2S)-1-[5-[2-(cyclohexylamino)-4-methyl-thiazol-5-yl]-2-methoxy-phenyl]sulfonylpyrrolidin-2-yl]methanol |
| S-169 | 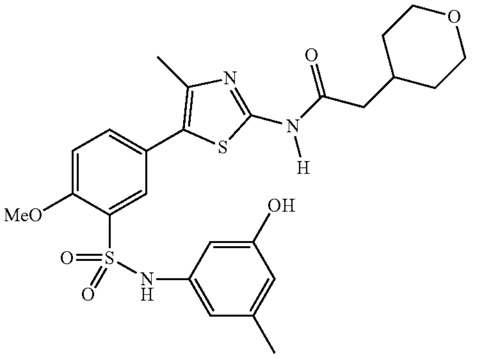 [SMILES: COc1ccc(-c2sc(NC(=O)CC3CCOCC3)nc2C)cc1S(=O)(=O)Nc1cc(C)cc(O)c1] | N-[5-[3-[(3-hydroxy-5-methyl-phenyl)sulfamoyl]-4-methoxy-phenyl]-4-methyl-thiazol-2-yl]-2-tetrahydropyran-4-yl-acetamide |
| S-170 | 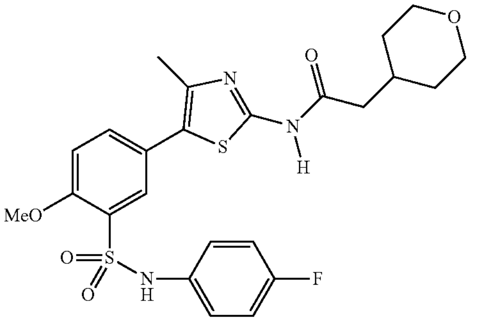 [SMILES: COc1ccc(-c2sc(NC(=O)CC3CCOCC3)nc2C)cc1S(=O)(=O)Nc1ccc(F)cc1] | N-[5-[3-[(4-fluorophenyl)sulfamoyl]-4-methoxy-phenyl]-4-methyl-thiazol-2-yl]-2-tetrahydropyran-4-yl-acetamide |

TABLE 1-continued

| Compounds | | |
|---|---|---|
| Compound | Structure | Name |
| S-171 | 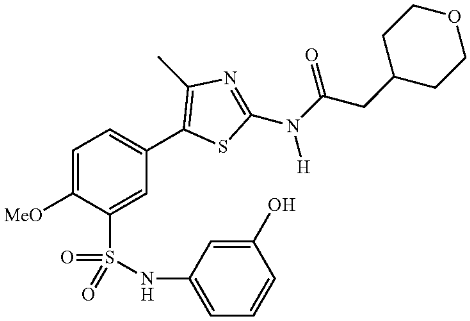 | N-[5-[3-[(3-hydroxyphenyl)sulfamoyl]-4-methoxy-phenyl]-4-methyl-thiazol-2-yl]-2-tetrahydropyran-4-yl-acetamide |
| S-172 | 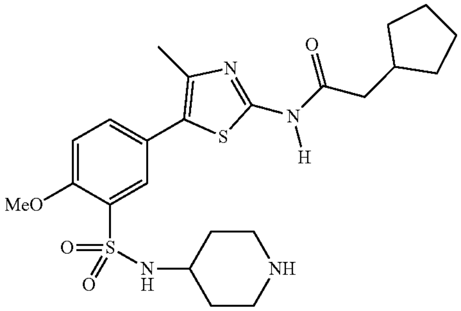 [SMILES: COc1ccc(-c2sc(NC(=O)CC3CCCC3)nc2C)cc1S(=O)(=O)NC1CCNCC1] | 2-cyclopentyl-N-[5-[4-methoxy-3-(4-piperidylsulfamoyl)phenyl]-4-methyl-thiazol-2-yl]acetamide; 2,2,2-trifluoroacetic acid |
| S-173 | 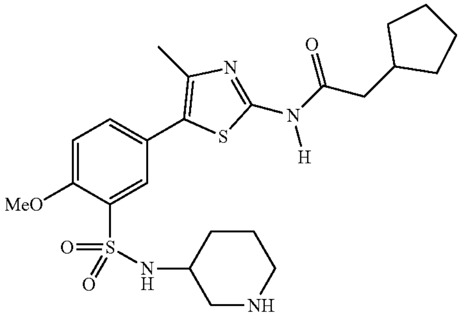 [SMILES: COc1ccc(-c2sc(NC(=O)CC3CCCC3)nc2C)cc1S(=O)(=O)NC1CCCNC1] | 2-cyclopentyl-N-[5-[4-methoxy-3-(3-piperidylsulfamoyl)phenyl]-4-methyl-thiazol-2-yl]acetamide; 2,2,2-trifluoroacetic acid |
| S-174 | 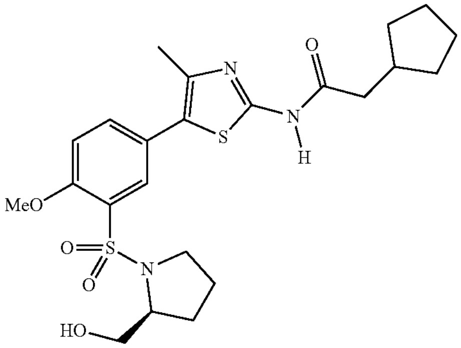 [SMILES: COc1ccc(-c2sc(NC(=O)CC3CCCC3)nc2C)cc1S(=O)(=O)N1CCC[C@H]1CO] | 2-cyclopentyl-N-[5-[3-[(2S)-2-(hydroxymethyl)pyrrolidin-1-yl]sulfonyl-4-methoxy-phenyl]-4-methyl-thiazol-2-yl]acetamide |

TABLE 1-continued

| Compounds | | |
|---|---|---|
| Compound | Structure | Name |
| S-175 | 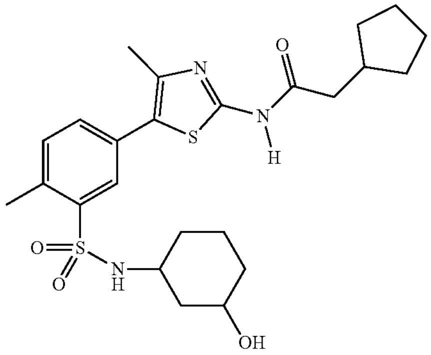 [SMILES: Cc1ccc(-c2sc(NC(=O)CC3CCCC3)nc2C)cc1S(=O)(=O)NC1CCCC(O)C1] | 2-cyclopentyl-N-[5-[3-[(3-hydroxycyclohexyl)sulfamoyl]-4-methyl-phenyl]-4-methyl-thiazol-2-yl]acetamide |
| S-176 | 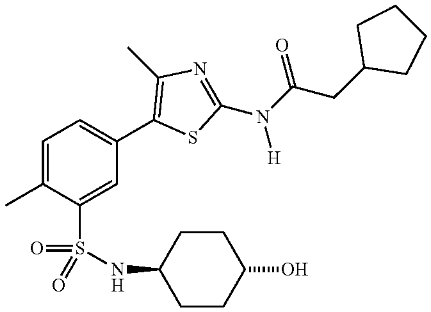 [SMILES: Cc1ccc(-c2sc(NC(=O)CC3CCCC3)nc2C)cc1S(=O)(=O)N[C@H]1CC[C@H](O)CC1] | 2-cyclopentyl-N-[5-[3-[(4-hydroxycyclohexyl)sulfamoyl]-4-methyl-phenyl]-4-methyl-thiazol-2-yl]acetamide |
| S-177 | 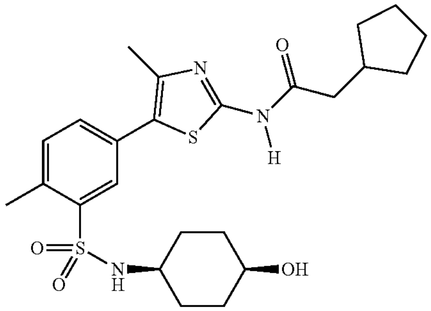 [SMILES: Cc1ccc(-c2sc(NC(=O)CC3CCCC3)nc2C)cc1S(=O)(=O)N[C@H]1CC[C@@H](O)CC1] | 2-cyclopentyl-N-[5-[3-[(4-hydroxycyclohexyl)sulfamoyl]-4-methyl-phenyl]-4-methyl-thiazol-2-yl]acetamide |
| S-178 | 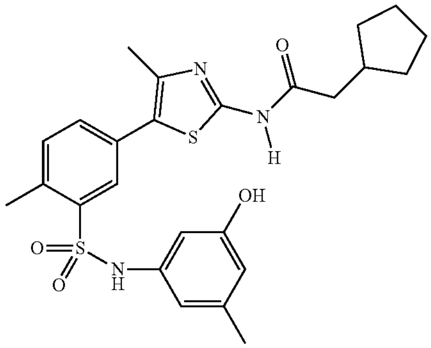 [SMILES: Cc1cc(O)cc(NS(=O)(=O)c2cc(-c3sc(NC(=O)CC4CCCC4)nc3C)ccc2C)c1] | 2-cyclopentyl-N-[5-[3-[(3-hydroxy-5-methyl-phenyl)sulfamoyl]-4-methyl-phenyl]-4-methyl-thiazol-2-yl]acetamide |

TABLE 1-continued

| Compounds | | |
|---|---|---|
| Compound | Structure | Name |
| S-179 | 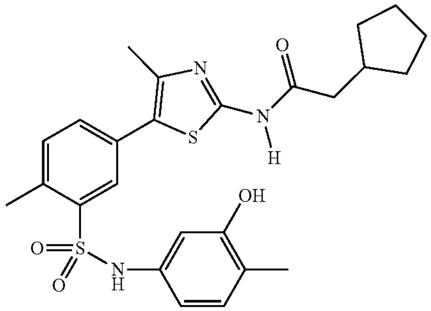 [SMILES: Cc1ccc(NS(=O)(=O)c2cc(-c3sc(NC(=O)CC4CCCC4)nc3C)ccc2C)cc1O] | 2-cyclopentyl-N-[5-[3-[(3-hydroxy-4-methyl-phenyl)sulfamoyl]-4-methyl-phenyl]-4-methyl-thiazol-2-yl]acetamide |
| S-180 | 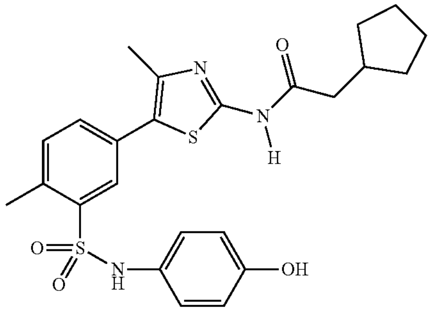 [SMILES: Cc1ccc(-c2sc(NC(=O)CC3CCCC3)nc2C)cc1S(=O)(=O)Nc1ccc(O)cc1] | 2-cyclopentyl-N-[5-[3-[(4-hydroxyphenyl)sulfamoyl]-4-methyl-phenyl]-4-methyl-thiazol-2-yl]acetamide |
| S-181 | 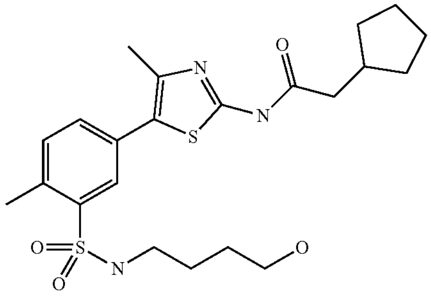 [SMILES: Cc1ccc(-c2sc(NC(=O)CC3CCCC3)nc2C)cc1S(=O)(=O)NCCCCO] | 2-cyclopentyl-N-[5-[3-(4-hydroxysulfamoyl)-4-methyl-phenyl]-4-methyl-thiazol-2-yl]acetamide |
| S-182 | 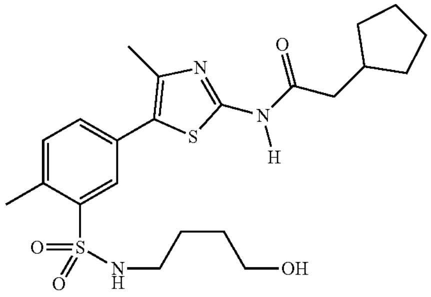 [SMILES: Cc1ccc(-c2sc(NC(=O)CC3CCCC3)nc2C)cc1S(=O)(=O)NCCCCO] | 2-cyclopentyl-N-[5-[3-(cyclopentylsulfamoyl)-4-methyl-phenyl]-4-methyl-thiazol-2-yl]acetamide |
| S-183 | 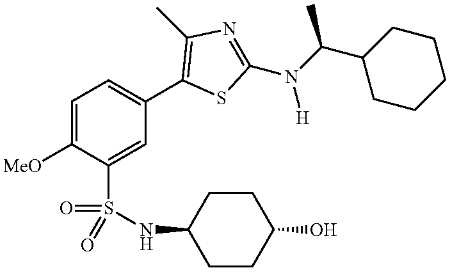 [SMILES: COc1ccc(-c2sc(N[C@@H](C)C3CCCCC3)nc2C)cc1S(=O)(=O)N[C@H]1CC[C@H](O)CC1] | 5-[2-[[(1S)-1-cyclohexylethyl]amino]-4-methyl-thiazol-5-yl]-N-(4-hydroxycyclohexyl)-2-methoxy-benzenesulfonamide |

TABLE 1-continued

| Compounds | | |
|---|---|---|
| Compound | Structure | Name |
| S-184 | 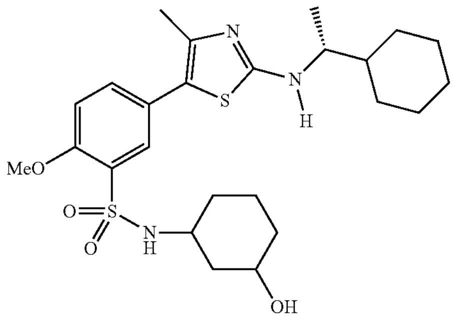 [SMILES: COc1ccc(-c2sc(N[C@H](C)C3CCCCC3)nc2C)cc1S(=O)(=O)NC1CCCC(O)C1] | 5-[2-[[(1R)-1-cyclohexylethyl]amino]-4-methyl-thiazol-5-yl]-N-(3-hydroxycyclohexyl)-2-methoxy-benzenesulfonamide |
| S-185 | 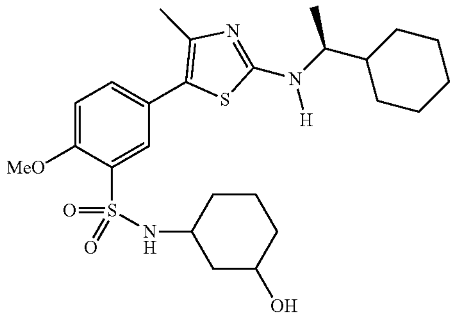 [SMILES: COc1ccc(-c2sc(N[C@@H](C)C3CCCCC3)nc2C)cc1S(=O)(=O)NC1CCCC(O)C1] | 5-[2-[[(1S)-1-cyclohexylethyl]amino]-4-methyl-thiazol-5-yl]-N-(3-hydroxycyclohexyl)-2-methoxy-benzenesulfonamide |
| S-186 | 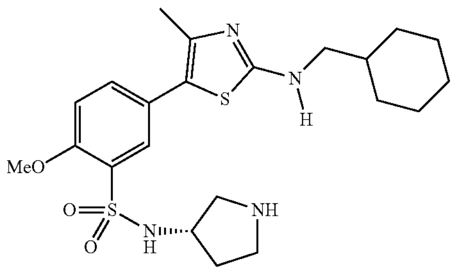 [SMILES: COc1ccc(-c2sc(NCC3CCCCC3)nc2C)cc1S(=O)(=O)N[C@H]1CCNC1] | 5-[2-(cyclohexylmethylamino)-4-methyl-thiazol-5-yl]-2-methoxy-N-[(3S)-pyrrolidin-3-yl]benzenesulfonamide |
| S-187 | 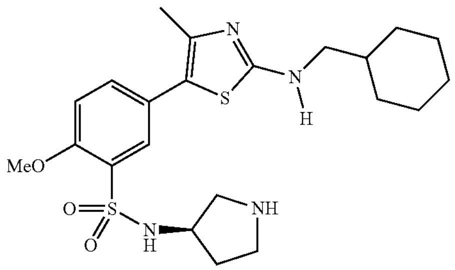 [SMILES: COc1ccc(-c2sc(NCC3CCCCC3)nc2C)cc1S(=O)(=O)N[C@@H]1CCNC1] | 5-[2-(cyclohexylmethylamino)-4-methyl-thiazol-5-yl]-2-methoxy-N-[(3R)-pyrrolidin-3-yl]benzenesulfonamide; 2,2,2-tifluoroacetic acid |
| S-188 | 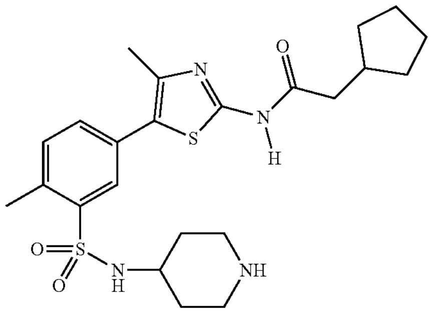 [SMILES: Cc1ccc(-c2sc(NC(=O)CC3CCCC3)nc2C)cc1S(=O)(=O)NC1CCNCC1] | 2-cyclopentyl-N-[4-methyl-5-[4-methyl-3-(4-piperidylsulfamoyl)phenyl]thiazol-2-yl]acetamide |

TABLE 1-continued

| Compound | Structure | Name |
|---|---|---|
| | Compounds | |
| S-189 | 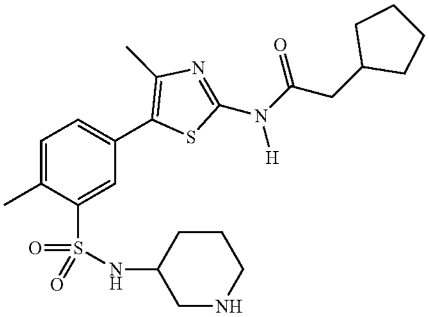 [SMILES: Cc1ccc(-c2sc(NC(=O)CC3CCCC3)nc2C)cc1S(=O)(=O)NC1CCCNC1] | 2-cyclopentyl-N-[4-methyl-5-[4-methyl-3-(3-piperidylsulfamoyl)phenyl]thiazol-2-yl]acetamide |
| S-190 | 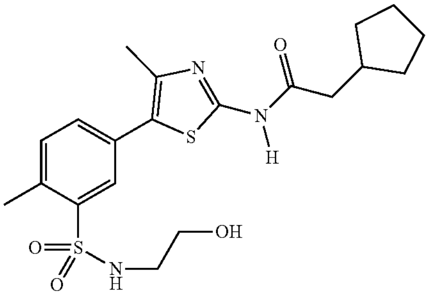 [SMILES: Cc1ccc(-c2sc(NC(=O)CC3CCCC3)nc2C)cc1S(=O)(=O)NCCO] | 2-cyclopentyl-N-[5-[3-(2-hydroxysulfamoyl)-4-methyl-phenyl]-4-methyl-thiazol-2-yl]acetamide |
| S-191 | 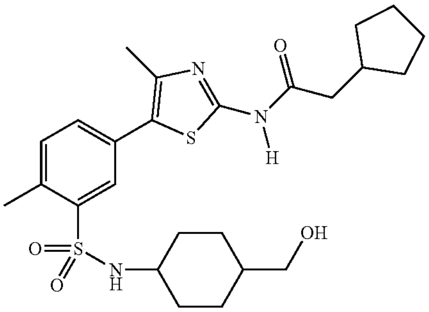 [SMILES: Cc1ccc(-c2sc(NC(=O)CC3CCCC3)nc2C)cc1S(=O)(=O)NC1CCC(CO)CC1] | 2-cyclopentyl-N-[5-[3-[[4-(hydroxymethyl)cyclohexyl]sulfamoyl]-4-methyl-phenyl]-4-methyl-thiazol-2-yl]acetamide |
| S-192 | 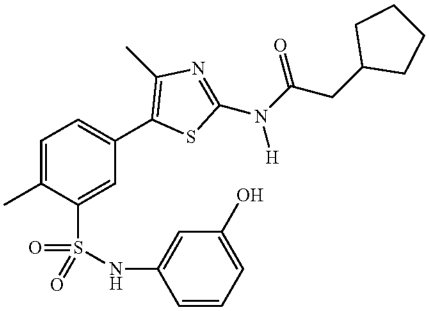 [SMILES: Cc1ccc(-c2sc(NC(=O)CC3CCCC3)nc2C)cc1S(=O)(=O)Nc1cccc(O)c1] | 2-cyclopentyl-N-[5-[3-[(3-hydroxyphenyl)sulfamoyl]-4-methyl-phenyl]-4-methyl-thiazol-2-yl]acetamide |
| S-193 | 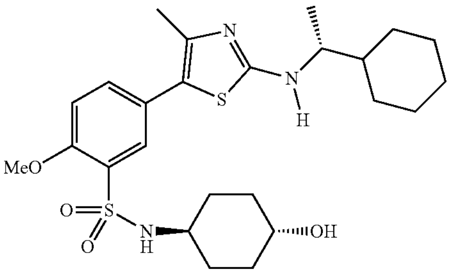 [SMILES: COc1ccc(-c2sc(N[C@H](C)C3CCCCC3)nc2C)cc1S(=O)(=O)N[C@H]1CC[C@H](O)CC1] | 5-[2-[[(1R)-1-cyclohexylethyl]amino]-4-methyl-thiazol-5-yl]-N-(4-hydroxycyclohexyl)-2-methoxy-benzenesulfonamide |

TABLE 1-continued

| Compounds | | |
|---|---|---|
| Compound | Structure | Name |
| S-194 | 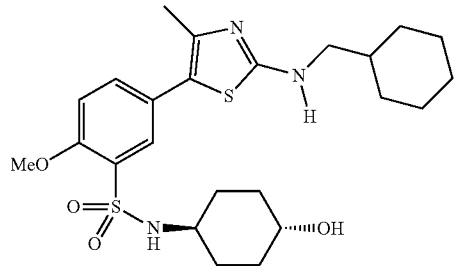 [SMILES: COc1ccc(-c2sc(NCC3CCCCC3)nc2C)cc1S(=O)(=O)N[C@H]1CC[C@H](O)CC1] | 5-[2-(cyclohexylmethylamino)-4-methyl-thiazol-5-yl]-N-(4-hydroxycyclohexyl)-2-methoxy-benzenesulfonamide |
| S-195 | 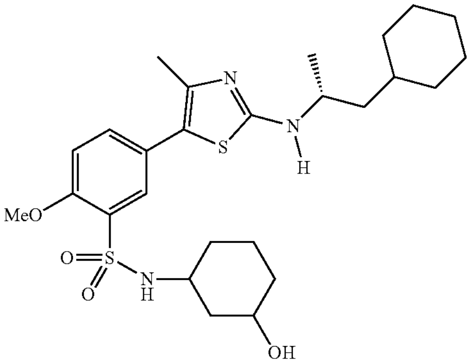 [SMILES: COc1ccc(-c2sc(N[C@H](C)CC3CCCCC3)nc2C)cc1S(=O)(=O)NC1CCCC(O)C1] | 5-[2-[[(1R)-2-cyclohexyl-1-methyl-ethyl]amino]-4-methyl-thiazol-5-yl]-N-(3-hydroxycyclohexyl)-2-methoxy-benzenesulfonamide |
| S-196 | 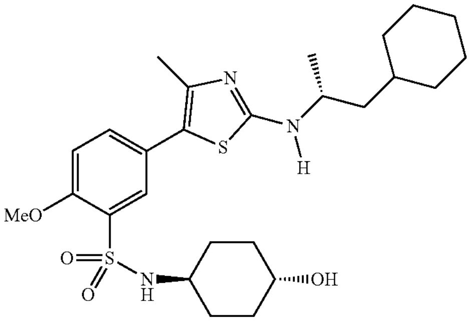 [SMILES: COc1ccc(-c2sc(N[C@H](C)CC3CCCCC3)nc2C)cc1S(=O)(=O)N[C@H]1CC[C@H](O)CC1] | 5-[2-[[(1R)-2-cyclohexyl-1-methyl-ethyl]amino]-4-methyl-thiazol-5-yl]-N-(4-hydroxycyclohexyl)-2-methoxy-benzenesulfonamide |
| S-197 | 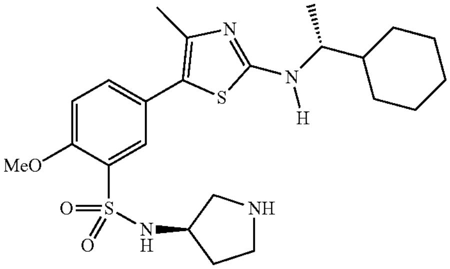 [SMILES: COc1ccc(-c2sc(N[C@H](C)C3CCCCC3)nc2C)cc1S(=O)(=O)N[C@@H]1CCNC1] | 5-[2-[[(1R)-1-cyclohexylethyl]amino]-4-methyl-thiazol-5-yl]-2-methoxy-N-[(3R)-pyrrolidin-3-yl]benzenesulfonamide |
| S-198 | 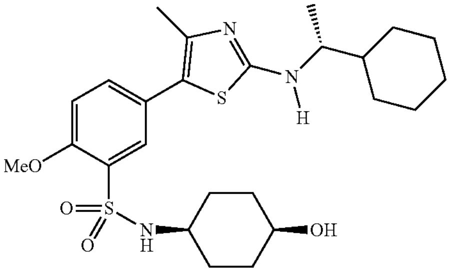 [SMILES: COc1ccc(-c2sc(N[C@H](C)C3CCCCC3)nc2C)cc1S(=O)(=O)N[C@H]1CC[C@@H](O)CC1] | 5-[-2[[(1R)-1-cyclohexylethyl]amino]-4-methyl-thiazol-5-yl]-N-(4-hydroxycyclohexyl)-2-methoxy-benzenesulfonamide |

TABLE 1-continued

| Compound | Structure | Name |
| --- | --- | --- |
| S-199 | 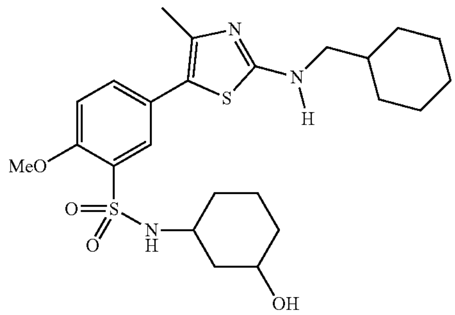 [SMILES: COc1ccc(-c2sc(NCC3CCCCC3)nc2C)cc1S(=O)(=O)NC1CCCC(O)C1] | 5-[2-(cyclohexylmethylamino)-4-methyl-thiazol-5-yl]-N-(3-hydroxycyclohexyl)-2-methoxy-benzenesulfonamide |
| S-200 | 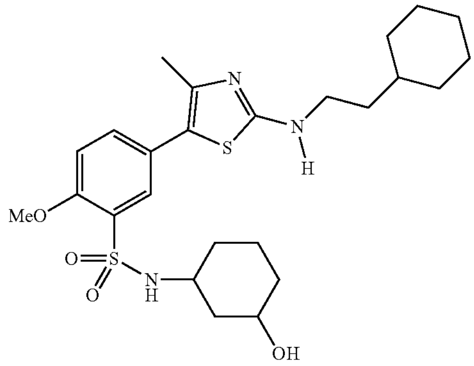 [SMILES: COc1ccc(-c2sc(NCCC3CCCCC3)nc2C)cc1S(=O)(=O)NC1CCCC(O)C1] | 5-[2-(2-cyclohexylethylamino)-4-methyl-thiazol-5-yl]-N-(3-hydroxycyclohexyl)-2-methoxy-benzenesulfonamide |
| S-201 | 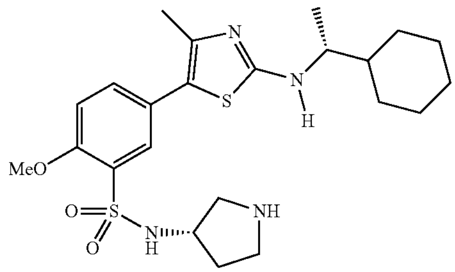 [SMILES: COc1ccc(-c2sc(N[C@H](C)C3CCCCC3)nc2C)cc1S(=O)(=O)N[C@H]1CCNC1] | 5-[2-[[(1R)-1-cyclohexylethyl]amino]-4-methyl-thiazol-5-yl]-2-methoxy-N-[(3S)-pyrrolidin-3-yl]benzenesulfonamide |
| S-202 | 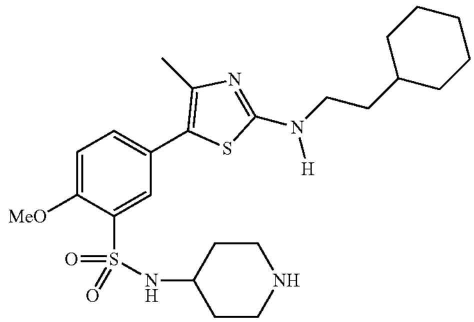 [SMILES: COc1ccc(-c2sc(NCCC3CCCCC3)nc2C)cc1S(=O)(=O)NC1CCNCC1] | 5-[2-(2-cyclohexylethylamino)-4-methyl-thiazol-5-yl]-2-methoxy-N-(4-piperidyl)benzenesulfonamide |
| S-203 | 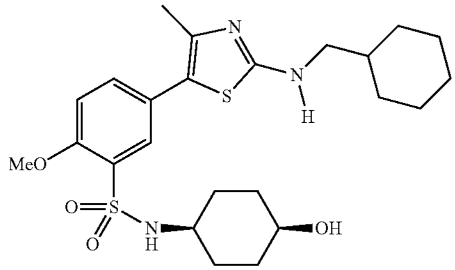 [SMILES: COc1ccc(-c2sc(NCC3CCCCC3)nc2C)cc1S(=O)(=O)N[C@H]1CC[C@@H](O)CC1] | 5-[2-(cyclohexylmethylamino)-4-methyl-thiazol-5-yl]-N-(4-hydroxycyclohexyl)-2-methoxy-benzenesulfonamide |

TABLE 1-continued

| Compounds | | |
|---|---|---|
| Compound | Structure | Name |
| S-204 | 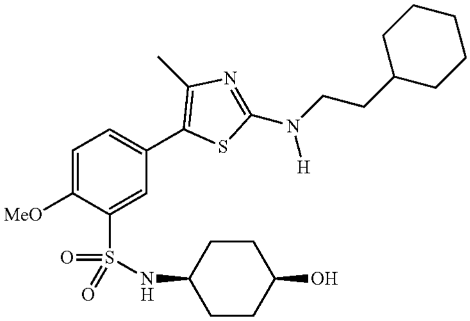 [SMILES: COc1ccc(-c2sc(NCCC3CCCCC3)nc2C)cc1S(=O)(=O)N[C@H]1CC[C@@H](O)CC1] | 5-[2-(2-cyclohexylethylamino)-4-methyl-thiazol-5-yl]-N-(4-hydroxycyclohexyl)-2-methoxy-benzenesulfonamide |
| S-205 | 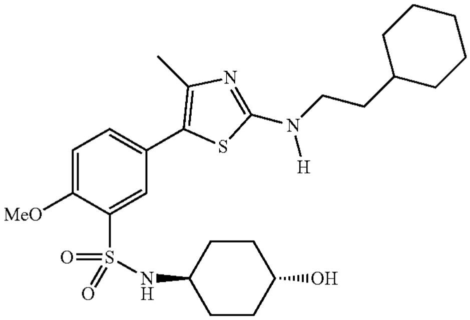 [SMILES: COc1ccc(-c2sc(NCCC3CCCCC3)nc2C)cc1S(=O)(=O)N[C@H]1CC[C@H](O)CC1] | 5-[2-(2-cyclohexylethylamino)-4-methyl-thiazol-5-yl]-N-(4-hydroxycyclohexyl)-2-methoxy-benzenesulfonamide |
| S-206 | 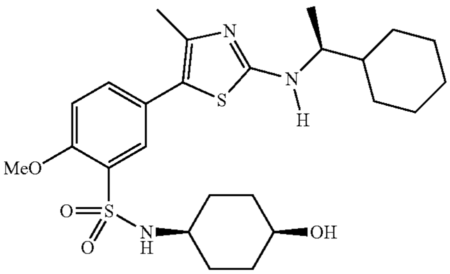 [SMILES: COc1ccc(-c2sc(N[C@@H](C)C3CCCCC3)nc2C)cc1S(=O)(=O)N[C@H]1CC[C@@H](O)CC1] | 5-[2-[[(1S)-1-cyclohexylethyl]amino]-4-methyl-thiazol-5-yl]-N-(4-hydroxycyclohexyl)-2-methoxy-benzenesulfonamide |
| S-207 | 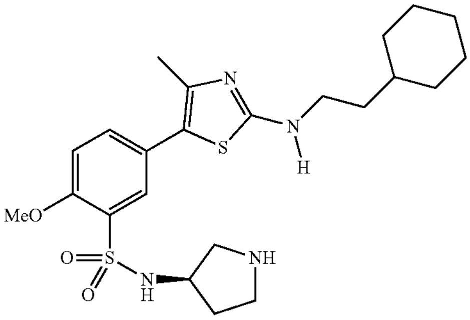 [SMILES: COc1ccc(-c2sc(NCCC3CCCCC3)nc2C)cc1S(=O)(=O)N[C@@H]1CCNC1] | 5-[2-(2-cyclohexylethylamino)-4-methyl-thiazol-5-yl]-2-methoxy-N-[(3R)-2-pyrrolidin-3-yl]benzenesulfonamide |

TABLE 1-continued

| Compounds | | |
|---|---|---|
| Compound | Structure | Name |
| S-208 | 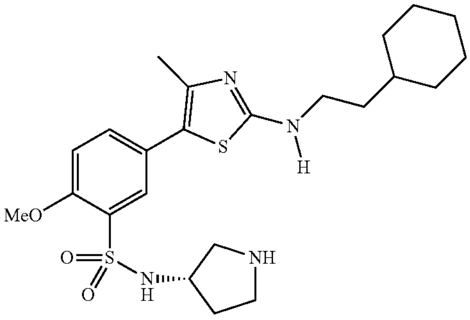 [SMILES: COc1ccc(-c2sc(NCCC3CCCCC3)nc2C)cc1S(=O)(=O)N[C@H]1CCNC1] | 5-[2-(2-cyclohexylethylamino)-4-methyl-thiazol-5-yl]-2-methoxy-N-[(3S)-pyrrolidin-3-yl]benzenesulfonamide |
| S-209 | 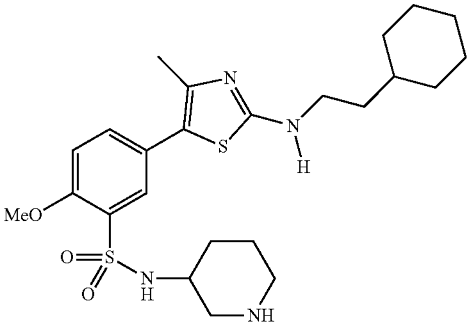 [SMILES: COc1ccc(-c2sc(NCCC3CCCCC3)nc2C)cc1S(=O)(=O)NC1CCCNC1] | 5-[2-(2-cyclohexylethylamino)-4-methyl-thiazol-5-yl]-2-methoxy-N-(3-piperidyl)benzenesulfonamide |
| S-210 | 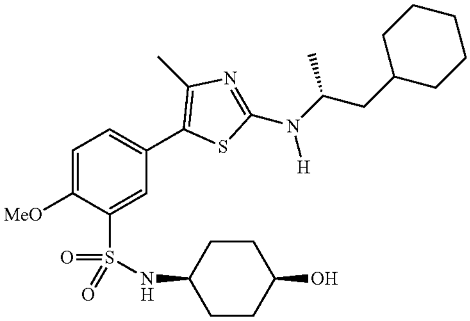 [SMILES: COc1ccc(-c2sc(N[C@H](C)CC3CCCCC3)nc2C)cc1S(=O)(=O)N[C@H]1CC[C@@H](O)CC1] | 5-[2-[[(1R)-2-cyclohexyl-1-methyl-ethyl]amino]-4-methyl-thiazol-5-yl]-N-(4-hydroxycyclohexyl)-2-methoxy-benzenesulfonamide |
| S-211 | 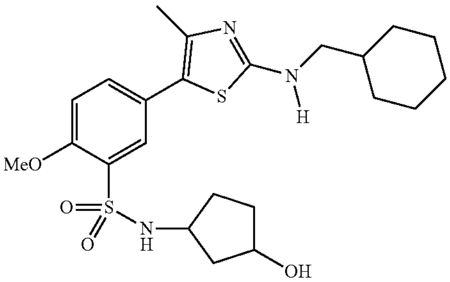 [SMILES: COc1ccc(-c2sc(NCC3CCCCC3)nc2C)cc1S(=O)(=O)NC1CCC(O)C1] | 5-[2-(cyclohexylmethylamino)-4-methyl-thiazol-5-yl]-N-(3-hydroxycyclopentyl)-2-methoxy-benzenesulfonamide |
| S-212 | 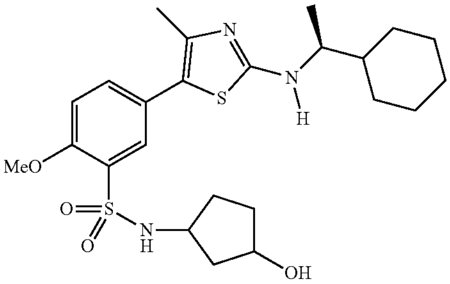 [SMILES: COc1ccc(-c2sc(N[C@@H](C)C3CCCCC3)nc2C)cc1S(=O)(=O)NC1CCC(O)C1] | 5-[2-[[(1S)-1-cyclohexylethyl]amino]-4-methyl-thiazol-5-yl]-N-(3-hydroxycyclopentyl)-2-methoxy-benzenesulfonamide |

TABLE 1-continued

| Compounds | | |
|---|---|---|
| Compound | Structure | Name |
| S-213 | 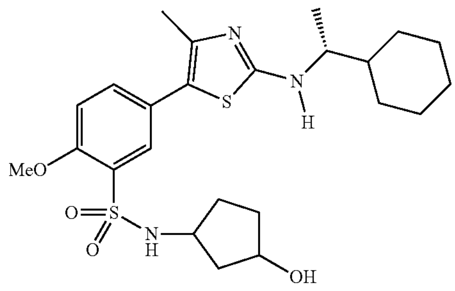 [SMILES: COc1ccc(-c2sc(N[C@H](C)C3CCCCC3)nc2C)cc1S(=O)(=O)NC1CCC(O)C1] | 5-[2-[[(1R)-1-cyclohexylethyl]amino]-4-methyl-thiazol-5-yl]-N-(3-hydroxycyclopentyl)-2-methoxy-benzenesulfonamide |
| S-214 | 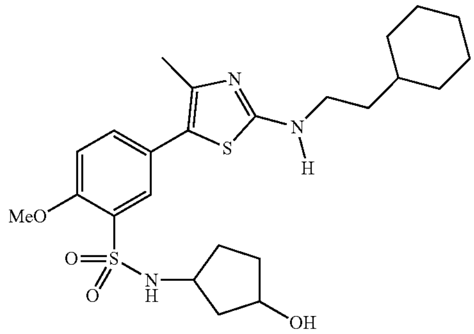 [SMILES: COc1ccc(-c2sc(NCCC3CCCCC3)nc2C)cc1S(=O)(=O)NC1CCC(O)C1] | 5-[2-(2-cyclohexylethylamino)-4-methyl-thiazol-5-yl]-N-(3-hydroxycyclopentyl)-2-methoxy-benzenesulfonamide |
| S-215 | 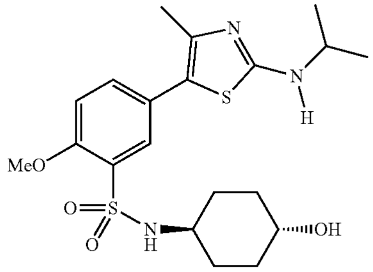 [SMILES: COc1ccc(-c2sc(NC(C)C)nc2C)cc1S(=O)(=O)N[C@H]1CC[C@H](O)CC1] | N-(4-hydroxycyclohexyl)-5-[2-(isopropylamino)-4-methyl-thiazol-5-yl]-2-methoxy-benzenesulfonamide |
| S-216 | 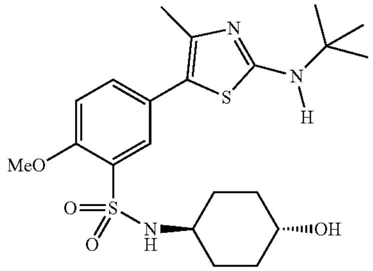 [SMILES: COc1ccc(-c2sc(NC(C)(C)C)nc2C)cc1S(=O)(=O)N[C@H]1CC[C@H](O)CC1] | 5-[2-(tert-butylamino)-4-methyl-thiazol-5-yl]-N-(4-hydroxycyclohexyl)-2-methoxy-benzenesulfonamide |
| S-217 | 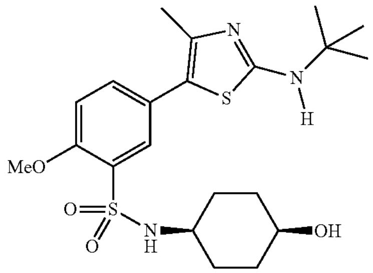 [SMILES: COc1ccc(-c2sc(NC(C)(C)C)nc2C)cc1S(=O)(=O)N[C@H]1CC[C@@H](O)CC1] | 5-[2-(tert-butylamino)-4-methyl-thiazol-5-yl]-N-(4-hydroxycyclohexyl)-2-methoxy-benzenesulfonamide |

TABLE 1-continued

| Compounds | | |
|---|---|---|
| Compound | Structure | Name |
| S-218 | 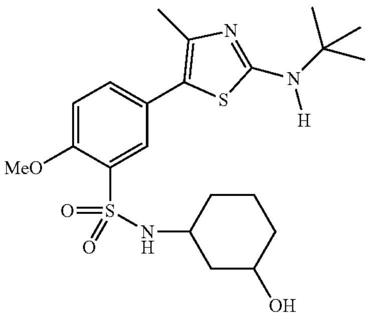 [SMILES: COc1ccc(-c2sc(NC(C)(C)C)nc2C)cc1S(=O)(=O)NC1CCCC(O)C1] | 5-[2-(tert-butylamino)-4-methyl-thiazol-5-yl]-N-(3-hydroxycyclohexyl)-2-methoxy-benzenesulfonamide |
| S-219 | 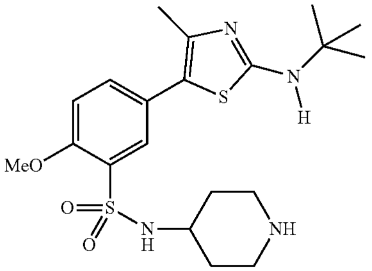 [SMILES: COc1ccc(-c2sc(NC(C)(C)C)nc2C)cc1S(=O)(=O)NC1CCNCC1] | 5-[2-(tert-butylamino)-4-methyl-thiazol-5-yl]-2-methoxy-N-(4-piperidyl)benzenesulfonamide |
| S-220 | 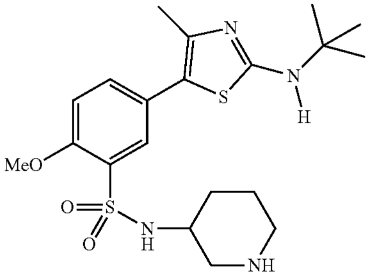 [SMILES: COc1ccc(-c2sc(NC(C)(C)C)nc2C)cc1S(=O)(=O)NC1CCCNC1] | 5-[2-(tert-butylamino)-4-methyl-thiazol-5-yl]-2-methoxy-N-(3-piperidyl)benzenesulfonamide |
| S-221 | 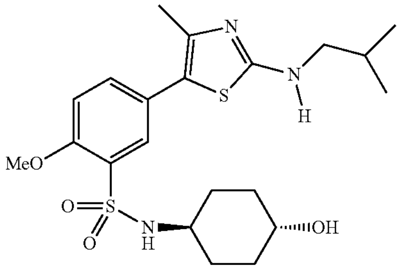 [SMILES: COc1ccc(-c2sc(NCC(C)C)nc2C)cc1S(=O)(=O)N[C@H]1CC[C@H](O)CC1] | N-(4-hydroxycyclohexyl)-5-[2-(isobutylamino)-4-methyl-thiazol-5-yl]-2-methoxy-benzenesulfonamide |
| S-222 | 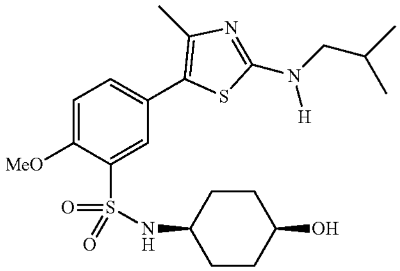 [SMILES: COc1ccc(-c2sc(NCC(C)C)nc2C)cc1S(=O)(=O)N[C@H]1CC[C@@H](O)CC1] | N-(4-hydroxycyclohexyl)-5-[2-(isobutylamino)-4-methyl-thiazol-5-yl]-2-methoxy-benzenesulfonamide |

TABLE 1-continued

| Compounds | | |
|---|---|---|
| Compound | Structure | Name |
| S-223 | 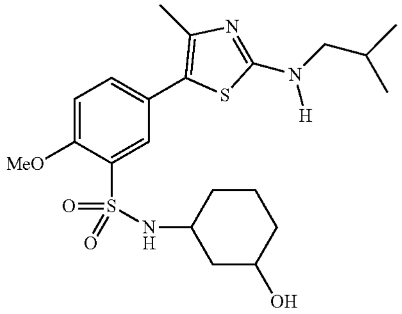 [SMILES: COc1ccc(-c2sc(NCC(C)C)nc2C)cc1S(=O)(=O)NC1CCCC(O)C1] | N-(3-hydroxycyclohexyl)-5-[2-(isobutylamino)-4-methyl-thiazol-5-yl]-2-methoxy-benzenesulfonamide; 2,2,2-trifluoroacetic acid |
| S-224 | 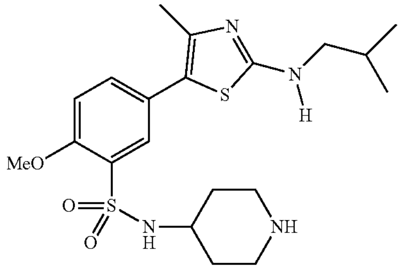 [SMILES: COc1ccc(-c2sc(NCC(C)C)nc2C)cc1S(=O)(=O)NC1CCNCC1] | 5-[2-(isobutylamino)-4-methyl-thiazol-5-yl]-2-methoxy-N-(4-piperidyl)benzenesulfonamide; 2,2,2-trifluoroacetic acid |
| S-225 | 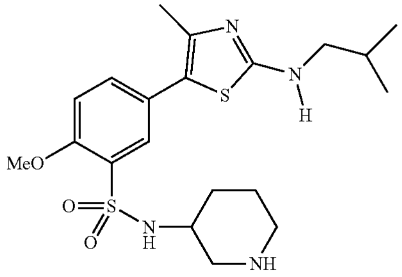 [SMILES: COc1ccc(-c2sc(NCC(C)C)nc2C)cc1S(=O)(=O)NC1CCCNC1] | 5-[2-(isobutylamino)-4-methyl-thiazol-5-yl]-2-methoxy-N-(3-piperidyl)benzenesulfonamide; 2,2,2-trifluoroacetic acid |
| S-226 | 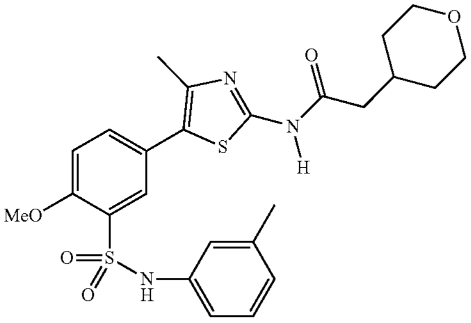 [SMILES: COc1ccc(-c2sc(NC(=O)CC3CCOCC3)nc2C)cc1S(=O)(=O)Nc1cccc(C)c1] | N-[5-[4-methoxy-3-(m-tolylsulfamoyl)phenyl]-4-methyl-thiazol-2-yl]-2-tetrahydropyran-4-yl-acetamide |
| S-227 | 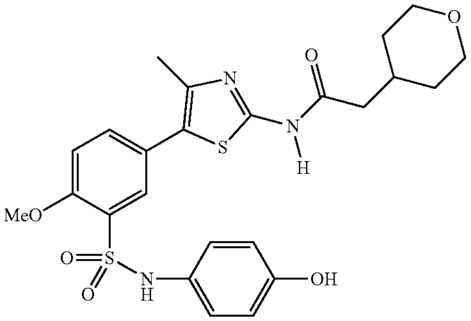 | N-[5-[3-[(4-hydroxyphenyl)sulfamoyl]-4-methoxy-phenyl]-4-methyl-thiazol-2-yl]-2-tetrahydropyran-4-yl-acetamide |

TABLE 1-continued

| Compound | Structure | Name |
|---|---|---|
| S-228 | 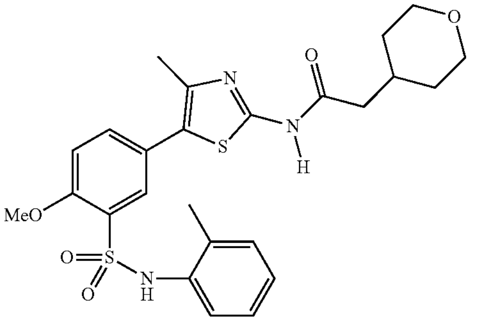 [SMILES: COc1ccc(-c2sc(NC(=O)CC3CCOCC3)nc2C)cc1S(=O)(=O)Nc1ccccc1C] | N-[5-[4-methoxy-3-(o-tolylsulfamoyl)phenyl]-4-methyl-thiazol-2-yl]-2-tetrahydropyran-4-yl-acetamide |
| S-229 | 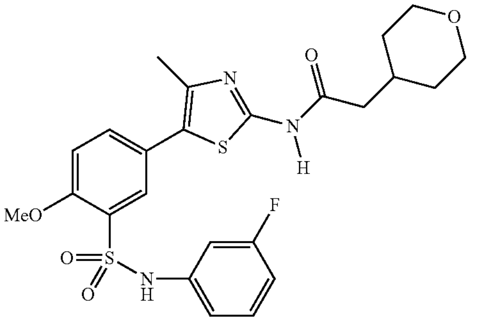 [SMILES: COc1ccc(-c2sc(NC(=O)CC3CCOCC3)nc2C)cc1S(=O)(=O)Nc1cccc(F)c1] | N-[5-[3-[(3-fluorophenyl)sulfamoyl]-4-methoxy-phenyl]-4-methyl-thiazol-2-yl]-2-tetrahydropyran-4-yl-acetamide |
| S-230 | 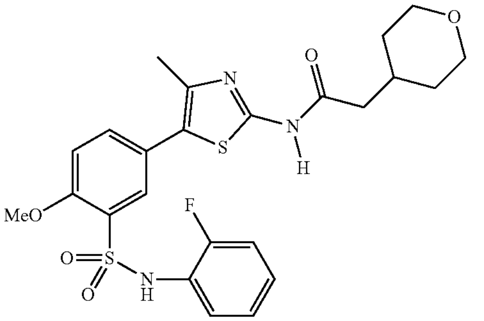 [SMILES: COc1ccc(-c2sc(NC(=O)CC3CCOCC3)nc2C)cc1S(=O)(=O)Nc1ccccc1F] | N-[5-[3-[(2-fluorophenyl)sulfamoyl]-4-methoxy-phenyl]-4-methyl-thiazol-2-yl]-2-tetrahydropyran-4-yl-acetamide |
| S-231 | 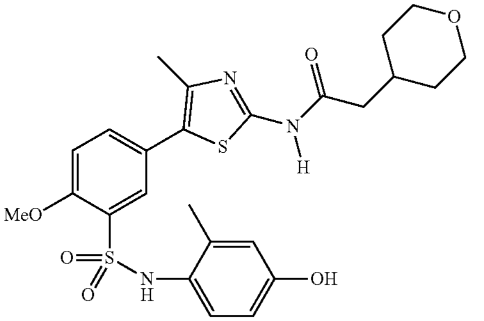 [SMILES: COc1ccc(-c2sc(NC(=O)CC3CCOCC3)nc2C)cc1S(=O)(=O)Nc1ccc(O)cc1C] | N-[5-[3-[(4-hydroxy-2-methyl-phenyl)sulfamoyl]-4-methoxy-phenyl]-4-methyl-thiazol-2-yl]-2-tetrahydropyran-4-yl-acetamide |

TABLE 1-continued

| Compounds | | |
|---|---|---|
| Compound | Structure | Name |
| S-232 | 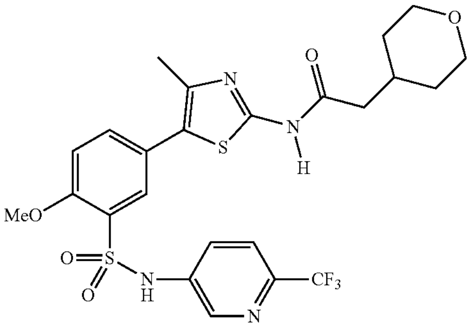 [SMILES: COc1ccc(-c2sc(NC(=O)CC3CCOCC3)nc2C)cc1S(=O)(=O)Nc1ccc(C(F)(F)F)nc1] | N-[5-[4-methoxy-3-[[6-(trifluoromethyl)-3-pyridyl]sulfamoyl]phenyl]-4-methyl-thiazol-2-yl]-2-tetrahydropyran-4-yl-acetamide |
| S-233 | 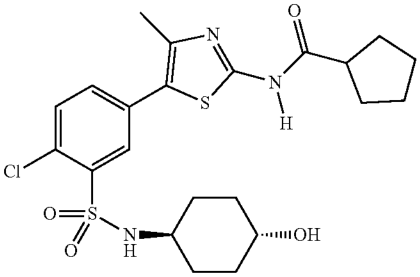 [SMILES: Cc1nc(NC(=O)C2CCCC2)sc1-c1ccc(Cl)c(S(=O)(=O)N[C@H]2CC[C@H](O)CC2)c1] | N-[5-[4-chloro-3-[(4-hydroxycyclohexyl)sulfamoyl]phenyl]-4-methyl-thiazol-2-yl]cyclopentanecarboxamide |
| S-234 | 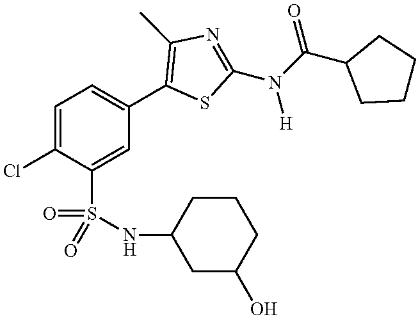 [SMILES: Cc1nc(NC(=O)C2CCCC2)sc1-c1ccc(Cl)c(S(=O)(=O)NC2CCCC(O)C2)c1] | N-[5-[4-chloro-3-[(3-hydroxycyclohexyl)sulfamoyl]phenyl]-4-methyl-thiazol-2-yl]cyclopentanecarboxamide |
| S-235 | 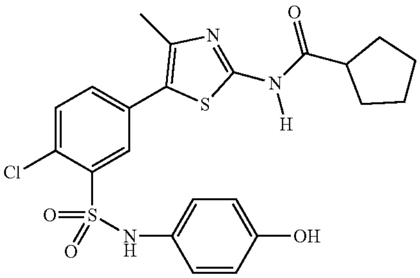 [SMILES: Cc1nc(NC(=O)C2CCCC2)sc1-c1ccc(Cl)c(S(=O)(=O)Nc2ccc(O)cc2)c1] | N-[5-[4-chloro-3-[(4-hydroxyphenyl)sulfamoyl]phenyl]-4-methyl-thiazol-2-yl]cyclopentanecarboxamide |
| S-236 | 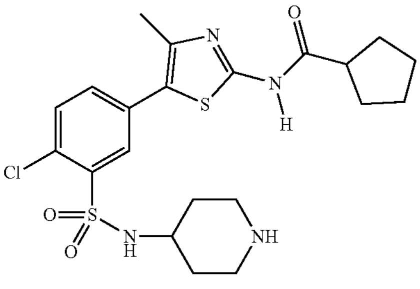 [SMILES: Cc1nc(NC(=O)C2CCCC2)sc1-c1ccc(Cl)c(S(=O)(=O)NC2CCNCC2)c1] | N-[5-[4-chloro-3-(4-piperidylsulfamoyl)phenyl]-4-methyl-thiazol-2-yl]cyclopentanecarboxamide |

TABLE 1-continued

| Compounds | | |
|---|---|---|
| Compound | Structure | Name |
| S-237 | 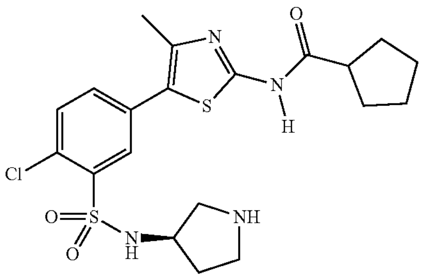 [SMILES: Cc1nc(NC(=O)C2CCCC2)sc1-c1ccc(Cl)c(S(=O)(=O)N[C@@H]2CCNC2)c1] | N-[5-[4-chloro-3-[[(3R)-pyrrolidin-3-yl]sulfamoyl]phenyl]-4-methyl-thiazol-2-yl]cyclopentanecarboxamide |
| S-238 | 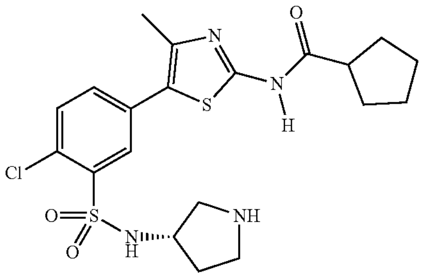 [SMILES: Cc1nc(NC(=O)C2CCCC2)sc1-c1ccc(Cl)c(S(=O)(=O)N[C@H]2CCNC2)c1] | N-[5-[4-chloro-3-[[(3S)-pyrrolidin-3-yl]sulfamoyl]phenyl]-4-methyl-thiazol-2-yl]cyclopentanecarboxamide |
| S-239 | 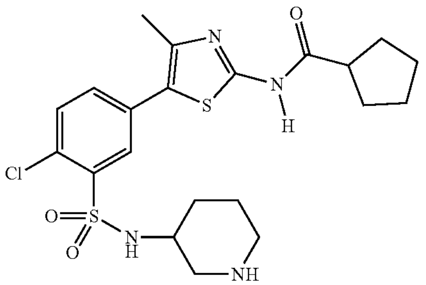 [SMILES: Cc1nc(NC(=O)C2CCCC2)sc1-c1ccc(Cl)c(S(=O)(=O)NC2CCCNC2)c1] | N-[5-[4-chloro-3-(3-piperidylsulfamoyl)phenyl]-4-methyl-thiazol-2-yl]cyclopentanecarboxamide |
| S-240 | 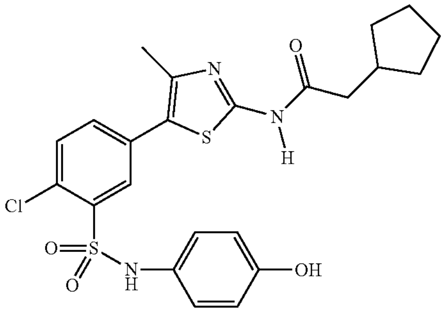 [SMILES: Cc1nc(NC(=O)CC2CCCC2)sc1-c1ccc(Cl)c(S(=O)(=O)Nc2ccc(O)cc2)c1] | N-[5-[4-chloro-3-[(4-hydroxyphenyl)sulfamoyl]phenyl]-4-methyl-thiazol-2-yl]-2-cyclopentyl-acetamide |
| S-241 | 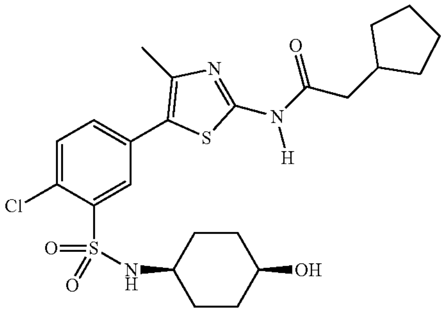 [SMILES: Cc1nc(NC(=O)CC2CCCC2)sc1-c1ccc(Cl)c(S(=O)(=O)N[C@H]2CC[C@@H](O)CC2)c1] | N-[5-[4-chloro-3-[(4-hydroxycyclohexyl)sulfamoyl]phenyl]-4-methyl-thiazol-2-yl]-2-cyclopentyl-acetamide |

TABLE 1-continued

| Compounds | | |
|---|---|---|
| Compound | Structure | Name |
| S-242 | 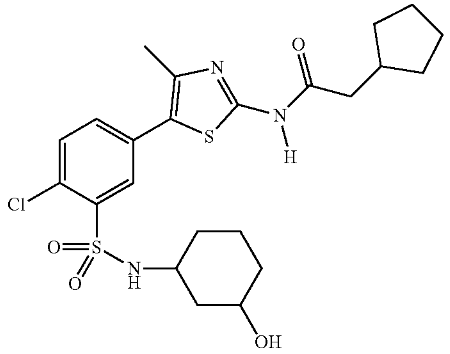 [SMILES: Cc1nc(NC(=O)CC2CCCC2)sc1-c1ccc(Cl)c(S(=O)(=O)NC2CCCC(O)C2)c1] | N-[5-[4-chloro-3-[(3-hydroxycyclohexyl)sulfamoyl]phenyl]-4-methyl-thiazol-2-yl]-2-cyclopentyl-acetamide |
| S-243 | 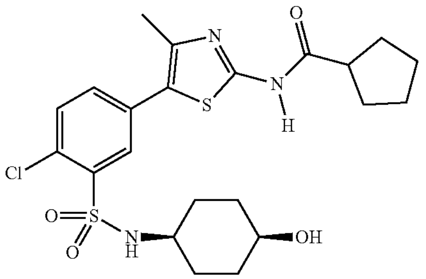 [SMILES: Cc1nc(NC(=O)C2CCCC2)sc1-c1ccc(Cl)c(S(=O)(=O)N[C@H]2CC[C@@H](O)CC2)c1] | N-[5-[4-chloro-3-[(4-hydroxycyclohexyl)sulfamoyl]phenyl]-4-methyl-thiazol-2-yl]cyclopentanecarboxamide |
| S-244 | 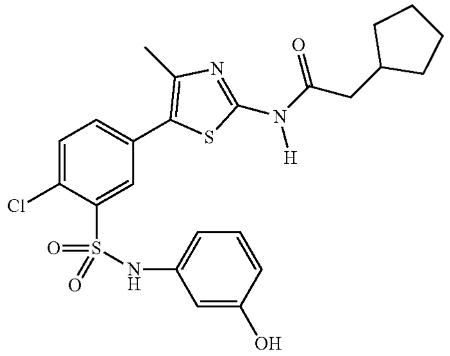 [SMILES: Cc1nc(NC(=O)CC2CCCC2)sc1-c1ccc(Cl)c(S(=O)(=O)Nc2cccc(O)c2)c1] | N-[5-[4-chloro-3-[(3-hydroxyphenyl)sulfamoyl]phenyl]-4-methyl-thiazol-2-yl]-2-cyclopentyl-acetamide |
| S-245 | 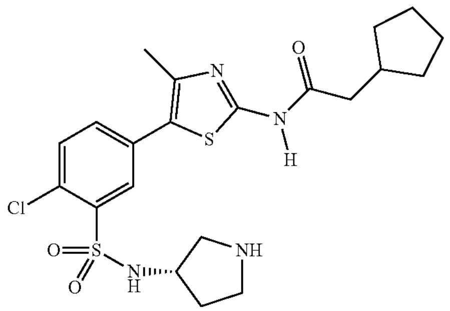 [SMILES: Cc1nc(NC(=O)CC2CCCC2)sc1-c1ccc(Cl)c(S(=O)(=O)N[C@H]2CCNC2)c1] | N-[5-[4-chloro-3-[[(3S)-pyrrolidin-3-yl]sulfamoyl]phenyl]-4-methyl-thiazol-2-yl]-2-cyclopentyl-acetamide; 2,2,2-trifluroroacetic acid |

TABLE 1-continued

| Compounds | | |
|---|---|---|
| Compound | Structure | Name |
| S-246 | 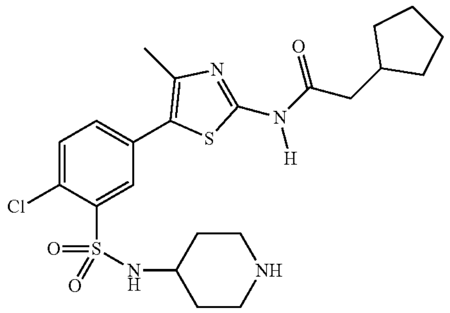 [SMILES: Cc1nc(NC(=O)CC2CCCC2)sc1-c1ccc(Cl)c(S(=O)(=O)NC2CCNCC2)c1] | N-[5-[4-chloro-3-(4-piperidylsulfamoyl)phenyl]-4-methyl-thiazol-2-yl]-2-cyclopentyl-acetamide |
| S-247 | 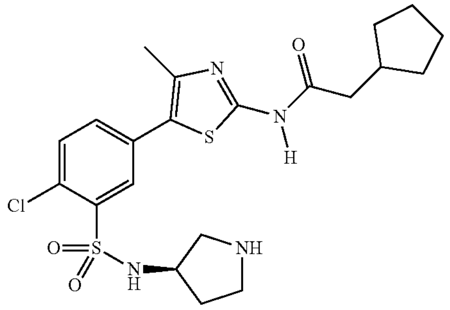 [SMILES: Cc1nc(NC(=O)CC2CCCC2)sc1-c1ccc(Cl)c(S(=O)(=O)N[C@@H]2CCNC2)c1] | N-[5-[4-chloro-3-[[(3R)-pyrrolidin-3-yl]sulfamoyl]phenyl]-4-methyl-thiazol-2-yl]-2-cyclopentyl-acetamide |
| S-248 | 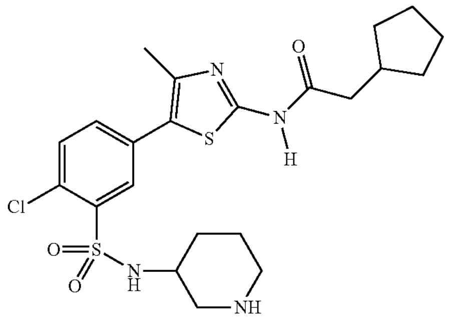 [SMILES: Cc1nc(NC(=O)CC2CCCC2)sc1-c1ccc(Cl)c(S(=O)(=O)NC2CCCNC2)c1] | N-[5-[4-chloro-3-(3-piperidylsulfamoyl)phenyl]-4-methyl-thiazol-2-yl]-2-cyclopentyl-acetamide |
| S-249 | 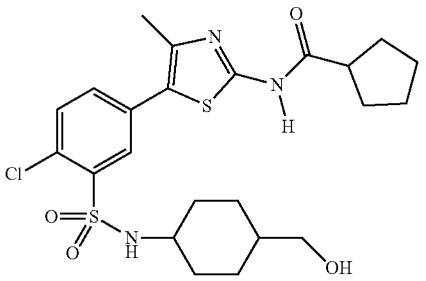 [SMILES: Cc1nc(NC(=O)C2CCCC2)sc1-c1ccc(Cl)c(S(=O)(=O)NC2CCC(CO)CC2)c1] | N-[5-[4-chloro-3-[[4-(hydroxymethyl)cyclohexyl]sulfamoyl]phenyl]-4-methyl-thiazol-2-yl]cyclopentanecarboxamide |
| S-250 | 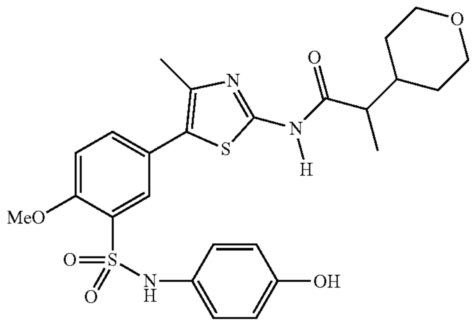 [SMILES: COc1ccc(-c2sc(NC(=O)C(C)C3CCOCC3)nc2C)cc1S(=O)(=O)Nc1ccc(O)cc1] | N-[5-[3-[(4-hydroxyphenyl)sulfamoyl]-4-methoxy-phenyl]-4-methyl-thiazol-2-yl]-2-tetrahydropyran-4-yl-propanamide |

TABLE 1-continued

| Compounds | | |
|---|---|---|
| Compound | Structure | Name |
| S-251 | 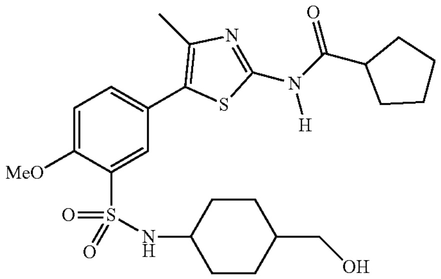 [SMILES: COc1ccc(-c2sc(NC(=O)C3CCCC3)nc2C)cc1S(=O)(=O)NC1CCC(CO)CC1] | N-[5-[3-[[4-(hydroxymethyl)cyclohexyl]sulfamoyl]-4-methoxy-phenyl]-4-methyl-thiazol-2-yl]cyclopentanecarboxamide |
| S-252 | 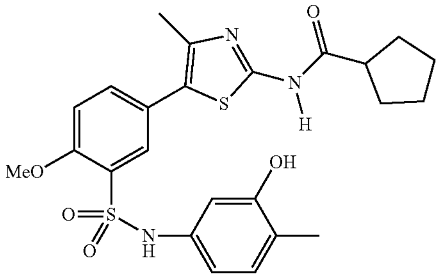 [SMILES: COc1ccc(-c2sc(NC(=O)C3CCCC3)nc2C)cc1S(=O)(=O)Nc1ccc(C)c(O)c1] | N-[5-[3-[(3-hydroxy-4-methyl-phenyl)sulfamoyl]-4-methoxy-phenyl]-4-methyl-thiazol-2-yl]cyclopentanecarboxamide |
| S-253 | 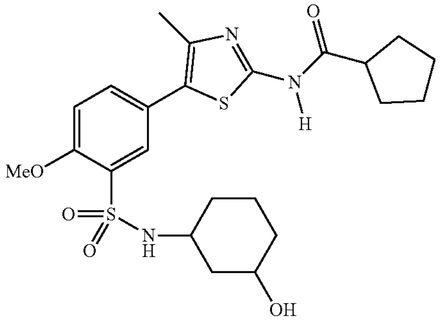 [SMILES: COc1ccc(-c2sc(NC(=O)C3CCCC3)nc2C)cc1S(=O)(=O)NC1CCCC(O)C1] | N-[5-[3-[(3-hydroxycyclohexyl)sulfamoyl]-4-methoxy-phenyl]-4-methyl-thiazol-2-yl]cyclopentanecarboxamide |
| S-254 | 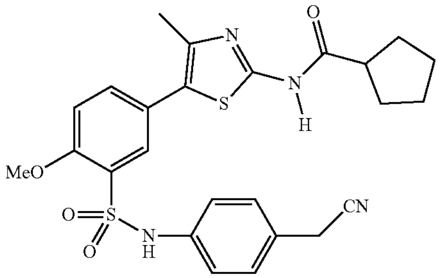 [SMILES: COc1ccc(-c2sc(NC(=O)C3CCCC3)nc2C)cc1S(=O)(=O)Nc1ccc(CC#N)cc1] | N-[5-[3-[[4-(cyanomethyl)phenyl]sulfamoyl]-4-methoxy-phenyl]-4-methyl-thiazol-2-yl]cyclopentanecarboxamide |
| S-255 | 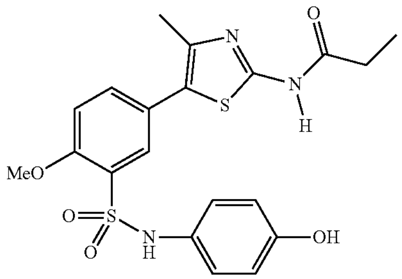 [SMILES: CCC(=O)Nc1nc(C)c(-c2ccc(OC)c(S(=O)(=O)Nc3ccc(O)cc3)c2)s1] | N-[5-[3-[(4-hydroxyphenyl)sulfamoyl]-4-methoxy-phenyl]-4-methyl-thiazol-2-yl]propanamide |

TABLE 1-continued
| Compounds | | |
|---|---|---|
| Compound | Structure | Name |
| S-256 | 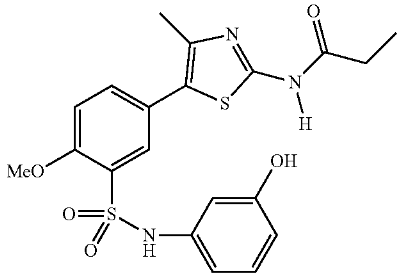 [SMILES: CCC(=O)Nc1nc(C)c(-c2ccc(OC)c(S(=O)(=O)Nc3cccc(O)c3)c2)s1] | N-[5-[3-[(3-hydroxyphenyl)sulfamoyl]-4-methoxy-phenyl]-4-methyl-thiazol-2-yl]propanamide |
| S-257 | 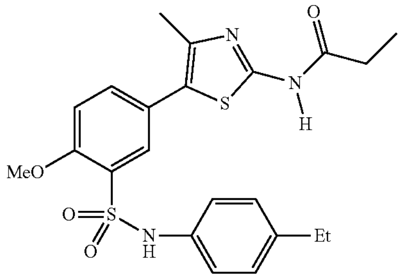 [SMILES: CCC(=O)Nc1nc(C)c(-c2ccc(OC)c(S(=O)(=O)Nc3ccc(CC)cc3)c2)s1] | N-[5-[3-[(4-ethylphenyl)sulfamoyl]-4-methoxy-phenyl]-4-methyl-thiazol-2-yl]propanamide |
| S-258 | 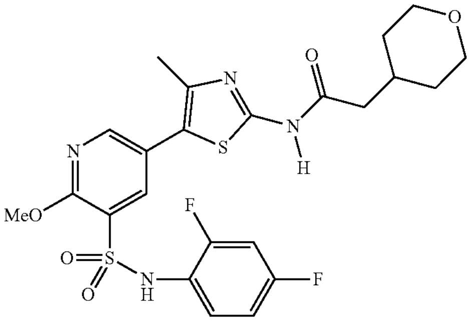 [SMILES: COc1ncc(-c2sc(NC(=O)CC3CCOCC3)nc2C)cc1S(=O)(=O)Nc1ccc(F)cc1F] | |
| S-259 | 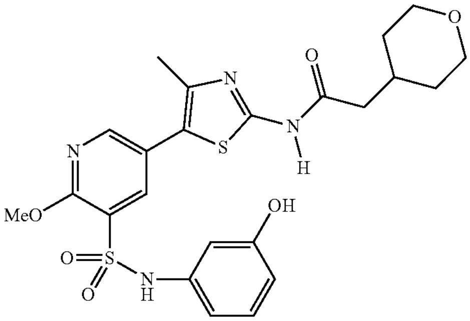 [SMILES: COc1ncc(-c2sc(NC(=O)CC3CCOCC3)nc2C)cc1S(=O)(=O)Nc1cccc(O)c1] | |
| S-260 | 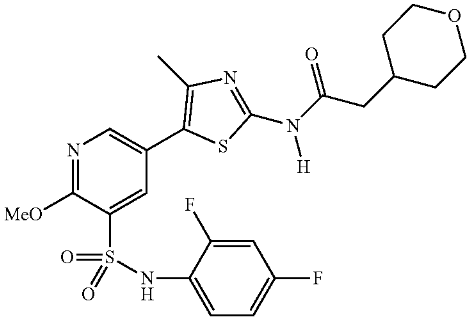 [SMILES: COc1ncc(-c2sc(NC(=O)CC3CCOCC3)nc2C)cc1S(=O)(=O)Nc1ccc(F)cc1F] | |

TABLE 1-continued
| Compounds | | |
|---|---|---|
| Compound | Structure | Name |
| S-261 | 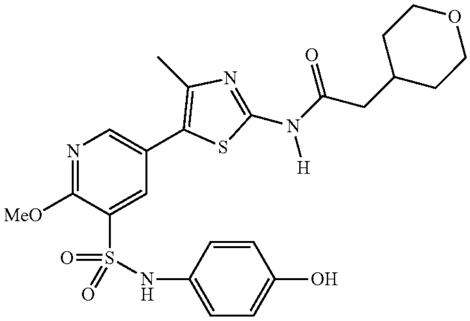 [SMILES: COc1ncc(-c2sc(NC(=O)CC3CCOCC3)nc2C)cc1S(=O)(=O)Nc1ccc(O)cc1] | |
| S-262 | 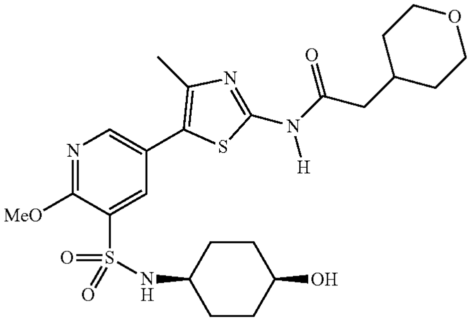 [SMILES: COc1ncc(-c2sc(NC(=O)CC3CCOCC3)nc2C)cc1S(=O)(=O)N[C@H]1CC[C@@H](O)CC1] | |
| S-263 | 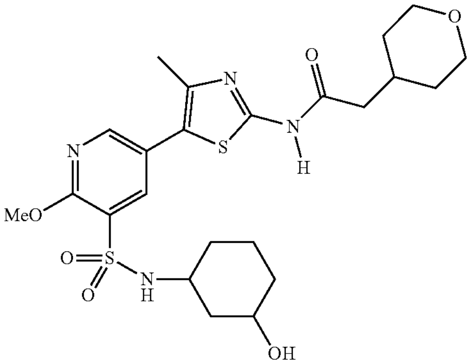 [SMILES: COc1ncc(-c2sc(NC(=O)CC3CCOCC3)nc2C)cc1S(=O)(=O)NC1CCCC(O)C1] | |
| S-264 | 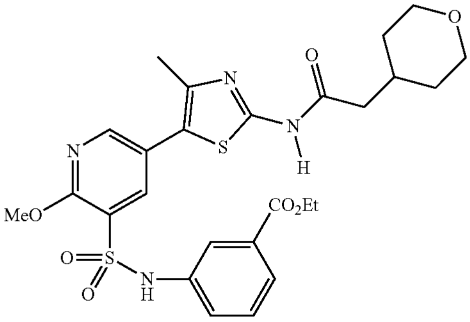 [SMILES: CCOC(=O)c1cccc(NS(=O)(=O)c2cc(-c3sc(NC(=O)CC4CCOCC4)nc3C)cnc2OC)c1] | |

TABLE 1-continued
| Compounds | | |
| --- | --- | --- |
| Compound | Structure | Name |
| S-265 | 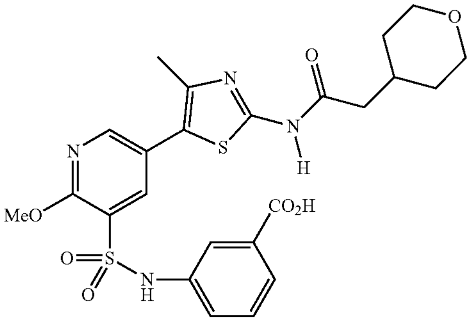 [SMILES: COc1ncc(-c2sc(NC(=O)CC3CCOCC3)nc2C)cc1S(=O)(=O)Nc1cccc(C(=O)O)c1] | |
| S-266 | 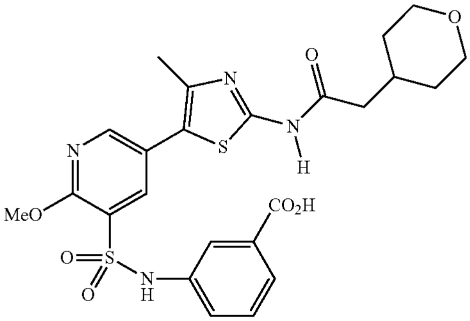 [SMILES: COc1ncc(-c2sc(NC(=O)CC3CCOCC3)nc2C)cc1S(=O)(=O)Nc1cccc(C(=O)O)c1] | |
| S-267 | 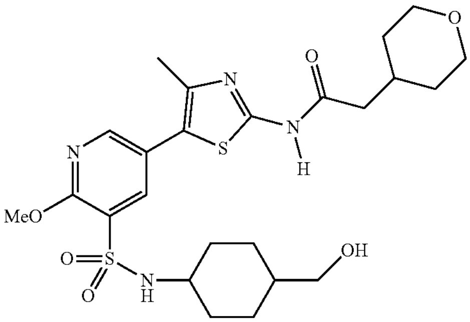 [SMILES: COc1ncc(-c2sc(NC(=O)CC3CCOCC3)nc2C)cc1S(=O)(=O)NC1CCC(CO)CC1] | |
| S-268 | 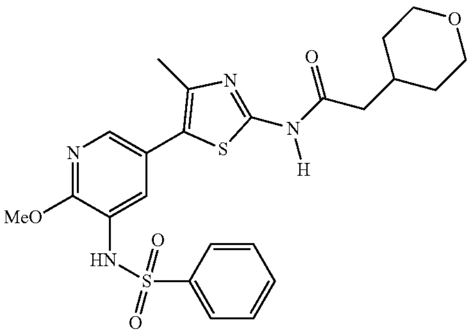 [SMILES: COc1ncc(-c2sc(NC(=O)CC3CCOCC3)nc2C)cc1NS(=O)(=O)c1ccccc1] | |

TABLE 1-continued
| Compounds | | |
|---|---|---|
| Compound | Structure | Name |
| S-269 | 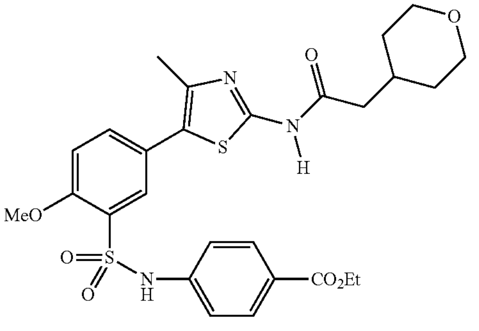 [SMILES: CCOC(=O)c1ccc(NS(=O)(=O)c2cc(-c3sc(NC(=O)CC4CCOCC4)nc3C)ccc2OC)cc1] | |
| S-270 | 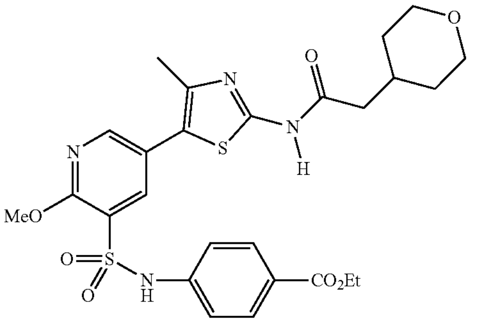 [SMILES: CCOC(=O)c1ccc(NS(=O)(=O)c2cc(-c3sc(NC(=O)CC4CCOCC4)nc3C)cnc2OC)cc1] | |
| S-271 | 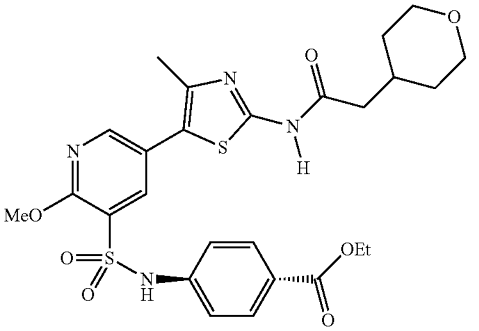 | |
| S-272 | 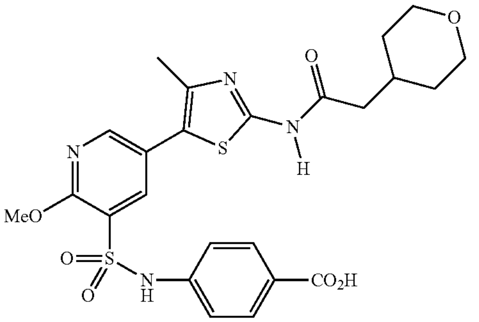 [SMILES: COc1ncc(-c2sc(NC(=O)CC3CCOCC3)nc2C)cc1S(=O)(=O)Nc1ccc(C(=O)O)cc1] | |

TABLE 1-continued

| Compounds | | |
|---|---|---|
| Compound | Structure | Name |
| S-273 | 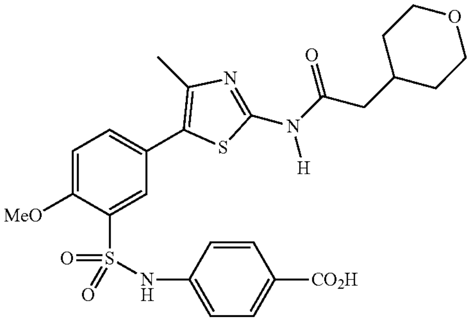 [SMILES: COc1ccc(-c2sc(NC(=O)CC3CCOCC3)nc2C)cc1S(=O)(=O)Nc1ccc(C(=O)O)cc1] | 4-(2-methoxy-5-(4-methyl-2-(2-(tetrahydro-2H-pyran-4-yl)acetamido)thiazol-5-yl)phenylsulfonamido)benzoic acid |
| S-274 | 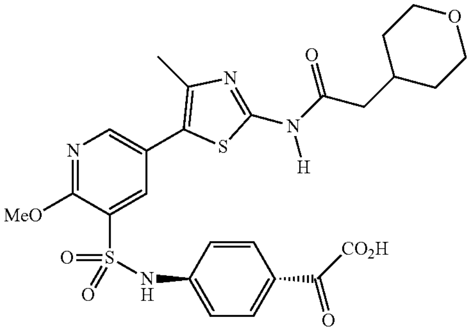 | 2-((1r,4r)-4-(2-methoxy-5-(4-methyl-2-(2-(tetrahydro-2H-pyran-4-yl)acetamido)thiazol-5-yl)pyridine-3-sulfonamido)cyclohexyl)-2-oxoacetic acid |
| S-275 | 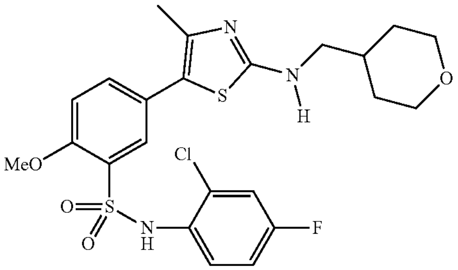 [SMILES: COc1ccc(-c2sc(NCC3CCOCC3)nc2C)cc1S(=O)(=O)Nc1ccc(F)cc1Cl] | N-(2-chloro-4-fluoro-phenyl)-2-methoxy-5-[2-methyl-2-(tetrahydropyran-4-ylmethylamino)thiazol-5-yl]benzenesulfonamide |
| S-276 | 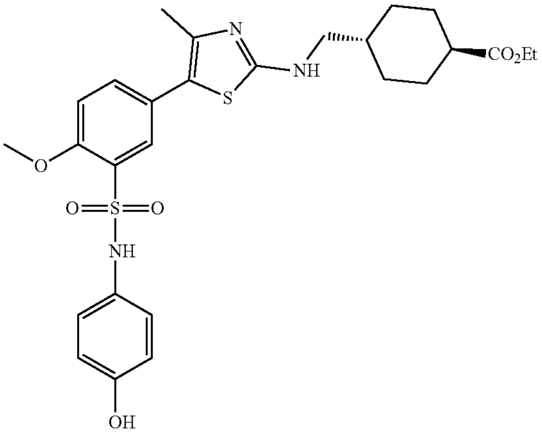 | 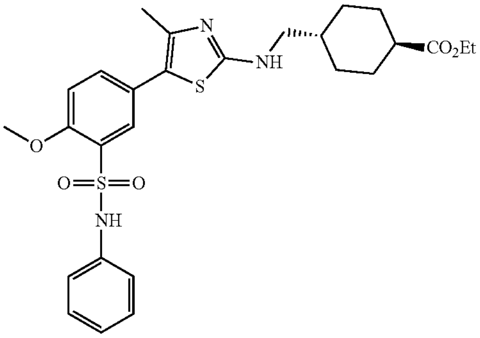 [SMILES: CCOC(=O)[C@H]1CC[C@H](CNc2nc(C)c(-c3ccc(OC)c(S(=O)(=O)Nc4ccccc4)c3)s2)CC1] |

TABLE 1-continued
| Compounds | | |
|---|---|---|
| Compound | Structure | Name |
| S-277 | 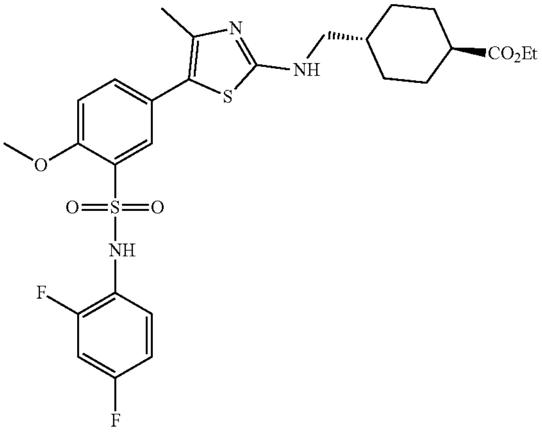 | |
| S-278 | 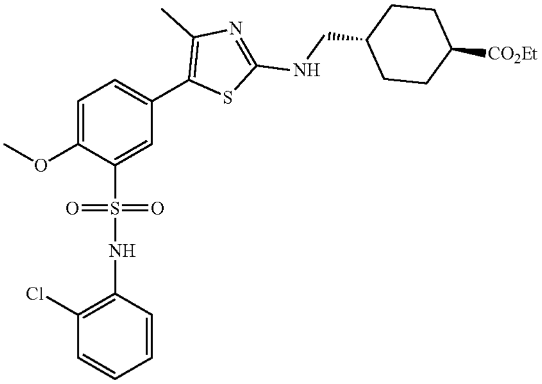 [SMILES: CCOC(=O)[C@H]1CC[C@H](CNc2nc(C)c(-c3ccc(OC)c(S(=O)(=O)Nc4ccccc4Cl)c3)s2)CC1] | |
| S-279 | 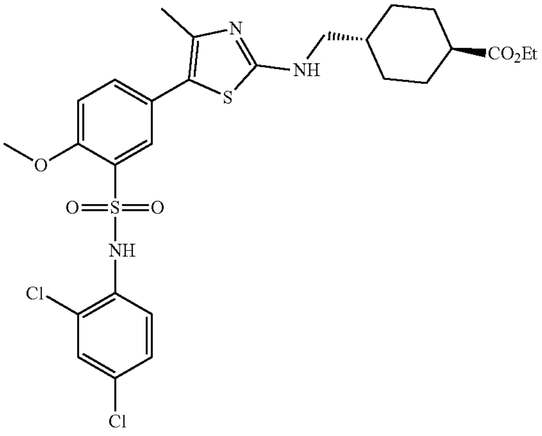 [SMILES: CCOC(=O)[C@H]1CC[C@H](CNc2nc(C)c(-c3ccc(OC)c(S(=O)(=O)Nc4ccc(Cl)cc4Cl)c3)s2)CC1] | |

TABLE 1-continued
| Compounds | | |
|---|---|---|
| Compound | Structure | Name |
| S-280 | 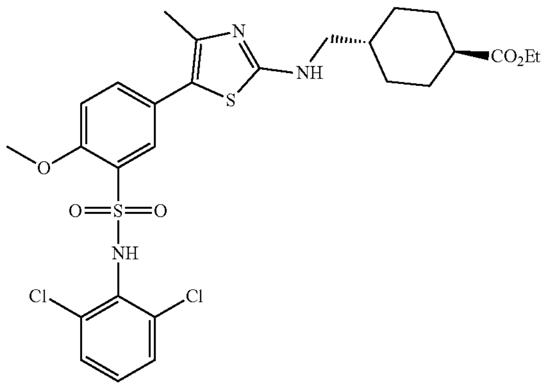 [SMILES: CCOC(=O)[C@H]1CC[C@H](CNc2nc(C)c(-c3ccc(OC)c(S(=O)(=O)Nc4c(Cl)cccc4Cl)c3)s2)CC1] | |
| S-281 | 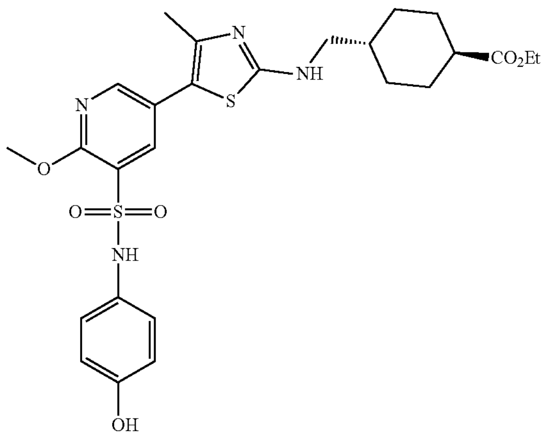 [SMILES: CCOC(=O)[C@H]1CC[C@H](CNc2nc(C)c(-c3cnc(OC)c(S(=O)(=O)Nc4ccc(O)cc4)c3)s2)CC1] | |
| S-282 | 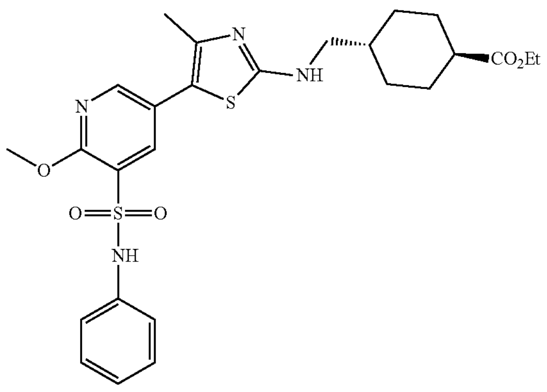 [SMILES: CCOC(=O)[C@H]1CC[C@H](CNc2nc(C)c(-c3cnc(OC)c(S(=O)(=O)Nc4ccccc4)c3)s2)CC1] | |

TABLE 1-continued
| Compounds | | |
|---|---|---|
| Compound | Structure | Name |
| S-283 | 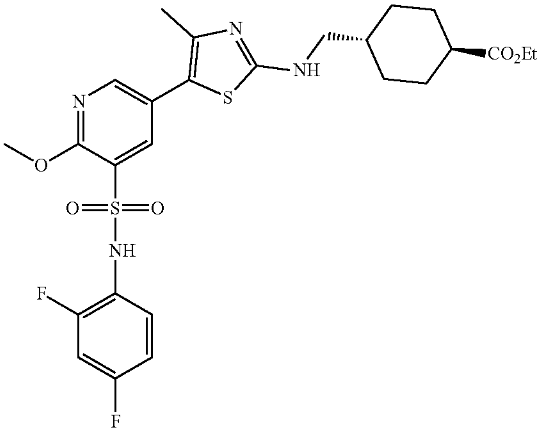 [SMILES: CCOC(=O)[C@H]1CC[C@H](CNc2nc(C)c(-c3cnc(OC)c(S(=O)(=O)Nc4ccc(F)cc4F)c3)s2)CC1] | |
| S-284 | 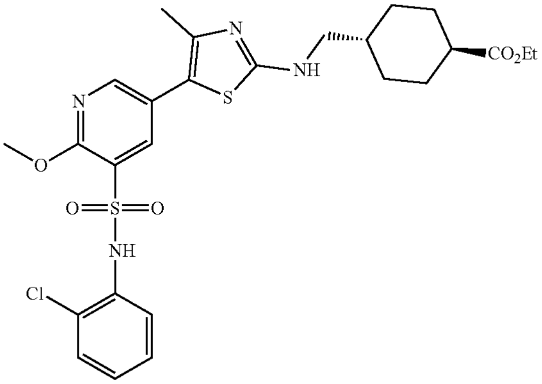 [SMILES: CCOC(=O)[C@H]1CC[C@H](CNc2nc(C)c(-c3cnc(OC)c(S(=O)(=O)Nc4ccccc4Cl)c3)s2)CC1] | |
| S-285 | 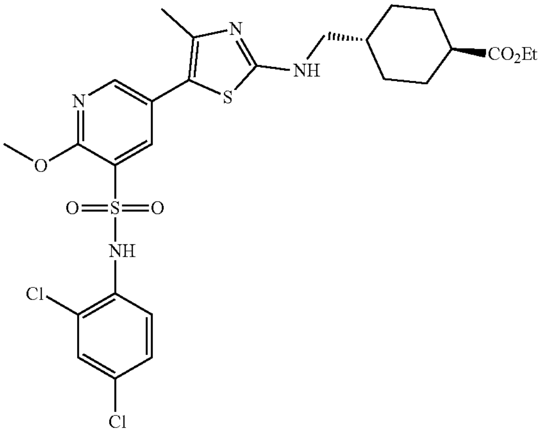 [SMILES: CCOC(=O)[C@H]1CC[C@H](CNc2nc(C)c(-c3cnc(OC)c(S(=O)(=O)Nc4ccc(Cl)cc4Cl)c3)s2)CC1] | |

TABLE 1-continued
| Compounds | | |
|---|---|---|
| Compound | Structure | Name |
| S-286 | 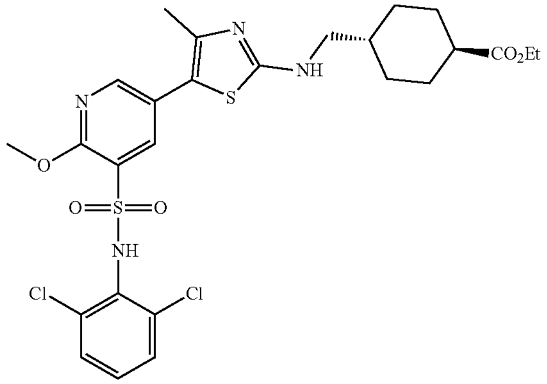 [SMILES: CCOC(=O)[C@H]1CC[C@H](CNc2nc(C)c(-c3cnc(OC)c(S(=O)(=O)Nc4c(Cl)cccc4Cl)c3)s2)CC1] | |
| S-287 | 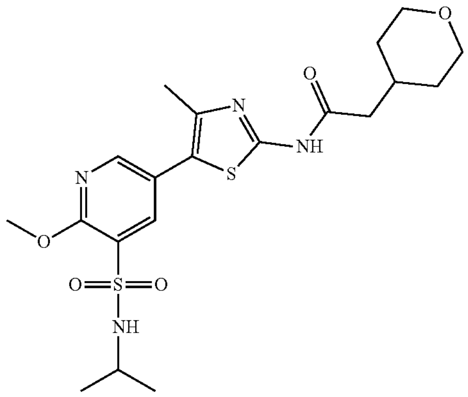 [SMILES: COc1ncc(-c2sc(NC(=O)CC3CCOCC3)nc2C)cc1S(=O)(=O)NC(C)C] | |
| S-288 | 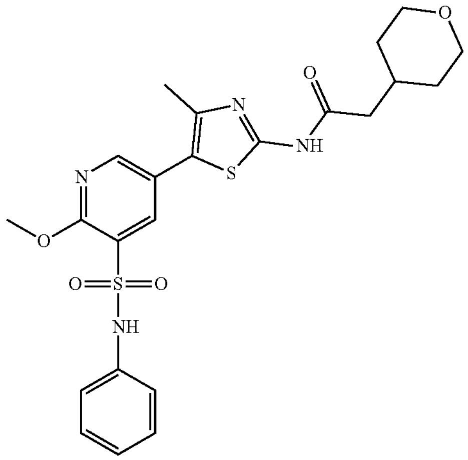 [SMILES: COc1ncc(-c2sc(NC(=O)CC3CCOCC3)nc2C)cc1S(=O)(=O)Nc1ccccc1] | |

TABLE 1-continued
| Compounds | | |
|---|---|---|
| Compound | Structure | Name |
| S-289 | 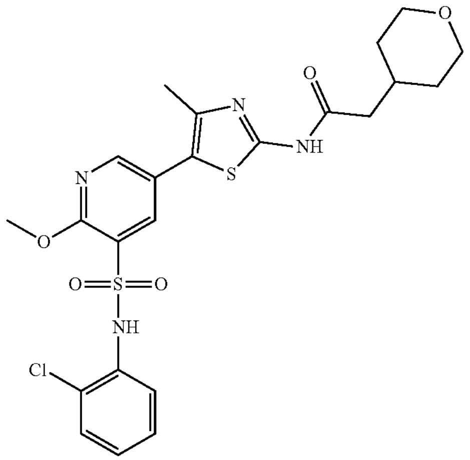 [SMILES: COc1ncc(-c2sc(NC(=O)CC3CCOCC3)nc2C)cc1S(=O)(=O)Nc1ccccc1Cl] | |
| S-290 | 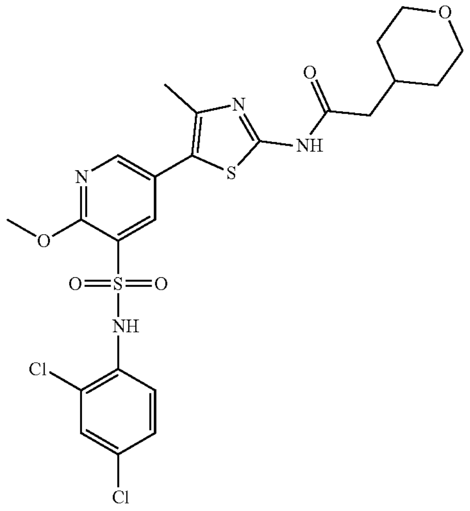 [SMILES: COc1ncc(-c2sc(NC(=O)CC3CCOCC3)nc2C)cc1S(=O)(=O)Nc1ccc(Cl)cc1Cl] | |
| S-291 | 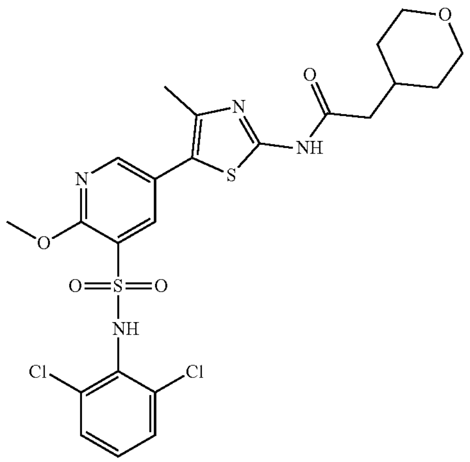 [SMILES: COc1ncc(-c2sc(NC(=O)CC3CCOCC3)nc2C)cc1S(=O)(=O)Nc1c(Cl)cccc1Cl] | |

TABLE 1-continued
| Compounds | | |
|---|---|---|
| Compound | Structure | Name |
| S-292 | 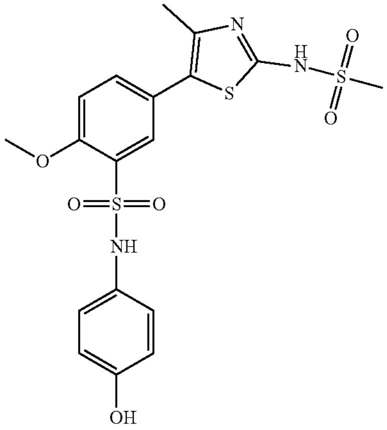 | |
| S-293 | 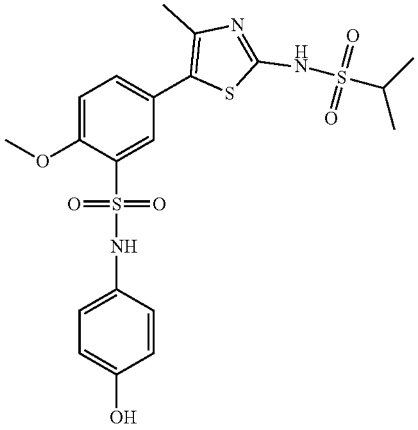 [SMILES: COc1ccc(-c2sc(NS(=O)(=O)C(C)C)nc2C)cc1S(=O)(=O)Nc1ccc(O)cc1] | |
| S-294 | 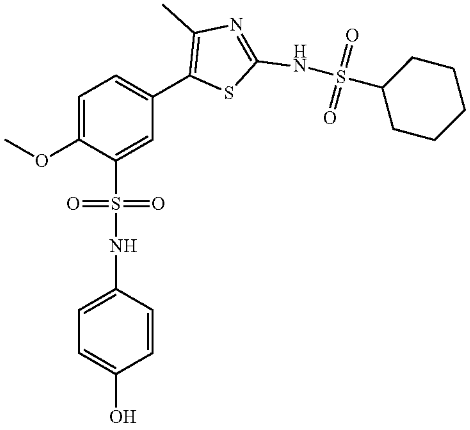 [SMILES: COc1ccc(-c2sc(NS(=O)(=O)C3CCCCC3)nc2C)cc1S(=O)(=O)Nc1ccc(O)cc1] | 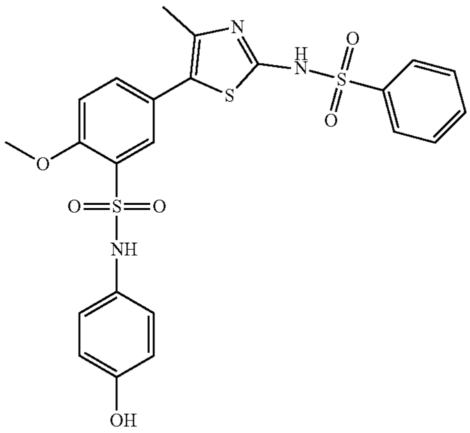 [SMILES: COc1ccc(-c2sc(NS(=O)(=O)c3ccccc3)nc2C)cc1S(=O)(=O)Nc1ccc(O)cc1] |

TABLE 1-continued
| Compounds | | |
|---|---|---|
| Compound | Structure | Name |
| S-295 | 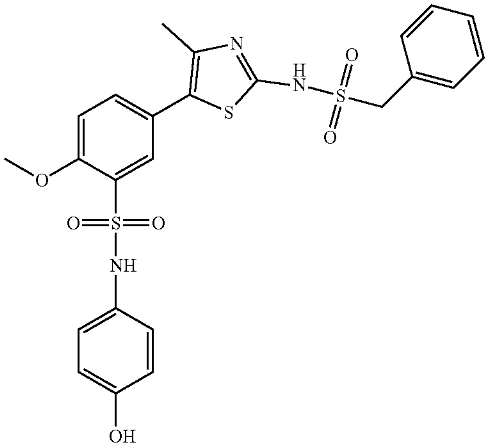 [SMILES: COc1ccc(-c2sc(NS(=O)(=O)Cc3ccccc3)nc2C)cc1S(=O)(=O)Nc1ccc(O)cc1] | |
| S-296 | 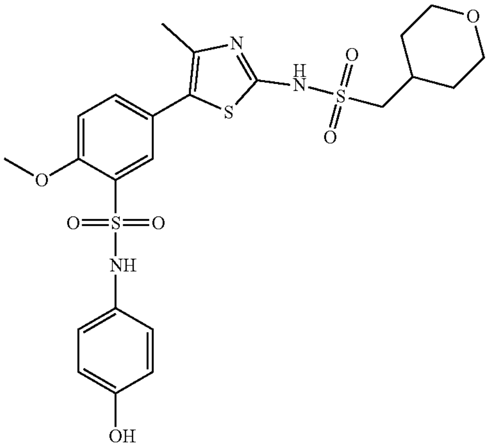 [SMILES: COc1ccc(-c2sc(NS(=O)(=O)CC3CCOCC3)nc2C)cc1S(=O)(=O)Nc1ccc(O)cc1] | |
| S-297 | 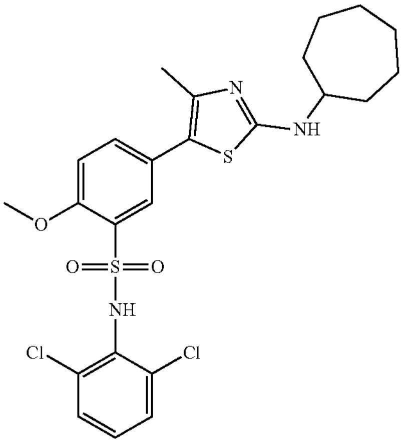 [SMILES: COc1ccc(-c2sc(NC3CCCCCC3)nc2C)cc1S(=O)(=O)Nc1c(Cl)cccc1Cl] | |

TABLE 1-continued
| Compounds | | |
|---|---|---|
| Compound | Structure | Name |
| S-298 | 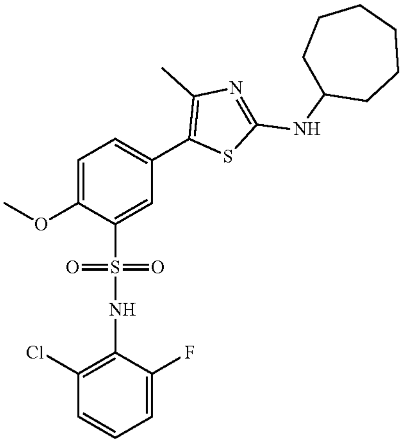 [SMILES: COc1ccc(-c2sc(NC3CCCCCC3)nc2C)cc1S(=O)(=O)Nc1c(F)cccc1Cl] | |
| S-299 | 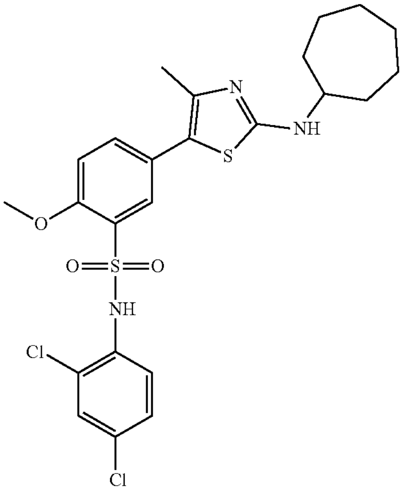 [SMILES: COc1ccc(-c2sc(NC3CCCCCC3)nc2C)cc1S(=O)(=O)Nc1ccc(Cl)cc1Cl] | |
| S-300 | 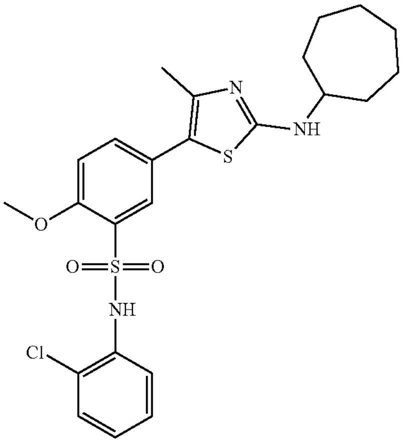 [SMILES: COc1ccc(-c2sc(NC3CCCCCC3)nc2C)cc1S(=O)(=O)Nc1ccccc1Cl] | |

TABLE 1-continued
| Compounds | | |
|---|---|---|
| Compound | Structure | Name |
| S-301 | 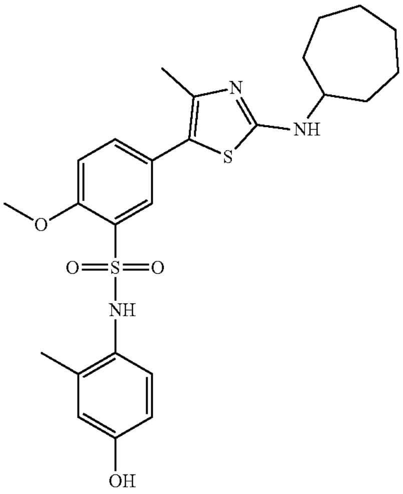 [SMILES: COc1ccc(-c2sc(NC3CCCCCC3)nc2C)cc1S(=O)(=O)Nc1ccc(O)cc1C] | |
| S-302 | 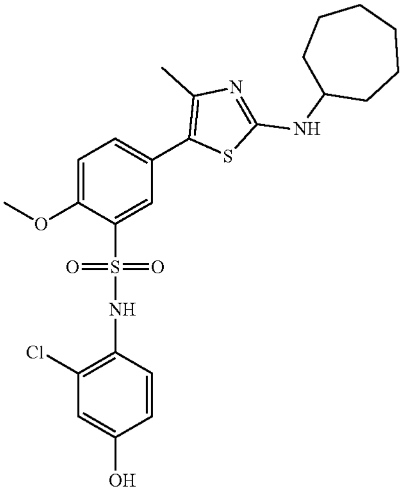 [SMILES: COc1ccc(-c2sc(NC3CCCCCC3)nc2C)cc1S(=O)(=O)Nc1ccc(O)cc1Cl] | |
| S-303 | 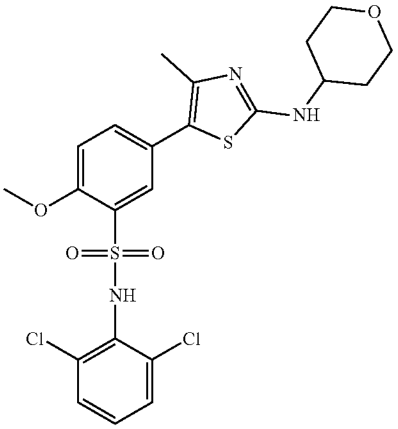 [SMILES: COc1ccc(-c2sc(NC3CCOCC3)nc2C)cc1S(=O)(=O)Nc1c(Cl)cccc1Cl] | |

TABLE 1-continued
| Compounds | | |
|---|---|---|
| Compound | Structure | Name |
| S-304 | 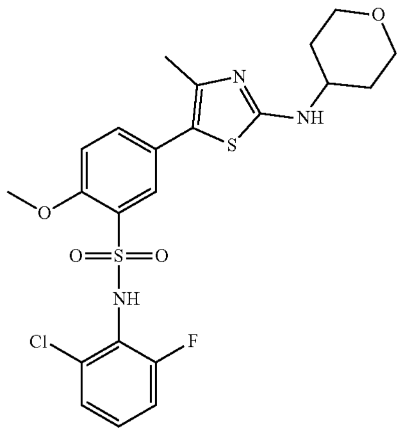 [SMILES: COc1ccc(-c2sc(NC3CCOCC3)nc2C)cc1S(=O)(=O)Nc1c(F)cccc1Cl] | |
| S-305 | 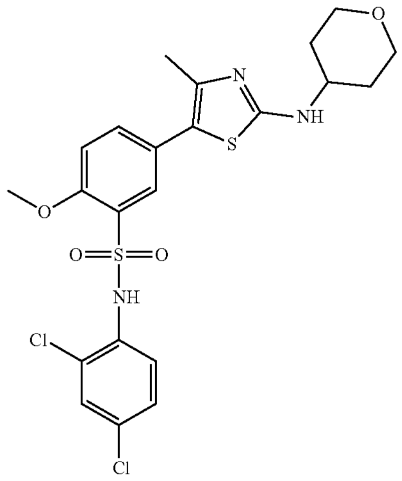 [SMILES: COc1ccc(-c2sc(NC3CCOCC3)nc2C)cc1S(=O)(=O)Nc1ccc(Cl)cc1Cl] | |
| S-306 | 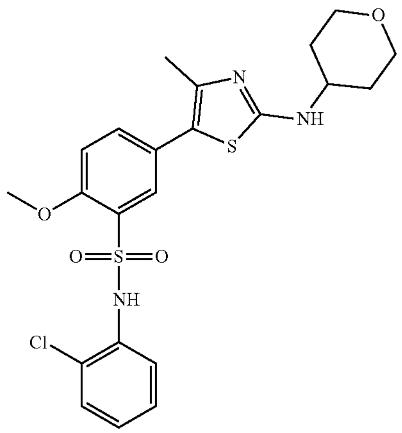 [SMILES: COc1ccc(-c2sc(NC3CCOCC3)nc2C)cc1S(=O)(=O)Nc1ccccc1Cl] | |

TABLE 1-continued
| Compounds | | |
|---|---|---|
| Compound | Structure | Name |
| S-307 | 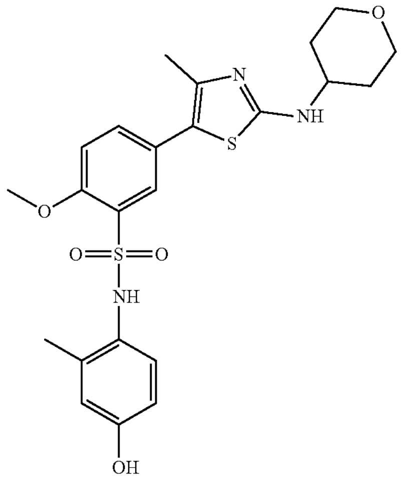 [SMILES: COc1ccc(-c2sc(NC3CCOCC3)nc2C)cc1S(=O)(=O)Nc1ccc(O)cc1C] | |
| S-308 | 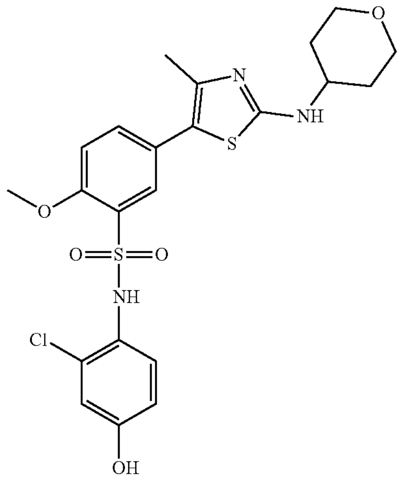 [SMILES: COc1ccc(-c2sc(NC3CCOCC3)nc2C)cc1S(=O)(=O)Nc1ccc(O)cc1Cl] | |
| S-309 | 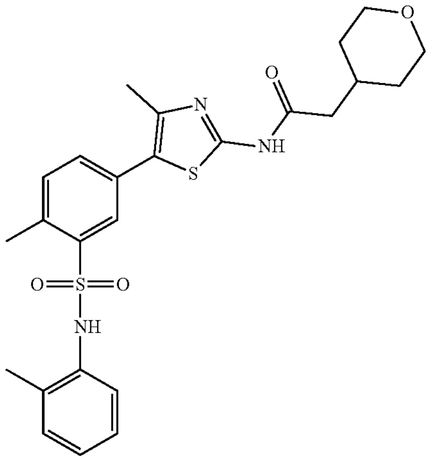 [SMILES: Cc1ccccc1NS(=O)(=O)c1cc(-c2sc(NC(=O)CC3CCOCC3)nc2C)ccc1C] | |

TABLE 1-continued
| Compounds | | |
|---|---|---|
| Compound | Structure | Name |
| S-310 | 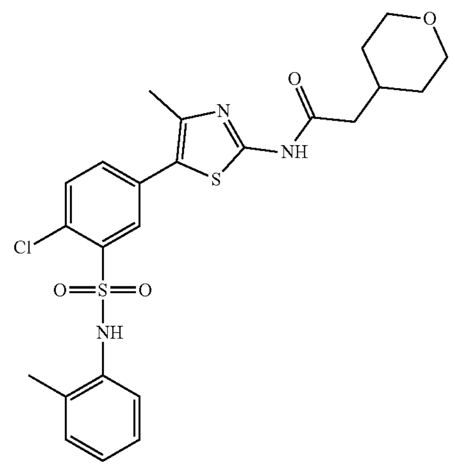 [SMILES: Cc1ccccc1NS(=O)(=O)c1cc(-c2sc(NC(=O)CC3CCOCC3)nc2C)ccc1Cl] | |
| S-311 | 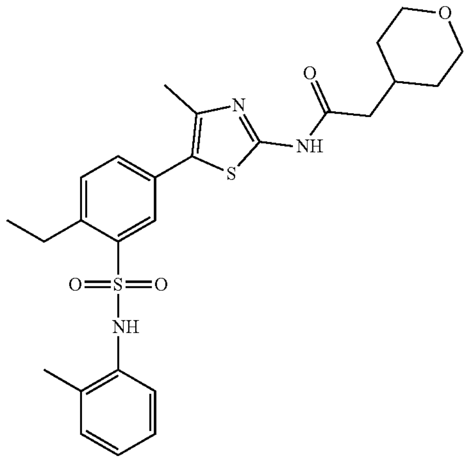 [SMILES: CCc1ccc(-c2sc(NC(=O)CC3CCOCC3)nc2C)cc1S(=O)(=O)Nc1ccccc1C] | |
| S-312 | 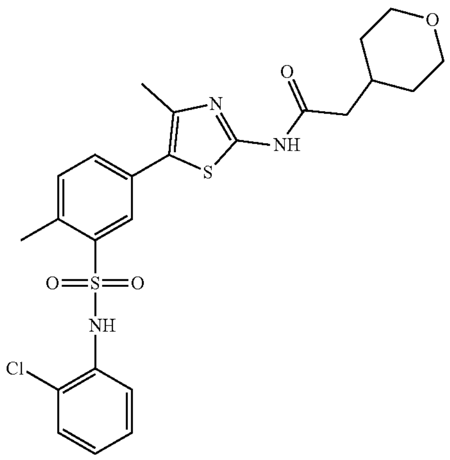 [SMILES: Cc1ccc(-c2sc(NC(=O)CC3CCOCC3)nc2C)cc1S(=O)(=O)Nc1ccccc1Cl] | |

TABLE 1-continued

| Compounds | | |
|---|---|---|
| Compound | Structure | Name |
| S-313 | 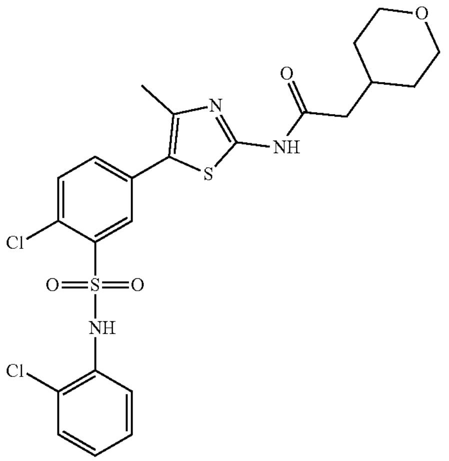 [SMILES: Cc1nc(NC(=O)CC2CCOCC2)sc1-c1ccc(Cl)c(S(=O)(=O)Nc2ccccc2Cl)c1] | |
| S-314 | 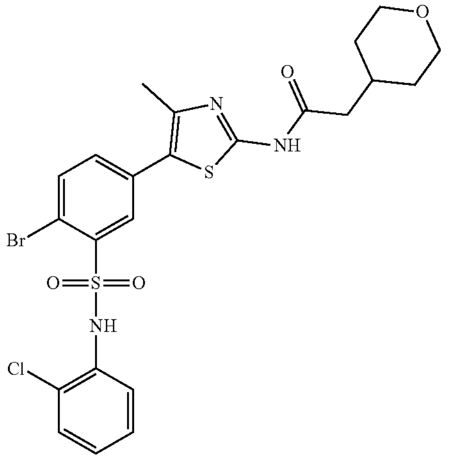 | |

In certain embodiments, the compound is described by the structure of one of the compounds of Table 1. It is understood that any of the compounds shown in Table 1 may be present in a salt form, such as a trifluoroacetate salt (e.g., $CF_3COOH$ salt). In some cases, the salt form of the compound is a pharmaceutically acceptable salt.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

PI-KINASE INHIBITION

As summarized above, aspects of the invention include PI4-kinase inhibiting compounds, and methods of inhibition using the same. The PI4-kinase inhibiting compounds are compounds that inhibit the activity of a PI4-kinase in a cell, upon contact with a cell or components thereof. In some instances, the types of cells in which the compounds of the invention exhibit activity are ones that have been infected with a pathogen, as described herein. By inhibiting a PI-kinase it is meant that the activity of the enzyme is decreased by a factor of 2 or more, such as 3 or more, 5 or more, 10 or more, 100 or more, or 1000 or more, relative to its normal activity (e.g., relative to a positive control).

In some embodiments, the subject compounds are inhibitors of a PI3-kinase. In some embodiments, the subject compounds are inhibitors of a PI4-kinase, such as a PI4-III-kinase (e.g., PI4-IIIα or PI4-IIIβ). In some embodiments, the subject compounds have a PI-kinase inhibition profile that reflects activity against two or more PI-kinases. In some embodiments, the subject compounds specifically inhibit both a type II PI3-kinase, such as PI3-kinase IIβ, and a type III PI4-kinase, such as PI4K-IIIα and/or PI4K-IIIβ). In some embodiments, the subject compounds specifically inhibit a PI4-kinase without undesired inhibition of protein kinases. In some embodiments, the subject compounds specifically inhibit a PI4-kinase without undesired inhibition of PI3-kinase. In some embodiments, the subject compounds specifically inhibit a PI4-kinase and/or a specific PI3-kinase subclass without undesired inhibition of other PI3-kinase subclasses or protein kinases.

In some embodiments, the compounds of the disclosure interfere with the interaction of a BAAPP domain with PIP2 in a pathogen (e.g., HCV). For example, the subject compounds may act by decreasing the levels of PIP2 either directly or indirectly that bind specifically to the BAAPP domain of the pathogen. In general, pathogens that include a BAAPP domain are susceptible to inhibition by the subject compounds.

In some embodiments, the subject compounds inhibit a PI4-kinase, as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 μM or less, such as 3 μM or less, 1 μM or less, 500 nM or less, 300 nM or less, 200nM or less, 100 nM or less, 50 nM or less, 30 nM or less, 10 nM or less, 5 nM or less, 3 nM or less, 1 nM or less, or even lower.

In some embodiments, the subject compounds inhibit a PI4-kinase, as determined by a kinase activity assay, e.g., by an assay that determines the level of incorporation of radiolabeled phosphate from [γ-$^{32}$P]-ATP into a substrate molecule after treatment with a subject compound, relative to a control, by measuring the beta-particle emission rate using a scintillation counter or phosphorimaging. In certain embodiments, the subject compounds have an $IC_{50}$ value for PI4K-IIIβ of less than about 1 μM, less than about 0.2 μM, less than about 0.1 μM, less than about 10 nM, less than about 1 nM, or even less, such as described in Tables 2-3. In certain embodiments, the subject compounds have an $IC_{50}$ value for PI4K-IIIα of less than about 50 μM, less than about 10 μM, less than about 1 μM, less than about 0.1 μM, less than about 10 nM, less than about 1 nM, or even less, such as described in Tables 2-3. In certain further embodiments, the subject compounds have an IC50 value for PI4K-IIIβ of 50 μM or less, [etc., etc.], 10 nM or less, 6 nM or less, or even less, such as described in Tables 2-3. In certain further embodiments, the subject compounds have an IC50 value for the PI3-kinase p110α-p85 complex of between about 8 and about 10 nM, between about 8 μM and about 10 μM, or even more. In certain further embodiments, the subject compounds have an IC50 value for the PI3-kinase p110γ-p85 complex of from about 2 to about 4 nM, of from about 4 μM to 5 μM, or even more, such as described herein. In certain further embodiments, the subject compounds have an IC50 value for the type II PI3-kinase beta of less than about 1 μM, less than about 150 nM, less than about 30 nM, or even less, such as described herein. In certain embodiments, the subject compounds have an IC50 value for type II PI3-kinase alpha of less than 10 μM. In certain further embodiments, more than one of the above criteria is independently satisfied by a particular compound.

In some embodiments, the potency of the PI4-kinase inhibiting compounds track with anti-infective (e.g., antiviral) activity. In some cases, the enzymatic and anti-infective activities of the subject compounds diverge. In some embodiments, the anti-infective activity of the subject compounds depends on a combination of inhibition of both PI4KIIIα and PI4KIIIβ, or a combination of inhibition of class III PI4-kinases and class II PI3-kinases (especially class II PI3-kinase beta). The subject compound may have increased specificity for one isoform of these PI-kinase family members.

In certain embodiments, the subject compounds have no significant effect on the viability of a mammalian cell, as determined by a cell cytotoxicity assay, e.g., as determined by administering a subject compound to a HeLa cell and determining the number of viable cells present. The subject compounds may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher. The subject compounds may exhibit a $CC_{50}$ value of 1 nM or higher, such as 100 nM or higher, 300 nM or higher, 1 μM or higher, 3 μM or higher, 5 μM or higher, 10 μM or higher, 20 μM or higher, 30 μM or higher, 50 μM or higher, or even higher.

In certain embodiments, the compounds have a therapeutic index (e.g., the ratio of a compound's cytotoxicity (e.g., cell cytotoxicity, CC50) to bioactivity (e.g., antiviral activity, EC50)) that is 20 or more, such as 50 or more, 100 or more, 200 or more, 300 or more, 400 or more, 500 or more, or even more.

As summarized above, aspects of the disclosure include methods of inhibiting a PI-kinase (e.g., a PI3, a PI4-IIIα, or a PI4-IIIβ kinase). A subject compound (e.g., as described herein) may inhibit at least one activity of the PI-kinase in the range of 10% to 100%, e.g., by 10% or more, 20% or more, 30% or more, 40% or more, 50% or more, 60% or more, 70% or more, 80% or more, or 90% or more. In certain assays, a subject compound may inhibit its target with an $IC_{50}$ of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining PI-kinase activity are numerous, and include but are not limited to cell-free assays, e.g., binding assays; assays using purified enzymes, cellular assays in which a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject compound that specifically inhibits a target PI-kinase. In certain embodiments, the sample is suspected of containing the PI-kinase and the subject method further comprises evaluating whether the compound inhibits the PI-kinase. In certain embodiments, the PI-kinase is a PI4-kinase or a PI-3 kinase.

In certain embodiments, the subject compound is a modified compound that includes a label, e.g., a fluorescent label, and the subject method further includes detecting the label, if present, in the sample, e.g., using optical detection.

In certain embodiments, the compound is modified with a support or with affinity groups that bind to a support (e.g. biotin), such that any sample that does not bind to the compound may be removed (e.g., by washing). The specifically bound target PI-kinase, if present, may then be detected using any convenient means, such as, using the binding of a labeled target specific probe, or using a fluorescent protein reactive reagent.

In another embodiment of the subject method, the sample is known to contain the target PI-kinase.

METHODS

Contrary to the classic paradigm of anti-infective therapy, the present disclosure provides methods of treating pathogen infection by targeting a host function and/or molecule upon which the pathogen is dependent, thereby decreasing the ability of the pathogen to avoid the therapeutic agent by mutation. In addition, by utilizing such a target, the methods of the disclosure allow combination therapies in which multiple targets are addressed, thereby increasing the ability to eliminate the infectious agent. The methods also provide a broad platform for anti-infective therapies by targeting a host function. In addition, in cases where the pathogen encodes its own PI-kinase(s), the present disclosure provides methods of treating pathogen infection by targeting the pathogen PI-kinase.

Pathogens of interest include those described in Glenn et al., "PIP-2 Inhibition-Based Antiviral and Anti-Hyperlipidemic Therapies" WO2009/148541, the disclosure of which is herein incorporated by reference in its entirety. Pathogens of interest include, but are not limited to, pathogens of the viral families Picornaviridae, Flaviviridae, Filoviridae, Caliciviridae, Coronavirinae, Hepeviridae, Bunyaviridae, Poxviridae and Orthomyxoviridae. In some embodiments, the pathogen is selected from hepacivirus (e.g., HCV), norovirus, hepevirus (e.g., HEV), betacoronvirus (e.g., SARS or MERS), rhinovirus (e.g., B or C), *P. falciparum*, Ebola virus, *Francisella tularensis*, hantavirus, vaccinia, smallpox, Japanese encephalitis virus, hepatitis A virus, and influenza virus, PolioVirus, Enterovirus (e.g., A-D), EV71, EV68, human rhinovirus, human poliovirus, hepatovirus (e.g., HAV), West Nile Virus, and Dengue Virus (e.g., 1-4).

In some embodiments, where the pathogen is HCV, useful compounds include those having a high first-pass effect and consequent low systemic bioavailability, which are targeted to the liver, and which are typically discarded in early drug development. In other embodiments for the treatment of HCV, the compound, or formulation, is modified for liver-specific targeting.

In some cases, the method is a method of inhibiting a PI4-kinase in a sample.

As such, aspects of the method include contacting a sample with a subject compound (e.g., as described above) under conditions by which the compound inhibits the PI4-kinase. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

The term "sample" as used herein relates to a material or mixture of materials, typically, although not necessarily, in fluid form, containing one or more components of interest.

In some embodiments, the subject method is a method of treating a subject for an infective disease. In some embodiments, the subject method includes administering to the subject an effective amount of a subject compound (e.g., as described herein) or a pharmaceutically acceptable salt thereof. The subject compound may be administered as part of a pharmaceutical composition (e.g., as described herein). In certain instances of the method, the compound that is administered is a compound of one of formulae (Ia)-(XLIX). In certain instances of the method, the compound that is administered is described by one of the compounds of Table 1.

In some embodiments, an "effective amount" is an amount of a subject compound that, when administered to an individual in one or more doses, in monotherapy or in combination therapy, is effective to reduce viral load in the individual by at least about 20% (20% suppression), at least about 30% (30% suppression), at least about 40% (40% suppression), at least about 50% (50% suppression), at least about 60% (60% suppression), at least about 70% (70% suppression), at least about 80% (80% suppression), or at least about 90% (90% suppression), compared to the load in the individual in the absence of treatment with the compound, or alternatively, compared to the bacterial load in the individual before or after treatment with the compound.

In some embodiments, an "effective amount" of a compound is an amount that, when administered in one or more doses to an individual having a viral infection, is effective to achieve a 1.5-log, a 2-log, a 2.5-log, a 3-log, a 3.5-log, a 4-log, a 4.5-log, or a 5-log reduction in virus in the serum of the individual.

In some embodiments, an effective amount of a compound is an amount that ranges from about 50 ng/ml to about 50 μg/ml (e.g., from about 50 ng/ml to about 40 μg/ml, from about 30 ng/ml to about 20 μg/ml, from about 50 ng/ml to about 10 μg/ml, from about 50 ng/ml to about 1 μg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 μg to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount can be a single dose amount or can be a total daily amount. The total daily amount can range from10 pg to 100 mg, or can range from 100 mg to about 500 mg, or can range from 500 mg to about 1000 mg.

In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Administration of an effective amount of a subject compound to an individual in need thereof can result in one or more of: 1) a reduction in viral load; 2) a reduction in viral load in a target biological sample; 3) a reduction in the spread of a virus from one cell to another cell in an individual; 4) a reduction in viral entry into (e.g., reduction of internalization of a virus into) a cell; 5) a reduction in time to seroconversion; 6) an increase in the rate of sustained response to therapy; 7) a reduction of morbidity or mortality in clinical outcomes; 8) shortening the total length of treatment when combined with other anti-viral agents; and 9) an improvement in an indicator of disease response (e.g., a reduction in one or more symptoms of a viral infection, such as fever, etc.). Any of a variety of methods can be used to determine whether a treatment method is effective. For example, a biological sample obtained from an individual who has been treated with a subject method can be assayed.

In some embodiments of the methods of treatment, the infective disease condition results from infection with a positive-stranded RNA virus, negative stranded RNA virus, or a DNA virus. In some embodiments, the infective disease condition results from infection with a pathogen selected from the group of viral families consisting of Picornaviridae, Flaviviridae, Filoviridae, Caliciviridae, Coronavirinae, Hepeviridae, Bunyaviridae, Poxviridae, and Orthomyxoviridae. In some embodiments, the infective disease condition results from infection with a pathogen selected from the phylum Apicomplexa or from the order Kinetoplastida. In some embodiments, the infective disease condition results from infection with a bacterium. In some embodiments, the infective disease condition results from infection with a pathogen selected from HCV, rhinovirus (e.g., A, B or C, as well as unclassified), *P. falciparum*, Ebola virus, *Francisella tularensis*, hantavirus, SARS virus, MERS virus, vaccinia, smallpox, Japanese encephalitis virus, hepatitis A virus, and influenza virus, Norovirus, PolioVirus, Enterovirus (e.g., A-D), HEV, EV71, EV68, West Nile Virus, and Dengue Virus (e.g., 1-4). In some embodiments, the pathogen is HCV. In some embodiments, the pathogen is rhinovirus or *P. falciparum*. In some embodiments, the pathogen is hepatitis A virus. In certain embodiments of the method of treatment, the pathogen is a virus selected from EV71, EV68, human rhinoviruses, HAV, HCV, norovirus and ebola virus. In some embodiments, the pathogen is hepatitis A virus. In certain cases, the virus is EV71 or EV68. In certain cases, the virus is a human rhinovirus. In certain cases, the virus is HAV. In certain cases, the virus is a norovirus. In certain cases, the virus is ebola virus. Any of the compounds described herein can be utilized in the subject methods of treatment. In certain instances, the compound is of one of formulae I-XLIX. In certain cases, the compound is one of the compounds of Table 1. In some cases, the compound that is utilized in the subject methods has broad spectrum activity against several of the pathogens (e.g., viruses) described herein. In certain instances, the compound has anti-viral activity against particular viruses, including one or more of the viruses described above.

In some embodiments, the pathogen is characterized by having a BAAPP domain that interacts with PIP-2, or a protein that binds $PI(4,5)P_2$ or PI(4)P. In some embodiments, the pathogen is characterized by having a protein that interacts with one or more PI-4 kinases or PI phosphatases. In some embodiments, the BAAPP domain is derived from NS5A or NS4B protein. In some embodiments, the infective disease condition is caused by infection of a pathogen susceptible to PI4-kinase inhibition. In some embodiments, the compound specifically inhibits the PI4-kinase. In some embodiments, the compound has broad spectrum activity against two or more pathogens. In some embodiments, the compound modulates the activity of PIP-2. In some embodiments, the compound interferes with the interaction of a BAAPP domain and PIP-2 of the pathogen. In some embodiments, the compound blocks pathogen replication.

In some embodiments, the subject method is a method of treating a subject for an elevated level of VLDL or LDL cholesterol. In some embodiments, the subject method includes administering to the subject an effective amount of a 2-aminophenylthiazole compound (e.g., as described above), alone or in combination with other drugs known to affect LDL or VLDL levels (e.g., 3-hydroxy-3-methylglutaryl-coenzyme A reductase inhibitors such as lovastatin, fluvastatin, atorvastatin, pravastatin, simvastatin, rosuvastatin, etc.; microsomal triglyceride transfer protein inhibitors such as lomitapide; inhibitors of intestinal cholesterol absorption such as ezetimibe; peroxisome proliferator-activated receptor type alpha activators such as fenofibrate).

In some embodiments, the subject is human. The subject may be in need of treatment for a viral infection, or may be at risk of a viral infection. In some instances, the subject methods include diagnosing a viral infection, including any one of the viruses described herein. In some embodiments, the compound is administered as a pharmaceutical preparation.

In some embodiments, the subject method is a method of inhibiting viral infection, the method including contacting virus-infected cells with an effective dose of a 2-aminophenylthiazole compound (e.g., as described above) to inhibit viral replication. In some embodiments, the method further includes contacting the cells with a second antiviral agent.

In some embodiments, the compound is formulated to be targeted to the liver.

In certain embodiments, the compound is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p 977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabelled and a secondary labeling agent is used for imaging.

UTILITY

The compounds and methods of the invention, e.g., as described herein, find use in a variety of applications. Applications of interest include, but are not limited to: research applications and therapeutic applications. Methods of the invention find use in a variety of different applications including any convenient application where inhibition of a PI4-kinase is desired.

The subject compounds and methods find use in a variety of research applications. The subject compounds and methods may be used in the optimization of the bioavailability and metabolic stability of compounds.

The subject compounds and methods find use in a variety of therapeutic applications. Therapeutic applications of interest include those applications in which pathogen infection is the cause or a compounding factor in disease progression. As such, the subject compounds find use in the treatment of a variety of different conditions in which the inhibition and/or treatment of viral infection in the host is desired. For example, the subject compounds and methods may find use in treating a pathogen caused infective disease (e.g., as described herein), such as HCV.

Pharmaceutical Compositions

The herein-discussed compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

In some embodiments, the subject compound and an antiviral agent, e.g. interferon, ribavirin, Enfuvirtide; RFI-641 (4,4"-bis-{4,6-bis-[3-(bis-carbamoylmethyl-sulfamoyl)-phenylamino]-(1,3,5) triazin-2-ylamino}-biphenyl-2, 2"-disulfonic acid); BMS-433771 (2H-Imidazo(4,5-c) pyridin-2-one, 1-cyclopropyl-1,3-dihydro-3-((1-(3-hydroxypropyl)-1H-benzimidazol-2-yl)methyl)); arildone; Pleconaril (3-(3,5-Dimethyl-4-(3-(3-methyl-5-isoxazolyl) propoxy)phenyl)-5-(trifluoromethyl)-1,2,4-oxadiazole); Amantadine (tricyclo[3.3.1.1.3,7]decane-1-amine hydrochloride); Rimantadine (alpha-methyltricyclo[3.3.1.1.3,7] decane-1-methanamine hydrochloride); Acyclovir (acycloguanosine); Valaciclovir; Penciclovir (9-(4-hydroxy-3-hydroxymethyl-but-1-yl)guanine); Famciclovir (diacetyl ester of 9-(4-hydroxy-3-hydroxymethyl-but-1-yl)-6-deoxyguanine); Gancyclovir (9-(1,3-dihydroxy-2-propoxymethyl)guanine); Ara-A (adenosine arabinoside); Zidovudine (3'-azido-2',3'-dideoxythymidine); Cidofovir (1-[(S)-3-hydroxy-2-(phosphonomethoxy)propyl]cytosine dihydrate); Dideoxyinosine (2',3'-dideoxyinosine); Zalcitabine (2',3'-dideoxycytidine); Stavudine (2',3'-didehydro-2',3'-dideoxythymidine); Lamivudine ((−)-β-L-3'-thia-2',3'-dideoxycytidine); Abacavir (1S,4R)-4-[2-amino-6-(cyclopropylamino)-9H-purin-9-yl]-2-cyclopentene-1-methanol succinate); Emtricitabine (−)-β-L-3'-thia-2',3'-dideoxy-5-fluorocytidine); Tenofovir disoproxil (Fumarate salt of bis(isopropoxycarbonyloxymethyl) ester of (R)-9-(2-phosphonylmethoxypropyl)adenine); Bromovinyl deoxyuridine (Brivudin); Iodo-deoxyuridine (Idoxuridine); Trifluorothymidine (Trifluridine); Nevirapine (11-cyclopropyl-5,11-dihydro-4-methyl-6H-dipyrido[3,2-b:2',3'-f][1,4]diazepin-6-one); Delavirdine (1-(5-methanesulfonamido-1H-indol-2-yl-carbonyl)-4-[3-(1-methylethyl-amino)pyridinyl) piperazine monomethane sulfonated); Efavirenz ((−)6-chloro-4-cyclopropylethynyl-4-trifluoromethyl-1,4-dihydro-2H-3,1-benzoxazin-2-one); Foscarnet (trisodium phosphonoformate); Ribavirin (1-β-D-ribofuranosyl-1H-1,2,4-triazole-3-carboxamide); Raltegravir (N-[(4-Fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide monopotassium salt); Neplanocin A; Fomivirsen; Saquinavir (SQ); Ritonavir ([5S-(5R,8R,10R,11R)]-10-hydroxy-2-methyl-5-(1-methylethyl)-1-[2-(methylethyl)-4-thiazolyl]-3,6-dioxo-8,11-bis (phenylmethyl)-2,4,7,12-tetraazatridecan-13-oic acid 5-thiazolylmethylester); Indinavir ([(1S,2R,5(S)-2,3,5-trideoxy-N-(2,3-dihydro-2-hydroxy-1H-inden-1-yl)-5-[2-[[(1,1-dimethylethyl)amino]carbonyl]-4-pyridinylmethyl)-1-piperazinyl]-2-(phenylmethyl-erythro)pentonamide); Amprenavir; Nelfinavir; Lopinavir; Atazanavir; Bevirimat; Indinavir; Relenza; Zanamivir; Oseltamivir; Tarvacin; etc. are administered to individuals in a formulation (e.g., in the same or in separate formulations) with a pharmaceutically acceptable excipient(s).

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional anti-viral agents of interest. Any convenient anti-viral agents can be utilized in the subject methods in conjunction with the subject compounds. In some instances, the additional agent is an anti-HCV therapeutic agent selected from: an HCV NS3 protease inhibitor, an HCV NS5B RNA-dependent RNA polymerase inhibitor, a thiazolide, a sustained release thiazolide, a nucleoside analog, an interferon-alpha or lambda, a pegylated interferon, ribavirin, levovirin, viramidine, a TLR7 agonist, a TLR9 agonist, a cyclophilin inhibitor, an alpha-glucosidase inhibitor, an NS5A inhibitor, an NS3 helicase inhibitor, clemizole or clemizole analog (such as the benzimidizole and indazole analogs described in U.S. patent applications Ser. Nos. 12/383,071 and 12/383,030), or other NS4B inhibitor including an NS4B amphipathic helix inhibitor. The subject compound and second antiviral agent, as well as additional therapeutic agents as described herein for combination therapies, can be administered orally, subcutaneously, intramuscularly, parenterally, or other route. The subject compound and second antiviral agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

In some embodiments, the subject compound and an antimalarial agent, e.g., chloroquine, primaquine, mefloquine, doxycycline, atovaquone-proguanil, quinine, quinidine, artesunate, artemether, lumefantrine; etc. are administered to individuals in a formulation (e.g., in the same or in separate formulations) with a pharmaceutically acceptable excipient(s). The subject compound and second antimalarial agent, as well as additional therapeutic agents as described herein for combination therapies, can be administered orally, subcutaneously, intramuscularly, parenterally, or other route. The subject compound and second antimalarial agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Although such may not be necessary, compounds and agents described herein can optionally be targeted to the liver, using any known targeting means. The compounds of the disclosure may be formulated with a wide variety of compounds that have been demonstrated to target compounds to hepatocytes. Such liver targeting compounds include, but are not limited to, asialoglycopeptides; basic polyamino acids conjugated with galactose or lactose residues; galactosylated albumin; asialoglycoprotein-poly-L-lysine) conjugates; lactosaminated albumin; lactosylated albumin-poly-L-lysine conjugates; galactosylated poly-L-lysine; galactose-PEG-poly-L-lysine conjugates; lactose-PEG-poly-L-lysine conjugates; asialofetuin; and lactosylated albumin.

The terms "targeting to the liver" and "hepatocyte targeted" refer to targeting of a compound to a hepatocyte, particularly a virally infected hepatocyte, such that at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, of the compound administered to the subject enters the liver via the hepatic portal and becomes associated with (e.g., is taken up by) a hepatocyte.

HCV infection is associated with liver fibrosis and in certain embodiments the inhibitors may be useful in treating liver fibrosis (particularly preventing, slowing of progression, etc.). The methods involve administering an compound of the disclosure as described above, in an amount effective to reduce viral load, thereby treating liver fibrosis in the subject. Treating liver fibrosis includes reducing the risk that liver fibrosis will occur; reducing a symptom associated with liver fibrosis; and increasing liver function.

Whether treatment with a compound as described herein is effective in reducing liver fibrosis is determined by any of a number of well-established techniques for measuring liver fibrosis and liver function. The benefit of anti-fibrotic therapy can be measured and assessed by using the Child-Pugh scoring system which comprises a multi-component point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

Treatment of liver fibrosis (e.g., reduction of liver fibrosis) can also be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) *Hepatol.* 31:241-246; and METAVIR (1994) *Hepatology* 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) *Hepatol.* 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) *J. Hepatol.* 13:372.

The Ishak scoring system is described in Ishak (1995) *J. Hepatol.* 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

In some embodiments, a therapeutically effective amount of a compound of the disclosure is an amount of compound that effects a change of one unit or more in the fibrosis stage based on pre- and post-therapy measures of liver function (e.g, as determined by biopsies). In particular embodiments, a therapeutically effective amount of the subject compound reduces liver fibrosis by at least one unit in the Child-Pugh, METAVIR, the Knodell, the Scheuer, the Ludwig, or the Ishak scoring system.

Secondary, or indirect, indices of liver function can also be used to evaluate the efficacy of treatment. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score. An effective amount of the subject compound is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

In some cases, a therapeutically effective amount of the subject compound is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Qualitative or quantitative tests of functional liver reserve can also be used to assess the efficacy of treatment with an agent. These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound in this context can be regarded as an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with the subject compound is effective in reducing the incidence of a disorder associated with cirrhosis of the liver can readily be determined by those skilled in the art.

Reduction in HCV viral load, as well as reduction in liver fibrosis, can be associated with an increase in liver function. Thus, the disclosure provides methods for increasing liver function, generally involving administering a therapeutically effective amount of a compound of the disclosure. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal range of alanine transaminase is from about 7 to about 56 units per liter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound in this context is one that is effective to increase liver function by at least about 10%, at least about 20%, at least about 30%, at least about 40%, at least about 50%, at least about 60%, at least about 70%, at least about 80%, or more. For example, a therapeutically effective amount of a compound is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

HCV infection is associated with hepatic cancer and in certain embodiments the present disclosure provides compositions and methods of reducing the risk that an individual will develop hepatic cancer. The methods involve administering the subject compound, as described above, wherein viral load is reduced in the individual, and wherein the risk that the individual will develop hepatic cancer is reduced. An effective amount of a compound is one that reduces the risk of hepatic cancer by at least about 10%, at least about 20%, at least about 25%, at least about 30%, at least about 35%, at least about 40%, at least about 45%, at least about 50%, at least about 55%, at least about 60%, at least about 65%, at least about 70%, or more. Whether the risk of hepatic cancer is reduced can be determined in, e.g., study groups, where individuals treated according to the subject methods have reduced incidence of hepatic cancer.

Subjects Amenable to Treatment using the Compounds of the Disclosure

Individuals who have been clinically diagnosed as infected with a pathogen of interest are suitable for treatment with the methods of the present disclosure. In particular embodiments of interest, individuals of interest for treatment according to the disclosure have detectable pathogen titer indicating active replication, for example an HCV titer of at least about $10^4$, at least about $10^5$, at least about $5\times10^5$, or at least about $10^6$, or greater than 2 million genome copies of HCV per milliliter of serum. Similar methods may be used to determine whether subjects infected with another pathogen are suitable for treatment using the subject methods.

The effectiveness of the anti-infective treatment may be determined using any convenient method. For example, whether a subject method is effective in treating a virus infection can be determined by measuring viral load, or by measuring a parameter associated with infection.

Viral load can be measured by measuring the titer or level of virus in serum. These methods include, but are not limited to, a quantitative polymerase chain reaction (PCR) and a branched DNA (bDNA) test. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1

Synthesis and Assays

In the assays described here, p110α-p85 complex and p110γ were acquired from Millipore. Assays were performed with Lα-phosphatidylinositol (Avanti) as described in Knight et al. Nat Protoc. 2007; 2 (10):2459-66. Inhibitor series were prepared 10% DMSO as 5× stocks for the assay. Assays of HsVps34 were performed as described in Knight et al, except that the final assay buffer composition used was changed to 20 mM HEPES 7.5, 100 mM NaCl, 3 mM MgCl, 1 mg/mL PI and 44 nM hvps34 was used in the assay. For inhibitors with an apparent IC50 less than or equal to 22 nM, values were reassayed using 4.4 nM hvps34 with 3 mM $MnCl_2$. COS-7 cells were cultured in 10 cm dishes and transfected at 70% confluence with 10 μg of plasmid DNA (HA-tagged bovine PI4KIIIβ, HA-tagged human PI4KIIIα) using Lipofectamine 2000 and 5 ml Opti-MEM following the manufacturer's instructions. After 5 hours the transfection medium was replaced with 10 ml complete DMEM. 36 hrs post transfection, cells were washed once with 5 ml PBS (pH 7.4) and lysed in 1 ml of lysis buffer (1) on ice. Lysates were collected by scraping and after 15 min they were centrifuged at 13,000 rpm for 10 min. To the lysates was added 200 μl of protein G Sepharose 4 fast flow beads that were prewashed with PBS and lysis buffer and 2 μg of anti-HA antibody. The tubes were then incubated overnight at 4 degrees C. in a tube rotator. The Sepharose beads in the lysate were washed twice with 150 mM NaCl in RIPA buffer, twice with RIPA buffer and once with kinase buffer (50 mM Tris/HCl, pH 7.5, 20 mM MgCl2, 1 mM EGTA, 1 mM PtdIns, 0.4% Triton X-100, 0.5 mg/mL BSA) and finally the beads were resuspended in 200 μL kinase buffer. Kinase reactions were run in a mixture of 45 μL of PI buffer (1 mM PI in kinase buffer), 10 μL of immunoprecipitated beads, 2 □L of inhibitors (dissolved and diluted in DMSO) or DMSO and 5 μL of [γ-$^{32}$P]-ATP (1 mM and 2 μCi/tube). The immunoprecipitates in PI buffer were pre-incubated with the drugs for 20 min prior the initiation of kinase reaction by adding ATP and the reactions were carried out for 30 min in 15 ml polypropolyne tubes. Reactions were terminated by addition of 3 ml of $CHCl_3$:$CH_3OH$:HCl (200:100:0.75) followed by 0.6 ml of 0.6N HCl to induce phase separation. The mixtures were vortexed, centrifuged at 2000 rpm for 2 min and the upper phase was discarded. To the lower phase was added 1.5 ml of $CHCl_3$:$CH_3OH$:0.6N HCl (3:48:47) and the mixture vortexed and centrifuged at 2000 rpm for 2 min. The lower phase was then transferred to counting vials and evaporated. Samples were counted in a scintillation beta counter after adding 5 ml of Instafluor (Perkin-Elmer).

Synthesis: Compounds may be synthesized using any convenient method. For example, by similar methods to those described by Shokat et al. "A pharmacological map of the PI3-K family defines a role for p110alpha in insulin signaling" Cell. 2006; 125(4):733-47. Starting materials are obtained from Aldrich or Alfa Aesar. Reactions are monitored by LC/MS and reaction products characterized by LC/MS and 1H NMR. Intermediates and final products are purified by silica gel chromatography or by reverse phase HPLC.

PI-kinase assay: Compounds are tested in C.1.1. PI kinase assays as described by Shokat et al., "A membrane capture assay for lipid kinase activity." Nat. Protoc. 2007; 2(10): 2459-66.

Anti-HCV assay: Anti-HCV assays are performed as described by Cho et al. "Identification of a class of HCV inhibitors directed against the nonstructural protein NS4B." Sci. Transl. Med. 2011; 2(15):15ra6.

Broad-spectrum anti-infective assays: Compounds are tested for activity against selected agents harboring proteins with BAAPP domains, or other PI-4 or PIP2 binding motifs, (i.e. Vaccinia virus, Japanese encephalitis virus, hepatitis A virus, and influenza virus) in clinical studies. Activity against multiple NIAID Category A, B, and C pathogens is assayed.

Vaccinia virus assay: Standard plaque assays are performed on CV-1 cells, using methods described by Glenn et al., "Amphipathic helix-dependent localization of NS5A mediates hepatitis C virus RNA replication." J. Virol. 2003; 77(10):6055-61, in the presence of vehicle or vehicle plus various concentrations of compound.

HAV assay: Huh7 cells harboring HAV replicons encoding a blasticidin resistance gene (Yang et al., "Disruption of innate immunity due to mitochondrial targeting of a picornaviral protease precursor." Proc Natl Acad Sci USA 2007; 104(17):7253-8) is grown in media containing blasticidin, with or without various concentrations of compound. Anti-HAV activity is assessed by both cell plating efficiency and HAV RNA levels using quantitative RT-PCR assays. A luciferase-linked HAV replicon for tranisient replication assays is used to evaluate the effects of HAV BAAPP domain mutants.

JEV assay: JEV assays are performed using both infectious virus in cell culture, as well as in an in vivo animal model, using similar methods to those described by Shah et al. "Molecular characterization of attenuated Japanese encephalitis live vaccine strain ML-17." Vaccine. 2006; 24(4):402-11.

Influenza virus assay: Influenza virus assays are performed using infectious virus in cell culture, using similar methods to those described by Hossain et al. "Establishment and characterization of a Madin-Darby canine kidney reporter cell line for influenza A virus assays." J. Clin. Microbiol. 48(7):2515-23.

*Plasmodium falciparum* assay: *Plasmodium falciparum* assays are performed using an erythrocyte-fed culture of *P. falciparum* ring forms, using similar methods to those described by Deu et al. "Functional Studies of *Plasmodium falciparum* Dipeptidyl Aminopeptidase I Using Small Molecule Inhibitors and Active Site Probes." Chemistry & Biology 17, 808-819.

Rhinovirus assay: Rhinovirus assays are performed by determining to what extent the compound protects HeLa S3 cells from the cytopathic effect of an inoculum of human rhinovirus 14, using similar methods to those described by Buckwold et al., "Synergistic In Vitro Interactions between Alpha Interferon and Ribavirin against Bovine Viral Diarrhea Virus and Yellow Fever Virus as Surrogate Models of Hepatitis C Virus Replication," Antimicrobial Agents and Chemotherapy 47(7), 2293-2298.

HAV assay: HAV assays are performed by co-culturing Huh7-derived cells harboring the blasticidin-selectable HAV replicon (HAV-Bla, described by Yang et al, "Disruption of innate immunity due to mitochondrial targeting of a picornaviral protease precursor", PNAS 104(17), 7253-7258) for over two weeks in DMEM with 10% FBS, 1% Pen-Strep, 1% L-Glutamine, 1% nonessential amino acids, and 4 μg/mL blasticidin, with various concentrations of compound or vehicle control in 6-well plates at a density of 1000 HAV-Bla cells per well and 1/72 confluent plate worth of Huh7 feeder cells per well. At the end of this culture, large colonies in each well are counted and an effective concentration at which plating efficiency is decreased by 50% (EC50) is calculated.

For all of the assays described above, EC50, EC90, and CC50 values are determined, and experiments are performed starting drug treatments at various times post initiation of infection to help localize the most sensitive aspects of each pathogen's life cycle to PI4-kinase inhibition.

Resistance assays: The capacity for emergence of resistance and its nature is determined using any convenient methods, for example methods that involve sequencing of any resistant isolates that are able to be propagated. Co-treatments with other drugs are also performed. Experiments are conducted under BL2+ conditions where appropriate.

Humanized mouse model: The performance characteristics of the compounds are assessed by dosing the compounds in a mouse model with a humanized liver to determine their in vivo pharmacokinetic (PK) and pharmacodynamic properties. This model consists of immunodeficient NOG mice (NOD/shi SCID Il2rg −/−) harboring a Herpes virus-derived thymidine kinase (TK) transgene under the control of an albumin promoter (Hasegawa et al., "The reconstituted 'humanized liver' in TK-NOG mice is mature and functional." Biochem Biophys Res Commun. 2011; 405(3):405-10). A brief exposure to ganciclovir targets destruction of the endogenous mouse liver, which is followed by the transplantation of human liver cells. High level engraftment of human hepatocytes can be achieved and efficient HCV infection established. A quantitative analysis of in vivo PK parameters and efficacy of the compounds and metabolites in the plasma of the humanized mice is performed.

PK and PD: Cohorts of humanized TK-NOG mice (e.g. 5 mice per treatment group) are gavaged with one dose of compound. Doses are chosen so as to maintain a concentration above the respective EC50s. Serial aliquots of plasma are obtained at baseline, 15 minutes, 30 minutes, 1 hr and 2 hr post dosing. Similarly treated groups of mice are sacrificed to analyze levels of the drugs and key metabolites in the liver. Concentrations of compounds and their metabolites are measured. PK parameters, such as Cmax, T½, AUC, and oral clearance are determined. Based on these parameters, cohorts of humanized TK-NOG mice (5 mice per treatment group) infected with HCV inoculums consisting of the infectious 2a clone (25) or de-identified patient-derived sera are gavaged (Glenn et al., "In vivo antiviral efficacy of prenylation inhibitors against hepatitis delta virus (HDV)." Journal of Clinical Investigation. 2003; 112(3):407-14) for multiple doses and serial serum aliquots are obtained and antiviral efficacy determined by measuring HCV titers by quantitative real-time PCR. Individually-treated mice can also serve as their own control wherein the HCV titers before, during, and after treatment can be used to assess antiviral efficacy wherein an antiviral effect in indicated by a drop in titer during the treatment phase compared to the pretreatment phase, with (in the case where the virus has not been completely eliminated during the treatment period) or without (in the case where the virus has been completely eliminated during the treatment period) an increase in titer following cessation of treatment.

Assessment of drug resistance: (In vitro) Huh7 cells harboring a bicistronic genotype 1b subgenomic replicon, wherein the first cistron encodes the neomycinphosphotransferase gene (which confers resistance to G418) and the second cistron encodes the HCV non-structural proteins required for RNA genome replication, are grown in media containing G418 plus increasing concentrations of compounds to select for drug resistant colonies. This, along with extraction of the replicons harbored in the resistant cells, sequencing to identify candidate resistance mutations, and cloning of these mutations back into a wild-type replicon to confirm they are truly causative of the resistance, is performed using convenient methods. In vivo) Inoculums consist of the infectious 2a clone and de-identified patient-derived sera. Once establishment of infection has been confirmed, humanized mice are treated by oral gavage with a resistance-promoting regimen of compounds involving progressive dose escalation from a low dose (0.1 mg/kg/day), with drug holidays. Serum samples for analysis are taken at time 0, and serially thereafter on a weekly basis. The focus is first on any samples that display a rebound in titer of greater than 1 log after a previous nadir. Standard DNA sequencing of individual clones isolated from RT-PCR cloning is performed. Ultradeep pyrosequencing is reserved to determine earliest evidence of any observed resistance. As a control, similar experiments with an HCV NS3 protease inhibitor (e.g. Boceprevir) are perfomed.

Example 2

Selected compounds of Table 1 were prepared and tested for inhibition activity in a variety of kinase assays.

TABLE 2

Comparison of PI4K and PI3K Kinase activity of select compounds

| Compound | PI4KIIIA | PI4KIIIB | PI3K p110a | PI3K p110g | PI3KC2B | PI3KC2G |
|---|---|---|---|---|---|---|
| S-1 | | A | D | D | D | A |
| S-8 | | B | | | | |
| S-9 | | A | | | | |
| S-25 | | B | | | | |
| S-28 | | C | | | | |
| S-29 | | B | | | | |
| S-37 | | B | | | | |
| S-41 | | A | | | | |
| S-43 | | B | | | | |
| S-46 | | B | | | | |
| S-49 | | A | | | | |
| S-50 | | B | | | | |
| S-52 | | B | | | | |
| S-53 | | B | | | | |
| S-54 | | C | | | | |
| S-78 | | C | | | | |
| S-81 | | B | | | | |
| S-91 | | B | | | | |
| S-92 | | C | | | | |
| S-94 | | C | | | | |
| S-95 | | B | | | | |
| S-98 | D | A | D | D | | |
| S-100 | D | B | | D | | C |
| S-101 | | C | | | | |
| S-102 | | B | | | | |
| S-103 | | C | | | | |
| S-107 | | C | | | | |
| S-109 | | B | | | | |
| S-111 | | B | | | | |
| S-115 | | A | | | | |
| S-118 | | B | | | | |
| S-119 | | B | | | | |

TABLE 2-continued

Comparison of PI4K and PI3K Kinase activity of select compounds

| Compound | PI4KIIIA | PI4KIIIB | PI3K p110a | PI3K p110g | PI3KC2B | PI3KC2G |
|---|---|---|---|---|---|---|
| S-121 | | C | | | | |
| S-122 | | B | | | | |
| S-123 | | A | | | | |
| S-127 | D | B | | D | | D |
| S-128 | D | B | | D | | D |
| S-129 | D | B | | D | | D |
| S-131 | D | B | | | | D |
| S-133 | | A | | | | |
| S-134 | | A | | | | |
| S-135 | | A | | | | |
| S-136 | | A | | | | |
| S-138 | | B | | | | |
| S-145 | B | A | D | D | | |
| S-146 | | B | | | | |
| S-147 | B | A | D | D | | |
| S-148 | B | A | D | D | | |
| S-149 | | A | | | | |
| S-150 | | B | | | | |
| S-151 | | A | | | | |
| S-152 | | A | | | | |
| S-153 | | A | | | | |
| S-154 | | B | | | | |
| S-155 | | B | | | | |
| S-156 | | A | | | | |
| S-157 | | B | | | | |
| S-159 | | B | | | | |
| S-160 | | A | | D | D | B |
| S-161 | | B | | | | |
| S-185 | | A | | | | |
| S-166 | | A | | | | |
| S-167 | | A | | | | |
| S-169 | A | A | D | D | | D |
| S-170 | A | A | D | D | | D |
| S-173 | | A | | | | |
| S-178 | | B | | | | |
| S-183 | | A | | | | |
| S-184 | | B | | | | |
| S-185 | | C | | | | |
| S-188 | | A | | | | |
| S-189 | | A | | | | |
| S-192 | | B | | | | |
| S-193 | | A | | | D | D |
| S-194 | | B | | | | |
| S-195 | | B | | | | |
| S-196 | | B | | | | |
| S-197 | | A | | | | |
| S-198 | | B | | | | |
| S-199 | | A | | | | |
| S-200 | | B | | | | |
| S-201 | | A | | | | |
| S-202 | | A | | | | |
| S-203 | | A | | | | |
| S-204 | | B | | | | |
| S-205 | | B | | | | |
| S-206 | | C | | | | |
| S-207 | | A | | | | |
| S-208 | | B | | | | |
| S-209 | | B | | | | |
| S-210 | | C | | | | |
| S-214 | D | B | | D | | D |
| S-215 | C | A | | D | D | C |
| S-216 | | A | | D | D | C |
| S-218 | | A | | | | |
| S-219 | | A | | | | |
| S-220 | | A | | | | |
| S-221 | | A | | | | |
| S-222 | | A | | | | |
| S-223 | | A | | | | |
| S-226 | | A | | | | |
| S-227 | | A | D | D | D | C |
| S-228 | | B | | | | |
| S-229 | | B | | | | |
| S-230 | | A | | | | |
| S-231 | | A | | D | D | B |
| S-234 | | B | | | | |

TABLE 2-continued

| Comparison of PI4K and PI3K Kinase activity of select compounds | | | | | | |
|---|---|---|---|---|---|---|
| Compound | PI4KIIIA | PI4KIIIB | PI3K p110a | PI3K p110g | PI3KC2B | PI3KC2G |
| S-235 | | B | | | | |
| S-253 | | B | | | | |
| S-258 | | C | | | | |
| S-259 | A | A | C | C | | C |
| S-260 | A | A | D | D | | D |
| S-261 | A | A | B | B | | B |
| S-262 | A | A | D | C | | B |
| S-263 | A | A | C | C | | B |
| S-265 | A | A | D | D | | C |

A = <100 nM;
B = 100 nM-1 uM;
C = 1-10 uM;
D = >10 uM

Example 3

Activity of Exemplary Compound (1)

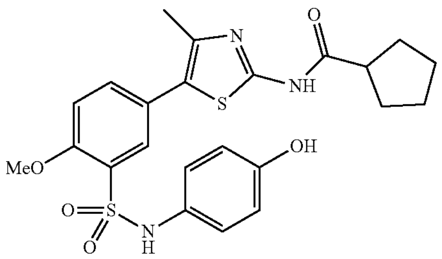

Compound 1 shown above exhibits activity against both PI4KIIIα (IC50 1.75 micromolar) and PI4KIIIβ (IC50 7 nanomolar) in in vitro enzyme assays.

To further confirm its mechanism of action the effect of (1) on PI-4 levels was determined in cells using immunofluorescence to monitor the intracellular localized pools of PI-4. The effect of (1) on intracellular pools of PIP2 was tested, which were predicted to be similarly sensitive to inhibition using (1). Indeed, a dose-dependent decrease in PI-4 and PIP2 was observed upon treatment with (1). As a control for non-specific effects on the cells, the latter were also co-stained with an antibody to ER-localized calnexin, which revealed that the effect on PI-4 and PIP2 occurred in the absence of any detectable effects on the ER.

Cell images show that (1) decreases PI(4)P and PI(4,5)$P_2$ (bottom panels) in a dose-dependent manner. Uninfected Huh7.5 cells or HCV-infected Huh7.5 cells were used. Cells were treated with 250 nm, 500 nM or 1 uM concentrations of (1) or vehicle control, and analyzed by immunofluorescence with antibodies to PI(4)P or PI(4,5)$P_2$ along with an antibody to calnexin to control for ER morphology.

The concentrations at which significant effects on PI-4 and PIP2 were observed in the target cells parallel the observed EC50 of 365 nM (CC50>10 micromolar) for PT423 against HCV in standard replication assays (Cho et al., "Identification of a class of HCV inhibitors directed against the nonstructural protein NS4B." Sci. Transl. Med. 2011; 2(15):15ra6). Consistent with its host PI4-kinase target, resistance was not able to be selected using the HCV replicon system.

Example 4

Table 4 shows the results of testing selected compounds for anti-viral ($EC_{50}$) activity in a HCV genotype 2a in Huh7.5 cells by luciferase reporter assay, for cell toxicity ($CC_{50}$) and metabolic halflife (t½), according to the methods described above.

TABLE 3

| Comparison of antiviral activity of select PI4K inhibitors. | | | | | | |
|---|---|---|---|---|---|---|
| Compounds | HCV2a $EC_{50}$ | HRV $EC_{50}$ | EV71 $EC_{50}$ | Ebola $EC_{50}$ | Norovirus $EC_{50}$ | HuH-7 $CC_{50}$ |
| S-1 | B | A | | | | E |
| S-29 | | A | | | | E |
| S-32 | D | A | | D | | E |
| S-66 | D | A | | | | E |
| S-85 | | A | | | | E |
| S-89 | | A | | | | E |
| S-98 | D | A | A | | D | E |
| S-106 | | A | | | | E |
| S-115 | C | A | | | | E |
| S-138 | C | A | | | | E |
| S227 | B | B | A | C | C | E |
| S-228 | C | A | | D | | E |
| S-260 | C | D | | | | E |
| S261 | B | D | | | | E |
| S-263 | B | D | | | | E |

A = <1 nM;
B = 1-100 nM;
C = 100 nM-1 uM;
D = 1-10 uM;
E = >10 uM

Notwithstanding the appended clauses, the disclosure set forth herein is also defined by the following clauses:

1. A compound described by the structure:

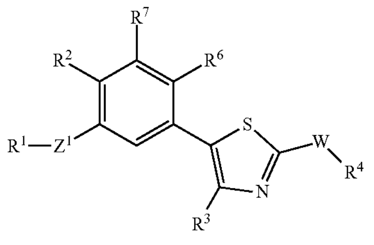

wherein: $Z^1$ and W are each independently a covalent bond or a linking functional group; $R^1$ is selected from an alkyl, an aryl, an alkyl-heterocycle and a heterocycle; $R^2$ is selected from hydrogen, a halogen, an alkyl and an alkoxy; $R^3$ is selected from hydrogen and an alkyl; $R^4$ is selected from an alkyl, an aralkyl, an aryl, an alkyl-cycloalkyl, a cycloalkyl, an alkyl-heterocycle, a heterocycle; and $R^6$ and $R^7$ are independently selected from hydrogen, an alkyl, an aryl, a hydroxy, an alkoxy, an aryloxy, a heterocycle, a cyano, a halogen, an amino, an acyl, an acyloxy, an amido and nitro.

2. The compound according to clause 1, wherein the compound is described by the structure:

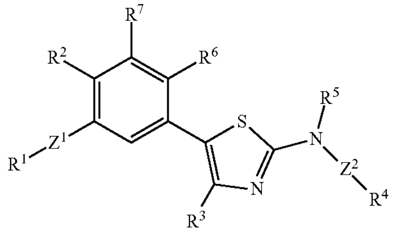

wherein: $Z^2$ is a covalent bond, or a linking functional group; and $R^5$ is selected from hydrogen and an alkyl.

3. The compound according to clause 1, wherein the compound is described by the structure:

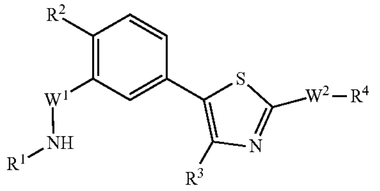

wherein: $R^1$ is selected from an aryl, an aralkyl, an alkyl-heterocycle, a heterocycle, a cycloalkyl and an alkyl-cycloalkyl; $R^2$ is hydrogen, alkyl or alkoxy; $R^3$ is alkyl; $R^4$ is alkyl, cycloalkyl, alkyl-cycloalkyl, heterocyclyl or alkyl-heterocyclyl; $W^1$ is $—SO_2—$ or $—C(=O)—$; and $W^2$ is a covalent bond, —NH—, or —NHCO—.

4. The compound according to clause 3, wherein the compound is described by the structure:

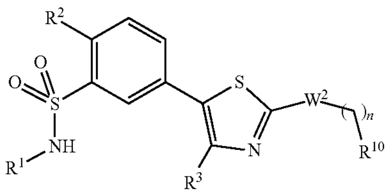

wherein: $R^1$ is $—(CH_2)_n—R^{20}$, where $R^{20}$ is an aryl, a cycloalkyl or a heterocycle and m is 0, 1 or 2; $R^2$ is an alkoxy; $R^3$ is an alkyl; $W^2$ is a covalent bond, —NH—, or —NHCO—; n is 0, 1, 2 or 3; and $R^{10}$ is a cyclopropyl, a cyclopentyl, a cyclohexyl, a piperidinyl or a pyrrolidinyl.

5. The compound according to any one of clauses 1 to 4 wherein $R^1$ or $R^{20}$ is described by the structure:

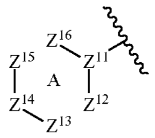

wherein A is a 6-membered aryl, heteroaryl, heterocyclyl, or cycloalkyl ring, wherein $Z^{11}$-$Z^{16}$ are independently selected from N, CR', NR and CR'R", where R is H, an alkyl, an aryl or a heterocycle; and R' and R" are independently selected from hydrogen, an alkyl, an aryl, a hydroxy, an alkoxy, an aryloxy, a heterocycle, a cyano, a halogen, an amino, an acyl, an acyloxy, an amido, and a nitro.

6. The compound according to any one of clauses 1 to 5, wherein $R^2$ is lower alkoxy.

7. The compound according to any one of clauses 1 to 6, wherein $R^3$ is lower alkyl.

8. The compound according to any one of clauses 1 to 7, wherein the compound is described by one of the following structures:

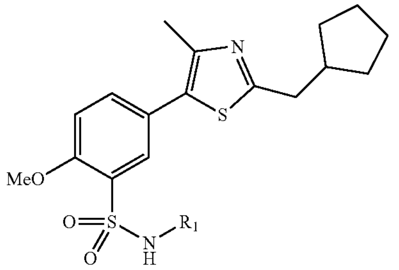

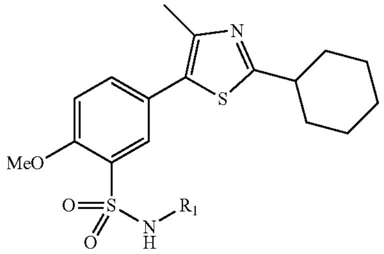

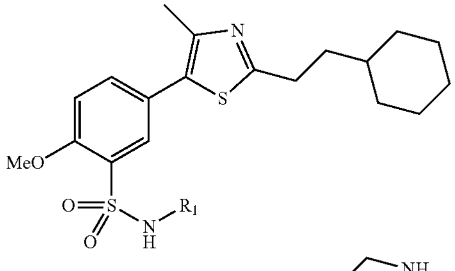

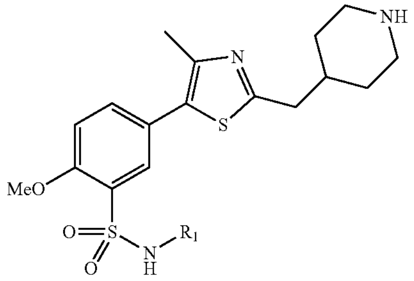

-continued

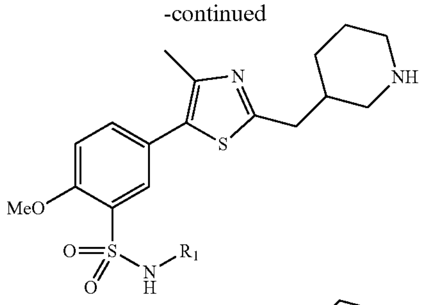

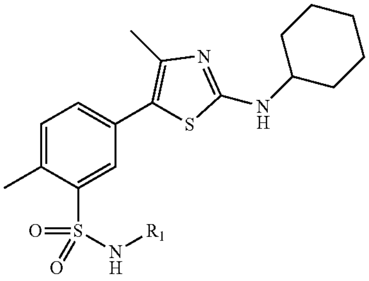

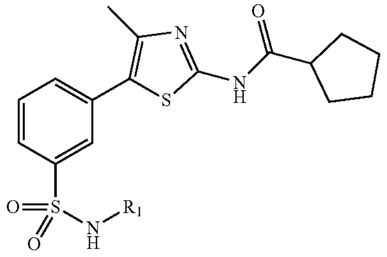

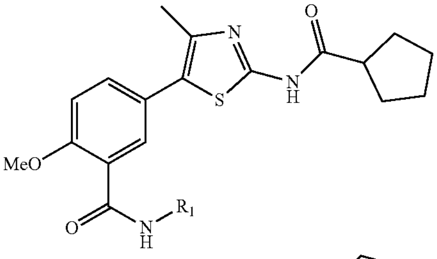

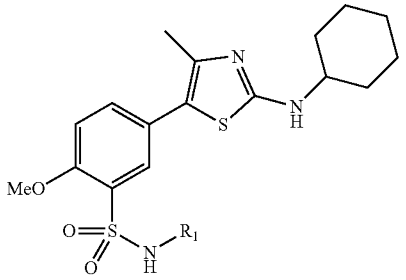

wherein $R^1$ is $-(CH_2)_m-R^{20}$, where $R^{20}$ is an aryl, a cycloalkyl or a heterocycle and m is 0, 1 or 2.

9. The compound according to any one of clauses 1 to 8, wherein $R^1$ or $R^{20}$ is described by one of the following structures:

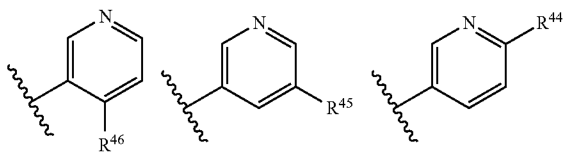

-continued

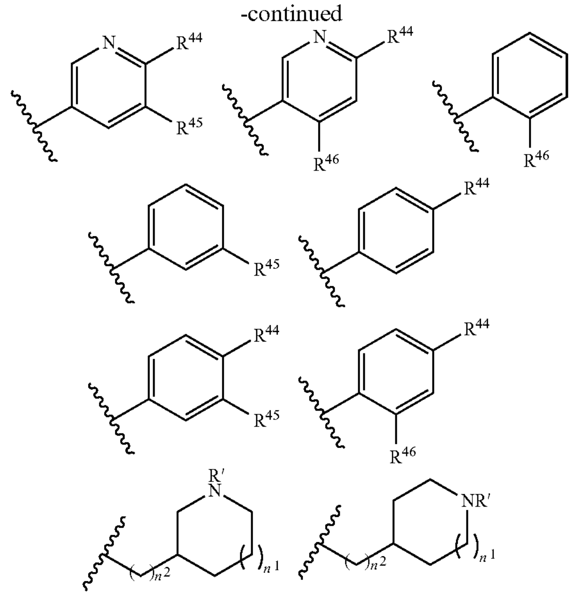

wherein $R^{44}$-$R^{46}$ are independently selected from hydrogen, an alkyl, an aryl, a hydroxy, an alkoxy, an aryloxy, a heterocycle, a cyano, a halogen, an amino, an acyl, an acyloxy, an amido, and a nitro; R' is hydrogen, an alkyl, an aryl or a heterocycle; $n^2$ is 0, 1, 2 or 3, and $n^1$ is 0, 1 or 2.

10. The compound according to any one of clauses 1 to 9, wherein the compound is described by a structure of Table 1.

11. An anti-infective pharmaceutical composition comprising the compound according to clause 1 and a pharmaceutically acceptable excipient.

12. A method of inhibiting a PI4-kinase, the method comprising contacting a sample comprising the PI4-kinase with the compound according to clause 1.

13. The method according to clause 12, wherein the PI4-kinase is a PI4-III kinase.

14. The method according to clause 13, wherein the PI4-III kinase is a PI4KIIIα- or PI4KIIIβ-kinase.

15. A method of treating a subject for an infective disease condition, the method comprising administering to the subject an effective amount of the compound according to clause 1.

16. The method according to clause 15, wherein the infective disease condition is caused by infection of a pathogen susceptible to PI4-kinase inhibition.

17. The method according to clause 16 wherein the infective disease condition results from infection with a pathogen selected from the group consisting of HCV, rhinovirus (e.g., B or C), *P. falciparum*, ebola virus, *francisella tularensis*, hantavirus, vaccinia, smallpox, Japanese encephalitis virus, hepatitis A virus, and influenza virus, PolioVirus, Enterovirus (e.g., A-D), West Nile Virus, cytomegalovirus, *P. aeruginosa*, and Dengue Virus (e.g., 1-4).

18. The method according to clause 17, wherein the pathogen is HCV.

19. The method according to clause 16, wherein the compound has broad-spectrum activity against two or more pathogens.

20. The method according to clause 16, wherein the compound modulates the activity of a PIP-2-dependent process.

21. The method according to clause 16, wherein the pathogen is characterized by having a BAAPP domain that interacts with PIP-2, wherein the BAAPP domain is derived from NS5A or NS4B protein.
22. A method of inhibiting viral infection, the method comprising contacting virus-infected cells with an effective dose of the compound according to clause 1 to inhibit viral replication.
23. The method according to clause 22, further comprising contacting the cells with a second antiviral agent.
24. The method according to clause 22, wherein the compound is formulated to be targeted to the liver.

What is claimed is:

1. A compound of the formula (XXI)

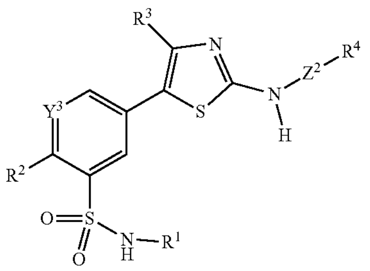

wherein:

$R^2$ is alkoxy or substituted alkoxy;

$R^3$ is hydrogen, lower alkyl or substituted lower alkyl;

$Y^3$ is CH;

$Z^2$ is absent;

$R^1$ is aryl, substituted aryl, alkyl, substituted alkyl, cycloalkyl, substituted cycloalkyl, heterocycle or substituted heterocycle; and $R^4$ is selected from alkyl, substituted alkyl, cycloalkyl, substituted cycloalkyl, alkyl-cycloalkyl, substituted alkyl-cycloalkyl, alkyl-aryl, substituted alkyl-aryl, aryl, substituted aryl, heterocycle, substituted heterocycle, alkyl-heterocycle and substituted alkyl-heterocycle, wherein the substituted alkyl, the substituted cycloalkyl, and the substituted alkyl-cycloalkyl are not substituted with an oxo or a thioketo;

or a prodrug thereof, or a pharmaceutically acceptable salt thereof.

2. A method of inhibiting a PI4-kinase, the method comprising contacting a sample comprising the PI4-kinase with the compound of claim 1.

3. The method of claim 2, wherein the PI4-kinase is a PI4-III kinase.

4. A method of treating a subject in need thereof for an infective disease condition, by inhibiting, relieving or causing regression of said disease condition, the method comprising administering to the subject a pharmaceutical composition comprising an effective amount of the compound of claim 1, or a pharmaceutically acceptable salt thereof, wherein the infective disease condition is caused by infection of a pathogen having a basic amino acid PIP-2 pincer (BAAPP) domain and is susceptible to PI4-kinase inhibition.

5. The method of claim 4, wherein the infective disease condition results from infection with a virus selected from the Picornaviridae, Flaviviridae, Caliciviridae, Filoviridae, Hepeviridae and Coronavirinae families.

6. The method of claim 5, wherein the infective disease condition results from infection with a virus from the Flaviviridae family.

7. The method of claim 5, wherein the infective disease condition results from infection with a pathogen selected from hepatitis C virus (HCV), rhinovirus, *P. falciparum*, ebola virus, *francisella tularensis*, hantavirus, SARS virus, MERS virus, vaccinia, smallpox, Japanese encephalitis virus, hepatitis A virus (HAV), influenza virus, norovirus, polio virus, enterovirus, hepatitis E virus (HEV), EV71, EV68, West Nile Virus, cytomegalovirus, *P. aeruginosa*, and Dengue virus.

8. The method of claim 7, wherein the pathogen is HCV.

9. The method of claim 7, wherein the pathogen is HAV.

10. The method of claim 7, wherein the pathogen is EV71 or EV68.

11. The method of claim 7, wherein the pathogen is human rhinovirus.

12. The method of claim 7, wherein the pathogen is norovirus.

13. The method of claim 7, wherein the pathogen is ebola virus.

14. The compound of claim 1, wherein $R^4$ is alkyl-aryl or substituted alkyl-aryl.

15. The compound of claim 1, wherein $R^4$ is alkyl-heterocycle or substituted alkyl-heterocycle.

16. The compound of claim 1, wherein $R^1$ is aryl, substituted aryl, heterocycle, or substituted heterocycle.

17. The compound of claim 16, wherein $R^1$ is aryl or substituted aryl.

18. The compound of claim 16, wherein $R^1$ is of the formula:

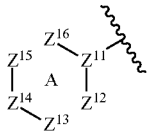

wherein $Z^{11}$, $Z^{12}$, $Z^{13}$, $Z^{14}$, $Z^{15}$, and $Z^{16}$ are each independently selected from N and CR';

wherein each R' is independently selected from hydrogen, alkyl, substituted alkyl, cyano, and halogen.

19. The compound of claim 18, wherein $Z^{11}$, $Z^{12}$, $Z^{13}$, and $Z^{15}$ are each CR'.

20. The compound of claim 18, wherein:

$R^2$ is alkoxy;

$R^3$ is lower alkyl; and $R^4$ is alkyl-aryl or substituted alkyl-aryl.

21. The compound of claim 18, wherein:

$R^2$ is alkoxy;

$R^3$ is lower alkyl; and $R^4$ is alkyl-heterocycle or substituted alkyl-heterocycle.

* * * * *

SEQUENCE LISTING

```
<160> NUMBER OF SEQ ID NOS: 1

<210> SEQ ID NO 1
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 1

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu
            20                  25
```